US011821042B2

(12) United States Patent
Cantley et al.

(10) Patent No.: US 11,821,042 B2
(45) Date of Patent: Nov. 21, 2023

(54) TARGETING CHROMOSOMAL INSTABILITY AND DOWNSTREAM CYTOSOLIC DNA SIGNALING FOR CANCER TREATMENT

(71) Applicants: Cornell University, Ithaca, NY (US); Memorial Sloan-Kettering Cancer Center, New York, NY (US)

(72) Inventors: Lewis C. Cantley, New York, NY (US); Bryan Ngo, New York, NY (US); Samuel F. Bakhoum, New York, NY (US)

(73) Assignees: Cornell University, Ithaca, NY (US); Memorial Sloan-Kettering Cancer Center, New York, NY (US)

( * ) Notice: Subject to any disclaimer, the term of this patent is extended or adjusted under 35 U.S.C. 154(b) by 475 days.

(21) Appl. No.: 16/629,512

(22) PCT Filed: Jul. 10, 2018

(86) PCT No.: PCT/US2018/041480
§ 371 (c)(1),
(2) Date: Jan. 8, 2020

(87) PCT Pub. No.: WO2019/014246
PCT Pub. Date: Jan. 17, 2019

(65) Prior Publication Data
US 2021/0130903 A1 May 6, 2021

Related U.S. Application Data

(60) Provisional application No. 62/530,661, filed on Jul. 10, 2017.

(51) Int. Cl.
| *C12Q 1/6886* | (2018.01) |
| *A61K 31/04* | (2006.01) |
| *C12N 15/113* | (2010.01) |
| *G01N 33/50* | (2006.01) |
| *A61K 48/00* | (2006.01) |

(52) U.S. Cl.
CPC ............ *C12Q 1/6886* (2013.01); *A61K 31/04* (2013.01); *A61K 48/0066* (2013.01); *C12N 15/113* (2013.01); *G01N 33/5011* (2013.01); *C12Q 2600/118* (2013.01); *C12Q 2600/136* (2013.01); *C12Q 2600/158* (2013.01); *G01N 33/5005* (2013.01); *G01N 2400/00* (2013.01)

(58) Field of Classification Search
CPC ............ C12Q 1/6886; C12Q 2600/118; C12Q 2600/136; C12Q 2600/158; G01N 33/5011; G01N 2400/00
See application file for complete search history.

(56) References Cited

U.S. PATENT DOCUMENTS

2017/0107577 A1   4/2017   Al-Ejeh

FOREIGN PATENT DOCUMENTS

| EP | 3045917 A2 | 7/2016 |
| JP | 2016-506408 A | 3/2016 |
| WO | WO2016044790 | * 3/2016 |
| WO | WO-2016044790 A1 | 3/2016 |
| WO | WO2016/176222 | * 11/2016 |
| WO | WO-2016176222 A1 | 11/2016 |
| WO | WO-2019014246 A1 | 1/2019 |

OTHER PUBLICATIONS

Ritter et al, Cell Cycle 14:3755-67, 2015 (Year: 2015).*
Heusinger et al, Frontiers, Feb. 8, 2017, article 198 (Year: 2017).*
Millet et al, JLB 94:941-951, Nov. 2013 (Year: 2013).*
"Mexican Application Serial No. MX/a/2020/000406, Voluntary Amendment filed May 19, 2021", (w/ English Claims), 125 pgs.
"Japanese Application Serial No. 2020-500887, Voluntary Amendment filed Jul. 8, 2021", (w/ English Claims), 14 pgs.
"European Application Serial No. 18746496.1, Communication Pursuant to Article 94(3) EPC dated Aug. 4, 2021", 8 pgs.
"Chinese Application Serial No. 201880058523.8, Amendment filed Oct. 9, 2020", (w/ English Translation), 25 pgs.
"European Application Serial No. 18746496.1, Response to Communication pursuant to Rules 161(1) and 162 EPC filed Aug. 17, 2020", 16 pgs.
"Japanese Application Serial No. 2020-500887, Voluntary Amendment filed May 12, 2020", (w/ Translation of English Claims'), 15 pgs.
"Miteiman Database of Chromosome Aberrations and Gene Fusions in Cancer", [online]. Retrieved from the Internet: <URL: https://mitelmandatabase.isb-cgc.org/>, (updated Oct. 15, 2020), 1 pg.
"Singaporean Application Serial No. 11202000132W, Voluntary Amendment filed Jul. 9, 2020", 19 pgs.

(Continued)

*Primary Examiner* — Lei Yao
(74) *Attorney, Agent, or Firm* — Schwegman Lundberg & Woessner, P.A.

(57) ABSTRACT

As described herein, chromosomal missegregations, chromosomal micronuclei, cytosolic DNA, and combinations thereof are indicative of metastatic cancer. Methods and compositions are described herein that are useful for detection and treatment of patients with chromosomal instabilities such as chromosomal missegregations, chromosomal micronuclei, cytosolic DNA, and combinations thereof. For example, some of the methods and compositions include use of kinesin-13 proteins such as Kif2b, MCAK/Kif2c, or KIF13A. The methods and compositions can also include inhibitors of STING, ENPP1, cGAS, NF-kB transcription factor p52, NF-kB transcription factor RelB, or any combination thereof. Methods are also described for identifying compounds that are effective for treatment of cancer, including metastatic cancer.

15 Claims, 44 Drawing Sheets
Specification includes a Sequence Listing.

(56) References Cited

OTHER PUBLICATIONS

Bakhoum, Samuel F., et al., "Chromosomal Instability Substantiates Poor Prognosis in Patients with Diffuse Large B-cell Lymphoma", Clinical Cancer Research 17(24), (2011), 7704-7711.

Bakhoum, Samuel F., et al., "DNA-Damage Response during Mitosis Induces Whole-Chromosome Missegregation", Cancer Discovery, 4(11), (Nov. 2014), 1281-1289.

Bakhoum, Samuel F., et al., "Numerical chromosomal instability mediates susceptibility to radiation treatment", Nature Communications, 6, Article No. 5990, (2015), 1-10.

Burrell, Rebecca, et al., "Replication stress links structural and numerical cancer chromosomal instability", Nature, 494, (2013), 492-496.

Burrell, Rebecca A., et al., "The causes and consequences of genetic heterogeneity in cancer evolution", Nature, 501, (2013), 338-345.

Cai, Xin, et al., "The cGAS-cGAMP-STING pathway of cytosolic DNA sensing and signaling". Molecular Cell, 54(2), (2014), 289-296.

Campbell, Peter J., "The patterns and dynamics of genomic instability in metastatic pancreatic cancer", Nature, vol. 467, (2010), 1109-1113.

Carter, Scott L., et al., "Absolute quantification of somatic DNA alterations in human cancer", Nature Biotechnology, 30, (2012), 14 pgs.

Crasta, Karen, et al., "DNA breaks and chromosome pulverization from errors in mitosis", Nature, 482(7383), (2012), 53-58 (8 pgs.).

Lau, Laura, et al., "DNA tumor virus oncogenes antagonize the cGAS-STING DNA-sensing pathway", Science, 350(6260), (2015), 568-571.

Lengauer, Christoph, et al., "Genetic instability in human cancers", Nature, 396(6625), (1998), 643-649.

Makohon-Moore, Alvin P., et al., "Limited heterogeneity of known driver gene mutations among the metastases of individual patients with pancreatic cancer", Nature Genetics, 49, (2017), 358-366.

Notta, Faiyaz, et al., "A renewed model of pancreatic cancer evolution based on genomic rearrangement patterns", Nature, 538(7625), (2016), 378-382 (21 pgs.).

Storchova, Zuzana, et al., "The consequences of tetraploidy and aneuploidy", Journal of Cell Science, 121(Pt 23), (2008), 3859-3866.

Sun, Lujun, et al., "Cyclic GMP-AMP Synthase Is a Cytosolic DNA Sensor That Activates the Type I Interferon Pathway", Science, 339(6129), (2013), 786-791.

Thompson, Sarah L., et al., "Examining the link between chromosomal instability and aneuploidy in human cells", Journal of Cell Biology, 180(4), (2008), 665-672.

Turajlic, Samra, et al., "Metastasis as an evolutionary process", Science, 352(6282), (2016), 169-175.

Zaki, Bassem, et al., "Chromosomal instability portends superior response of rectal adenocarcinoma to chemoradiation therapy", Cancer, 120(11), (2014), 1733-1742.

"Australian Application Serial No. 2018300007, Voluntary Amendment dated Sep. 30, 2022", 12 pgs.

"Chinese Application Serial No. 201880058523.8, Office Action dated Aug. 26, 2022", 9 pgs.

"Japanese Application Serial No. 2020-500887, Notification of Reasons for Refusal dated Apr. 25, 2022", (w/ English Translation), 14 pgs.

"Japanese Application Serial No. 2020-500887, Response filed Jul. 20, 2022 to Notification of Reasons for Refusal dated Apr. 25, 2022", (w/ English Translation of Claims), 37 pgs.

"Singaporean Application Serial No. 11202000132W, Response filed Feb. 3, 2022 to Written Opinion dated Sep. 3, 2021", (w/ English Translation of Claims), 13 pgs.

Baud, Veronique, et al., "Post-Translational Modifications of RelB NF-kB Subunit and Associated Functions", *Cells*, vol. 5: 22, (2016), 1-11.

Orr, Bernardo, et al., "Adaptive resistance to an inhibitor of chromosomalinstability in humancancer cells", *Cell Rep.*, vol. 17, (2016), 1755-1763.

Tozawa, Keiichi, "The role of NF-kB in urologic disease and therapeutic application", (w/ Partial Translation), *Nagoya Med. J.* vol. 51, (2006), 171-174.

Xu, Y, et al., "RelB Enhances Prostate Cancer Growth: Implications for the Role of the Nuclear Factor-κB Alternative Pathway in Tumorigenicity", *Cancer Res.* vol. 69, (2009), 3267-3271.

"International Application Serial No. PCT/US2018/041480, International Preliminary Report on Patentability dated Sep. 4, 2019", 15 pgs.

"International Application Serial No. PCT/US2018/041480, International Search Report dated Nov. 6, 2018", 8 pgs.

"International Application Serial No. PCT/US2018/041480, Invitation to Pay Add'l Fees and Partial Search Report dated Sep. 11, 2018", 7 pgs.

"International Application Serial No. PCT/US2018/041480, Written Opinion dated Nov. 6, 2018", 13 pgs.

Andreas, Ritter, et al., "Functional analysis of phosphorylation of the mitotic centromere-associated kinesin by Aurora B kinase in human tumor cells", Cell Cycle, vol. 14, No. 23, (Jul. 6, 2015), 3755-3767.

Elena, Heusinger, et al., "Primate Lentiviruses Modulate NF-[kappa]B Activity by Multiple Mechanisms to Fine-Tune Viral and Cellular Gene Expression", Frontiers in Microbiology, vol. 8, (Feb. 14, 2017), 12 pgs.

Samuel, F Bakhoum, et al., "Chromosomal instability drives metastasis through a cytosolic DNA response", Nature, vol. 553, No. 7689, (Jan. 25, 2018), 467-472.

Samuel, F Bakhoum, et al., "Genome stability is ensured by temporal control of kinetochore-microtubule dynamics", Nature Cell Biology, vol. 11, No. 1, (Dec. 7, 2008), 27-35.

"European Application Serial No. 18746496.1, Communication Pursuant to Article 94(3) EPC dated Mar. 21, 2023", 11 pgs.

"Chinese Application Serial No. 201880058523.8, Office Action dated Aug. 12, 2023", w machine English Translation, 11 pgs.

\* cited by examiner

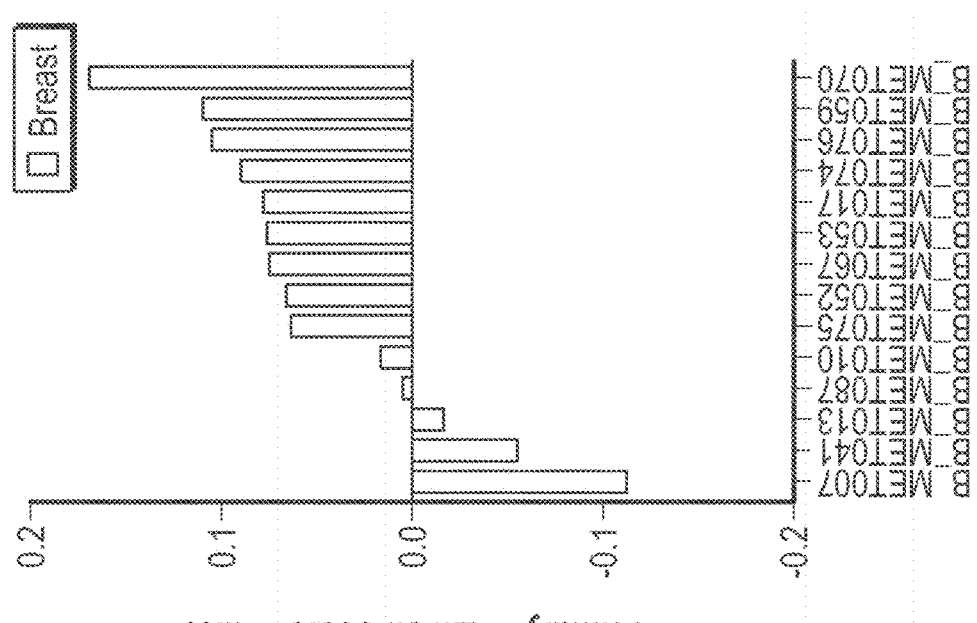
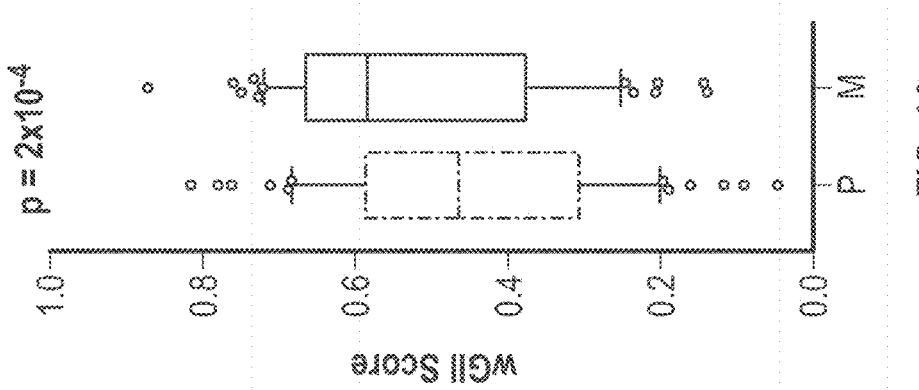
FIG. 1A
FIG. 1B-1

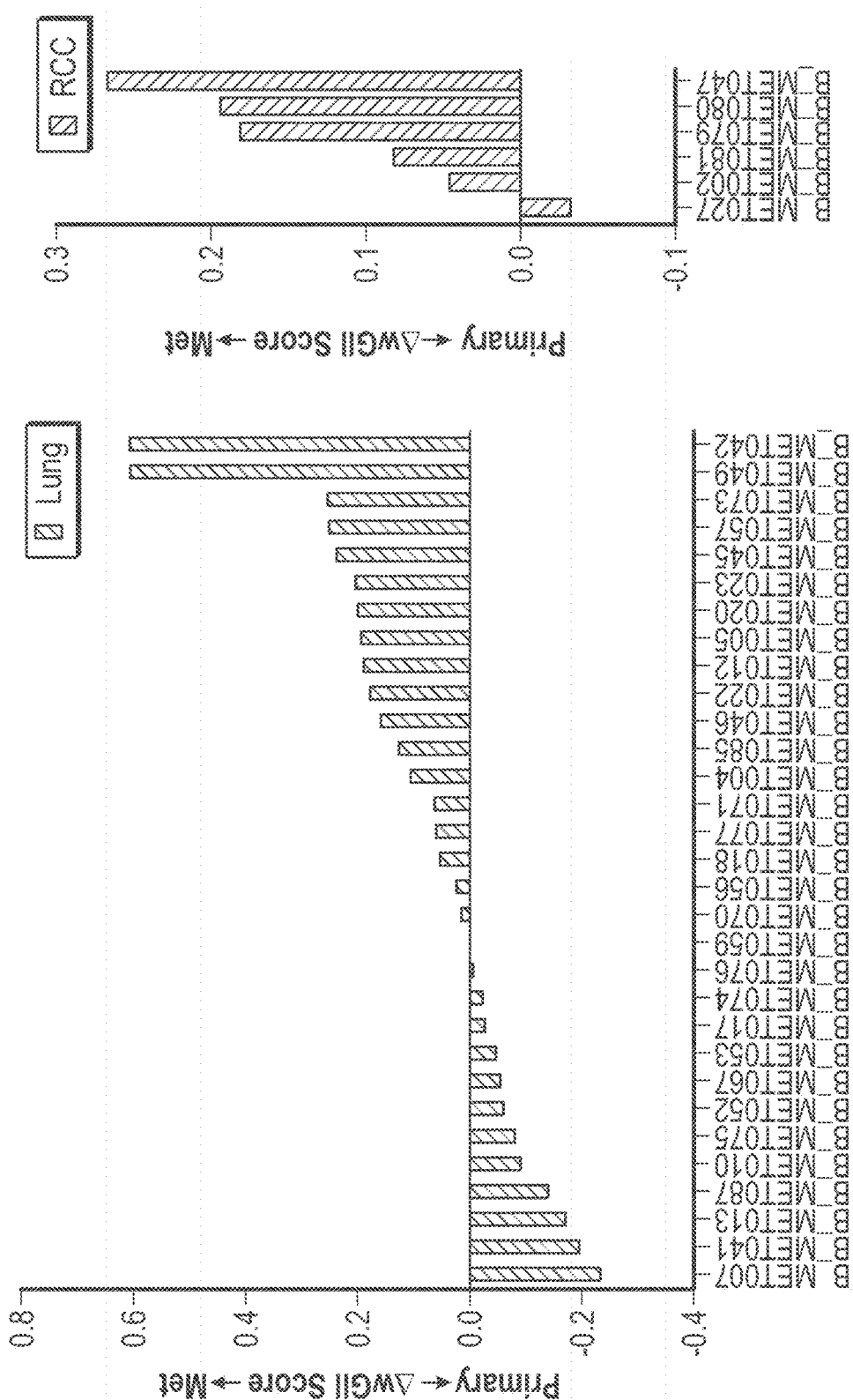

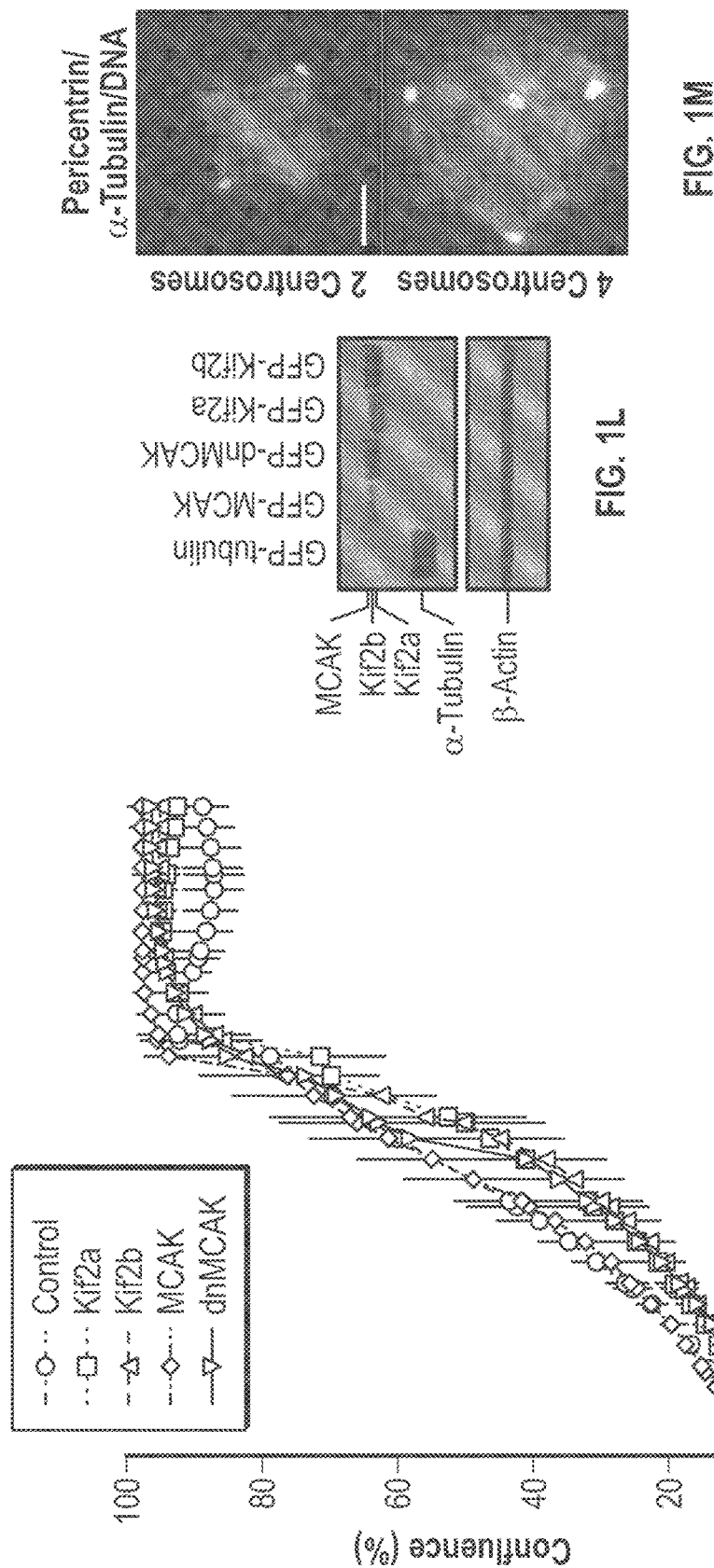

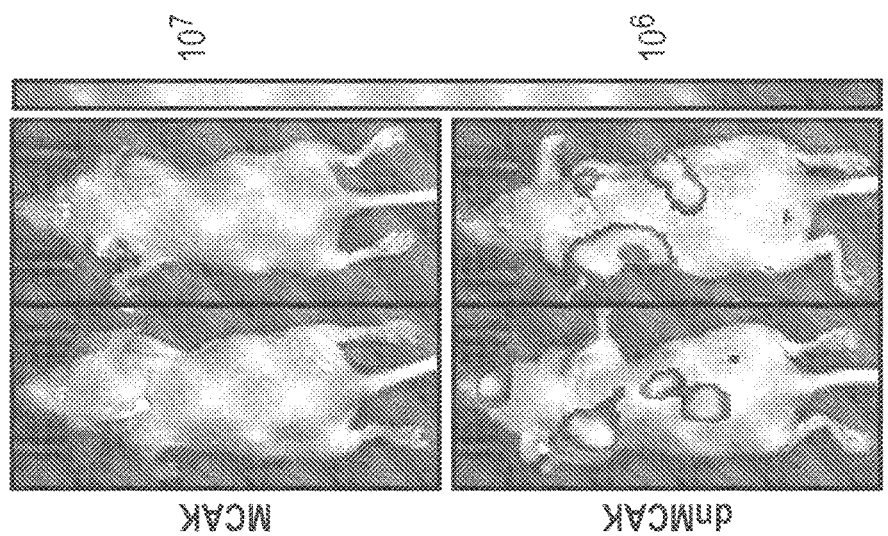
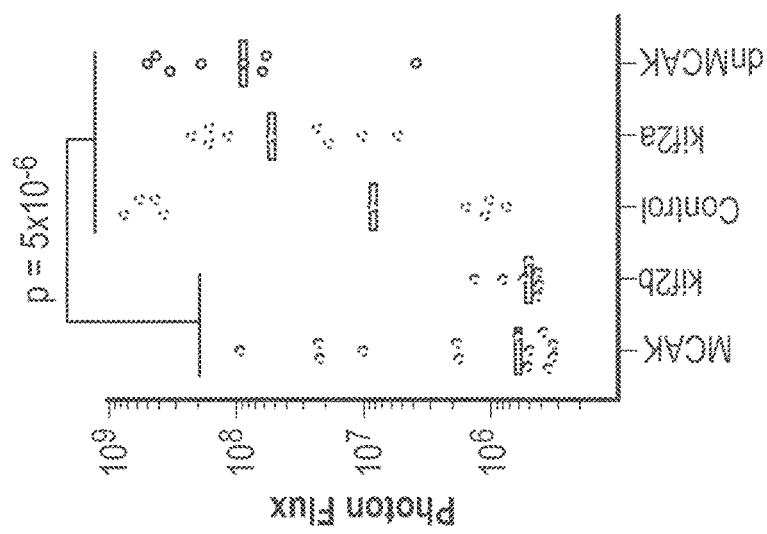
FIG. 2C-1
FIG. 2C-2

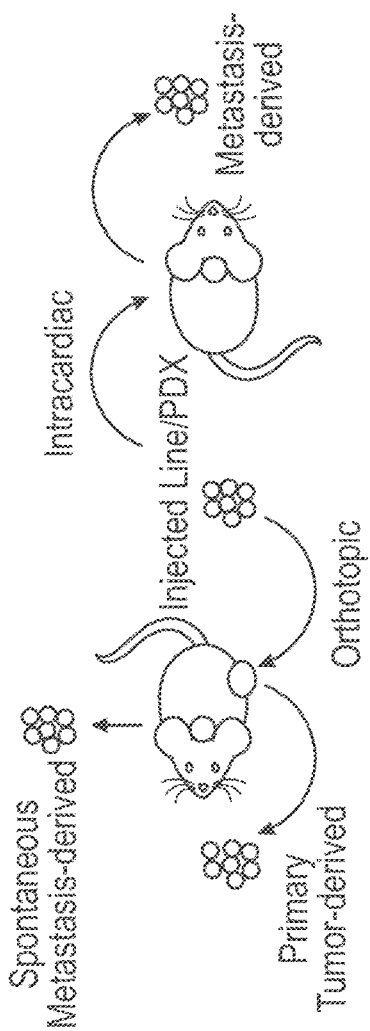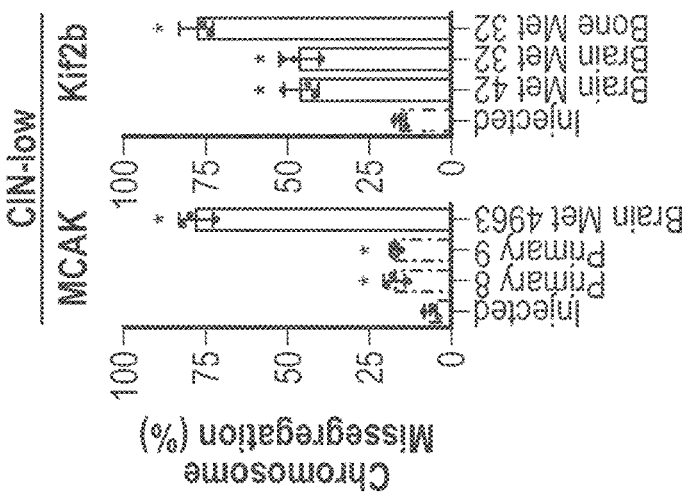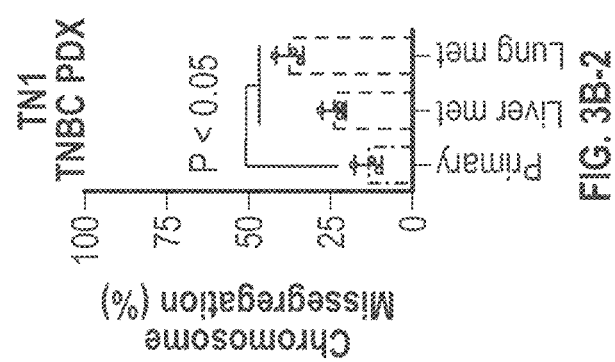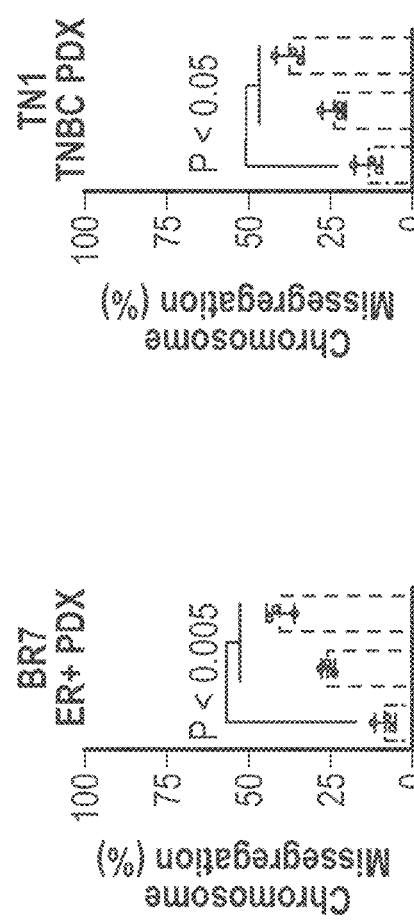

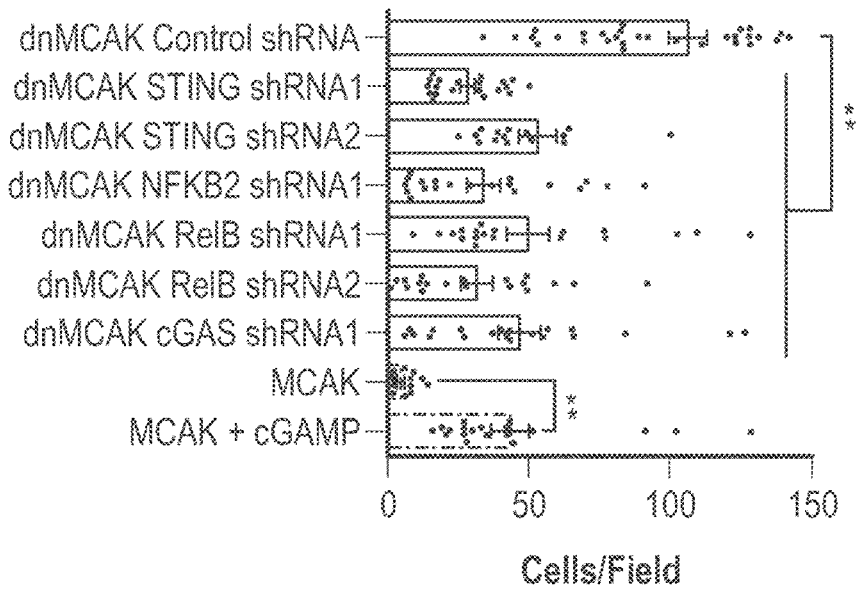
FIG. 6H
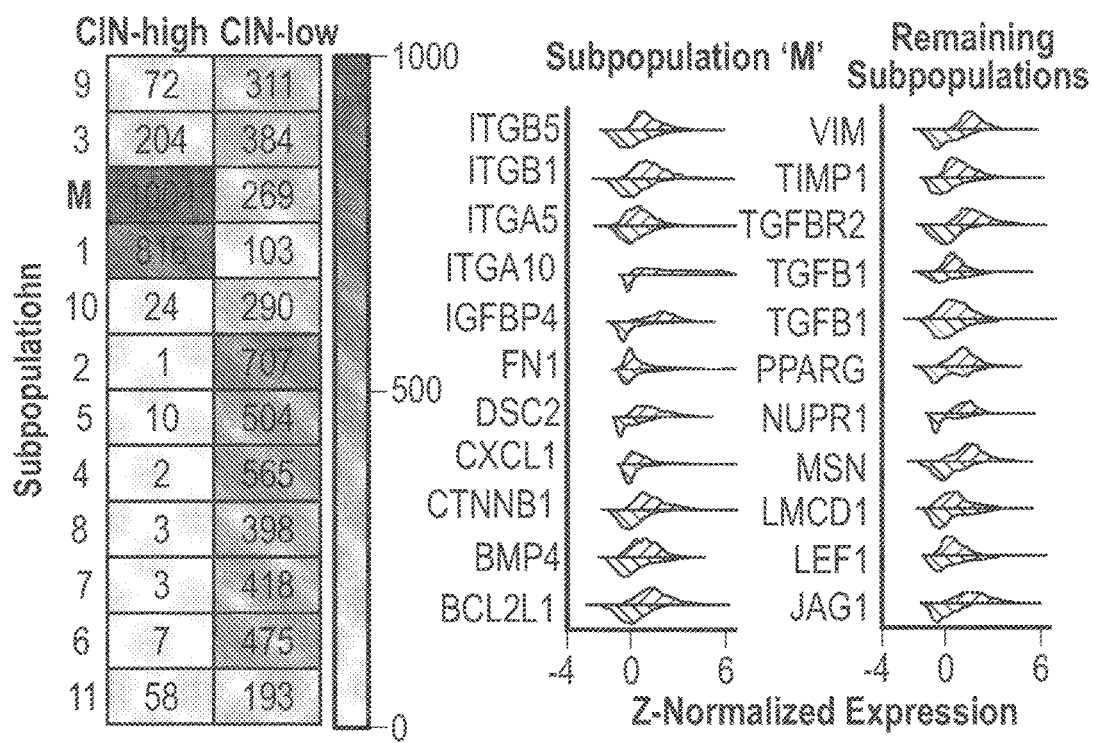
FIG. 6I
FIG. 6J

SEQUENCE LISTING

```
<160> NUMBER OF SEQ ID NOS: 61

<210> SEQ ID NO 1
<211> LENGTH: 673
<212> TYPE: PRT
<213> ORGANISM: Homo sapiens

<400> SEQUENCE: 1

Met Ala Ser Gln Phe Cys Leu Pro Glu Ser Pro Cys Leu Ser Pro Leu
1               5                   10                  15

Lys Pro Leu Lys Pro His Phe Gly Asp Ile Gln Glu Gly Ile Tyr Val
            20                  25                  30

Ala Ile Gln Arg Ser Asp Lys Arg Ile His Leu Ala Val Val Thr Glu
        35                  40                  45

Ile Asn Arg Glu Asn Tyr Trp Val Thr Val Glu Trp Val Glu Lys Ala
    50                  55                  60

Val Lys Lys Gly Lys Lys Ile Asp Leu Glu Thr Ile Leu Leu Leu Asn
65                  70                  75                  80

Pro Ala Leu Asp Ser Ala Glu His Pro Met Pro Pro Pro Leu Ser
                85                  90                  95

Pro Leu Ala Leu Ala Pro Ser Ser Ala Ile Arg Asp Gln Arg Thr Ala
            100                 105                 110

Thr Lys Trp Val Ala Met Ile Pro Gln Lys Asn Gln Thr Ala Ser Gly
        115                 120                 125

Asp Ser Leu Asp Val Arg Val Pro Ser Lys Pro Cys Leu Met Lys Gln
130                 135                 140

Lys Lys Ser Pro Cys Leu Trp Glu Ile Gln Lys Leu Gln Glu Gln Arg
145                 150                 155                 160

Glu Lys Arg Arg Arg Leu Gln Gln Glu Ile Arg Ala Arg Arg Ala Leu
            165                 170                 175

Asp Val Asn Thr Arg Asn Pro Asn Tyr Glu Ile Met His His Met Ile Glu
        180                 185                 190

Glu Tyr Arg Arg His Leu Asp Ser Ser Lys Ile Ser Val Leu Glu Pro
    195                 200                 205

Pro Gln Glu His Arg Ile Cys Val Cys Val Arg Lys Arg Pro Leu Asn
    210                 215                 220

Gln Arg Glu Thr Thr Leu Lys Asp Leu Asp Ile Ile Thr Val Pro Ser
225                 230                 235                 240

Asp Asn Val Val Met Val His Glu Ser Lys Gln Lys Val Asp Leu Thr
                245                 250                 255
```

```
Arg Tyr Leu Gln Asn Gln Thr Phe Cys Phe Asp His Ala Phe Asp Asp
            260                 265                 270

Lys Ala Ser Asn Glu Leu Val Tyr Gln Phe Thr Ala Gln Pro Leu Val
        275                 280                 285

Glu Ser Ile Phe Arg Lys Gly Met Ala Thr Cys Phe Ala Tyr Gly Gln
    290                 295                 300

Thr Gly Ser Gly Lys Thr Tyr Thr Met Gly Gly Asp Phe Ser Gly Thr
305                 310                 315                 320

Ala Gln Asp Cys Ser Lys Gly Ile Tyr Ala Leu Val Ala Gln Asp Val
                325                 330                 335

Phe Leu Leu Leu Arg Asn Ser Thr Tyr Glu Lys Leu Asp Leu Lys Val
            340                 345                 350

Tyr Gly Thr Phe Phe Glu Ile Tyr Gly Gly Lys Val Tyr Asp Leu Leu
        355                 360                 365

Asn Trp Lys Lys Lys Leu Gln Val Leu Glu Asp Gly Asn Gln Gln Ile
    370                 375                 380

Gln Val Val Gly Leu Gln Glu Lys Glu Val Cys Cys Val Glu Glu Val
385                 390                 395                 400

Leu Asn Leu Val Glu Ile Gly Asn Ser Cys Arg Thr Ser Arg Gln Thr
                405                 410                 415

Pro Val Asn Ala His Ser Ser Arg Ser His Ala Val Phe Gln Ile Ile
            420                 425                 430

Leu Lys Ser Gly Arg Ile Met His Gly Lys Phe Ser Leu Val Asp Leu
        435                 440                 445

Ala Gly Asn Glu Arg Gly Ala Asp Thr Thr Lys Ala Ser Arg Lys Arg
    450                 455                 460

Gln Leu Glu Gly Ala Glu Ile Asn Lys Ser Leu Leu Ala Leu Lys Glu
465                 470                 475                 480

Cys Ile Leu Ala Leu Gly Gln Asn Lys Pro His Thr Pro Phe Arg Ala
                485                 490                 495

Ser Lys Leu Thr Leu Val Leu Arg Asp Ser Phe Ile Gly Gln Asn Ser
            500                 505                 510

Ser Thr Cys Met Ile Ala Thr Ile Ser Pro Gly Met Thr Ser Cys Glu
        515                 520                 525

Asn Thr Leu Asn Thr Leu Arg Tyr Ala Asn Arg Val Lys Lys Leu Asn
    530                 535                 540

Val Asp Val Arg Pro Tyr His Arg Gly His Tyr Pro Ile Gly His Glu
545                 550                 555                 560

Ala Pro Arg Met Leu Lys Ser His Ile Gly Asn Ser Glu Met Ser Leu
                565                 570                 575

Gln Arg Asp Glu Phe Ile Lys Ile Pro Tyr Val Gln Ser Glu Glu Gln
            580                 585                 590

Lys Glu Ile Glu Glu Val Glu Thr Leu Pro Thr Leu Leu Gly Lys Asp
        595                 600                 605

Thr Thr Ile Ser Gly Lys Gly Ser Ser Gln Trp Leu Glu Asn Ile Gln
    610                 615                 620

Glu Arg Ala Gly Gly Val His His Asp Ile Asp Phe Cys Ile Ala Arg
625                 630                 635                 640

Ser Leu Ser Ile Leu Glu Gln Lys Ile Asp Ala Leu Thr Glu Ile Gln
                645                 650                 655

Lys Lys Leu Lys Leu Leu Leu Ala Asp Leu His Val Lys Ser Lys Val
            660                 665                 670

Glu
```

<210> SEQ ID NO 2
<211> LENGTH: 2335
<212> TYPE: PRT
<213> ORGANISM: Homo sapiens

<400> SEQUENCE: 2

```
Gly Thr Ala Gly Thr Gly Gly Cys Cys Cys Ala Gly Thr Cys Cys
1               5                   10                  15

Gly Gly Gly Cys Cys Cys Gly Cys Gly Cys Gly Cys Thr Ala
            20                  25                  30

Gly Gly Cys Thr Cys Ala Cys Ala Ala Gly Gly Cys Ala Gly Gly
            35                  40                  45

Cys Ala Cys Ala Gly Ala Cys Thr Gly Cys Ala Ala Cys Cys Thr
        50                  55                  60

Gly Cys Thr Cys Ala Gly Thr Gly Cys Thr Cys Gly Gly Gly Cys
65                  70                  75                  80

Gly Cys Thr Thr Cys Ala Gly Gly Cys Thr Gly Gly Cys Thr Thr Gly
            85                  90                  95

Gly Gly Thr Cys Cys Thr Gly Cys Thr Gly Cys Thr Cys Ala Ala
            100                 105                 110

Cys Cys Cys Cys Ala Ala Gly Gly Cys Cys Cys Thr Gly Gly Ala
        115                 120                 125

Gly Cys Gly Cys Thr Cys Cys Cys Thr Gly Ala Thr Ala Cys Cys Thr
        130                 135                 140

Cys Cys Ala Thr Cys Ala Cys Thr Cys Ala Cys Cys Ala Thr Gly Gly
145                 150                 155                 160

Cys Cys Ala Gly Cys Cys Ala Gly Thr Thr Cys Thr Gly Cys Cys Thr
            165                 170                 175

Cys Cys Cys Thr Gly Ala Ala Thr Cys Cys Cys Ala Thr Gly Thr
        180                 185                 190

Cys Thr Cys Thr Cys Gly Cys Cys Cys Thr Gly Ala Ala Ala Cys
        195                 200                 205

Cys Cys Thr Thr Gly Ala Ala Gly Cys Cys Ala Cys Ala Thr Thr Thr
        210                 215                 220

Cys Gly Gly Ala Gly Ala Cys Ala Thr Cys Cys Ala Ala Gly Ala Gly
225                 230                 235                 240

Gly Gly Cys Ala Thr Cys Thr Ala Cys Gly Thr Gly Gly Cys Gly Ala
            245                 250                 255

Thr Cys Cys Ala Gly Cys Gly Cys Ala Gly Thr Gly Ala Cys Ala Ala
        260                 265                 270

Gly Cys Gly Gly Ala Thr Cys Cys Ala Cys Cys Thr Cys Gly Cys Thr
            275                 280                 285

Gly Thr Gly Gly Thr Cys Ala Cys Gly Gly Ala Gly Ala Thr Cys Ala
        290                 295                 300

Ala Cys Ala Gly Ala Gly Ala Ala Ala Cys Thr Ala Thr Thr Gly
305                 310                 315                 320

Gly Gly Thr Cys Ala Cys Gly Gly Thr Ala Gly Ala Gly Thr Gly Gly
            325                 330                 335

Gly Thr Gly Gly Ala Gly Ala Ala Ala Gly Cys Ala Gly Thr Cys Ala
            340                 345                 350

Ala Ala Ala Ala Gly Gly Cys Ala Ala Gly Ala Ala Gly Ala Thr
        355                 360                 365

Thr Gly Ala Cys Cys Thr Gly Gly Ala Gly Ala Cys Cys Ala Thr Ala
```

```
                370                 375                 380
Cys Thr Cys Cys Thr Gly Cys Thr Gly Ala Ala Thr Cys Cys Ala Gly
385                 390                 395                 400

Cys Thr Cys Thr Gly Gly Ala Cys Thr Cys Thr Gly Cys Thr Gly Ala
                405                 410                 415

Ala Cys Ala Cys Cys Cys Cys Ala Thr Gly Cys Cys Gly Cys Cys Cys
                420                 425                 430

Cys Cys Gly Cys Cys Cys Thr Thr Ala Thr Cys Cys Cys Cys Cys Thr
            435                 440                 445

Thr Gly Gly Cys Thr Cys Thr Gly Gly Cys Gly Cys Cys Cys Thr Cys
            450                 455                 460

Thr Thr Cys Gly Gly Cys Cys Ala Thr Cys Ala Gly Gly Gly Ala Cys
465                 470                 475                 480

Cys Ala Gly Cys Gly Thr Ala Cys Cys Gly Cys Cys Ala Cys Gly Ala
                485                 490                 495

Ala Ala Thr Gly Gly Gly Thr Thr Gly Cys Gly Ala Thr Gly Ala Thr
                500                 505                 510

Cys Cys Cys Cys Cys Ala Gly Ala Ala Ala Ala Cys Cys Ala Ala Ala
            515                 520                 525

Ala Cys Ala Gly Cys Cys Thr Cys Ala Gly Gly Gly Ala Cys Ala
            530                 535                 540

Gly Cys Cys Thr Gly Gly Ala Thr Gly Thr Gly Ala Gly Gly Gly Thr
545                 550                 555                 560

Cys Cys Cys Cys Ala Gly Cys Ala Ala Ala Cys Cys Thr Thr Gly Thr
                565                 570                 575

Cys Thr Gly Ala Thr Gly Ala Ala Gly Cys Ala Gly Ala Ala Ala Ala
                580                 585                 590

Ala Gly Thr Cys Thr Cys Cys Thr Gly Cys Cys Thr Cys Thr Cys Thr Gly
            595                 600                 605

Gly Gly Ala Ala Ala Thr Cys Cys Ala Gly Ala Ala Ala Cys Thr Gly
            610                 615                 620

Cys Ala Gly Gly Ala Gly Cys Ala Gly Cys Gly Gly Gly Ala Ala Ala
625                 630                 635                 640

Ala Gly Cys Gly Cys Ala Gly Gly Gly Cys Gly Thr Gly Cys Ala
                645                 650                 655

Gly Cys Ala Gly Gly Ala Gly Ala Thr Cys Cys Gly Ala Gly Cys Thr
            660                 665                 670

Ala Gly Ala Cys Gly Cys Gly Cys Cys Thr Cys Gly Ala Thr Gly
            675                 680                 685

Thr Cys Ala Ala Thr Ala Cys Cys Ala Gly Ala Ala Ala Cys Cys Cys
            690                 695                 700

Cys Ala Ala Cys Thr Ala Cys Gly Ala Ala Ala Thr Cys Ala Thr Gly
705                 710                 715                 720

Cys Ala Cys Ala Thr Gly Ala Thr Cys Gly Ala Ala Gly Ala Gly Thr
                725                 730                 735

Ala Thr Cys Gly Cys Ala Gly Gly Cys Ala Cys Cys Thr Gly Gly Ala
                740                 745                 750

Cys Ala Gly Cys Ala Gly Cys Ala Ala Gly Ala Thr Cys Thr Cys Ala
            755                 760                 765

Gly Thr Cys Cys Thr Gly Gly Ala Gly Cys Cys Cys Cys Gly Cys
            770                 775                 780

Ala Ala Gly Ala Ala Cys Ala Thr Cys Gly Cys Ala Thr Cys Thr Gly
785                 790                 795                 800
```

-continued

```
Cys Gly Thr Cys Thr Gly Cys Gly Thr Gly Ala Gly Ala Ala Gly
                805                 810                 815
Cys Gly Gly Cys Cys Thr Cys Thr Cys Ala Ala Cys Cys Ala Gly Cys
            820                 825                 830
Gly Ala Gly Ala Gly Ala Cys Ala Ala Cys Cys Thr Ala Ala Ala
                835                 840                 845
Gly Gly Ala Cys Cys Thr Gly Gly Ala Thr Ala Thr Cys Ala Thr Cys
        850                 855                 860
Ala Cys Cys Gly Thr Cys Cys Cys Thr Cys Gly Gly Ala Cys Ala
865                 870                 875                 880
Ala Thr Gly Thr Gly Gly Thr Thr Ala Thr Gly Gly Thr Gly Cys Ala
                885                 890                 895
Thr Gly Ala Gly Thr Cys Cys Ala Ala Gly Cys Ala Ala Ala Gly
                900                 905                 910
Gly Thr Gly Gly Ala Cys Cys Thr Cys Ala Cys Thr Cys Gly Cys Thr
            915                 920                 925
Ala Cys Cys Thr Gly Cys Ala Gly Ala Ala Cys Cys Ala Gly Ala Cys
930                 935                 940
Cys Thr Thr Cys Thr Gly Cys Thr Thr Cys Gly Ala Cys Cys Ala Thr
945                 950                 955                 960
Gly Cys Cys Thr Thr Cys Gly Ala Thr Gly Ala Cys Ala Ala Ala Gly
            965                 970                 975
Cys Cys Thr Cys Cys Ala Ala Cys Gly Ala Gly Thr Thr Gly Gly Thr
        980                 985                 990
Gly Thr Ala Cys Cys Ala Gly Thr Thr Cys Ala Cys Cys Gly Cys Cys
            995                 1000                1005
Cys Ala Gly Cys Cys Ala Cys Thr Gly Gly Thr Gly Gly Ala Gly Thr
    1010                1015                1020
Cys Cys Ala Thr Cys Thr Thr Cys Cys Gly Cys Ala Ala Gly Gly Gly
1025                1030                1035                1040
Cys Ala Thr Gly Gly Cys Cys Ala Cys Cys Thr Gly Cys Thr Thr Thr
            1045                1050                1055
Gly Cys Cys Thr Ala Thr Gly Gly Gly Cys Ala Gly Ala Cys Gly Gly
        1060                1065                1070
Gly Ala Ala Gly Thr Gly Gly Gly Ala Ala Gly Ala Cys Gly Thr Ala
            1075                1080                1085
Cys Ala Cys Cys Ala Thr Gly Gly Thr Gly Gly Ala Gly Ala Cys
        1090                1095                1100
Thr Thr Thr Thr Cys Ala Gly Gly Ala Ala Cys Gly Gly Cys Cys Cys
1105                1110                1115                1120
Ala Ala Gly Ala Thr Thr Gly Thr Thr Cys Thr Ala Ala Gly Gly Gly
                1125                1130                1135
Cys Ala Thr Thr Thr Ala Thr Gly Cys Thr Cys Thr Gly Gly Thr Gly
            1140                1145                1150
Gly Cys Ala Cys Ala Gly Gly Ala Thr Gly Thr Cys Thr Thr Thr Cys
        1155                1160                1165
Thr Cys Cys Thr Gly Cys Thr Cys Ala Gly Ala Ala Ala Cys Thr Cys
    1170                1175                1180
Cys Ala Cys Ala Thr Ala Thr Gly Ala Gly Ala Ala Gly Cys Thr Gly
1185                1190                1195                1200
Gly Ala Cys Cys Thr Cys Ala Ala Ala Gly Thr Cys Thr Ala Thr Gly
        1205                1210                1215
```

-continued

Gly Gly Ala Cys Ala Thr Thr Thr Thr Thr Thr Gly Ala Gly Ala Thr
            1220                1225                1230

Thr Thr Ala Thr Gly Gly Gly Gly Gly Cys Ala Ala Gly Gly Thr Gly
        1235                1240                1245

Thr Ala Thr Gly Ala Thr Thr Thr Gly Thr Thr Gly Ala Ala Cys Thr
        1250                1255                1260

Gly Gly Ala Ala Gly Ala Ala Gly Ala Ala Gly Cys Thr Gly Cys Ala
1265                1270                1275                1280

Ala Gly Thr Cys Cys Thr Thr Gly Ala Gly Gly Ala Thr Gly Gly Cys
                1285                1290                1295

Ala Ala Thr Cys Ala Gly Cys Ala Ala Ala Thr Cys Cys Ala Ala Gly
                1300                1305                1310

Thr Gly Gly Thr Cys Gly Gly Gly Cys Thr Gly Cys Ala Gly Gly Ala
            1315                1320                1325

Gly Ala Ala Ala Gly Ala Gly Gly Thr Gly Thr Gly Thr Thr Gly Thr
        1330                1335                1340

Gly Thr Gly Gly Ala Gly Gly Ala Ala Gly Thr Gly Cys Thr Gly Ala
1345                1350                1355                1360

Ala Cys Cys Thr Gly Gly Thr Gly Gly Ala Ala Ala Thr Ala Gly Gly
            1365                1370                1375

Gly Ala Ala Thr Ala Gly Cys Thr Gly Thr Cys Gly Gly Ala Cys Thr
        1380                1385                1390

Thr Cys Cys Ala Gly Gly Cys Ala Ala Ala Cys Ala Cys Cys Thr Gly
            1395                1400                1405

Thr Cys Ala Ala Cys Gly Cys Thr Cys Ala Cys Thr Cys Ala Thr Cys
        1410                1415                1420

Cys Ala Gly Gly Ala Gly Cys Cys Ala Thr Gly Cys Ala Gly Thr Gly
1425                1430                1435                1440

Thr Thr Cys Cys Ala Gly Ala Thr Cys Ala Thr Cys Thr Gly Thr Ala
            1445                1450                1455

Ala Gly Thr Cys Ala Gly Gly Ala Cys Gly Gly Ala Thr Ala Ala Thr
            1460                1465                1470

Gly Cys Ala Thr Gly Gly Cys Ala Ala Gly Thr Thr Thr Thr Cys Cys
        1475                1480                1485

Cys Thr Cys Gly Thr Thr Gly Ala Thr Thr Thr Ala Gly Cys Thr Gly
            1490                1495                1500

Gly Gly Ala Ala Thr Gly Ala Ala Ala Gly Ala Gly Gly Ala Gly Cys
1505                1510                1515                1520

Ala Gly Ala Thr Ala Cys Ala Ala Cys Cys Ala Ala Gly Gly Cys Cys
            1525                1530                1535

Ala Gly Cys Cys Gly Gly Ala Ala Ala Ala Gly Gly Cys Ala Gly Cys
            1540                1545                1550

Thr Gly Gly Ala Ala Gly Gly Gly Gly Cys Ala Gly Ala Gly Ala Thr
        1555                1560                1565

Thr Ala Ala Cys Ala Ala Gly Ala Gly Thr Cys Thr Thr Cys Thr Ala
        1570                1575                1580

Gly Cys Cys Cys Thr Cys Ala Ala Gly Ala Ala Thr Gly Thr Ala
1585                1590                1595                1600

Thr Thr Cys Thr Gly Gly Cys Thr Thr Thr Gly Gly Gly Thr Cys Ala
            1605                1610                1615

Gly Ala Ala Cys Ala Ala Gly Cys Cys Thr Cys Ala Cys Ala Cys Cys
        1620                1625                1630

Cys Cys Ala Thr Thr Cys Ala Gly Ala Gly Cys Cys Ala Gly Cys Ala

-continued

```
        1635                1640                1645

Ala Ala Cys Thr Cys Ala Cys Ala Cys Thr Gly Gly Thr Gly Cys Thr
    1650                1655                1660

Cys Cys Gly Gly Gly Ala Cys Thr Cys Cys Thr Thr Thr Ala Thr Ala
1665                1670                1675                1680

Gly Gly Cys Cys Ala Gly Ala Ala Cys Thr Cys Cys Thr Cys Cys Ala
                1685                1690                1695

Cys Thr Thr Gly Cys Ala Thr Gly Ala Thr Thr Gly Cys Thr Ala Cys
            1700                1705                1710

Cys Ala Thr Cys Thr Cys Thr Cys Cys Gly Gly Gly Gly Ala Thr Gly
        1715                1720                1725

Ala Cys Cys Thr Cys Thr Thr Gly Thr Gly Ala Ala Ala Ala Cys Ala
    1730                1735                1740

Cys Thr Cys Thr Cys Ala Ala Cys Ala Cys Thr Thr Thr Ala Ala Gly
1745                1750                1755                1760

Ala Thr Ala Thr Gly Cys Ala Ala Ala Cys Ala Gly Ala Gly Thr Ala
                1765                1770                1775

Ala Ala Ala Ala Ala Ala Thr Thr Ala Ala Ala Thr Gly Thr Ala Gly
            1780                1785                1790

Ala Thr Gly Thr Ala Ala Gly Gly Cys Cys Cys Thr Ala Cys Cys Ala
        1795                1800                1805

Thr Cys Gly Thr Gly Gly Cys Cys Ala Cys Thr Ala Thr Cys Cys Gly
    1810                1815                1820

Ala Thr Thr Gly Gly Ala Cys Ala Thr Gly Ala Gly Gly Cys Ala Cys
1825                1830                1835                1840

Cys Ala Ala Gly Gly Ala Thr Gly Thr Thr Ala Ala Ala Ala Ala Gly
                1845                1850                1855

Thr Cys Ala Cys Ala Thr Cys Gly Gly Ala Ala Ala Thr Thr Cys Ala
            1860                1865                1870

Gly Ala Ala Ala Thr Gly Thr Cys Cys Cys Thr Thr Cys Ala Gly Ala
        1875                1880                1885

Gly Gly Gly Ala Thr Gly Ala Ala Thr Thr Thr Ala Thr Thr Ala Ala
    1890                1895                1900

Ala Ala Thr Ala Cys Cys Thr Thr Ala Thr Gly Thr Ala Cys Ala Gly
1905                1910                1915                1920

Ala Gly Thr Gly Ala Gly Gly Ala Gly Cys Ala Gly Ala Ala Ala Gly
                1925                1930                1935

Ala Gly Ala Thr Thr Gly Ala Ala Gly Ala Gly Gly Thr Thr Gly Ala
            1940                1945                1950

Ala Ala Cys Ala Thr Thr Ala Cys Cys Cys Ala Cys Thr Cys Thr Gly
        1955                1960                1965

Thr Thr Ala Gly Gly Gly Ala Ala Gly Gly Ala Thr Ala Cys Cys Ala
    1970                1975                1980

Cys Ala Ala Thr Thr Thr Cys Ala Gly Gly Gly Ala Ala Gly Gly Gly
1985                1990                1995                2000

Ala Thr Cys Thr Ala Gly Cys Cys Ala Ala Thr Gly Gly Cys Thr Gly
                2005                2010                2015

Gly Ala Ala Ala Ala Cys Ala Thr Cys Cys Ala Gly Gly Ala Gly Ala
            2020                2025                2030

Gly Ala Gly Cys Thr Gly Gly Thr Gly Gly Ala Gly Thr Ala Cys Ala
        2035                2040                2045

Cys Cys Ala Thr Gly Ala Thr Ala Thr Thr Gly Ala Thr Thr Thr Thr
    2050                2055                2060
```

-continued

Thr Gly Cys Ala Thr Thr Gly Cys Cys Cys Gly Gly Thr Cys Thr Thr
            2065                2070                2075                2080

Thr Gly Thr Cys Cys Ala Thr Thr Thr Gly Gly Ala Gly Cys Ala
            2085                2090                2095

Gly Ala Ala Ala Ala Thr Thr Gly Ala Thr Gly Cys Thr Cys Thr Gly
            2100                2105                2110

Ala Cys Cys Gly Ala Gly Ala Thr Cys Cys Ala Ala Ala Gly Ala
            2115                2120                2125

Ala Ala Cys Thr Gly Ala Ala Ala Thr Thr Ala Thr Thr Ala Cys Thr
            2130                2135                2140

Ala Gly Cys Thr Gly Ala Cys Cys Thr Cys Cys Ala Cys Gly Thr Gly
            2145                2150                2155                2160

Ala Ala Gly Ala Gly Cys Ala Ala Gly Gly Thr Ala Gly Ala Gly Thr
            2165                2170                2175

Gly Ala Ala Gly Cys Cys Ala Ala Thr Gly Gly Cys Gly Ala Gly Ala
            2180                2185                2190

Gly Ala Thr Cys Ala Gly Gly Thr Cys Cys Gly Ala Ala Ala Thr Gly
            2195                2200                2205

Cys Thr Gly Cys Ala Thr Thr Gly Cys Thr Gly Cys Ala Gly Thr Thr
            2210                2215                2220

Thr Cys Cys Ala Cys Cys Ala Cys Thr Cys Thr Thr Ala Thr Ala Cys
2225                2230                2235                2240

Ala Gly Gly Ala Ala Ala Ala Cys Thr Gly Thr Cys Ala Ala Ala
            2245                2250                2255

Thr Thr Ala Thr Cys Thr Ala Ala Ala Gly Ala Thr Cys Cys Thr Cys
            2260                2265                2270

Cys Thr Gly Ala Gly Ala Ala Gly Cys Thr Thr Ala Ala Ala Ala Cys
            2275                2280                2285

Ala Thr Cys Thr Thr Ala Ala Ala Thr Ala Cys Ala Cys Thr Gly
            2290                2295                2300

Ala Thr Gly Gly Gly Ala Ala Ala Cys Ala Thr Gly Cys Thr Cys Thr
2305                2310                2315                2320

Thr Thr Cys Thr Thr Cys Thr Gly Cys Cys Thr Cys Thr Gly Thr
            2325                2330                2335

<210> SEQ ID NO 3
<211> LENGTH: 725
<212> TYPE: PRT
<213> ORGANISM: Homo sapiens

<400> SEQUENCE: 3

Met Ala Met Asp Ser Ser Leu Gln Ala Arg Leu Phe Pro Gly Leu Ala
1               5                   10                  15

Ile Lys Ile Gln Arg Ser Asn Gly Leu Ile His Ser Ala Asn Val Arg
            20                  25                  30

Thr Val Asn Leu Glu Lys Ser Cys Val Ser Val Glu Trp Ala Glu Gly
        35                  40                  45

Gly Ala Thr Lys Gly Lys Glu Ile Asp Phe Asp Asp Val Ala Ala Ile
    50                  55                  60

Asn Pro Glu Leu Leu Gln Leu Leu Pro Leu His Pro Lys Asp Asn Leu
65                  70                  75                  80

Pro Leu Gln Glu Asn Val Thr Ile Gln Lys Gln Lys Arg Arg Ser Val
                85                  90                  95

Asn Ser Lys Ile Pro Ala Pro Lys Glu Ser Leu Arg Ser Arg Ser Thr

```
            100                 105                 110
Arg Met Ser Thr Val Ser Glu Leu Arg Ile Thr Ala Gln Glu Asn Asp
            115                 120                 125

Met Glu Val Glu Leu Pro Ala Ala Asn Ser Arg Lys Gln Phe Ser
            130                 135             140

Val Pro Pro Ala Pro Thr Arg Pro Ser Cys Pro Ala Val Ala Glu Ile
145             150                 155                 160

Pro Leu Arg Met Val Ser Glu Glu Met Glu Glu Gln Val His Ser Ile
                165                 170                 175

Arg Gly Ser Ser Ser Ala Asn Pro Val Asn Ser Val Arg Arg Lys Ser
                180                 185                 190

Cys Leu Val Lys Glu Val Glu Lys Met Lys Asn Lys Arg Glu Glu Lys
            195                 200                 205

Lys Ala Gln Asn Ser Glu Met Arg Met Lys Arg Ala Gln Glu Tyr Asp
            210                 215                 220

Ser Ser Phe Pro Asn Trp Glu Phe Ala Arg Met Ile Lys Glu Phe Arg
225             230                 235                 240

Ala Thr Leu Glu Cys His Pro Leu Thr Met Thr Asp Pro Ile Glu Glu
                245                 250                 255

His Arg Ile Cys Val Cys Val Arg Lys Arg Pro Leu Asn Lys Gln Glu
                260                 265                 270

Leu Ala Lys Lys Glu Ile Asp Val Ile Ser Ile Pro Ser Lys Cys Leu
            275                 280                 285

Leu Leu Val His Glu Pro Lys Leu Lys Val Asp Leu Thr Lys Tyr Leu
            290                 295                 300

Glu Asn Gln Ala Phe Cys Phe Asp Phe Ala Phe Asp Glu Thr Ala Ser
305             310                 315                 320

Asn Glu Val Val Tyr Arg Phe Thr Ala Arg Pro Leu Val Gln Thr Ile
                325                 330                 335

Phe Glu Gly Gly Lys Ala Thr Cys Phe Ala Tyr Gly Gln Thr Gly Ser
                340                 345                 350

Gly Lys Thr His Thr Met Gly Gly Asp Leu Ser Gly Lys Ala Gln Asn
            355                 360                 365

Ala Ser Lys Gly Ile Tyr Ala Met Ala Ser Arg Asp Val Phe Leu Leu
            370                 375                 380

Lys Asn Gln Pro Cys Tyr Arg Lys Leu Gly Leu Glu Val Tyr Val Thr
385             390                 395                 400

Phe Phe Glu Ile Tyr Asn Gly Lys Leu Phe Asp Leu Leu Asn Lys Lys
                405                 410                 415

Ala Lys Leu Arg Val Leu Glu Asp Gly Lys Gln Gln Val Gln Val Val
                420                 425                 430

Gly Leu Gln Glu His Leu Val Asn Ser Ala Asp Asp Val Ile Lys Met
            435                 440                 445

Leu Asp Met Gly Ser Ala Cys Arg Thr Ser Gly Gln Thr Phe Ala Asn
            450                 455                 460

Ser Asn Ser Ser Arg Ser His Ala Cys Phe Gln Ile Ile Leu Arg Ala
465             470                 475                 480

Lys Gly Arg Met His Gly Lys Phe Ser Leu Val Asp Leu Ala Gly Asn
                485                 490                 495

Glu Arg Gly Ala Asp Thr Ser Ser Ala Asp Arg Gln Thr Arg Met Glu
            500                 505                 510

Gly Ala Glu Ile Asn Lys Ser Leu Leu Ala Leu Lys Glu Cys Ile Arg
            515                 520                 525
```

```
Ala Leu Gly Gln Asn Lys Ala His Thr Pro Phe Arg Glu Ser Lys Leu
            530                 535                 540

Thr Gln Val Leu Arg Asp Ser Phe Ile Gly Glu Asn Ser Arg Thr Cys
545                 550                 555                 560

Met Ile Ala Thr Ile Ser Pro Gly Ile Ser Ser Cys Glu Tyr Thr Leu
                565                 570                 575

Asn Thr Leu Arg Tyr Ala Asp Arg Val Lys Glu Leu Ser Pro His Ser
            580                 585                 590

Gly Pro Ser Gly Glu Gln Leu Ile Gln Met Glu Thr Glu Glu Met Glu
        595                 600                 605

Ala Cys Ser Asn Gly Ala Leu Ile Pro Gly Asn Leu Ser Lys Glu Glu
        610                 615                 620

Glu Glu Leu Ser Ser Gln Met Ser Ser Phe Asn Glu Ala Met Thr Gln
625                 630                 635                 640

Ile Arg Glu Leu Glu Glu Lys Ala Met Glu Glu Leu Lys Glu Ile Ile
                645                 650                 655

Gln Gln Gly Pro Asp Trp Leu Glu Leu Ser Glu Met Thr Glu Gln Pro
            660                 665                 670

Asp Tyr Asp Leu Glu Thr Phe Val Asn Lys Ala Glu Ser Ala Leu Ala
            675                 680                 685

Gln Gln Ala Lys His Phe Ser Ala Leu Arg Asp Val Ile Lys Ala Leu
        690                 695                 700

Arg Leu Ala Met Gln Leu Glu Glu Gln Ala Ser Arg Gln Ile Ser Ser
705                 710                 715                 720

Lys Lys Arg Pro Gln
                725

<210> SEQ ID NO 4
<211> LENGTH: 2886
<212> TYPE: DNA
<213> ORGANISM: Homo sapiens

<400> SEQUENCE: 4
acgcttgcgc gcgggattta aactgcggcg gtttacgcgg cgttaagact tcgtagggtt        60
agcgaaattg aggtttcttg gtattgcgcg tttctcttcc ttgctgactc tccgaatggc       120
catggactcg tcgcttcagg cccgcctgtt tcccggtctc gctatcaaga tccaacgcag       180
taatggttta attcacagtg ccaatgtaag gactgtgaac ttggagaaat cctgtgtttc       240
agtggaatgg gcagaaggag gtgccacaaa gggcaaagag attgattttg atgatgtggc       300
tgcaataaac ccagaactct acagcttcct cccttacat ccgaaggaca atctgccctt        360
gcaggaaaat gtaacaatcc agaaacaaaa acggagatcc gtcaactcca aaattcctgc       420
tccaaaagaa agtcttcgaa gccgctccac tcgcatgtcc actgtctcag agcttcgcat       480
cacggctcag gagaatgaca tggaggtgga gctgcctgca gctgcaaact cccgcaagca       540
gttttcagtt cctcctgccc ccactaggcc ttcctgccct gcagtggctg aaataccatt       600
gaggatggtc agcgaggaga tggaagagca agtccattcc atccgtggca gctcttctgc       660
aaaccctgtg aactcagttc ggaggaaatc atgtcttgtg aaggaagtgg aaaaaatgaa       720
gaacaagcga gaagagaaga aggcccagaa ctctgaaatg agaatgaaga gagctcagga       780
gtatgacagt agtttttccaa actgggaatt tgcccgaatg attaaagaat tcgggctac        840 tttggaatgt catccactta ctatgactga tcctatcgaa gagcacagaa tatgtgtctg       900
tgttaggaaa cgcccactga ataagcaaga attggccaag aaagaaattg atgtgatttc       960
```

```
cattcctagc aagtgtctcc tcttggtaca tgaacccaag ttgaaagtgg acttaacaaa    1020
gtatctggag aaccaagcat tctgctttga ctttgcattt gatgaaacag cttcgaatga    1080
agttgtctac aggttcacag caaggccact ggtacagaca atctttgaag gtggaaaagc    1140
aacttgtttt gcatatggcc agacaggaag tggcaagaca catactatgg gcggagacct    1200
ctctgggaaa gcccagaatg catccaaagg gatctatgcc atggcctccc gggacgtctt    1260
cctcctgaag aatcaaccct gctaccggaa gttgggcctg aagtctatg tgacattctt     1320 cgagatctac aatgggaagc tgtttgacct gctcaacaag aaggccaagc tgcgcgtgct    1380
ggaggacggc aagcaacagg tgcaagtggt ggggctgcag gagcatctgg ttaactctgc    1440
tgatgatgtc atcaagatgc tcgacatggg cagcgcctgc agaacctctg gcagacatt     1500 tgccaactcc aattcctccc gctcccacgc gtgcttccaa attattcttc gagctaaagg    1560
gagaatgcat ggcaagttct ctttggtaga tctggcaggg aatgagcgag gcgcagacac    1620
ttccagtgct gaccggcaga cccgcatgga gggcgcagaa atcaacaaga gtctcttagc    1680
cctgaaggag tgcatcaggg ccctgggaca gaacaaggct cacacccgt tccgtgagag     1740 caagctgaca caggtgctga gggactcctt cattggggag aactctagga cttgcatgat    1800
tgccacgatc tcaccaggca taagctcctg tgaatatact ttaaacaccc tgagatatgc    1860
agacagggtc aaggagctga gcccccacag tgggcccagt ggagagcagt tgattcaaat    1920
ggaaacagaa gagatggaag cctgctctaa cggggcgctg attccaggca atttatccaa    1980
ggaagaggag gaactgtctt cccagatgtc cagctttaac gaagccatga ctcagatcag    2040
ggagctggag gagaaggcta tggaagagct caaggagatc atacagcaag gaccagactg    2100
gcttgagctc tctgagatga ccgagcagcc agactatgac ctggagacct tgtgtaacaa    2160
agcggaatct gctctggccc agcaagccaa gcatttctca gccctgcgag atgtcatcaa    2220 ggcccttacgc ctggccatgc agctggaaga gcaggctagc agacaaataa gcagcaagaa    2280
acggccccag tgacgactgc aaataaaaat ctgtttggtt tgacacccag cctcttccct    2340
ggccctcccc agagaacttt gggtacctgg tgggtctagg cagggtctga gctgggacag    2400
gttctggtaa atgccaagta tgggggcatc tgggcccagg gcagctgggg aggggggtcag   2460 agtgacatgg gacactcctt ttctgttcct cagttgtcgc cctcacgaga ggaaggagct    2520
cttagttacc ctttttgtgtt gcccttctttt ccatcaaggg gaatgttctc agcatagagc  2580
tttctccgca gcatcctgcc tgcgtggact ggctgctaat ggagagctcc ctggggttgt    2640
cctggctctg gggagagaga cggagccttt agtacagcta tctgctggct ctaaaccttc    2700
tacgcctttg ggccgagcac tgaatgtctt gtactttaaa aaaatgtttc tgagacctct    2760
ttctacttta ctgtctccct agagtcctag aggatcccta ctgttttctg ttttatgtgt    2820
ttatacattg tatgtaacaa taaagagaaa aaataaaaaa aaaaaaaaaa aaaaaaaaa     2880 aaaaaa                                                               2886
```

<210> SEQ ID NO 5
<211> LENGTH: 1805
<212> TYPE: PRT
<213> ORGANISM: Homo sapiens

<400> SEQUENCE: 5

Met Ser Asp Thr Lys Val Lys Val Ala Val Arg Val Arg Pro Met Asn
 1               5                  10                  15

Arg Arg Glu Leu Glu Leu Asn Thr Lys Cys Val Val Glu Met Glu Gly

```
            20                  25                  30
Asn Gln Thr Val Leu His Pro Pro Ser Asn Thr Lys Gln Gly Glu
            35                  40                  45
Arg Lys Pro Pro Lys Val Phe Ala Phe Asp Tyr Cys Phe Trp Ser Met
 50                      55                  60
Asp Glu Ser Asn Thr Thr Lys Tyr Ala Gly Gln Glu Val Val Phe Lys
 65                  70                  75                  80
Cys Leu Gly Glu Gly Ile Leu Glu Lys Ala Phe Gln Gly Tyr Asn Ala
                 85                  90                  95
Cys Ile Phe Ala Tyr Gly Gln Thr Gly Ser Gly Lys Ser Phe Ser Met
                100                 105                 110
Met Gly His Ala Glu Gln Leu Gly Leu Ile Pro Arg Leu Cys Cys Ala
                115                 120                 125
Leu Phe Lys Arg Ile Ser Leu Glu Gln Asn Glu Ser Gln Thr Phe Lys
                130                 135                 140
Val Glu Val Ser Tyr Met Glu Ile Tyr Asn Glu Lys Val Arg Asp Leu
145                 150                 155                 160
Leu Asp Pro Lys Gly Ser Arg Gln Ser Leu Lys Val Arg Glu His Lys
                165                 170                 175
Val Leu Gly Pro Tyr Val Asp Gly Leu Ser Gln Leu Ala Val Thr Ser
                180                 185                 190
Phe Glu Asp Ile Glu Ser Leu Met Ser Glu Gly Asn Lys Ser Arg Thr
                195                 200                 205
Val Ala Ala Thr Asn Met Asn Glu Glu Ser Ser Arg Ser His Ala Val
                210                 215                 220
Phe Asn Ile Ile Ile Thr Gln Thr Leu Tyr Asp Leu Gln Ser Gly Asn
225                 230                 235                 240
Ser Gly Glu Lys Val Ser Lys Val Ser Leu Val Asp Leu Ala Gly Ser
                245                 250                 255
Glu Arg Val Ser Lys Thr Gly Ala Ala Gly Glu Arg Leu Lys Glu Gly
                260                 265                 270
Ser Asn Ile Asn Lys Ser Leu Thr Thr Leu Gly Leu Val Ile Ser Ser
                275                 280                 285
Leu Ala Asp Gln Ala Ala Gly Lys Gly Lys Ser Lys Phe Val Pro Tyr
                290                 295                 300
Arg Asp Ser Val Leu Thr Trp Leu Leu Lys Asp Asn Leu Gly Gly Asn
305                 310                 315                 320
Ser Gln Thr Ser Met Ile Ala Thr Ile Ser Pro Ala Ala Asp Asn Tyr
                325                 330                 335
Glu Glu Thr Leu Ser Thr Leu Arg Tyr Ala Asp Arg Ala Lys Arg Ile
                340                 345                 350
Val Asn His Ala Val Val Asn Glu Asp Pro Asn Ala Lys Val Ile Arg
                355                 360                 365
Glu Leu Arg Glu Glu Val Glu Lys Leu Arg Glu Gln Leu Ser Gln Ala
                370                 375                 380
Glu Ala Met Lys Ala Pro Glu Leu Lys Glu Lys Leu Glu Glu Ser Glu
385                 390                 395                 400
Lys Leu Ile Lys Glu Leu Thr Val Thr Trp Glu Glu Lys Leu Arg Lys
                405                 410                 415
Thr Glu Glu Ile Ala Gln Glu Arg Gln Arg Gln Leu Glu Ser Met Gly
                420                 425                 430
Ile Ser Leu Glu Met Ser Gly Ile Lys Val Gly Asp Asp Lys Cys Tyr
                435                 440                 445
```

-continued

```
Leu Val Asn Leu Asn Ala Asp Pro Ala Leu Asn Glu Leu Leu Val Tyr
    450                 455                 460

Tyr Leu Lys Asp His Thr Arg Val Gly Ala Asp Thr Ser Gln Asp Ile
465                 470                 475                 480

Gln Leu Phe Gly Ile Gly Ile Gln Pro Gln His Cys Glu Ile Asp Ile
                485                 490                 495

Ala Ser Asp Gly Asp Val Thr Leu Thr Pro Lys Glu Asn Ala Arg Ser
                500                 505                 510

Cys Val Asn Gly Thr Leu Val Cys Ser Thr Thr Gln Leu Trp His Gly
                515                 520                 525

Asp Arg Ile Leu Trp Gly Asn Asn His Phe Phe Arg Ile Asn Leu Pro
            530                 535                 540

Lys Arg Lys Arg Arg Asp Trp Leu Lys Asp Phe Glu Lys Glu Thr Gly
545                 550                 555                 560

Pro Pro Glu His Asp Leu Asp Ala Ala Ser Glu Ala Ser Ser Glu Pro
                565                 570                 575

Asp Tyr Asn Tyr Glu Phe Ala Gln Met Glu Val Ile Met Lys Thr Leu
            580                 585                 590

Asn Ser Asn Asp Pro Val Gln Asn Val Val Gln Val Leu Glu Lys Gln
            595                 600                 605

Tyr Leu Glu Glu Lys Arg Ser Ala Leu Glu Glu Gln Arg Leu Met Tyr
            610                 615                 620

Glu Arg Glu Leu Glu Gln Leu Arg Gln Gln Leu Ser Pro Asp Arg Gln
625                 630                 635                 640

Pro Gln Ser Ser Gly Pro Asp Arg Leu Ala Tyr Ser Ser Gln Thr Ala
                645                 650                 655

Gln Gln Lys Val Thr Gln Trp Ala Glu Glu Arg Asp Glu Leu Phe Arg
            660                 665                 670

Gln Ser Leu Ala Lys Leu Arg Glu Gln Leu Val Lys Ala Asn Thr Leu
            675                 680                 685

Val Arg Glu Ala Asn Phe Leu Ala Glu Glu Met Ser Lys Leu Thr Asp
690                 695                 700

Tyr Gln Val Thr Leu Gln Ile Pro Ala Ala Asn Leu Ser Ala Asn Arg
705                 710                 715                 720

Lys Arg Gly Ala Ile Val Ser Glu Pro Ala Ile Gln Val Arg Arg Lys
                725                 730                 735

Gly Lys Ser Thr Gln Val Trp Thr Ile Glu Lys Leu Glu Asn Lys Leu
            740                 745                 750

Ile Asp Met Arg Asp Leu Tyr Gln Glu Trp Lys Glu Lys Val Pro Glu
            755                 760                 765

Ala Lys Arg Leu Tyr Gly Lys Arg Gly Asp Pro Phe Tyr Glu Ala Gln
770                 775                 780

Glu Asn His Asn Leu Ile Gly Val Ala Asn Val Phe Leu Glu Cys Leu
785                 790                 795                 800

Phe Cys Asp Val Lys Leu Gln Tyr Ala Val Pro Ile Ile Ser Gln Gln
                805                 810                 815

Gly Glu Val Ala Gly Arg Leu His Val Glu Val Met Arg Val Thr Gly
                820                 825                 830

Ala Val Pro Glu Arg Val Val Glu Asp Ser Ser Glu Asn Ser Ser
                835                 840                 845

Glu Ser Gly Ser Leu Glu Val Val Asp Ser Ser Gly Glu Ile Ile His
850                 855                 860
```

```
Arg Val Lys Lys Leu Thr Cys Arg Val Lys Ile Lys Glu Ala Thr Gly
865                 870                 875                 880

Leu Pro Leu Asn Leu Ser Asn Phe Val Phe Cys Gln Tyr Thr Phe Trp
                885                 890                 895

Asp Gln Cys Glu Ser Thr Val Ala Ala Pro Val Val Asp Pro Glu Val
            900                 905                 910

Pro Ser Pro Gln Ser Lys Asp Ala Gln Tyr Thr Val Thr Phe Ser His
        915                 920                 925

Cys Lys Asp Tyr Val Val Asn Val Thr Glu Glu Phe Leu Glu Phe Ile
    930                 935                 940

Ser Asp Gly Ala Leu Ala Ile Glu Val Trp Gly His Arg Cys Ala Gly
945                 950                 955                 960

Asn Gly Ser Ser Ile Trp Glu Val Asp Ser Leu His Ala Lys Thr Arg
                965                 970                 975

Thr Leu His Asp Arg Trp Asn Glu Val Thr Arg Arg Ile Glu Met Trp
            980                 985                 990

Ile Ser Ile Leu Glu Leu Asn Glu Leu Gly Tyr Ala Ala Val Glu
        995                 1000                1005

Leu His Gln Ala Lys Asp Val Asn Thr Gly Gly Ile Phe Gln Leu Arg
    1010                1015                1020

Gln Gly His Ser Arg Arg Val Gln Val Thr Val Lys Pro Val Gln His
1025                1030                1035                1040

Ser Gly Thr Leu Pro Leu Met Val Glu Ala Ile Leu Ser Val Ser Ile
                1045                1050                1055

Gly Cys Val Thr Ala Arg Ser Thr Lys Leu Gln Arg Gly Leu Asp Ser
            1060                1065                1070

Tyr Gln Arg Asp Asp Glu Asp Gly Asp Met Asp Ser Tyr Gln Glu
        1075                1080                1085

Glu Asp Leu Asn Cys Val Arg Glu Arg Trp Ser Asp Ala Leu Ile Lys
    1090                1095                1100

Arg Arg Glu Tyr Leu Asp Glu Gln Ile Lys Lys Val Ser Asn Lys Thr
1105                1110                1115                1120

Glu Lys Thr Glu Asp Asp Val Glu Arg Glu Ala Gln Leu Val Glu Gln
                1125                1130                1135

Trp Val Gly Leu Thr Glu Glu Arg Asn Ala Val Leu Val Pro Ala Pro
            1140                1145                1150

Gly Ser Gly Ile Pro Gly Ala Pro Ala Asp Trp Ile Pro Pro Gly
        1155                1160                1165

Met Glu Thr His Ile Pro Val Leu Phe Leu Asp Leu Asn Ala Asp Asp
    1170                1175                1180

Leu Ser Ala Asn Glu Gln Leu Val Gly Pro His Ala Ser Gly Val Asn
1185                1190                1195                1200

Ser Ile Leu Pro Lys Glu His Gly Ser Gln Phe Phe Tyr Leu Pro Ile
                1205                1210                1215

Ile Lys His Ser Asp Asp Glu Val Ser Ala Thr Ala Ser Trp Asp Ser
            1220                1225                1230

Ser Val His Asp Ser Val His Leu Asn Arg Val Thr Pro Gln Asn Glu
        1235                1240                1245

Arg Ile Tyr Leu Ile Val Lys Thr Thr Val Gln Leu Ser His Pro Ala
    1250                1255                1260

Ala Met Glu Leu Val Leu Arg Lys Arg Ile Ala Ala Asn Ile Tyr Asn
1265                1270                1275                1280

Lys Gln Ser Phe Thr Gln Ser Leu Lys Arg Arg Ile Ser Leu Lys Asn
```

-continued

```
                1285                1290                1295
Ile Phe Tyr Ser Cys Gly Val Thr Tyr Glu Ile Val Ser Asn Ile Pro
            1300                1305                1310
Lys Ala Thr Glu Glu Ile Glu Asp Arg Glu Thr Leu Ala Leu Leu Ala
            1315                1320                1325
Ala Arg Ser Glu Asn Glu Gly Thr Ser Asp Gly Glu Thr Tyr Ile Glu
            1330                1335                1340
Lys Tyr Thr Arg Gly Val Leu Gln Val Glu Asn Ile Leu Ser Leu Glu
1345                1350                1355                1360
Arg Leu Arg Gln Ala Val Thr Val Lys Glu Ala Leu Ser Thr Lys Ala
            1365                1370                1375
Arg His Ile Arg Arg Ser Leu Ser Thr Pro Asn Val His Asn Val Ser
            1380                1385                1390
Ser Ser Arg Pro Asp Leu Ser Gly Phe Asp Glu Asp Asp Lys Gly Trp
            1395                1400                1405
Pro Glu Asn Gln Leu Asp Met Ser Asp Tyr Ser Ser Tyr Gln Asp
            1410                1415                1420
Val Ala Cys Tyr Gly Thr Leu Pro Arg Asp Ser Pro Arg Arg Asn Lys
1425                1430                1435                1440
Glu Gly Cys Thr Ser Glu Thr Pro His Ala Leu Thr Val Ser Pro Phe
            1445                1450                1455
Lys Ala Phe Ser Pro Gln Pro Lys Phe Phe Lys Pro Leu Met Pro
            1460                1465                1470
Val Lys Glu Glu His Lys Lys Arg Ile Ala Leu Glu Ala Arg Pro Leu
            1475                1480                1485
Leu Ser Gln Glu Ser Met Pro Pro Gln Ala His Asn Pro Gly Cys
            1490                1495                1500
Ile Val Pro Ser Gly Ser Asn Gly Ser Ser Met Pro Val Glu His Asn
1505                1510                1515                1520
Ser Lys Arg Glu Lys Lys Ile Asp Ser Glu Glu Glu Asn Glu Leu
            1525                1530                1535
Glu Ala Ile Asn Arg Lys Leu Ile Ser Ser Gln Pro Tyr Val Pro Val
            1540                1545                1550
Glu Phe Ala Asp Phe Ser Val Tyr Asn Ala Ser Leu Glu Asn Arg Glu
            1555                1560                1565
Trp Phe Ser Ser Lys Val Asp Leu Ser Asn Ser Arg Val Leu Glu Lys
            1570                1575                1580
Glu Val Ser Arg Ser Pro Thr Thr Ser Ser Ile Thr Ser Gly Tyr Phe
1585                1590                1595                1600
Ser His Ser Ala Ser Asn Ala Thr Leu Ser Asp Met Val Val Pro Ser
            1605                1610                1615
Ser Asp Ser Ser Asp Gln Leu Ala Ile Gln Thr Lys Asp Ala Asp Ser
            1620                1625                1630
Thr Glu His Ser Thr Pro Ser Leu Val His Asp Phe Arg Pro Ser Ser
            1635                1640                1645
Asn Lys Glu Leu Thr Glu Val Glu Lys Gly Leu Val Lys Asp Lys Ile
            1650                1655                1660
Ile Val Val Pro Leu Lys Glu Asn Ser Ala Leu Ala Lys Gly Ser Pro
1665                1670                1675                1680
Ser Ser Gln Ser Ile Pro Glu Lys Asn Ser Lys Ser Leu Cys Arg Thr
            1685                1690                1695
Gly Ser Cys Ser Glu Leu Asp Ala Cys Pro Ser Lys Ile Ser Gln Pro
            1700                1705                1710
```

Ala Arg Gly Phe Cys Pro Arg Glu Val Thr Val Glu His Thr Thr Asn
    1715                1720                1725

Ile Leu Glu Asp His Ser Phe Thr Glu Phe Met Gly Val Ser Glu Gly
    1730                1735                1740

Lys Asp Phe Asp Gly Leu Thr Asp Ser Ser Ala Gly Glu Leu Ser Ser
1745                1750                1755                1760

Arg Arg Ser Leu Pro Asn Lys Thr Gly Gly Lys Thr Val Ser Asp Gly
                1765                1770                1775

Leu His His Pro Ser Gln Leu His Ser Lys Leu Glu Asn Asp Gln Val
            1780                1785                1790

Ile Ile Pro Glu Ala Ala Phe Trp Val Leu Cys Cys Gln
        1795                1800                1805

<210> SEQ ID NO 6
<211> LENGTH: 6005
<212> TYPE: DNA
<213> ORGANISM: Homo sapiens

<400> SEQUENCE: 6

```
cgggatggcc cgcgcgcctc ggcgctgcct ctcggagctc acggcggagc ggcggcggcc    60
gcgctcgagg ggcgcgcggc tgcagcggcg gcggcgccgc gcgtgagggg ccgcctaagg   120
ccgagcgggc gcggcgagcg gccgggcgag cgcagccaac atgtcggata ccaaggtaaa   180
agttgccgtc cgggtccggc ccatgaaccg acgagaactg aactgaaca ccaagtgcgt    240
ggtggagatg gaagggaatc aaacggtcct gcaccctcct ccttctaaca ccaaacaggg   300
agaaaggaaa cctcccaagg tatttgcctt tgattattgc ttttggtcca tggatgaatc   360
taacactaca aaatacgctg gtcaagaagt ggttttcaag tgccttgggg aaggaattct   420
tgaaaaagcc tttcaggggt ataatgcgtg tattttttgca tatggacaga caggttcggg   480
aaaatccttt tccatgatgg gccatgctga gcagctgggc cttattccaa ggctctgctg   540
tgctttattt aaaaggatct ctttggagca aaatgagtca cagacccttta aagttgaagt   600
gtcctatatg gaaatttata tgagaaaagt tcgggatctt ttagacccca agggagtag    660
acagtctctt aaagttcgag aacataaagt tttgggacca tatgtagatg gtttatctca   720
actagctgtc actagttttg aggatattga gtcattgatg tctgagggaa ataagtctcg   780
aacggtagct gctaccaaca tgaacgaaga agcagccgc tcccatgctg tgttcaacat   840
cataatcaca cagacacttt atgacctgca gtctgggaat tccggggaga agtcagtaa   900
ggtcagcttg gtagacctgg cgggtagcga aagagtatct aaaacaggag ctgcaggaga   960
gcgactgaaa gaaggcagca acattaacaa atcgcttaca accttggggt tggttatatc  1020
atcactggct gaccaggcag ctggcaaggg taaaagcaaa tttgtgcctt atcgagattc  1080
agtcctcact tggctgctta aggacaactt ggggggcaac agccaaacct ctatgatagc  1140
cacaatcagc ccagccgcag acaactatga agagaccctc tccacattaa gatatgcaga  1200
ccgagccaaa aggattgtga accatgctgt tgtgaatgag accccaacg caaaagtgat   1260
ccgagaactg cggaggaag tcgagaaact gagagagcag ctctctcagg cagaggccat   1320
gaaggcccct gaactgaagg agaagctcga agagtctgaa agctgataa agaactaac    1380
agtgacttgg gaagagaagc tgagaaaaac agaagagata gcacaggaaa gacaacgaca  1440
acttgaaagc atggggattt ccctggagat gtccggtatc aaggtggggg atgacaaatg  1500
ctacttagtc aatctgaatg cagaccctgc tcttaacgaa cttctgggttt attatttaaa  1560
```

-continued

| | |
|---|---|
| ggatcacacc agggtgggtg cagatacctc tcaagatatc cagctttttg gcataggaat | 1620 |
| tcagcctcag cactgtgaga ttgacattgc atctgatgga gacgtcactc tcactccaaa | 1680 |
| agaaaatgca aggtcctgtg tgaacggcac ccttgtgtgc agtaccaccc agctgtggca | 1740 |
| tggtgaccga atcctatggg gaataatca cttttttaga ataaacttac ctaagaggaa | 1800 |
| acgtcgagat tggttgaaag actttgaaaa agaaacgggc ccgccagagc atgacctgga | 1860 |
| tgcagccagt gaggcttcct ctgaaccaga ctataactat gaatttgcac agatggaagt | 1920 |
| tatcatgaaa accctgaata gtaatgaccc agttcaaaat gtggttcagg tcctggagaa | 1980 |
| acaataccta gaagaaaaga gaagtgccct agaggagcag cggctcatgt atgagcggga | 2040 |
| actggagcaa ctccgccagc agctctcccc cgacaggcag ccacagagta gcggccctga | 2100 |
| ccgcctggcc tacagcagcc agacagcgca gcagaaggtg acccagtggg cagaagagag | 2160 |
| ggatgaactc ttccgacaaa gcctggcaaa actgcgagag cagctggtta aagctaatac | 2220 |
| cttggtgagg gaagcaaact tcctggctga ggaaatgagc aaactcaccg attaccaagt | 2280 |
| gactcttcag atccctgctg caaacctcag tgccaatagg aagagaggtg caatagtgag | 2340 |
| tgaaccagct atccaagtga ggaggaaagg aaagagcacc caagtgtgga ccattgagaa | 2400 |
| gctggagaat aaattaattg acatgagaga ccttttaccaa gaatggaagg aaaaagttcc | 2460 |
| tgaggcaaag agactctacg aaaacgagg tgacccttc tatgaagccc aagaaaatca | 2520 |
| caacctcatc ggggtggcga atgtattctt ggaatgcctc ttctgtgatg tgaaacttca | 2580 |
| gtatgcagtc cctatcatca gccagcaggg ggaggttgca gggcgtctcc acgtggaagt | 2640 |
| gatgcgtgtt acaggagctg ttccagagcg tgtggtggag gatgactctt cggagaattc | 2700 |
| cagtgaaagt gggagccttg aagtcgtaga cagcagcggg gaaatcattc accgagtcaa | 2760 |
| aaagctgaca tgtcgggtaa aaattaaga agcaacgggg ctgcccttaa acctctcaaa | 2820 |
| ttttgtcttc tgtcaataca cattctggga ccagtgtgag tctacggtgg ctgccccggt | 2880 |
| ggtggacccc gaggtgcctt caccacagtc caaggatgcc cagtacacag tgaccttctc | 2940 |
| ccactgtaag gactatgtgg tgaatgtaac agaagaattt ctggagttca tttcagatgg | 3000 |
| agcactggcc attgaagtat ggggccaccg gtgtgctgga aatggcagct ccatctggga | 3060 |
| ggtcgattct cttcatgcta agacaagaac actgcatgac aggtggaatg aagtaacgcg | 3120 |
| aagaatagaa atgtggatct ccatattaga attgaatgag ttaggagagt atgctgcagt | 3180 |
| ggaacttcat caggcaaaag atgtcaacac aggaggcatc tttcaactta gacagggtca | 3240 |
| ttcccgtaga gtacaagtca cggtgaaacc tgtgcagcat tcagggacac tgccacttat | 3300 |
| ggttgaagcc atcctgtcag tatccatcgg ctgtgtaact gccaggtcca ccaaactcca | 3360 |
| aagagggctg gacagttacc agagagatga tgaggatggt gatgatatgg atagttatca | 3420 |
| ggaagaagac ttaaactgcg taagggagag gtggtcagat gcactcatta aacgacgaga | 3480 |
| atacctggat gaacagataa aaaagtcag caataaaaca gagaaaacag aggacgatgt | 3540 |
| ggagcgggaa gcccagcttg tggagcagtg ggtagggctg actgaggaaa ggaatgctgt | 3600 |
| gctggtgcca gccccaggca gtgggattcc tggggcacct gccgactgga tcccacctcc | 3660 |
| tggaatggaa acccacatac cagttctctt cctcgatttg aatgcggatg acctcagtgc | 3720 |
| caatgagcag cttgttggcc ccatgcatc cggcgtgaac tccatcctgc caaggagca | 3780 |
| tggcagccag tttttctacc tgcccatcat aaagcacagt gatgatgagg tttcagccac | 3840 |
| agcctcttgg gattcctcgg tgcatgattc tgttcacttg aatagggtca caccacagaa | 3900 |
| tgaaaggatt tacctaattg tgaaaaccac agttcaactc agccaccctg ctgctatgga | 3960 |

-continued

```
gttagtatta cgaaaacgaa ttgcagccaa tatttacaac aaacagagtt tcacgcagag    4020
tttgaagagg agaatatccc tgaaaaatat attttattcc tgtggtgtaa cctatgaaat    4080
agtatccaat ataccaaagg caactgagga gatagaggac cgggaaacgc tggctctcct    4140
ggcagcaagg agtgaaaacg aaggcacatc agatggggag acgtacattg agaagtacac    4200
tcgaggcgtg ctgcaggtgg aaaacattct gagtcttgaa cggctccggc aggccgtcac    4260
agtcaaagaa gcactttcca ccaaagcccg gcacattcgg aggagcctca gtacaccaaa    4320
tgttcataat gtctcttcca gccgaccgga cctttctggc tttgatgaag atgacaaggg    4380
ttggccagag aaccagttgg acatgtctga ctatagctcc agttaccaag atgtagcatg    4440
ttatggaact ttacccaggg attctcctcg aaggaataaa gaaggttgta catcagagac    4500
tcctcatgcc ttaaccgtca gccctttaa agcattctct cctcagccac caaagttttt    4560
caagccccta atgcctgtaa agaggagca taagaaaagg atagccctgg aagcaaggcc    4620
tcttctaagc caggagagca tgcctccacc tcaggcacat aaccctggct gcattgtacc    4680
ctcaggaagc aatggcagca gcatgccagt agaacacaat agcaaacgtg agaagaagat    4740
tgactctgag gaggaagaaa atgagctgga agctattaac aggaagctaa taagttcaca    4800
gccttatgta cctgtggagt ttgctgactt cagtgtttac aatgccagct ggagaacag    4860 ggaatggttt tcctctaaag tagatctgtc aaactcacgg gtcttggaga agaagtgtc    4920 ccgtagccct accaccagca gtattaccag tggctacttt cccacagtg cctccaatgc    4980 caccctgtct gacatggtgg tccctctag tgacagctca gaccagctgg ccattcagac    5040
gaaggatgca gactccaccg agcactccac accatcgctt gtgcatgatt tcaggccgtc    5100
ctcaaacaaa gagttgacag aagtcgaaaa aggcttggta aaggacaaga taattgtggt    5160
gccactcaag gaaacagtg ccttagccaa agggagccca tcatcccaga gcatccctga    5220
gaaaaactcc aaatcactgt gcaggactgg ctcatgttca gaactagatg cctgccccag    5280
caaaattagc cagccagcca ggggattctg ccccagggag gtgacggtag aacacaccac    5340
caacatcctt gaagaccatt ctttcacaga atttatggga gtgtcagagg gaaaagattt    5400
tgatggtttg acagattctt ctgctggaga gctttccagt aggaggagtc taccaaataa    5460
aacaggcggc aagactgtct ccgatgggct ccaccacccc agccagctgc attccaagtt    5520
agagaatgac caggtaataa ttccagaggc agccttttgg gttctgtgct gtcaatgagt    5580
atgtctaact gtatgtcaac cccagaggcc cttcaccgca acaacttggt aggaaagatt    5640
catccagttg tttgtgacag caaagatgag cccacagaga agcaggctca cttcctgcac    5700
agctgtctct gtcggagagc aagtctgttt tgggaactag aacgcaattg tgaaattata    5760
agaccagtgg attttttac ctggcacatg ggttggtgtt gaatgaagtg ttcagatgga    5820
taaggatcaa tctcatattc attccctggg atgtttagtt accagttttc ccaaagtgtt    5880
ctggtagcat ctaccatatt tcatcaaatc tgtgattcct ttgattatta tatgaaccat    5940
tattttatgt atcattaaga aaaatactg ccaattaaac tctgtcatat caacaaaaaa    6000
aaaaa                                                                6005
```

<210> SEQ ID NO 7
<211> LENGTH: 725
<212> TYPE: PRT
<213> ORGANISM: Homo sapiens

<400> SEQUENCE: 7

-continued

```
Met Ala Met Asp Ser Ser Leu Gln Ala Arg Leu Phe Pro Gly Leu Ala
1               5                   10                  15

Ile Lys Ile Gln Arg Ser Asn Gly Leu Ile His Ser Ala Asn Val Arg
            20                  25                  30

Thr Val Asn Leu Glu Lys Ser Cys Val Ser Val Glu Trp Ala Glu Gly
        35                  40                  45

Gly Ala Thr Lys Gly Lys Glu Ile Asp Phe Asp Asp Val Ala Ala Ile
    50                  55                  60

Asn Pro Glu Leu Leu Gln Leu Pro Leu His Pro Lys Asp Asn Leu
65                  70                  75                  80

Pro Leu Gln Glu Asn Val Thr Ile Gln Lys Gln Lys Arg Arg Ser Val
                85                  90                  95

Asn Ser Lys Ile Pro Ala Pro Lys Glu Ser Leu Arg Ser Arg Ser Thr
            100                 105                 110

Arg Met Ser Thr Val Ser Glu Leu Arg Ile Thr Ala Gln Glu Asn Asp
            115                 120                 125

Met Glu Val Glu Leu Pro Ala Ala Ala Asn Ser Arg Lys Gln Phe Ser
130                 135                 140

Val Pro Pro Ala Pro Thr Arg Pro Ser Cys Pro Ala Val Ala Glu Ile
145                 150                 155                 160

Pro Leu Arg Met Val Ser Glu Met Glu Glu Gln Val His Ser Ile
                165                 170                 175

Arg Gly Ser Ser Ser Ala Asn Pro Val Asn Ser Val Arg Arg Lys Ser
            180                 185                 190

Cys Leu Val Lys Glu Val Glu Lys Met Lys Asn Lys Arg Glu Glu Lys
            195                 200                 205

Lys Ala Gln Asn Ser Glu Met Arg Met Lys Arg Ala Gln Glu Tyr Asp
210                 215                 220

Ser Ser Phe Pro Asn Trp Glu Phe Ala Arg Met Ile Lys Glu Phe Arg
225                 230                 235                 240

Ala Thr Leu Glu Cys His Pro Leu Thr Met Thr Asp Pro Ile Glu Glu
                245                 250                 255

His Arg Ile Cys Val Cys Val Arg Lys Arg Pro Leu Asn Lys Gln Glu
            260                 265                 270

Leu Ala Lys Lys Glu Ile Asp Val Ile Ser Ile Pro Ser Lys Cys Leu
            275                 280                 285

Leu Leu Val His Glu Pro Lys Leu Lys Val Asp Leu Thr Lys Tyr Leu
            290                 295                 300

Glu Asn Gln Ala Phe Cys Phe Asp Phe Ala Phe Asp Glu Thr Ala Ser
305                 310                 315                 320

Asn Glu Val Val Tyr Arg Phe Thr Ala Arg Pro Leu Val Gln Thr Ile
                325                 330                 335

Phe Glu Gly Gly Lys Ala Thr Cys Phe Ala Tyr Gly Gln Thr Gly Ser
            340                 345                 350

Gly Lys Thr His Thr Met Gly Gly Asp Leu Ser Gly Lys Ala Gln Asn
            355                 360                 365

Ala Ser Lys Gly Ile Tyr Ala Met Ala Ser Arg Asp Val Phe Leu Leu
370                 375                 380

Lys Asn Gln Pro Cys Tyr Arg Lys Leu Gly Leu Glu Val Tyr Val Thr
385                 390                 395                 400

Phe Phe Glu Ile Tyr Asn Gly Lys Leu Phe Asp Leu Leu Asn Lys Lys
                405                 410                 415

Ala Lys Leu Arg Val Leu Glu Asp Gly Lys Gln Gln Val Gln Val Val
```

```
                420            425              430
Gly Leu Gln Glu His Leu Val Asn Ser Ala Asp Val Ile Lys Met
              435                440               445
Ile Asp Met Gly Ser Ala Cys Arg Thr Ser Gly Gln Thr Phe Ala Asn
            450                455                460
Ser Asn Ser Ser Arg Ser His Ala Cys Phe Gln Ile Ile Leu Arg Ala
465                470                475                480
Lys Gly Arg Met His Gly Lys Phe Ser Leu Val Asp Leu Ala Gly Asn
                485                490                495
Glu Arg Gly Ala Asp Thr Ser Ser Ala Asp Arg Gln Thr Arg Met Glu
              500                505                510
Gly Ala Glu Ile Asn Lys Ser Leu Leu Ala Leu Lys Glu Cys Ile Arg
            515                520                525
Ala Leu Gly Gln Asn Lys Ala His Thr Pro Phe Arg Glu Ser Lys Leu
            530                535                540
Thr Gln Val Leu Arg Asp Ser Phe Ile Gly Glu Asn Ser Arg Thr Cys
545                550                555                560
Met Ile Ala Thr Ile Ser Pro Gly Ile Ser Ser Cys Glu Tyr Thr Leu
                565                570                575
Asn Thr Leu Arg Tyr Ala Asp Arg Val Lys Glu Leu Ser Pro His Ser
                580                585                590
Gly Pro Ser Gly Glu Gln Leu Ile Gln Met Thr Glu Glu Met Glu
              595                600                605
Ala Cys Ser Asn Gly Ala Leu Ile Pro Gly Asn Leu Ser Lys Glu Glu
            610                615                620
Glu Glu Leu Ser Ser Gln Met Ser Ser Phe Asn Glu Ala Met Thr Gln
625                630                635                640
Ile Arg Glu Leu Glu Glu Lys Ala Met Glu Leu Lys Glu Ile Ile
                645                650                655
Gln Gln Gly Pro Asp Trp Leu Glu Leu Ser Glu Met Thr Glu Gln Pro
              660                665                670
Asp Tyr Asp Leu Glu Thr Phe Val Asn Lys Ala Glu Ser Ala Leu Ala
            675                680                685
Gln Gln Ala Lys His Phe Ser Ala Leu Arg Asp Val Ile Lys Ala Leu
            690                695                700
Arg Leu Ala Met Gln Leu Glu Glu Gln Ala Ser Arg Gln Ile Ser Ser
705                710                715                720
Lys Lys Arg Pro Gln
              725

<210> SEQ ID NO 8
<211> LENGTH: 2896
<212> TYPE: DNA
<213> ORGANISM: Homo sapiens

<400> SEQUENCE: 8
acgcttgcgc gcgggattta aactgcggcg gtttacgcgg cgttaagact tcgtagggtt    60
agcgaaattg aggtttcttg gtattgcgcg tttctcttcc ttgctgactc tccgaatggc   120
catggactcg tcgcttcagg cccgcctgtt tcccggtctc gctatcaaga tccaacgcag   180
taatggttta attcacagtg ccaatgtaag gactgtgaac ttggagaaat cctgtgtttc   240
agtggaatgg gcagaaggag gtgccacaaa gggcaaagag attgattttg atgatgtggc   300
tgcaataaac ccagaactct tacagcttct tcccttacat ccgaaggaca atctgcccat   360
```

```
gcaggaaaat gtaacaatcc agaaacaaaa acggagatcc gtcaactcca aaattcctgc      420
tccaaaagaa agtcttcgaa gccgctccac tcgcatgtcc actgtctcag agcttcgcat      480
cacggctcag gagaatgaca tggaggtgga gctgcctgca gctgcaaact cccgcaagca      540
gttttcagtt cctcctgccc ccactaggcc ttcctgccct gcagtggctg aaataccatt      600
gaggatggtc agcgaggaga tggaagagca agtccattcc atccgaggca gctcttctgc      660
aaaccctgtg aactcagttc ggaggaaatc atgtcttgtg aaggaagtgg aaaaaatgaa      720
gaacaagcga gaagagaaga aggcccagaa ctctgaaatg agaatgaaga gagctcagga      780
gtatgacagt agttttccaa actgggaatt tgcccgaatg attaaagaat ttcgggctac      840
tttggaatgt catccactta ctatgactga tcctatcgaa gagcacagaa tatgtgtctg      900
tgttaggaaa cgcccactga ataagcaaga attggccaag aaagaaattg atgtgatttc      960
cattcctagc aagtgtctcc tcttggtaca tgaacccaag ttgaaagtgg acttaacaaa     1020
gtatctggag aaccaagcat ctgctttga ctttgcattt gatgaaacag cttcgaatga     1080
agttgtctac aggttcacag caaggccact ggtacagaca atctttgaag gtggaaaagc     1140
aacttgtttt gcatatggcc agacaggaag tggcaagaca catactatgg gcggagacct     1200
ctctgggaaa gcccagaatg catccaaagg gatctatgcc atggcctccc gggacgtctt     1260
cctcctgaag aatcaaccct gctaccggaa gttgggcctg gaagtctatg tgacattctt     1320
cgagatctac aatgggaagc tgtttgacct gctcaacaag aaggccaagc tgcgcgtgct     1380
ggaggacggc aagcaacagg tgcaagtggt ggggctgcag gagcatctgg ttaactctgc     1440
tgatgatgtc atcaagatga tcgacatggg cagcgcctgc agaacctctg gcagacatt      1500 tgccaactcc aattcctccc gctcccacgc gtgcttccaa attattcttc gagctaaagg     1560
gagaatgcat ggcaagttct ctttggtaga tctggcaggg aatgagcgag cgcggacac      1620 ttccagtgct gaccggcaga cccgcatgga gggcgcagaa atcaacaaga gtctcttagc     1680
cctgaaggag tgcatcaggg ccctgggaca gaacaaggct cacacccgt tccgtgagag      1740 caagctgaca caggtgctga gggactcctt cattggggag aactctagga cttgcatgat     1800
tgccacgatc tcaccaggca taagctcctg tgaatatact ttaaacaccc tgagatatgc     1860
agacagggtc aaggagctga gcccccacag tgggcccagt ggagagcagt tgattcaaat     1920
ggaaacagaa gagatggaag cctgctctaa cggggcgctg attccaggca atttatccaa     1980
ggaagaggag gaactgtctt cccagatgtc cagctttaac gaagccatga ctcagatcag     2040
ggagctggag gagaaggcta tggaagagct caaggagatc atacagcaag accagactg      2100 gcttgagctc tctgagatga ccgagcagcc agactatgac ctggagacct tgtgtaacaa     2160
agcggaatct gctctggccc agcaagccaa gcatttctca gccctgcgag atgtcatcaa     2220
ggccttgcgc ctggccatgc agctggaaga gcaggctagc agacaaataa gcagcaagaa     2280
acggccccag tgacgactgc aaataaaaat ctgtttggtt tgacacccag cctcttccct     2340
ggccctcccc agagaacttt gggtacctgg tgggtctagg cagggtctga gctgggacag     2400
gttctggtaa atgccaagta tggggggcatc tgggcccagg gcagctgggg aggggtcag      2460 agtgacatgg gacactcctt ttctgttcct cagttgtcgc cctcacgaga ggaaggagct     2520
cttagttacc cttttgtgtt gcccttcttt ccatcaaggg gaatgttctc agcatagagc     2580
tttctccgca gcatcctgcc tgcgtggact ggctgctaat ggagagctcc ctggggttgt     2640
cctggctctg gggagagaga cggagccttt agtacagcta tctgctggct ctaaaccttc     2700
tacgcctttg ggccgagcac tgaatgtctt gtactttaaa aaaatgtttc tgagacctct     2760
```

-continued

```
ttctacttta ctgtctccct agagatccta gaggatccct actgttttct gttttatgtg      2820
tttatacatt gtatgtaaca ataaagagaa aaataaatc agctgtttaa gtgtgtggaa       2880
aaaaaaaaaa aaaaaa                                                      2896
```

<210> SEQ ID NO 9
<211> LENGTH: 859
<212> TYPE: PRT
<213> ORGANISM: Homo sapiens

<400> SEQUENCE: 9

Met Leu Pro Val Tyr Gln Glu Val Lys Pro Asn Pro Leu Gln Asp Ala
1               5                   10                  15

Asn Leu Cys Ser Arg Val Phe Phe Trp Trp Leu Asn Pro Leu Phe Lys
            20                  25                  30

Ile Gly His Lys Arg Arg Leu Glu Glu Asp Met Tyr Ser Val Leu
        35                  40                  45

Pro Glu Asp Arg Ser Gln His Leu Gly Glu Leu Gln Gly Phe Trp
    50                  55                  60

Asp Lys Glu Val Leu Arg Ala Glu Asn Asp Ala Gln Lys Pro Ser Leu
65                  70                  75                  80

Thr Arg Ala Ile Ile Lys Cys Tyr Trp Lys Ser Tyr Leu Val Leu Gly
                85                  90                  95

Ile Phe Thr Leu Ile Glu Glu Ser Ala Lys Val Ile Gln Pro Ile Phe
            100                 105                 110

Leu Gly Lys Ile Ile Asn Tyr Phe Glu Asn Tyr Asp Pro Met Asp Ser
        115                 120                 125

Val Ala Leu Asn Thr Ala Tyr Ala Tyr Ala Thr Val Leu Thr Phe Cys
    130                 135                 140

Thr Leu Ile Leu Ala Ile Leu His His Leu Tyr Phe Tyr His Val Gln
145                 150                 155                 160

Cys Ala Gly Met Arg Leu Arg Val Ala Met Cys His Met Ile Tyr Arg
                165                 170                 175

Lys Ala Leu Arg Leu Ser Asn Met Ala Met Gly Lys Thr Thr Thr Gly
            180                 185                 190

Gln Ile Val Asn Leu Leu Ser Asn Asp Val Asn Lys Phe Asp Gln Val
        195                 200                 205

Thr Val Phe Leu His Phe Leu Trp Ala Gly Pro Leu Gln Ala Ile Ala
    210                 215                 220

Val Thr Ala Leu Leu Trp Met Glu Ile Gly Ile Ser Cys Leu Ala Gly
225                 230                 235                 240

Met Ala Val Leu Ile Ile Leu Pro Leu Gln Ser Cys Phe Gly Lys
                245                 250                 255

Leu Phe Ser Ser Leu Arg Ser Lys Thr Ala Thr Phe Thr Asp Ala Arg
            260                 265                 270

Ile Arg Thr Met Asn Glu Val Ile Thr Gly Ile Arg Ile Ile Lys Met
        275                 280                 285

Tyr Ala Trp Glu Lys Ser Phe Ser Asn Leu Ile Thr Asn Leu Arg Lys
    290                 295                 300

Lys Glu Ile Ser Lys Ile Leu Arg Ser Cys Leu Arg Gly Met Asn
305                 310                 315                 320

Leu Ala Ser Phe Phe Ser Ala Ser Lys Ile Ile Val Phe Val Thr Phe
                325                 330                 335

Thr Thr Tyr Val Leu Leu Gly Ser Val Ile Thr Ala Ser Arg Val Phe

```
                340                 345                 350
Val Ala Val Thr Leu Tyr Gly Ala Val Arg Leu Thr Val Thr Leu Phe
            355                 360                 365

Phe Pro Ser Ala Ile Glu Arg Val Ser Glu Ala Ile Val Ser Ile Arg
    370                 375                 380

Arg Ile Gln Thr Phe Leu Leu Asp Glu Ile Ser Gln Arg Asn Arg
385                 390                 395                 400

Gln Leu Pro Ser Asp Gly Lys Lys Met Val His Val Gln Asp Phe Thr
                405                 410                 415

Ala Phe Trp Asp Lys Ala Ser Glu Thr Pro Thr Leu Gln Gly Leu Ser
            420                 425                 430

Phe Thr Val Arg Pro Gly Glu Leu Leu Ala Val Val Gly Pro Val Gly
            435                 440                 445

Ala Gly Lys Ser Ser Leu Leu Ser Ala Val Leu Gly Glu Leu Ala Pro
        450                 455                 460

Ser His Gly Leu Val Ser Val His Gly Arg Ile Ala Tyr Val Ser Gln
465                 470                 475                 480

Gln Pro Trp Val Phe Ser Gly Thr Leu Arg Ser Asn Ile Leu Phe Gly
                485                 490                 495

Lys Lys Tyr Glu Lys Glu Arg Tyr Glu Lys Val Ile Lys Ala Cys Ala
                500                 505                 510

Leu Lys Lys Asp Leu Gln Leu Leu Glu Asp Gly Asp Leu Thr Val Ile
            515                 520                 525

Gly Asp Arg Gly Thr Thr Leu Ser Gly Gly Gln Lys Ala Arg Val Asn
    530                 535                 540

Leu Ala Arg Ala Val Tyr Gln Asp Ala Asp Ile Tyr Leu Leu Asp Asp
545                 550                 555                 560

Pro Leu Ser Ala Val Asp Ala Glu Val Ser Arg His Leu Phe Glu Leu
                565                 570                 575

Cys Ile Cys Gln Ile Leu His Glu Lys Ile Thr Ile Leu Val Thr His
            580                 585                 590

Gln Leu Gln Tyr Leu Lys Ala Ala Ser Gln Ile Leu Ile Leu Lys Asp
        595                 600                 605

Gly Lys Met Val Gln Lys Gly Thr Tyr Thr Glu Phe Leu Lys Ser Gly
    610                 615                 620

Ile Asp Phe Gly Ser Leu Leu Lys Lys Asp Asn Glu Glu Ser Glu Gln
625                 630                 635                 640

Pro Pro Val Pro Gly Thr Pro Thr Leu Arg Asn Arg Thr Phe Ser Glu
                645                 650                 655

Ser Ser Val Trp Ser Gln Gln Ser Ser Arg Pro Ser Leu Lys Asp Gly
            660                 665                 670

Ala Leu Glu Ser Gln Asp Thr Glu Asn Val Pro Val Thr Leu Ser Glu
        675                 680                 685

Glu Asn Arg Ser Glu Gly Lys Val Gly Phe Gln Ala Tyr Lys Asn Tyr
    690                 695                 700

Phe Arg Ala Gly Ala His Trp Ile Val Phe Ile Phe Leu Ile Leu Leu
705                 710                 715                 720

Asn Thr Ala Ala Gln Val Ala Tyr Val Leu Gln Asp Trp Trp Leu Ser
                725                 730                 735

Tyr Trp Ala Asn Lys Gln Ser Met Leu Asn Val Thr Val Asn Gly Gly
            740                 745                 750

Gly Asn Val Thr Glu Lys Leu Asp Leu Asn Trp Tyr Leu Gly Ile Tyr
        755                 760                 765
```

```
Ser Gly Leu Thr Val Ala Thr Val Leu Phe Gly Ile Ala Arg Ser Leu
    770                 775                 780

Leu Val Phe Tyr Val Leu Val Asn Ser Ser Gln Thr Leu His Asn Lys
785                 790                 795                 800

Met Phe Glu Ser Ile Leu Lys Ala Pro Val Leu Phe Phe Asp Arg Asn
                805                 810                 815

Pro Ile Gly Arg Ile Leu Asn Arg Phe Ser Lys Asp Ile Gly His Leu
            820                 825                 830

Asp Asp Leu Leu Pro Leu Thr Phe Leu Asp Phe Ile Gln Arg Trp Asp
        835                 840                 845

Leu Ala Val Leu Ser Trp Leu Val Ser Asn Ser
    850                 855

<210> SEQ ID NO 10
<211> LENGTH: 2890
<212> TYPE: DNA
<213> ORGANISM: Homo sapiens

<400> SEQUENCE: 10
ggccggagcc ccagcatccc tgcttgaggt ccaggagcgg agcccgcggc caccgccgcc      60
tgatcagcgc gaccccggcc cgcgcccgcc ccgccggca agatgctgcc cgtgtaccag     120
gaggtgaagc ccaaccccgct gcaggacgcg aacctctgct cacgcgtgtt cttctggtgg    180
ctcaatccct tgtttaaaat tggccataaa cggagattag aggaagatga tatgtattca    240
gtgctgccag aagaccgctc acagcacctt ggagaggagt tgcaagggtt ctgggataaa    300
gaagttttaa gagctgagaa tgacgcacag aagccttctt taacaagagc aatcataaag    360
tgttactgga atcttatttt agttttggga atttttacgt taattgagga aagtgccaaa    420
gtaatccagc ccatattttt gggaaaaatt attaattatt ttgaaaatta tgatcccatg    480
gattctgtgg ctttgaacac agcgtacgcc tatgccacgg tgctgacttt ttgcacgctc    540
attttggcta tactgcatca cttatatttt tatcacgttc agtgtgctgg gatgaggtta    600
cgagtagcca tgtgccatat gatttatcgg aaggcacttc gtcttagtaa catgccatg     660 gggaagacaa ccacaggcca gatagtcaat ctgctgtcca atgatgtgaa caagtttgat    720
caggtgacag tgttcttaca cttcctgtgg gcaggaccac tgcaggcgat cgcagtgact    780
gccctactct ggatggagat aggaatatcg tgccttgctg gatggcagt tctaatcatt    840 ctcctgccct tgcaaagctg ttttgggaag ttgttctcat cactgaggag taaaactgca    900
actttcacgg atgccaggat caggaccatg aatgaagtta taactggtat aaggataata    960
aaaatgtacg cctgggaaaa gtcatttttca atcttatta ccaatttgag aaagaaggag   1020
atttccaaga ttctgagaag ttcctgcctc agggggatga atttggcttc gttttttcagt  1080 gcaagcaaaa tcatcgtgtt tgtgaccttc accacctacg tgctcctcgg cagtgtgatc   1140
acagccagcc gcgtgttcgt ggcagtgacg ctgtatgggg ctgtgcggct gacggttacc   1200
ctcttcttcc cctcagccat tgagagggtg tcagaggcaa tcgtcagcat ccgaagaatc   1260
cagacctttt tgctacttga tgagatatca cagcgcaacc gtcagctgcc gtcagatggt   1320
aaaaagatgg tgcatgtgca ggattttact gcttttttggg ataaggcatc agagacccca   1380
actctacaag gcctttcctt tactgtcaga cctggcgaat tgttagctgt ggtcggcccc   1440
gtgggagcag ggaagtcatc actgttaagt gccgtgctcg gggaattggc ccaagtcac   1500 gggctggtca gcgtgcatgg aagaattgcc tatgtgtctc agcagccctg ggtgttctcg   1560
```

```
ggaactctga ggagtaatat tttatttggg aagaaatacg aaaaggaacg atatgaaaaa    1620
gtcataaagg cttgtgctct gaaaaaggat ttacagctgt tggaggatgg tgatctgact    1680
gtgataggag atcggggaac cacgctgagt ggagggcaga agcacgggt aaaccttgca     1740 agagcagtgt atcaagatgc tgacatctat ctcctggacg atcctctcag tgcagtagat    1800
gcggaagtta gcagacactt gttcgaactg tgtatttgtc aaattttgca tgagaagatc    1860
acaattttag tgactcatca gttgcagtac ctcaaagctg caagtcagat tctgatattg    1920
aaagatggta aaatggtgca aagggggact tacactgagt tcctaaaatc tggtatagat    1980
tttggctccc ttttaaagaa ggataatgag gaaagtgaac aacctccagt tccaggaact    2040
cccacactaa ggaatcgtac cttctcagag tcttcggttt ggtctcaaca atcttctaga    2100
ccctccttga agatggtgc tctggagagc caagatacag agaatgtccc agttacacta     2160
tcagaggaga accgttctga aggaaaagtt ggttttcagg cctataagaa ttacttcaga    2220
gctggtgctc actggattgt cttcattttc cttattctcc taaacactgc agctcaggtt    2280
gcctatgtgc ttcaagattg gtggctttca tactgggcaa acaaacaaag tatgctaaat    2340
gtcactgtaa atggaggagg aaatgtaacc gagaagctag atcttaactg gtacttagga    2400
atttattcag gtttaactgt agctaccgtt ctttttggca tagcaagatc tctattggta    2460
ttctacgtcc ttgttaactc ttcacaaact ttgcacaaca aaatgtttga gtcaattctg    2520
aaagctccgg tattattctt tgatagaaat ccaataggaa gaattttaaa tcgtttctcc    2580
aaagacattg acacttgga tgatttgctg ccgctgacgt ttttagattt catccagaga    2640
tgggatctcg ctgtgttgtc ctggctggtc tcaaactcct aggctcaagc aatcctcctc    2700
cctcctcaag caaacctcag tgctgggatt ataggcatga gccactgtac ctggctaaat    2760 gttgttttt tgatattcaa ttttttgttta tagaattttc atttgttttg ctcttatact    2820
tttcatcttt ttatgtttat tgaccaatta aatatcattt gggtaagcac ctaaaaaaaa    2880
aaaaaaaaaa                                                            2890
```

<210> SEQ ID NO 11
<211> LENGTH: 655
<212> TYPE: PRT
<213> ORGANISM: Homo sapiens

<400> SEQUENCE: 11

```
Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
```

```
            130                 135                 140
Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
                180                 185                 190

Arg Thr Ser Ile Gly Met Glu Leu Ile Thr Asp Pro Ser Ile Leu Phe
                195                 200                 205

Leu Asp Glu Pro Thr Thr Gly Leu Asp Ser Ser Thr Ala Asn Ala Val
210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
                260                 265                 270

Ala Leu Gly Tyr Phe Glu Ser Ala Gly Tyr His Cys Glu Ala Tyr Asn
                275                 280                 285

Asn Pro Ala Asp Phe Phe Leu Asp Ile Ile Asn Gly Asp Ser Thr Ala
290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
                340                 345                 350

Ser Gly Gly Glu Lys Lys Lys Ile Thr Val Phe Lys Glu Ile Ser
                355                 360                 365

Tyr Thr Thr Ser Phe Cys His Gln Leu Arg Trp Val Ser Lys Arg Ser
                370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
                420                 425                 430

Leu Thr Thr Asn Gln Cys Phe Ser Ser Val Ser Ala Val Glu Leu Phe
                435                 440                 445

Val Val Glu Lys Lys Leu Phe Ile His Glu Tyr Ile Ser Gly Tyr Tyr
450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Ala Lys Ala Asp Ala Phe Phe Val Met Met Phe Thr
                500                 505                 510

Leu Met Met Val Ala Tyr Ser Ala Ser Ser Met Ala Leu Ala Ile Ala
                515                 520                 525

Ala Gly Gln Ser Val Val Ser Val Ala Thr Leu Leu Met Thr Ile Cys
                530                 535                 540

Phe Val Phe Met Met Ile Phe Ser Gly Leu Leu Val Asn Leu Thr Thr
545                 550                 555                 560
```

```
Ile Ala Ser Trp Leu Ser Trp Leu Gln Tyr Phe Ser Ile Pro Arg Tyr
            565                 570                 575

Gly Phe Thr Ala Leu Gln His Asn Glu Phe Leu Gly Gln Asn Phe Cys
        580                 585                 590

Pro Gly Leu Asn Ala Thr Gly Asn Asn Pro Cys Asn Tyr Ala Thr Cys
    595                 600                 605

Thr Gly Glu Glu Tyr Leu Val Lys Gln Gly Ile Asp Leu Ser Pro Trp
610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 12
<211> LENGTH: 2247
<212> TYPE: DNA
<213> ORGANISM: Homo sapiens

<400> SEQUENCE: 12
```

| | | | | | |
|---|---|---|---|---|---|
| accgtgcaca | tgcttggtgg | tcttgttaag | tggaaactgc | tgctttagag | tttgtttgga | 60 |
| aggtccgggt | gactcatccc | aacatttaca | tccttaattg | ttaaagcgct | gcctccgagc | 120 |
| gcacgcatcc | tgagatcctg | agcctttggt | taagaccgag | ctctattaag | ctgaaaagat | 180 |
| aaaaactctc | cagatgtctt | ccagtaatgt | cgaagttttt | atcccagtgt | cacaaggaaa | 240 |
| caccaatggc | ttccccgcga | cagcttccaa | tgacctgaag | gcatttactg | aaggagctgt | 300 |
| gttaagtttt | cataacatct | gctatcgagt | aaaactgaag | agtggctttc | taccttgtcg | 360 |
| aaaaccagtt | gagaaagaaa | tattatcgaa | tatcaatggg | atcatgaaac | ctggtctcaa | 420 |
| cgccatcctg | ggacccacag | gtggaggcaa | atcttcgtta | ttagatgtct | tagctgcaag | 480 |
| gaaagatcca | agtggattat | ctggagatgt | tctgataaat | ggagcaccgc | gacctgccaa | 540 |
| tttcaaatgt | aattcaggtt | acgtggtaca | agatgatgtt | gtgatgggca | ctctgacggt | 600 |
| gagagaaaac | ttacagttct | cagcagctct | tcggcttgca | caactatga | cgaatcatga | 660 |
| aaaaaacgaa | cggattaaca | gggtcattca | agagttaggt | ctggataaag | tggcagactc | 720 |
| caaggttgga | actcagttta | tccgtggtgt | gtctggagga | gaaagaaaaa | ggactagtat | 780 |
| aggaatggag | cttatcactg | atccttccat | cttgttcttg | gatgagccta | caactggctt | 840 |
| agactcaagc | acagcaaatg | ctgtcctttt | gctcctgaaa | aggatgtcta | agcagggacg | 900 |
| aacaatcatc | ttctccattc | atcagcctcg | atattccatc | ttcaagttgt | ttgatagcct | 960 |
| cacttattg | gcctcaggaa | gacttatgtt | ccacgggcct | gctcaggagg | ccttgggata | 1020 |
| ctttgaatca | gctggttatc | actgtgaggc | ctataataac | cctgcagact | tcttcttgga | 1080 |
| catcattaat | ggagattcca | ctgctgtggc | attaaacaga | gaagaagact | taaagccac | 1140 |
| agagatcata | gagccttcca | agcaggataa | gccactcata | gaaaaattag | cggagattta | 1200 |
| tgtcaactcc | tccttctaca | aagagacaaa | agctgaatta | catcaacttt | ccggggggtga | 1260 |
| gaagaagaag | aagatcacag | tcttcaagga | gatcagctac | accacctcct | tctgtcatca | 1320 |
| actcagatgg | gtttccaagc | gttcattcaa | aaacttgctg | gtaatcccc | aggcctctat | 1380 |
| agctcagatc | attgtcacag | tcgtactggg | actggttata | ggtgccattt | actttgggct | 1440 |
| aaaaatgat | tctactggaa | tccagaacag | agctgggtt | ctcttcttcc | tgacgaccaa | 1500 |
| ccagtgtttc | agcagtgttt | cagccgtgga | actctttgtg | gtagagaaga | agctcttcat | 1560 |

```
acatgaatac atcagcggat actacagagt gtcatcttat ttccttggaa aactgttatc    1620
tgatttatta cccatgagga tgttaccaag tattatattt acctgtatag tgtacttcat    1680
gttaggattg aaggcaaagg cagatgcctt cttcgttatg atgtttaccc ttatgatggt    1740
ggcttattca gccagttcca tggcactggc catagcagca ggtcagagtg tggtttctgt    1800
agcaacactt ctcatgacca tctgttttgt gtttatgatg attttttcag gtctgttggt    1860
caatctcaca accattgcat cttggctgtc atggcttcag tacttcagca ttccacgata    1920
tggatttacg gctttgcagc ataatgaatt tttgggacaa aacttctgcc caggactcaa    1980
tgcaacagga aacaatcctt gtaactatgc aacatgtact ggcgaagaat atttggtaaa    2040
gcagggcatc gatctctcac cctggggctt gtggaagaat cacgtggcct tggcttgtat    2100
gattgttatt ttcctcacaa ttgcctacct gaaattgtta tttcttaaaa aatattctta    2160
aatttcccct taattcagta tgatttatcc tcacataaaa aagaagcact ttgattgaag    2220
tattcaaaaa aaaaaaaaaa aaaaaaa                                        2247
```

<210> SEQ ID NO 13
<211> LENGTH: 379
<212> TYPE: PRT
<213> ORGANISM: Homo sapiens

<400> SEQUENCE: 13

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255
```

```
Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375

<210> SEQ ID NO 14
<211> LENGTH: 2223
<212> TYPE: DNA
<213> ORGANISM: Homo sapiens

<400> SEQUENCE: 14
tataaaaata gctcttgtta ccggaaataa ctgttcattt ttcactcctc cctcctaggt     60 cacactttc agaaaaagaa tctgcatcct ggaaaccaga agaaaatat gagacgggga     120 atcatcgtgt gatgtgtgtg ctgcctttgg ctgagtgtgt ggagtcctgc tcaggtgtta    180
ggtacagtgt gtttgatcgt ggtggcttga ggggaacccg ctgttcagag ctgtgactgc    240
ggctgcactc agagaagctg cccttggctg ctcgtagcgc cgggccttct ctcctcgtca    300
tcatccagag cagccagtgt ccgggaggca gaagatgccc cactccagcc tgcatccatc    360
catcccgtgt cccaggggtc acggggccca gaaggcagcc ttggttctgc tgagtgcctg    420
cctggtgacc ctttgggggc taggagagcc accagagcac actctccggt acctggtgct    480
ccacctagcc tccctgcagc tgggactgct gttaaacggg gtctgcagcc tggctgagga    540
gctgcgccac atccactcca ggtaccgggg cagctactgg aggactgtgc gggcctgcct    600
gggctgcccc ctccgccgtg gggccctgtt gctgctgtcc atctatttct actactccc    660 cccaaatgcg gtcggcccgc ccttcacttg gatgcttgcc ctcctgggcc tctcgcaggc    720
actgaacatc ctcctgggcc tcaagggcct ggccccagct gagatctctg cagtgtgtga    780
aaaagggaat ttcaacgtgg cccatgggct ggcatggtca tattacatcg gatatctgcg    840
gctgatcctg ccagagctcc aggcccggat tcgaacttac aatcagcatt acaacaacct    900
gctacggggt gcagtgagcc agcggctgta tattctcctc ccattggact gtggggtgcc    960
tgataacctg agtatggctg accccaacat tcgcttcctg gataaactgc ccagcagac    1020 cggtgaccat gctggcatca aggatcgggt ttacagcaac agcatctatg agcttctgga   1080
gaacgggcag cgggcgggca cctgtgtcct ggagtacgcc accccttgc agactttgtt   1140 tgccatgtca caatacagtc aagctggctt tagccgggag ataggcttg agcaggccaa   1200 actcttctgc cggacacttg aggacatcct ggcagatgcc cctgagtctc agaacaactg   1260
ccgcctcatt gcctaccagg aacctgcaga tgacagcagc ttctcgctgt cccaggaggt   1320
tctccggcac ctgcggcagg aggaaaagga agaggttact gtgggcagct tgaagacctc   1380
```

```
agcggtgccc agtacctcca cgatgtccca agagcctgag ctcctcatca gtggaatgga    1440
aaagcccctc cctctccgca cggatttctc ttgagaccca gggtcaccag gccagagcct    1500
ccagtggtct ccaagcctct ggactggggg ctctcttcag tggctgaatg tccagcagag    1560
ctatttcctt ccacaggggg ccttgcaggg aagggtccag gacttgacat cttaagatgc    1620
gtcttgtccc cttgggccag tcatttcccc tctctgagcc tcggtgtctt caacctgtga    1680
aatgggatca taatcactgc cttacctccc tcacggttgt tgtgaggact gagtgtgtgg    1740 aagttttca  taaactttgg atgctagtgt acttaggggg tgtgccaggt gtctttcatg    1800
gggccttcca gacccactcc ccaccttct  ccccttcctt tgcccgggga cgccgaactc    1860
tctcaatggt atcaacaggc tccttcgccc tctggctcct ggtcatgttc cattattggg    1920
gagccccagc agaagaatgg agaggaggag gaggctgagt ttggggtatt gaatcccccg    1980
gctcccaccc tgcagcatca aggttgctat ggactctcct gccgggcaac tcttgcgtaa    2040
tcatgactat ctctaggatt ctggcaccac ttccttccct ggcccttaa  gcctagctgt    2100 gtatcggcac cccacccca  ctagagtact ccctctcact tgcggtttcc ttatactcca    2160
cccctttctc aacggtcctt ttttaaagca catctcagat tacccaaaaa aaaaaaaaa    2220 aaa                                                                  2223
```

<210> SEQ ID NO 15
<211> LENGTH: 522
<212> TYPE: PRT
<213> ORGANISM: Homo sapiens

<400> SEQUENCE: 15

```
Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30

Asp Pro Thr Glu Ser Pro Ala Ala Pro Glu Ala Ala Leu Pro Lys Ala
        35                  40                  45

Gly Lys Phe Gly Pro Ala Arg Lys Ser Gly Ser Arg Gln Lys Lys Ser
    50                  55                  60

Ala Pro Asp Thr Gln Glu Arg Pro Val Arg Ala Thr Gly Ala Arg
65                  70                  75                  80

Ala Lys Lys Ala Pro Gln Arg Ala Gln Asp Thr Gln Pro Ser Asp Ala
                85                  90                  95

Thr Ser Ala Pro Gly Ala Glu Gly Leu Glu Pro Ala Ala Arg Glu
            100                 105                 110

Pro Ala Leu Ser Arg Ala Gly Ser Cys Arg Gln Arg Gly Ala Arg Cys
        115                 120                 125

Ser Thr Lys Pro Arg Pro Pro Gly Pro Trp Asp Val Pro Ser Pro
    130                 135                 140

Gly Leu Pro Val Ser Ala Pro Ile Leu Arg Arg Asp Ala Ala Pro
145                 150                 155                 160

Gly Ala Ser Lys Leu Arg Ala Val Leu Glu Lys Leu Lys Leu Ser Arg
                165                 170                 175

Asp Asp Ile Ser Thr Ala Ala Gly Met Val Lys Gly Val Val Asp His
            180                 185                 190

Leu Leu Leu Arg Leu Lys Cys Asp Ser Ala Phe Arg Gly Val Gly Leu
        195                 200                 205

Leu Asn Thr Gly Ser Tyr Tyr Glu His Val Lys Ile Ser Ala Pro Asn
    210                 215                 220
```

```
Glu Phe Asp Val Met Phe Lys Leu Glu Val Pro Arg Ile Gln Leu Glu
225                 230                 235                 240

Glu Tyr Ser Asn Thr Arg Ala Tyr Tyr Phe Val Lys Phe Lys Arg Asn
            245                 250                 255

Pro Lys Glu Asn Pro Leu Ser Gln Phe Leu Glu Gly Glu Ile Leu Ser
        260                 265                 270

Ala Ser Lys Met Leu Ser Lys Phe Arg Lys Ile Ile Lys Glu Glu Ile
    275                 280                 285

Asn Asp Ile Lys Asp Thr Asp Val Ile Met Lys Arg Lys Arg Gly Gly
290                 295                 300

Ser Pro Ala Val Thr Leu Leu Ile Ser Glu Lys Ile Ser Val Asp Ile
305                 310                 315                 320

Thr Leu Ala Leu Glu Ser Lys Ser Ser Trp Pro Ala Ser Thr Gln Glu
                325                 330                 335

Gly Leu Arg Ile Gln Asn Trp Leu Ser Ala Lys Val Arg Lys Gln Leu
            340                 345                 350

Arg Leu Lys Pro Phe Tyr Leu Val Pro Lys His Ala Lys Glu Gly Asn
        355                 360                 365

Gly Phe Gln Glu Glu Thr Trp Arg Leu Ser Phe Ser His Ile Glu Lys
    370                 375                 380

Glu Ile Leu Asn Asn His Gly Lys Ser Lys Thr Cys Cys Glu Asn Lys
385                 390                 395                 400

Glu Glu Lys Cys Cys Arg Lys Asp Cys Leu Lys Leu Met Lys Tyr Leu
                405                 410                 415

Leu Glu Gln Leu Lys Glu Arg Phe Lys Asp Lys Lys His Leu Asp Lys
            420                 425                 430

Phe Ser Ser Tyr His Val Lys Thr Ala Phe Phe His Val Cys Thr Gln
        435                 440                 445

Asn Pro Gln Asp Ser Gln Trp Asp Arg Lys Asp Leu Gly Leu Cys Phe
    450                 455                 460

Asp Asn Cys Val Thr Tyr Phe Leu Gln Cys Leu Arg Thr Glu Lys Leu
465                 470                 475                 480

Glu Asn Tyr Phe Ile Pro Glu Phe Asn Leu Phe Ser Ser Asn Leu Ile
                485                 490                 495

Asp Lys Arg Ser Lys Glu Phe Leu Thr Lys Gln Ile Glu Tyr Glu Arg
            500                 505                 510

Asn Asn Glu Phe Pro Val Phe Asp Glu Phe
        515                 520

<210> SEQ ID NO 16
<211> LENGTH: 1802
<212> TYPE: DNA
<213> ORGANISM: Homo sapiens

<400> SEQUENCE: 16
agcctggggt tccccttcgg gtcgcagact cttgtgtgcc cgccagtagt gcttggtttc      60
caacagctgc tgctggctct tcctcttgcg gccttttcct gaaacggatt cttctttcgg    120
ggaacagaaa gcgccagcca tgcagccttg gcacggaaag gccatgcaga gagcttccga    180
ggccggagcc actgccccca aggcttccgc acggaatgcc aggggcgccc cgatggatcc    240
caccgagtct ccggctgccc ccgaggccgc cctgcctaag gcgggaaagt tcggccccgc    300
caggaagtcg ggatcccggc agaaaaagag cgccccggac acccaggaga ggccgcccgt    360
ccgcgcaact ggggcccgcg ccaaaaaggc ccctcagcgc gcccaggaca cgcagccgtc    420
```

-continued

```
tgacgccacc agcgccctg gggcagaggg gctggagcct cctgcggctc gggagccggc    480
tctttccagg gctggttctt gccgccagag gggcgcgcgc tgctccacga agccaagacc    540
tccgcccggg ccctgggacg tgcccagccc cggcctgccg gtctcggccc ccattctcgt    600
acggagggat gcggcgcctg gggcctcgaa gctccgggcg gttttggaga agttgaagct    660
cagccgcgat gatatctcca cggcggcggg gatggtgaaa ggggttgtgg accacctgct    720
gctcagactg aagtgcgact ccgcgttcag aggcgtcggg ctgctgaaca ccggagcta    780 ctatgagcac gtgaagattt ctgcacctaa tgaatttgat gtcatgttta aactggaagt    840
ccccagaatt caactagaag aatattccaa cactcgtgca tattactttg tgaaatttaa    900
aagaaatccg aaagaaaatc ctctgagtca gttttagaa ggtgaaatat tatcagcttc    960
taagatgctg tcaaagttta ggaaaatcat taaggaagaa attaacgaca ttaaagatac   1020
agatgtcatc atgaagagga aagaggagg gagccctgct gtaacacttc ttattagtga   1080
aaaaatatct gtggatataa ccctggcttt ggaatcaaaa agtagctggc ctgctagcac   1140
ccaagaaggc ctgcgcattc aaaactggct ttcagcaaaa gttaggaagc aactacgact   1200
aaagccattt taccttgtac ccaagcatgc aaaggaagga aatggtttcc aagaagaaac   1260
atggcggcta tccttctctc acatcgaaaa ggaaattttg aacaatcatg gaaaatctaa   1320
aacgtgctgt gaaaacaaag aagagaaatg ttgcaggaaa gattgtttaa actaatgaa    1380 atacctttta gaacagctga agaaaggtt taaagacaaa aaacatctgg ataaattctc   1440
ttcttatcat gtgaaaactg ccttctttca cgtatgtacc cagaaccctc aagacagtca   1500
gtgggaccgc aaagacctgg gcctctgctt tgataactgc gtgacatact tcttcagtg    1560 cctcaggaca gaaaaacttg agaattattt tattcctgaa ttcaatctat tctctagcaa   1620
cttaattgac aaaagaagta aggaatttct gacaaagcaa attgaatatg aaagaaacaa   1680
tgagtttcca gtttttgatg aattttgaga ttgtattttt agaaagatct aagaactaga   1740
gtcaccctaa atcctggaga atacaagaaa aatttgaaaa ggggccagac gctgtggctc   1800
ac                                                                 1802
```

<210> SEQ ID NO 17
<211> LENGTH: 900
<212> TYPE: PRT
<213> ORGANISM: Homo sapiens

<400> SEQUENCE: 17

Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp

```
            115                 120                 125
Met Thr Ala Gln Phe Asn Asn Leu Gly Val Leu His Val Thr Lys Lys
130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
            195                 200                 205

Leu Lys Pro Val Ile Ser Gln Pro Ile His Asp Ser Lys Ser Pro Gly
        210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350

Gly Ser His Met Gly Gly Gly Ser Gly Gly Ala Ala Gly Gly Tyr Gly
            355                 360                 365

Gly Ala Gly Gly Gly Gly Ser Leu Gly Phe Phe Pro Ser Ser Leu Ala
        370                 375                 380

Tyr Ser Pro Tyr Gln Ser Gly Ala Gly Pro Met Gly Cys Tyr Pro Gly
385                 390                 395                 400

Gly Gly Gly Gly Ala Gln Met Ala Ala Thr Val Pro Ser Arg Asp Ser
                405                 410                 415

Gly Glu Glu Ala Ala Glu Pro Ser Ala Pro Ser Arg Thr Pro Gln Cys
            420                 425                 430

Glu Pro Gln Ala Pro Glu Met Leu Gln Arg Ala Arg Glu Tyr Asn Ala
            435                 440                 445

Arg Leu Phe Gly Leu Ala Gln Arg Ser Ala Arg Ala Leu Leu Asp Tyr
        450                 455                 460

Gly Val Thr Ala Asp Ala Arg Ala Leu Leu Ala Gly Gln Arg His Leu
465                 470                 475                 480

Leu Thr Ala Gln Asp Glu Asn Gly Asp Thr Pro Leu His Leu Ala Ile
                485                 490                 495

Ile His Gly Gln Thr Ser Val Ile Glu Gln Ile Val Tyr Val Ile His
            500                 505                 510

His Ala Gln Asp Leu Gly Val Val Asn Leu Thr Asn His Leu His Gln
            515                 520                 525

Thr Pro Leu His Leu Ala Val Ile Thr Gly Gln Thr Ser Val Val Ser
        530                 535                 540
```

Phe Leu Leu Arg Val Gly Ala Asp Pro Ala Leu Leu Asp Arg His Gly
545                 550                 555                 560

Asp Ser Ala Met His Leu Ala Leu Arg Ala Gly Ala Gly Ala Pro Glu
            565                 570                 575

Leu Leu Arg Ala Leu Leu Gln Ser Gly Ala Pro Ala Val Pro Gln Leu
        580                 585                 590

Leu His Met Pro Asp Phe Glu Gly Leu Tyr Pro Val His Leu Ala Val
    595                 600                 605

Arg Ala Arg Ser Pro Glu Cys Leu Asp Leu Leu Val Asp Ser Gly Ala
610                 615                 620

Glu Val Glu Ala Thr Glu Arg Gln Gly Gly Arg Thr Ala Leu His Leu
625                 630                 635                 640

Ala Thr Glu Met Glu Glu Leu Gly Leu Val Thr His Leu Val Thr Lys
            645                 650                 655

Leu Arg Ala Asn Val Asn Ala Arg Thr Phe Ala Gly Asn Thr Pro Leu
        660                 665                 670

His Leu Ala Ala Gly Leu Gly Tyr Pro Thr Leu Thr Arg Leu Leu Leu
    675                 680                 685

Lys Ala Gly Ala Asp Ile His Ala Glu Asn Glu Glu Pro Leu Cys Pro
690                 695                 700

Leu Pro Ser Pro Pro Thr Ser Asp Ser Asp Ser Glu Gly Pro
705                 710                 715                 720

Glu Lys Asp Thr Arg Ser Ser Phe Arg Gly His Thr Pro Leu Asp Leu
            725                 730                 735

Thr Cys Ser Thr Lys Val Lys Thr Leu Leu Leu Asn Ala Ala Gln Asn
        740                 745                 750

Thr Met Glu Pro Pro Leu Thr Pro Ser Pro Ala Gly Pro Gly Leu
    755                 760                 765

Ser Leu Gly Asp Thr Ala Leu Gln Asn Leu Glu Gln Leu Leu Asp Gly
770                 775                 780

Pro Glu Ala Gln Gly Ser Trp Ala Glu Leu Ala Glu Arg Leu Gly Leu
785                 790                 795                 800

Arg Ser Leu Val Asp Thr Tyr Arg Gln Thr Thr Ser Pro Ser Gly Ser
            805                 810                 815

Leu Leu Arg Ser Tyr Glu Leu Ala Gly Gly Asp Leu Ala Gly Leu Leu
        820                 825                 830

Glu Ala Leu Ser Asp Met Gly Leu Glu Glu Gly Val Arg Leu Leu Arg
    835                 840                 845

Gly Pro Glu Thr Arg Asp Lys Leu Pro Ser Thr Ala Glu Val Lys Glu
850                 855                 860

Asp Ser Ala Tyr Gly Ser Gln Ser Val Glu Gln Glu Ala Glu Lys Leu
865                 870                 875                 880

Gly Pro Pro Pro Glu Pro Pro Gly Gly Leu Cys His Gly His Pro Gln
            885                 890                 895

Pro Gln Val His
        900

<210> SEQ ID NO 18
<211> LENGTH: 3129
<212> TYPE: DNA
<213> ORGANISM: Homo sapiens

<400> SEQUENCE: 18
gcctcccgcc cctcccgtcg cgagggcggg gccagtggcg tcatttccag gcccgccccc    60

-continued

| | |
|---|---|
| tccggccccg cctcccctctg gtattttcgg gactttccta agctgctcta actttcctgc | 120 |
| cccttccccg gccaagccca actccggatc tcgctctcca ccggatctca cccgccacac | 180 |
| ccggacaggc ggctggagga ggcgggcgtc taaaattctg ggaagcagaa cctggccgga | 240 |
| gccactagac agagccgggc ctagcccaga gacatggaga gttgctacaa cccaggtctg | 300 |
| gatggtatta ttgaatatga tgatttcaaa ttgaactcct ccattgtgga acccaaggag | 360 |
| ccagccccag aaacagctga tggcccctac ctggtgatcg tggaacagcc taagcagaga | 420 |
| ggcttccgat ttcgatatgg ctgtgaaggc ccctcccatg gaggactgcc cggtgcctcc | 480 |
| agtgagaagg gccgaaagac ctatcccact gtcaagatct gtaactacga gggaccagcc | 540 |
| aagatcgagg tggacctggt aacacacagt gacccacctc gtgctcatgc ccacagtctg | 600 |
| gtgggcaagc aatgctcgga gctggggatc tgcgccgttt ctgtggggcc caaggacatg | 660 |
| actgcccaat taacaacct gggtgtcctg catgtgacta agaagaacat gatggggact | 720 |
| atgatacaaa aacttcagag gcagcggctc cgctctaggc cccagggcct tacggaggcc | 780 |
| gagcagcggg agctggagca agaggccaaa gaactgaaga aggtgatgga tctgagtata | 840 |
| gtgcggctgc gcttctctgc cttccttaga gccagtgatg gctccttctc cctgcccctg | 900 |
| aagccagtca tctcccagcc catccatgac agcaaatctc cggggggcatc aaacctgaag | 960 |
| atttctcgaa tggacaagac agcaggctct gtgcggggtg gagatgaagt ttatctgctt | 1020 |
| tgtgacaagg tgcagaaaga tgacattgag gttcggttct atgaggatga tgagaatgga | 1080 |
| tggcaggcct ttggggactt ctctcccaca gatgtgcata acagtatgc cattgtgttc | 1140 |
| cggacacccc cctatcacaa gatgaagatt gagcggcctg taacagtgtt tctgcaactg | 1200 |
| aaacgcaagc gaggagggga cgtgtctgat tccaaacagt tcacctatta ccctctggtg | 1260 |
| gaagacaagg aagaggtgca gcggaagcgg aggaaggcct tgcccaccttt ctcccagccc | 1320 |
| ttcggggtg gctcccacat gggtggaggc tctggggtg cagccggggg ctacggagga | 1380 |
| gctggaggag gtggcagcct cggtttcttc ccctcctccc tggcctacag cccctaccag | 1440 |
| tccggcgcgg gccccatggg ctgctacccg ggaggcgggg gcggggcgca gatgccgcc | 1500 |
| acggtgccca gcagggactc cggggaggaa gccgcgcgagc cgagcgcccc ctccaggacc | 1560 |
| ccccagtgcg agccgcaggc cccggagatg ctgcagcgag ctcgagagta caacgcgcgc | 1620 |
| ctgttcggcc tggcgcagcg cagcgcccga gccctactcg actacggcgt caccgcggac | 1680 |
| gcgcgcgcgc tgctggcggg acagcgccac ctgctgacgg cgcaggacga aacggagac | 1740 |
| acaccactgc acctagccat catccacggg cagaccagtg tcattgagca gatagtctat | 1800 |
| gtcatccacc acgcccagga cctcggcgtt gtcaacctca ccaaccacct gcaccagacg | 1860 |
| cccctgcacc tggcggtgat cacggggcag acgagtgtgg tgagctttct gctgcgggta | 1920 |
| ggtgcagacc cagctctgct ggatcggcat ggagactcag ccatgcatct ggcgctgcgg | 1980 |
| gcaggcgctg tgctcctga gctgctgcgt gcactgcttc agagtggagc tcctgctgtg | 2040 |
| ccccagctgt tgcatatgcc tgactttgag ggactgtatc cagtacacct ggcggtccga | 2100 |
| gcccgaagcc ctgagtgcct ggatctgctg gtggacagtg gggctgaagt ggaggccaca | 2160 |
| gagcggcagg ggggacgaac agccttgcat ctagccacag agatggagga ctggggttg | 2220 |
| gtcacccatc tggtcaccaa gctccgggcc aacgtgaacg ctcgcacctt gcgggaaac | 2280 |
| acacccctgc acctggcagc tggactgggg tacccgaccc tcacccgcct ccttctgaag | 2340 |
| gctggtgctg acatccatgc tgaaaacgag gagcccctgt gcccactgcc ttcaccccct | 2400 |

-continued

```
acctctgata gcgactcgga ctctgaaggg cctgagaagg acacccgaag cagcttccgg    2460
ggccacacgc ctcttgacct cacttgcagc accaaggtga agaccttgct gctaaatgct    2520
gctcagaaca ccatggagcc acccctgacc ccgcccagcc cagcagggcc gggactgtca    2580
cttggtgata cagctctgca gaacctggag cagctgctag acgggccaga agcccagggc    2640
agctgggcag agctggcaga gcgtctgggg ctgcgcagcc tggtagacac gtaccgacag    2700
acaacctcac ccagtggcag cctcctgcgc agctacgagc tggctggcgg ggacctggca    2760
ggtctactgg aggccctgtc tgacatgggc ctagaggagg gagtgaggct gctgaggggt    2820
ccagaaaccc gagacaagct gcccagcaca gcagaggtga aggaagacag tgcgtacggg    2880
agccagtcag tggagcagga ggcagagaag ctgggcccac cccctgagcc accaggaggg    2940
ctctgccacg gcaccccca gcctcaggtg cactgacctg ctgcctgccc ccagcccct    3000 tcccggaccc cctgtacagc gtccccacct atttcaaatc ttatttaaca ccccacaccc    3060 accctcagt tgggacaaat aaaggattct catgggaagg ggaggacccc tccttcccaa    3120
cttatggca                                                             3129
```

<210> SEQ ID NO 19
<211> LENGTH: 579
<212> TYPE: PRT
<213> ORGANISM: Homo sapiens

<400> SEQUENCE: 19

```
Met Leu Arg Ser Gly Pro Ala Ser Gly Pro Ser Val Pro Thr Gly Arg
1               5                   10                  15

Ala Met Pro Ser Arg Arg Val Ala Arg Pro Pro Ala Ala Pro Glu Leu
            20                  25                  30

Gly Ala Leu Gly Ser Pro Asp Leu Ser Ser Leu Ser Leu Ala Val Ser
        35                  40                  45

Arg Ser Thr Asp Glu Leu Glu Ile Ile Asp Glu Tyr Ile Lys Glu Asn
    50                  55                  60

Gly Phe Gly Leu Asp Gly Gly Gln Pro Gly Pro Gly Glu Gly Leu Pro
65                  70                  75                  80

Arg Leu Val Ser Arg Gly Ala Ala Ser Leu Ser Thr Val Thr Leu Gly
                85                  90                  95

Pro Val Ala Pro Pro Ala Thr Pro Pro Trp Gly Cys Pro Leu Gly
            100                 105                 110

Arg Leu Val Ser Pro Ala Pro Gly Pro Gly Pro Gln Pro His Leu Val
        115                 120                 125

Ile Thr Glu Gln Pro Lys Gln Arg Gly Met Arg Phe Arg Tyr Glu Cys
    130                 135                 140

Glu Gly Arg Ser Ala Gly Ser Ile Leu Gly Glu Ser Ser Thr Glu Ala
145                 150                 155                 160

Ser Lys Thr Leu Pro Ala Ile Glu Leu Arg Asp Cys Gly Gly Leu Arg
                165                 170                 175

Glu Val Glu Val Thr Ala Cys Leu Val Trp Lys Asp Trp Pro His Arg
            180                 185                 190

Val His Pro His Ser Leu Val Gly Lys Asp Cys Thr Asp Gly Ile Cys
        195                 200                 205

Arg Val Arg Leu Arg Pro His Val Ser Pro Arg His Ser Phe Asn Asn
    210                 215                 220

Leu Gly Ile Gln Cys Val Arg Lys Lys Glu Ile Glu Ala Ala Ile Glu
225                 230                 235                 240
```

Arg Lys Ile Gln Leu Gly Ile Asp Pro Tyr Asn Ala Gly Ser Leu Lys
        245                 250                 255

Asn His Gln Glu Val Asp Met Asn Val Val Arg Ile Cys Phe Gln Ala
        260                 265                 270

Ser Tyr Arg Asp Gln Gln Gly Gln Met Arg Arg Met Asp Pro Val Leu
        275                 280                 285

Ser Glu Pro Val Tyr Asp Lys Lys Ser Thr Asn Thr Ser Glu Leu Arg
        290                 295                 300

Ile Cys Arg Ile Asn Lys Glu Ser Gly Pro Cys Thr Gly Gly Glu Glu
305                 310                 315                 320

Leu Tyr Leu Leu Cys Asp Lys Val Gln Lys Glu Asp Ile Ser Val Val
                325                 330                 335

Phe Ser Arg Ala Ser Trp Glu Gly Arg Ala Asp Phe Ser Gln Ala Asp
                340                 345                 350

Val His Arg Gln Ile Ala Ile Val Phe Lys Thr Pro Pro Tyr Glu Asp
                355                 360                 365

Leu Glu Ile Val Glu Pro Val Thr Val Asn Val Phe Leu Gln Arg Leu
        370                 375                 380

Thr Asp Gly Val Cys Ser Glu Pro Leu Pro Phe Thr Tyr Leu Pro Arg
385                 390                 395                 400

Asp His Asp Ser Tyr Gly Val Asp Lys Lys Arg Lys Arg Gly Met Pro
                405                 410                 415

Asp Val Leu Gly Glu Leu Asn Ser Ser Asp Pro His Gly Ile Glu Ser
                420                 425                 430

Lys Arg Arg Lys Lys Lys Pro Ala Ile Leu Asp His Phe Leu Pro Asn
        435                 440                 445

His Gly Ser Gly Pro Phe Leu Pro Pro Ser Ala Leu Leu Pro Asp Pro
        450                 455                 460

Asp Phe Phe Ser Gly Thr Val Ser Leu Pro Gly Leu Glu Pro Pro Gly
465                 470                 475                 480

Gly Pro Asp Leu Leu Asp Asp Gly Phe Ala Tyr Asp Pro Thr Ala Pro
                485                 490                 495

Thr Leu Phe Thr Met Leu Asp Leu Leu Pro Pro Ala Pro Pro His Ala
                500                 505                 510

Ser Ala Val Val Cys Ser Gly Gly Ala Gly Ala Val Val Gly Glu Thr
        515                 520                 525

Pro Gly Pro Glu Pro Leu Thr Leu Asp Ser Tyr Gln Ala Pro Gly Pro
        530                 535                 540

Gly Asp Gly Gly Thr Ala Ser Leu Val Gly Ser Asn Met Phe Pro Asn
545                 550                 555                 560

His Tyr Arg Glu Ala Ala Phe Gly Gly Gly Leu Leu Ser Pro Gly Pro
                565                 570                 575

Glu Ala Thr

<210> SEQ ID NO 20
<211> LENGTH: 2297
<212> TYPE: DNA
<213> ORGANISM: Homo sapiens

<400> SEQUENCE: 20
ggccccgcgc cccgcgcagc cccgggcgcc gcgcgtcctg cccggcctgc ggccccagcc    60
cttgcgccgc tcgtccgacc cgcgatcgtc caccagaccg tgcctcccgg ccgcccggcc   120
ggcccgcgtg catgcttcgg tctgggccag cctctgggcc gtccgtcccc actggccggg   180

```
ccatgccgag tcgccgcgtc gccagaccgc cggctgcgcc ggagctgggg gccttagggt    240 ccccgacct ctcctcactc tcgctcgccg tttccaggag cacagatgaa ttggagatca     300
tcgacgagta catcaaggag aacggcttcg gcctggacgg gggacagccg ggcccgggcg    360
aggggctgcc acgcctggtg tctcgcgggg ctgcgtccct gagcacggtc accctgggcc    420
ctgtggcgcc cccagccacg ccgccgcctt ggggctgccc cctgggccga ctagtgtccc    480
cagcgccggg cccgggcccg cagccgcacc tggtcatcac ggagcagccc aagcagcgcg    540
gcatgcgctt ccgctacgag tgcgagggcc gctcggccgg cagcatcctt ggggagagca    600
gcaccgaggc cagcaagacg ctgcccgcca tcgagctccg ggattgtgga gggctgcggg    660
aggtggaggt gactgcctgc ctggtgtgga aggactggcc tcaccgagtc cacccccaca    720
gcctcgtggg gaaagactgc accgacggca tctgcagggt gcggctccgg cctcacgtca    780
gcccccggca cagttttaac aacctgggca tccagtgtgt gaggaagaag gagattgagg    840
ctgccattga gcggaagatt caactgggca ttgaccccta caacgctggg tccctgaaga    900
accatcagga agtagacatg aatgtggtga ggatctgctt ccaggcctca tatcgggacc    960
agcagggaca gatgcgccgg atggatcctg tgctttccga gcccgtctat gacaagaaat    1020
ccacaaacac atcagagctg cggatttgcc gaattaacaa ggaaagcggg ccgtgcaccg    1080
gtggcgagga gctctacttg ctctgcgaca aggtgcagaa agaggacata tcagtggtgt    1140
tcagcagggc ctcctgggaa ggtcgggctg acttctccca ggccgacgtg caccgccaga    1200
ttgccattgt gttcaagacg ccgccctacg aggacctgga gattgtcgag cccgtgacag    1260
tcaacgtctt cctgcagcgg ctcaccgatg gggtctgcag cgagccattg cctttcacgt    1320
acctgcctcg cgaccatgac agctacggcg tggacaagaa gcggaaacgg gggatgcccg    1380
acgtccttgg ggagctgaac agctctgacc cccatggcat cgagagcaaa cggcggaaga    1440
aaaagccggc catcctggac cacttcctgc ccaaccacgg ctcaggcccg ttcctcccgc    1500
cgtcagccct gctgccagac cctgacttct ctctggcac cgtgtccctg cccggcctgg    1560 agcccctgg cgggcctgac ctcctggacg atggctttgc ctacgaccct acggccccca    1620
cactcttcac catgctggac ctgctgcccc cggcaccgcc acacgctagc gctgttgtgt    1680
gcagcggagg tgccggggcc gtggttgggg agaccccgg ccctgaacca ctgacactgg    1740
actcgtacca ggcccgggc cccggggatg gaggcaccgc cagccttgtg ggcagcaaca    1800
tgttccccaa tcattaccgc gaggcggcct ttggggggcgg cctcctatcc ccggggcctg    1860
aagccacgta gccccgcgat gccagaggag gggcactggg tggggaggga ggtgaggag     1920 ccgtgcaatc ccaaccagga tgtctagcac ccccatcccc ttggcccttc ctcatgcttc    1980
tgaagtggac atattcagcc ttggcgagaa gctccgttgc acgggtttcc ccttgagccc    2040
attttacaga tgaggaaact gagtccggag aggaaaaggg acatggctcc cgtgcactag    2100
cttgttacag ctgcctctgt ccccacatgt ggggcacct tctccagtag gattcggaaa     2160
agattgtaca tatgggagga gggggcagat tcctggccct ccctcccag acttgaaggt     2220 gggggtagg ttggttgttc agagtcttcc caataaagat gagttttga gcctccggga     2280 aaaaaaaaaa aaaaaaa                                                  2297
```

<210> SEQ ID NO 21
<211> LENGTH: 925
<212> TYPE: PRT
<213> ORGANISM: Homo sapiens

<400> SEQUENCE: 21

-continued

```
Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
            35                  40                  45

Leu Leu Ala Pro Met Asp Val Gly Glu Pro Leu Glu Lys Ala Ala
        50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                85                  90                  95

Leu Lys Pro Ser Cys Ala Lys Glu Val Lys Ser Cys Lys Gly Arg Cys
            100                 105                 110

Phe Glu Arg Thr Phe Gly Asn Cys Arg Cys Asp Ala Ala Cys Val Glu
            115                 120                 125

Leu Gly Asn Cys Cys Leu Asp Tyr Gln Glu Thr Cys Ile Glu Pro Glu
        130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
            195                 200                 205

Thr Pro Pro Thr Leu Leu Phe Ser Leu Asp Gly Phe Arg Ala Glu Tyr
        210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285

Ser Leu Lys Ser Lys Glu Lys Phe Asn Pro Glu Trp Tyr Lys Gly Glu
        290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
        370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415
```

```
Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
                500                 505                 510

Tyr Leu Asp Pro Gln Trp Gln Leu Ala Leu Asn Pro Ser Glu Arg Lys
            515                 520                 525

Tyr Cys Gly Ser Gly Phe His Gly Ser Asp Asn Val Phe Ser Asn Met
        530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
    770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
```

```
                        835                 840                 845
Glu Asn Leu Asp Thr Leu Ala Phe Ile Leu Pro His Arg Thr Asp Asn
            850                 855                 860
Ser Glu Ser Cys Val His Gly Lys His Asp Ser Ser Trp Val Glu Glu
865                 870                 875                 880
Leu Leu Met Leu His Arg Ala Arg Ile Thr Asp Val Glu His Ile Thr
                        885                 890                 895
Gly Leu Ser Phe Tyr Gln Gln Arg Lys Glu Pro Val Ser Asp Ile Leu
            900                 905                 910
Lys Leu Lys Thr His Leu Pro Thr Phe Ser Gln Glu Asp
            915                 920                 925

<210> SEQ ID NO 22
<211> LENGTH: 7442
<212> TYPE: DNA
<213> ORGANISM: Homo sapiens

<400> SEQUENCE: 22
ccggagcggc cggggccacg atggagcgcg acggctgcgc ggggggcggg agccgcggcg      60
gcgagggcgg gcgcgctccc cgggagggcc cggcggggaa cggccgcgat cggggccgca     120
gccacgctgc cgaggcgccc ggggacccgc aggcggccgc gtccttgctg cccctatgg     180 acgtggggga ggagccgctg gagaaggcgg cgcgcgcccg cactgccaag gaccccaaca     240
cctataaagt actctcgctg gtattgtcag tatgtgtgtt aacaacaata cttggttgta     300
tatttgggtt gaaaccaagc tgtgccaaag aagttaaaag ttgcaaaggt cgctgtttcg     360
agagaacatt tgggaactgt cgctgtgatg ctgcctgtgt tgagcttgga aactgctgtt     420
tagattacca ggagacgtgc atagaaccag aacatatatg gacttgcaac aaattcaggt     480
gtggtgagaa aaggttgacc agaagcctct gtgcctgttc agatgactgc aaggacaagg     540
gcgactgctg catcaactac agttctgtgt gtcaaggtga aaaagttgg gtagaagaac     600 catgtgagag cattaatgag ccacagtgcc agcagggtt tgaaacgcct cctaccctct     660
tattttcttt ggatggattc agggcagaat atttacacac ttggggtgga cttcttcctg     720
ttattagcaa actaaaaaaa tgtggaacat atactaaaaa catgagaccg gtatatccaa     780
caaaaacttt ccccaatcac tacagcattg tcaccggatt gtatccagaa tctcatggca     840
taatcgacaa taaaatgtat gatcccaaaa tgaatgcttc cttttcactt aaaagtaaag     900
agaaatttaa tcctgagtgg tacaaaggag aaccaatttg ggtcacagct aagtatcaag     960
gcctcaagtc tggcacattt ttctggccag atcagatgt ggaaattaac ggaatttttcc    1020 cagacatcta taaatgtat aatggttcag taccatttga agaaaggatt ttagctgttc    1080
ttcagtggct acagcttcct aaagatgaaa gaccacactt ttacactctg tatttagaag    1140
aaccagattc ttcaggtcat tcatatggac cagtcagcag tgaagtcatc aaagccttgc    1200
agagggttga tggtatggtt ggtatgctga tggatggtct gaaagagctg aacttgcaca    1260
gatgcctgaa cctcatcctt atttcagatc atggcatgga caaggcagt tgtaagaaat    1320 acatatatct gaataaatat ttgggggatg ttaaaaatat taaagttatc tatgacctg    1380 cagctcgatt gagaccctct gatgtcccag ataaatacta ttcatttaac tatgaaggca    1440
ttgcccgaaa tctttcttgc cgggaaccaa ccagcacctt caaaccttac ctgaaacatt    1500
tcttacctaa gcgtttgcac tttgctaaga gtgatagaat tgagcccttg acattctatt    1560
tggaccctca gtggcaactt gcattgaatc cctcagaaag gaaatattgt ggaagtggat    1620
```

```
ttcatggctc tgacaatgta tttttcaaata tgcaagccct ctttgttggc tatggacctg    1680
gattcaagca tggcattgag gctgacacct ttgaaaacat tgaagtctat aacttaatgt    1740
gtgatttact gaatttgaca ccggctccta ataacggaac tcatggaagt cttaaccacc    1800
ttctaaagaa tcctgtttat acgccaaagc atcccaaaga agtgcacccc ctggtacagt    1860
gccccttcac aagaaacccc agagataacc ttggctgctc atgtaaccct tcgatttgc     1920 cgattgagga ttttcaaaca cagttcaatc tgactgtggc agaagagaag attattaagc    1980
atgaaacttt accctatgga agacctagag ttctccagaa ggaaaacacc atctgtcttc    2040
tttcccagca ccagtttatg agtggataca gccaagacat cttaatgccc ctttggacat    2100
cctataccgt ggacagaaat gacagtttct ctacggaaga cttctccaac tgtctgtacc    2160
aggactttag aattcctctt agtcctgtcc ataaatgttc attttataaa ataacacca     2220 aagtgagtta cgggttcctc tccccaccac aactaaataa aaattcaagt ggaatatatt    2280
ctgaagcttt gcttactaca aatatagtgc caatgtacca gagttttcaa gttatatggc    2340
gctactttca tgacacccta ctgcgaaagt atgctgaaga agaaatggt gtcaatgtcg     2400 tcagtggtcc tgtgtttgac tttgattatg atggacgttg tgattcctta gagaatctga    2460
ggcaaaaaag aagagtcatc cgtaaccaag aaatttttgat ccaactcac ttctttattg     2520 tgctaacaag ctgtaaagat acatctcaga cgcctttgca ctgtgaaaac ctagacacct    2580
tagctttcat tttgcctcac aggactgata acagcgagag ctgtgtgcat gggaagcatg    2640
actcctcatg ggttgaagaa ttgttaatgt tacacagagc acggatcaca gatgttgagc    2700
acatcactgg actcagcttc tatcaacaaa gaaagagcc agtttcagac attttaaagt     2760
tgaaaacaca tttgccaacc tttagccaag aagactgata tgtttttat ccccaaacac     2820 catgaatctt tttgagagaa ccttatattt tatatagtcc tctagctaca ctattgcatt    2880
gttcagaaac tgtcgaccag agttagaacg gagccctcgg tgatgcggac atctcaggga    2940
aacttgcgta ctcagcacag cagtggagag tgttcctgtt gaatcttgca catatttgaa    3000
tgtgtaagca ttgtatacat tgatcaagtt cgggggaata aagacagacc acacctaaaa    3060
ctgcctttct gcttctctta aaggagaagt agctgtgaac attgtctgga taccagatat    3120
ttgaatcttt cttactattg gtaataaacc ttgatggcat tgggcaaaca gtagactttat  3180 agtagggttg gggtagccca tgttatgtga ctatctttat gagaatttta aagtggttct    3240
ggatatcttt taacttggag tttcatttct tttcattgta atcaaaaaaa aaattaacag    3300
aagccaaaat acttctgaga ccttgtttca atctttgctg tatatcccct caaaatccaa    3360
gttattaatc ttatgtgttt tctttttaat tttttgattg gatttcttta gatttaatgg    3420
ttcaaatgag ttcaactttg agggacgatc tttgaatata cttacctatt ataaaatctt    3480
actttgtatt tgtatttaaa aagaaaaat attcctatcc tgctcactgg taattaacat    3540
aggtttaaaa tggcttcaaa tgtggcccta tagacggtta aaattgtacc ttatcttggc    3600
aaaacttcag agcaccagtc agtgcatgca aggtgccatt ttttattgag atgcttagaa    3660
tgtttctttc tgtgcacaag acttacccta ccagcagcag agccattctc tgttgagtgg    3720
ttcattttga agttccacag attgaagaga acatgccacc aatcacctca catcttcttg    3780
gtggacatga taaatgacac aatgaacttg atttctttac taccttgact gtagcttttt    3840
atccctacct gtgaaccttc aaagactgca ttaacttttta ggctacatag gtccaattga    3900
ggtataatat cagtacacca aagattttta tatgtccttc gtgtgaccat tcttcaacgg    3960
cctaagggcc agctgcaaag acttttggaa aatacaattt acaactcaaa attatttaat    4020
```

```
aatttaggaa gttgcttttt ttttttttttt ttttcagtcc tgcagtttcc tgaagctctg    4080
tatatgatat tttttttcagc ctgcttctct ctgttgttca gattaggtaa ttttattctt    4140
ctgtctcgaa gctcactgat tctttattct gtctaatctg ttctgctgtt gagcccattt    4200
attcctgatt tttatatttt agttattgta tgttttattt ctaaaatttc cattcagttt    4260
ttctttatat cttctatttg ctgagaattt ctgtctcttt gctgagactt tctacgtttt    4320
catttgtttc aagtgcattt atacttgctt gttgaagaat ttttatgatg gctgctgtaa    4380
aatccttatc agataattcc aacatctgtc acctcattgt ttgcatctac tgatggtctt    4440
ttttccattc ggaaacattt tcctgtttct tggtgtgtgg aatgattttt tattgaaacc    4500
tggatatttt taggtattat gttatgagac tatgggtctt atttaaacct tctgctttag    4560
ccaactttct cagataccac cacagcaggg gaattgggag cactgcttca ttattaccag    4620
gtgtggctag gagtccaggt tccccagtca gcctcccttt atactgagta acagggtccc    4680
ctcattacta ctgggcaagg tgagaattca gtttcccatt aggtctttat tgattcttcc    4740
ctggctggaa tgtgcagcgg cacctttttgg tgcaccctgg gaatctccac taatgctatg    4800
ggacagagtg accaggaaga gcttcattac accaggtggg aatgaaattc ccagtagcct    4860
acacagcctt ctccgacacc actctggagt tgtattcttc cagcacacaa acatacacaa    4920
tttaactcaa agcatcttag cagagcttaa ttaaatggat agatgcctgt tcccttttgct    4980 ggataccaag aatacaaaag tcagggagtt ggggcacctc tttacagctt ggtgagagtg    5040
taagtctgga ctcccacatc agcatttgct ggtatgggtg gggccatggt gtttttccat    5100
ggtgtttggt tggagtacag ccttttttac ccttgcttgg ctaccctttt ctggtccttt    5160
ggcaggagag agcaggactc tcttagggct ttttttttccc ctgcatttat tgacatttcc    5220
aggttgctga ctttttcagc tccaagttgg aaatatatga gctgaaaaga aaatgtaggg    5280
aactcatcac agtgttgtta cttgggcccc aatgttccta gcctattttc tgtctactat    5340
tcagagtctt gctgtgtttt aatataatat ccaggatttt tatatgcatt tagcagaagg    5400
atgtctactc tgcctttgta gaagtgtctc actgatttttt acatattttt ccagcacaca    5460
aacatacaca atttaactca aagcatctta gcagagctta ttaaatgga tagatgtctg    5520 ttccctttgc tggacgccaa gaatacaaaa aagaacaagt gacaatttttc tctgtcttag    5580 ggagaagaga cagcagaagt gtaaatgatc cctaaagagt gatagatgtt atcatgaagc    5640
cacaggaggg gtgccaggct gcacaaaaga gacactggat gcttcttggt agtagaggca    5700
gtggcttccc agccttgggg ctaaggcttg tagggtgaat tggaacttttt cagatgagca    5760 aggcaaagaa gggaccttct aacattcctt ggatggaaca tttttgacat tttcccattt    5820
acagctactt atattttcta caagtgtcac tgtgaccaac ttatgtacac atactttttc    5880
ttgcttagtt ataataatct gttcttaaag aaaatgtcag tctctacatt ctatgctgac    5940
tgttaaggaa agagcaccca catctgctcc tacttagctt ttttctgtg gttcttacac    6000 agtattcctt tttttctttt cttgaaagag actcctcctt tcttttctttt tcttgaaaga    6060 gttttaaaca gataagatgg caaaagtgac tgatctctac tcccccagtt tgaatggtaa    6120
atttgaatgg taaaattccca tgaacatata tggaaatgtc tttatcctac tttctccaat    6180
aaaggctgtt cttagctttt caaatgcaaa gtgaaacctt tatttatctt gatttctttt    6240
tttttttttt tttttttttt ttttttgaga tgctctgtca cccaggctgg agtgcagtgg    6300
caagatcttg gctcactgca agctccgcct cccaggttca cgccattctc ctggctcagc    6360
```

```
ctcccgagta actgggacta caggcacctg ccgtcacgcc tggctaattt tttgtatttt    6420
tagtagagaa tggagtttca ccgtgttagc caggatggtc tcgatctcct gaccttgtga    6480
tctgcccgcc tcggcctccc aaagtgctgg gattacaggc tcgagccact gcctccagcc    6540
tatcctgatt tctactgtca tgcctcacat cagtcctttt tttttttttt gagacagagt    6600
ctcgctctgt ggcccaggct agactgcagt ggcatgatct cggctcactg caacctccac    6660
ctccggggtt ctagcaattc tcctgcctca gcctcctgag tagctgggat tataggcgca    6720
tgccacacct ggcttttgt atttagtgg agatggggtt tcactgtgtt gctcaggctg    6780
gtcttgatct cctgagctca gacaatcccc ccgccttggc ctcccaaagt gctaggatta    6840
taggcgagag ctgctgtgtg cttcttaagt gaggtaagta acttccatag aaaatttcca    6900
tcagttcatt catgaaagaa caagaacct ggcaaaactt aaaaaaacgt ttccaagaat    6960
cagataaaag aggacaaacc ttagggagaa gaaggcagct gctcatttcc agcaggggaa    7020
gtagctgcat agagtacaag gactggtagg cctgttggct gttcctgttt aaggagacaa    7080
gatgggcatg aacagggac cacccctcc tctgggagaa gctgttaccc ccttcacttt    7140
tcctcctctg tcattaccca caatcactct ccttctttgc gctatggtag gtgtttaccc    7200
atcataggaa tgggcatttg aactttgaaa ctgaatgtgg tgattacact tcatgctgaa    7260
gcttttcaca tgagtgcttt cataagcatt aagtaaaatt ttataatgac tgcagtccaa    7320
ggacattttc cctggttttt ggccagtcta aatattgtaa gagagagaga agaaaagtgt    7380
acggaatata attgtctcta agctaagaaa tgtggatgtt caaataaaac atacgtacag    7440
aa                                                                  7442
```

<210> SEQ ID NO 23
<211> LENGTH: 435
<212> TYPE: PRT
<213> ORGANISM: Homo sapiens

<400> SEQUENCE: 23

Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45

Glu Tyr Tyr Glu Pro Gln His Arg Ile Cys Cys Ser Arg Cys Pro Pro
    50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
    130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

```
Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
    210                 215                 220

Met Leu Met Leu Ala Val Leu Leu Pro Leu Ala Phe Phe Leu Leu Leu
225                 230                 235                 240

Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
    290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335

Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
        355                 360                 365

Leu Gly Gly Pro Pro Gly Pro Gly Asp Leu Pro Ala Thr Pro Glu Pro
    370                 375                 380

Pro Tyr Pro Ile Pro Glu Glu Gly Asp Pro Gly Pro Pro Gly Leu Ser
385                 390                 395                 400

Thr Pro His Gln Glu Asp Gly Lys Ala Trp His Leu Ala Glu Thr Glu
                405                 410                 415

His Cys Gly Ala Thr Pro Ser Asn Arg Gly Pro Arg Asn Gln Phe Ile
            420                 425                 430

Thr His Asp
        435

<210> SEQ ID NO 24
<211> LENGTH: 2283
<212> TYPE: DNA
<213> ORGANISM: Homo sapiens

<400> SEQUENCE: 24
gctttcccgg ccgcccctcc cgccccgcat cgaggcagac aagcctgttc ctcttccctg      60
ggctgcgatt gcgacaggcc ggcctggctc ccagcgctcc ctgtcccgc  cccgcggcca     120 gctcgctcca ctcccacttc ctgagctccg ccatgggagc cctggaggcc cggcctggcc     180
gctcccggcc ctggggtgca catcggccct gagtcccgtc caggctctg  gctcgggca     240 gccgccgcca ccgctgccca ggacgtcggg cctcctgcct tcctcccagg ccccacgtt     300 gctggccgcc tggccgagtg gccgccatgc tcctgccttg gccacctct  gccccggcc     360 tggcctgggg gcctctggtg ctgggcctct tcgggctcct ggcagcatcg cagccccagg     420
cggtgcctcc atatgcgtcg gagaaccaga cctgcaggga ccaggaaaag gaatactatg     480
agccccagca ccgcatctgc tgctcccgct gcccgccagg cacctatgtc tcagctaaat     540
gtagccgcat ccgggacaca gtttgtgcca catgtgccga gaattcctac aacgagcact     600
```

```
ggaactacct gaccatctgc cagctgtgcc gcccctgtga cccagtgatg ggcctcgagg    660
agattgcccc ctgcacaagc aaacggaaga cccagtgccg ctgccagccg ggaatgttct    720
gtgctgcctg ggccctcgag tgtacacact gcgagctact ttctgactgc ccgcctggca    780
ctgaagccga gctcaaagat gaagttggga agggtaacaa ccactgcgtc ccctgcaagg    840
ccgggcactt ccagaatacc tcctccccca gcgcccgctg ccagcccac accaggtgtg     900 agaaccaagg tctggtggag gcagctccag gcactgccca gtccgacaca acctgcaaaa    960
atccattaga gccactgccc ccagagatgt caggaaccat gctgatgctg gccgttctgc    1020
tgccactggc cttctttctg ctccttgcca ccgtcttctc ctgcatctgg aagagccacc    1080
cttctctctg caggaaactg ggatcgctgc tcaagaggcg tccgcaggga gagggaccca    1140
atcctgtagc tggaagctgg gagcctccga aggcccatcc atacttccct gacttggtac    1200
agccactgct acccatttct ggagatgttt ccccagtatc cactgggctc cccgcagccc    1260
cagttttgga ggcaggggtg ccgcaacagc agagtcctct ggacctgacc agggagccgc    1320
agttggaacc cggggagcag agccaggtgg cccacgtac caatggcatt catgtcaccg     1380
gcgggtctat gactatcact ggcaacatct acatctacaa tggaccagta ctgggggggac    1440 caccgggtcc tggagacctc ccagctaccc ccgaacctcc atacccatt cccgaagagg     1500 gggaccctgg ccctcccggg ctctctacac cccaccagga agatggcaag gcttggcacc    1560
tagcggagac agagcactgt ggtgccacac cctctaacag ggcccaagg aaccaattta     1620 tcacccatga ctgactgagt ctgagaaaag gcagaagaag gggggcacaa gggcaccttc    1680
tcccttgagg ctgccctgcc cacgtgggat tcacagggc ctgagtaggg cccggggaag     1740
cagagcccta agggattaag gctcagacac ctctgagagc aggtgggcac tggctgggta    1800
cggtgccctc cacaggactc tccctactgc ctgagcaaac ctgaggcctc ccggcagacc    1860
cacccacccc ctggggctgc tcagcctcag gcacggacag ggcacatgat accaactgct    1920
gcccactacg gcacgccgca ccggagcacg gcaccgaggg agccgccaca cggtcacctg    1980
caaggacgtc acgggcccct ctaaaggatt cgtggtgctc atccccaagc ttcagagacc    2040 ctttgggggtt ccacacttca cgtggactga ggtagaccct gcatgaagat gaaattatag    2100
ggaggacgct ccttccctcc cctcctagag gagaggaaag ggagtcatta acaactaggg    2160
ggttgggtag gattcctagg tatggggaag agttttggaa ggggaggaaa atggcaagtg    2220
tatttatatt gtaaccacat gcaaataaaa agaatgggac ctagataaaa aaaaaaaaaa    2280
aaa                                                                   2283

<210> SEQ ID NO 25
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 25
ttcatattca atttgctttg tc                                               22

<210> SEQ ID NO 26
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 26
```

```
ttagttttaa acaatctttc ct                                              22

<210> SEQ ID NO 27
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 27
ttctaaaaac tgactcagag ga                                              22

<210> SEQ ID NO 28
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 28
ttcagttgca gaaacactgt ta                                              22

<210> SEQ ID NO 29
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 29
tcatcatatt caataatacc at                                              22

<210> SEQ ID NO 30
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 30
tgaagttttt gtatcatagt cc                                              22

<210> SEQ ID NO 31
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 31
ttcctcatct gtaaaatggg ct                                              22

<210> SEQ ID NO 32
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 32
taatgattgg ggaacatgtt gc                                              22

<210> SEQ ID NO 33
<211> LENGTH: 22
<212> TYPE: DNA
```

-continued

<213> ORGANISM: Artificial Sequence
<220> FEATURE:
<223> OTHER INFORMATION: A synthetic oligonucleotide sequence

<400> SEQUENCE: 33
tttcttgtca tagacgggct cg                                    22

<210> SEQ ID NO 34
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 34
tcaaaaactc atctttattg gg                                    22

<210> SEQ ID NO 35
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 35
ttatgatccc atttcacagg tt                                    22

<210> SEQ ID NO 36
<211> LENGTH: 22
<212> TYPE: DNA
<213> ORGANISM: Artificial Sequence
<220> FEATURE:
<223> OTHER INFORMATION: A synthetic oligonucleotide sequence

<400> SEQUENCE: 36
tctcaagaga aatccgtgcg ga                                    22

<210> SEQ ID NO 37
<211> LENGTH: 420
<212> TYPE: PRT
<213> ORGANISM: Homo sapiens

<400> SEQUENCE: 37

Met Phe Ser Pro Gly Gln Glu Glu His Cys Ala Pro Asn Lys Glu Pro
1               5                   10                  15

Val Lys Tyr Gly Glu Leu Val Val Leu Gly Tyr Asn Gly Ala Leu Pro
            20                  25                  30

Asn Gly Asp Arg Gly Arg Arg Lys Ser Arg Phe Ala Leu Tyr Lys Arg
        35                  40                  45

Pro Lys Ala Asn Gly Val Lys Pro Ser Thr Val His Val Ile Ser Thr
    50                  55                  60

Pro Gln Ala Ser Lys Ala Ile Ser Cys Lys Gly Gln His Ser Ile Ser
65                  70                  75                  80

Tyr Thr Leu Ser Arg Asn Gln Thr Val Val Glu Tyr Thr His Asp
                85                  90                  95

Lys Asp Thr Asp Met Phe Gln Val Gly Arg Ser Thr Glu Ser Pro Ile
            100                 105                 110

Asp Phe Val Val Thr Asp Thr Ile Ser Gly Ser Gln Asn Thr Asp Glu
        115                 120                 125

Ala Gln Ile Thr Gln Ser Thr Ile Ser Arg Phe Ala Cys Arg Ile Val
    130                 135                 140

```
Cys Asp Arg Asn Glu Pro Tyr Thr Ala Arg Ile Phe Ala Ala Gly Phe
145                 150                 155                 160

Asp Ser Ser Lys Asn Ile Phe Leu Gly Glu Lys Ala Ala Lys Trp Lys
                165                 170                 175

Asn Pro Asp Gly His Met Asp Gly Leu Thr Thr Asn Gly Val Leu Val
            180                 185                 190

Met His Pro Arg Gly Gly Phe Thr Glu Glu Ser Gln Pro Gly Val Trp
        195                 200                 205

Arg Glu Ile Ser Val Cys Gly Asp Val Tyr Thr Leu Arg Glu Thr Arg
    210                 215                 220

Ser Ala Gln Gln Arg Gly Lys Leu Val Glu Ser Glu Thr Asn Val Leu
225                 230                 235                 240

Gln Asp Gly Ser Leu Ile Asp Leu Cys Gly Ala Thr Leu Leu Trp Arg
                245                 250                 255

Thr Ala Asp Gly Leu Phe His Thr Pro Thr Gln Lys His Ile Glu Ala
            260                 265                 270

Leu Arg Gln Glu Ile Asn Ala Ala Arg Pro Gln Cys Pro Val Gly Leu
        275                 280                 285

Asn Thr Leu Ala Phe Pro Ser Ile Asn Arg Lys Glu Val Val Glu Glu
    290                 295                 300

Lys Gln Pro Trp Ala Tyr Leu Ser Cys Gly His Val His Gly Tyr His
305                 310                 315                 320

Asn Trp Gly His Arg Ser Asp Thr Glu Ala Asn Glu Arg Glu Cys Pro
                325                 330                 335

Met Cys Arg Thr Val Gly Pro Tyr Val Pro Leu Trp Leu Gly Cys Glu
            340                 345                 350

Ala Gly Phe Tyr Val Asp Ala Gly Pro Pro Thr His Ala Phe Thr Pro
        355                 360                 365

Cys Gly His Val Cys Ser Glu Lys Ser Ala Lys Tyr Trp Ser Gln Ile
    370                 375                 380

Pro Leu Pro His Gly Thr His Ala Phe His Ala Ala Cys Pro Phe Cys
385                 390                 395                 400

Ala Thr Gln Leu Val Gly Glu Gln Asn Cys Ile Lys Leu Ile Phe Gln
                405                 410                 415

Gly Pro Ile Asp
            420

<210> SEQ ID NO 38
<211> LENGTH: 396
<212> TYPE: PRT
<213> ORGANISM: Homo sapiens

<400> SEQUENCE: 38

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
        50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95
```

```
His Arg Leu Glu Arg Ala Ala Ser Ala Asn Thr Val Arg Ser Phe
            100                 105                 110
His His Glu Glu Ser Leu Glu Leu Pro Glu Thr Ser Gly Lys Thr
        115                 120                 125
Thr Arg Arg Phe Phe Asn Leu Ser Ser Ile Pro Thr Glu Phe
130                 135                 140
Ile Thr Ser Ala Glu Leu Gln Val Phe Arg Glu Gln Met Gln Asp Ala
145                 150                 155                 160
Leu Gly Asn Asn Ser Ser Phe His His Arg Ile Asn Ile Tyr Glu Ile
                165                 170                 175
Ile Lys Pro Ala Thr Ala Asn Ser Lys Phe Pro Val Thr Arg Leu Leu
            180                 185                 190
Asp Thr Arg Leu Val Asn Gln Asn Ala Ser Arg Trp Glu Ser Phe Asp
        195                 200                 205
Val Thr Pro Ala Val Met Arg Trp Thr Ala Gln Gly His Ala Asn His
    210                 215                 220
Gly Phe Val Val Glu Val Ala His Leu Glu Glu Lys Gln Gly Val Ser
225                 230                 235                 240
Lys Arg His Val Arg Ile Ser Arg Ser Leu His Gln Asp Glu His Ser
                245                 250                 255
Trp Ser Gln Ile Arg Pro Leu Leu Val Thr Phe Gly His Asp Gly Lys
            260                 265                 270
Gly His Pro Leu His Lys Arg Glu Lys Arg Gln Ala Lys His Lys Gln
        275                 280                 285
Arg Lys Arg Leu Lys Ser Ser Cys Lys Arg His Pro Leu Tyr Val Asp
    290                 295                 300
Phe Ser Asp Val Gly Trp Asn Asp Trp Ile Val Ala Pro Pro Gly Tyr
305                 310                 315                 320
His Ala Phe Tyr Cys His Gly Glu Cys Pro Phe Pro Leu Ala Asp His
                325                 330                 335
Leu Asn Ser Thr Asn His Ala Ile Val Gln Thr Leu Val Asn Ser Val
            340                 345                 350
Asn Ser Lys Ile Pro Lys Ala Cys Cys Val Pro Thr Glu Leu Ser Ala
        355                 360                 365
Ile Ser Met Leu Tyr Leu Asp Glu Asn Glu Lys Val Val Leu Lys Asn
    370                 375                 380
Tyr Gln Asp Met Val Val Glu Gly Cys Gly Cys Arg
385                 390                 395
```

<210> SEQ ID NO 39
<211> LENGTH: 462
<212> TYPE: PRT
<213> ORGANISM: Homo sapiens

<400> SEQUENCE: 39

```
Met Leu Leu Leu Ala Arg Cys Leu Leu Val Leu Val Ser Ser Leu
1               5                   10                  15
Leu Val Cys Ser Gly Leu Ala Cys Gly Pro Gly Arg Gly Phe Gly Lys
            20                  25                  30
Arg Arg His Pro Lys Lys Leu Thr Pro Leu Ala Tyr Lys Gln Phe Ile
        35                  40                  45
Pro Asn Val Ala Glu Lys Thr Leu Gly Ala Ser Gly Arg Tyr Glu Gly
    50                  55                  60
Lys Ile Ser Arg Asn Ser Glu Arg Phe Lys Glu Leu Thr Pro Asn Tyr
```

```
            65                  70                  75                  80
Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Thr Ala Gly Ile
            420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser
    450                 455                 460

<210> SEQ ID NO 40
<211> LENGTH: 480
<212> TYPE: PRT
<213> ORGANISM: Homo sapiens
```

<400> SEQUENCE: 40

```
Met Gly Ser Lys Ala Ser Ser Pro His Gly Leu Gly Ser Pro Leu Val
1               5                   10                  15

Ala Ser Pro Arg Leu Glu Lys Arg Leu Gly Gly Leu Ala Pro Gln Arg
            20                  25                  30

Gly Ser Arg Ile Ser Val Leu Ser Ala Ser Pro Val Ser Asp Val Ser
        35                  40                  45

Tyr Met Phe Gly Ser Ser Gln Ser Leu Leu His Ser Ser Asn Ser Ser
    50                  55                  60

His Gln Ser Ser Arg Ser Leu Glu Ser Pro Ala Asn Ser Ser Ser
65                  70                  75                  80

Ser Leu His Ser Leu Gly Ser Val Ser Leu Cys Thr Arg Pro Ser Asp
                85                  90                  95

Phe Gln Ala Pro Arg Asn Pro Thr Leu Thr Met Gly Gln Pro Arg Thr
                100                 105                 110

Pro His Ser Pro Pro Leu Ala Lys Glu His Ala Ser Ser Cys Pro Pro
            115                 120                 125

Ser Ile Thr Asn Ser Met Val Asp Ile Pro Ile Val Leu Ile Asn Gly
130                 135                 140

Cys Pro Glu Pro Gly Ser Ser Pro Pro Gln Arg Thr Pro Gly His Gln
145                 150                 155                 160

Asn Ser Val Gln Pro Gly Ala Ala Ser Pro Ser Asn Pro Cys Pro Ala
                165                 170                 175

Thr Arg Ser Asn Ser Gln Thr Leu Ser Asp Ala Pro Phe Thr Thr Cys
            180                 185                 190

Pro Glu Gly Pro Ala Arg Asp Met Gln Pro Thr Met Lys Phe Val Met
        195                 200                 205

Asp Thr Ser Lys Tyr Trp Phe Lys Pro Asn Ile Thr Arg Glu Gln Ala
    210                 215                 220

Ile Glu Leu Leu Arg Lys Glu Pro Gly Ala Phe Val Ile Arg Asp
225                 230                 235                 240

Ser Ser Ser Tyr Arg Gly Ser Phe Gly Leu Ala Leu Lys Val Gln Glu
                245                 250                 255

Val Pro Ala Ser Ala Gln Ser Arg Pro Gly Glu Asp Ser Asn Asp Leu
            260                 265                 270

Ile Arg His Phe Leu Ile Glu Ser Ala Lys Gly Val His Leu Lys
        275                 280                 285

Gly Ala Asp Glu Glu Pro Tyr Phe Gly Ser Leu Ser Ala Phe Val Cys
    290                 295                 300

Gln His Ser Ile Met Ala Leu Ala Leu Pro Cys Lys Leu Thr Ile Pro
305                 310                 315                 320

Gln Arg Glu Leu Gly Gly Ala Asp Gly Ala Ser Asp Ser Thr Asp Ser
                325                 330                 335

Pro Ala Ser Cys Gln Lys Lys Ser Ala Gly Cys His Thr Leu Tyr Leu
            340                 345                 350

Ser Ser Val Ser Val Glu Thr Leu Thr Gly Ala Leu Ala Val Gln Lys
        355                 360                 365

Ala Ile Ser Thr Thr Phe Glu Arg Asp Ile Leu Pro Thr Pro Thr Val
    370                 375                 380

Val His Phe Lys Val Thr Glu Gln Gly Ile Thr Leu Thr Asp Val Gln
385                 390                 395                 400

Arg Lys Val Phe Phe Arg Arg His Tyr Pro Leu Thr Thr Leu Arg Phe
```

```
                405                 410                 415
Cys Gly Met Asp Pro Glu Gln Arg Lys Trp Gln Lys Tyr Cys Lys Pro
            420                 425                 430

Ser Trp Ile Phe Gly Phe Val Ala Lys Ser Gln Thr Glu Pro Gln Glu
            435                 440                 445

Asn Val Cys His Leu Phe Ala Glu Tyr Asp Met Val Gln Pro Ala Ser
        450                 455                 460

Gln Val Ile Gly Leu Val Thr Ala Leu Leu Gln Asp Ala Glu Arg Met
465                 470                 475                 480

<210> SEQ ID NO 41
<211> LENGTH: 219
<212> TYPE: PRT
<213> ORGANISM: Homo sapiens

<400> SEQUENCE: 41

Met Ala Ser Val Thr Asp Gly Lys Thr Gly Val Lys Asp Ala Ser Asp
1               5                   10                  15

Gln Asn Phe Asp Tyr Met Phe Lys Leu Leu Ile Ile Gly Asn Ser Ser
            20                  25                  30

Val Gly Lys Thr Ser Phe Leu Phe Arg Tyr Ala Asp Asp Thr Phe Thr
        35                  40                  45

Pro Ala Phe Val Ser Thr Val Gly Ile Asp Phe Lys Val Lys Thr Val
    50                  55                  60

Tyr Arg His Glu Lys Arg Val Lys Leu Gln Ile Trp Asp Thr Ala Gly
65                  70                  75                  80

Gln Glu Arg Tyr Arg Thr Ile Thr Thr Ala Tyr Tyr Arg Gly Ala Met
                85                  90                  95

Gly Phe Ile Leu Met Tyr Asp Ile Thr Asn Glu Glu Ser Phe Asn Ala
            100                 105                 110

Val Gln Asp Trp Ala Thr Gln Ile Lys Thr Tyr Ser Trp Asp Asn Ala
        115                 120                 125

Gln Val Ile Leu Val Gly Asn Lys Cys Asp Met Glu Glu Glu Arg Val
    130                 135                 140

Val Pro Thr Glu Lys Gly Gln Leu Leu Ala Glu Gln Leu Gly Phe Asp
145                 150                 155                 160

Phe Phe Glu Ala Ser Ala Lys Glu Asn Ile Ser Val Arg Gln Ala Phe
                165                 170                 175

Glu Arg Leu Val Asp Ala Ile Cys Asp Lys Met Ser Asp Ser Leu Asp
            180                 185                 190

Thr Asp Pro Ser Met Leu Gly Ser Ser Lys Asn Thr Arg Leu Ser Asp
        195                 200                 205

Thr Pro Pro Leu Leu Gln Gln Asn Cys Ser Cys
    210                 215

<210> SEQ ID NO 42
<211> LENGTH: 1607
<212> TYPE: PRT
<213> ORGANISM: Homo sapiens

<400> SEQUENCE: 42

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
```

```
                35                  40                  45
Asn Cys Lys Ala Glu Gly Arg Pro Thr Pro Thr Ile Glu Trp Tyr Lys
 50                  55                  60

Gly Gly Glu Arg Val Glu Thr Asp Lys Asp Asp Pro Arg Ser His Arg
 65                  70                  75                  80

Met Leu Leu Pro Ser Gly Ser Leu Phe Phe Leu Arg Ile Val His Gly
                 85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
                115                 120                 125

Leu Arg Asp Asp Phe Arg Gln Asn Pro Ser Asp Val Met Val Ala Val
                130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
                195                 200                 205

Glu Arg Glu Ser Glu Val Ala Glu Leu Thr Val Leu Glu Arg Pro Ser
                210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
                260                 265                 270

Asp His Thr Leu Lys Ile Arg Lys Val Thr Ala Gly Asp Met Gly Ser
                275                 280                 285

Tyr Thr Cys Val Ala Glu Asn Met Val Gly Lys Ala Glu Ala Ser Ala
                290                 295                 300

Thr Leu Thr Val Gln Val Gly Ser Glu Pro Pro His Phe Val Val Lys
305                 310                 315                 320

Pro Arg Asp Gln Val Val Ala Leu Gly Arg Thr Val Thr Phe Gln Cys
                325                 330                 335

Glu Ala Thr Gly Asn Pro Gln Pro Ala Ile Phe Trp Arg Arg Glu Gly
                340                 345                 350

Ser Gln Asn Leu Leu Phe Ser Tyr Gln Pro Pro Gln Ser Ser Ser Arg
                355                 360                 365

Phe Ser Val Ser Gln Thr Gly Asp Leu Thr Ile Thr Asn Val Gln Arg
                370                 375                 380

Ser Asp Val Gly Tyr Tyr Ile Cys Gln Thr Leu Asn Val Ala Gly Ser
385                 390                 395                 400

Ile Ile Thr Lys Ala Tyr Leu Glu Val Thr Asp Val Ile Ala Asp Arg
                405                 410                 415

Pro Pro Pro Val Ile Arg Gln Gly Pro Val Asn Gln Thr Val Ala Val
                420                 425                 430

Asp Gly Thr Phe Val Leu Ser Cys Val Ala Thr Gly Ser Pro Val Pro
                435                 440                 445

Thr Ile Leu Trp Arg Lys Asp Gly Val Leu Val Ser Thr Gln Asp Ser
450                 455                 460
```

```
                     -continued

Arg Ile Lys Gln Leu Glu Asn Gly Val Leu Gln Ile Arg Tyr Ala Lys
465                 470                 475                 480

Leu Gly Asp Thr Gly Arg Tyr Thr Cys Ile Ala Ser Thr Pro Ser Gly
            485                 490                 495

Glu Ala Thr Trp Ser Ala Tyr Ile Glu Val Gln Glu Phe Gly Val Pro
                500                 505                 510

Val Gln Pro Pro Arg Pro Thr Asp Pro Asn Leu Ile Pro Ser Ala Pro
            515                 520                 525

Ser Lys Pro Glu Val Thr Asp Val Ser Arg Asn Thr Val Thr Leu Ser
530                 535                 540

Trp Gln Pro Asn Leu Asn Ser Gly Ala Thr Pro Thr Ser Tyr Ile Ile
545                 550                 555                 560

Glu Ala Phe Ser His Ala Ser Gly Ser Ser Trp Gln Thr Val Ala Glu
                565                 570                 575

Asn Val Lys Thr Glu Thr Ser Ala Ile Lys Gly Leu Lys Pro Asn Ala
            580                 585                 590

Ile Tyr Leu Phe Leu Val Arg Ala Ala Asn Ala Tyr Gly Ile Ser Asp
        595                 600                 605

Pro Ser Gln Ile Ser Asp Pro Val Lys Thr Gln Asp Val Leu Pro Thr
    610                 615                 620

Ser Gln Gly Val Asp His Lys Gln Val Gln Arg Glu Leu Gly Asn Ala
625                 630                 635                 640

Val Leu His Leu His Asn Pro Thr Val Leu Ser Ser Ser Ile Glu
                645                 650                 655

Val His Trp Thr Val Asp Gln Gln Ser Gln Tyr Ile Gln Gly Tyr Lys
            660                 665                 670

Ile Leu Tyr Arg Pro Ser Gly Ala Asn His Gly Glu Ser Asp Trp Leu
        675                 680                 685

Val Phe Glu Val Arg Thr Pro Ala Lys Asn Ser Val Val Ile Pro Asp
    690                 695                 700

Leu Arg Lys Gly Val Asn Tyr Glu Ile Lys Ala Arg Pro Phe Phe Asn
705                 710                 715                 720

Glu Phe Gln Gly Ala Asp Ser Glu Ile Lys Phe Ala Lys Thr Leu Glu
                725                 730                 735

Glu Ala Pro Ser Ala Pro Pro Gln Gly Val Thr Val Ser Lys Asn Asp
            740                 745                 750

Gly Asn Gly Thr Ala Ile Leu Val Ser Trp Gln Pro Pro Glu Asp
        755                 760                 765

Thr Gln Asn Gly Met Val Gln Glu Tyr Lys Val Trp Cys Leu Gly Asn
    770                 775                 780

Glu Thr Arg Tyr His Ile Asn Lys Thr Val Asp Gly Ser Thr Phe Ser
785                 790                 795                 800

Val Val Ile Pro Phe Leu Val Pro Gly Ile Arg Tyr Ser Val Glu Val
                805                 810                 815

Ala Ala Ser Thr Gly Ala Gly Ser Gly Val Lys Ser Glu Pro Gln Phe
            820                 825                 830

Ile Gln Leu Asp Ala His Gly Asn Pro Val Ser Pro Glu Asp Gln Val
        835                 840                 845

Ser Leu Ala Gln Gln Ile Ser Asp Val Val Lys Gln Pro Ala Phe Ile
    850                 855                 860

Ala Gly Ile Gly Ala Ala Cys Trp Ile Ile Leu Met Val Phe Ser Ile
865                 870                 875                 880
```

-continued

Trp Leu Tyr Arg His Arg Lys Lys Arg Asn Gly Leu Thr Ser Thr Tyr
                885             890                 895

Ala Gly Ile Arg Lys Val Thr Tyr Gln Arg Gly Gly Glu Ala Val Ser
            900             905                 910

Ser Gly Gly Arg Pro Gly Leu Leu Asn Ile Ser Glu Pro Ala Ala Gln
            915                 920             925

Pro Trp Leu Ala Asp Thr Trp Pro Asn Thr Gly Asn Asn His Asn Asp
930             935                 940

Cys Ser Ile Ser Cys Cys Thr Ala Gly Asn Gly Asn Ser Asp Ser Asn
945             950                 955                 960

Leu Thr Thr Tyr Ser Arg Pro Ala Asp Cys Ile Ala Asn Tyr Asn Asn
                965                 970                 975

Gln Leu Asp Asn Lys Gln Thr Asn Leu Met Leu Pro Glu Ser Thr Val
            980                 985                 990

Tyr Gly Asp Val Asp Leu Ser Asn Lys Ile Asn Glu Met Lys Thr Phe
            995                 1000                1005

Asn Ser Pro Asn Leu Lys Asp Gly Arg Phe Val Asn Pro Ser Gly Gln
        1010                1015                1020

Pro Thr Pro Tyr Ala Thr Thr Gln Leu Ile Gln Ser Asn Leu Ser Asn
1025                1030                1035                1040

Asn Met Asn Asn Gly Ser Gly Asp Ser Gly Glu Lys His Trp Lys Pro
                1045                1050                1055

Leu Gly Gln Gln Lys Gln Glu Val Ala Pro Val Gln Tyr Asn Ile Val
                1060                1065                1070

Glu Gln Asn Lys Leu Asn Lys Asp Tyr Arg Ala Asn Asp Thr Val Pro
                1075                1080                1085

Pro Thr Ile Pro Tyr Asn Gln Ser Tyr Asp Gln Asn Thr Gly Gly Ser
            1090                1095                1100

Tyr Asn Ser Ser Asp Arg Gly Ser Ser Thr Ser Gly Ser Gln Gly His
1105                1110                1115                1120

Lys Lys Gly Gly Ala Arg Thr Pro Lys Val Pro Lys Gln Gly Gly Met
                1125                1130                1135

Asn Trp Ala Asp Leu Leu Pro Pro Pro Pro Ala His Pro Pro Pro His
                1140                1145                1150

Ser Asn Ser Glu Glu Tyr Asn Ile Ser Val Asp Glu Ser Tyr Asp Gln
                1155                1160                1165

Glu Met Pro Cys Pro Val Pro Pro Ala Arg Met Tyr Leu Gln Gln Asp
            1170                1175                1180

Glu Leu Glu Glu Glu Asp Glu Arg Gly Pro Thr Pro Pro Val Arg
1185                1190                1195                1200

Gly Ala Ala Ser Ser Pro Ala Ala Val Ser Tyr Ser His Gln Ser Thr
                1205                1210                1215

Ala Thr Leu Thr Pro Ser Pro Gln Glu Glu Leu Gln Pro Met Leu Gln
                1220                1225                1230

Asp Cys Pro Glu Glu Thr Gly His Met Gln His Gln Pro Asp Arg Arg
            1235                1240                1245

Arg Gln Pro Val Ser Pro Pro Pro Pro Arg Pro Ile Ser Pro Pro
        1250                1255                1260

His Thr Tyr Gly Tyr Ile Ser Gly Pro Leu Val Ser Asp Met Asp Thr
1265                1270                1275                1280

Asp Ala Pro Glu Glu Glu Asp Glu Ala Asp Met Glu Val Ala Lys
            1285                1290                1295

Met Gln Thr Arg Arg Leu Leu Leu Arg Gly Leu Glu Gln Thr Pro Ala 1300                1305                1310
         Ser Ser Val Gly Asp Leu Glu Ser Ser Val Thr Gly Ser Met Ile Asn
                     1315                1320                1325

Gly Trp Gly Ser Ala Ser Glu Glu Asp Asn Ile Ser Ser Gly Arg Ser
                     1330                1335                1340

Ser Val Ser Ser Ser Asp Gly Ser Phe Phe Thr Asp Ala Asp Phe Ala
         1345                1350                1355                1360

Gln Ala Val Ala Ala Ala Ala Glu Tyr Ala Gly Leu Lys Val Ala Arg
                     1365                1370                1375

Arg Gln Met Gln Asp Ala Ala Gly Arg Arg His Phe His Ala Ser Gln
                     1380                1385                1390

Cys Pro Arg Pro Thr Ser Pro Val Ser Thr Asp Ser Asn Met Ser Ala
                     1395                1400                1405

Ala Val Met Gln Lys Thr Arg Pro Ala Lys Lys Leu Lys His Gln Pro
                     1410                1415                1420

Gly His Leu Arg Arg Glu Thr Tyr Thr Asp Asp Leu Pro Pro Pro Pro
         1425                1430                1435                1440

Val Pro Pro Pro Ala Ile Lys Ser Pro Thr Ala Gln Ser Lys Thr Gln
                     1445                1450                1455

Leu Glu Val Arg Pro Val Val Pro Lys Leu Pro Ser Met Asp Ala
                     1460                1465                1470

Arg Thr Asp Arg Ser Ser Asp Arg Lys Gly Ser Ser Tyr Lys Gly Arg
                     1475                1480                1485

Glu Val Leu Asp Gly Arg Gln Val Val Asp Met Arg Thr Asn Pro Gly
                     1490                1495                1500

Asp Pro Arg Glu Ala Gln Gln Gln Asn Asp Gly Lys Gly Arg Gly
         1505                1510                1515                1520

Asn Lys Ala Ala Lys Arg Asp Leu Pro Pro Ala Lys Thr His Leu Ile
                     1525                1530                1535

Gln Glu Asp Ile Leu Pro Tyr Cys Arg Pro Thr Phe Pro Thr Ser Asn
                     1540                1545                1550

Asn Pro Arg Asp Pro Ser Ser Ser Ser Met Ser Ser Arg Gly Ser
                     1555                1560                1565

Gly Ser Arg Gln Arg Glu Gln Ala Asn Val Gly Arg Arg Asn Ile Ala
                     1570                1575                1580

Glu Met Gln Val Leu Gly Gly Tyr Glu Arg Gly Glu Asp Asn Asn Glu
         1585                1590                1595                1600

Glu Leu Glu Glu Thr Glu Ser
                     1605

<210> SEQ ID NO 43
<211> LENGTH: 545
<212> TYPE: PRT
<213> ORGANISM: Homo sapiens

<400> SEQUENCE: 43

Met Asn Glu Leu Pro Arg Asp Thr Cys Gly Asn His Thr Asn Gln Leu
1               5                   10                  15

Asp Gly Thr Lys Glu Glu Arg Glu Leu Pro Arg Val Ile Lys Thr Ser
            20                  25                  30

Gly Ser Met Pro Asp Asp Ala Ser Leu Asn Ser Thr Thr Leu Ser Asp
        35                  40                  45

Ala Ser Gln Asp Lys Glu Gly Ser Phe Ala Val Pro Arg Ser Asp Ser
    50                  55                  60

```
Val Ala Ile Leu Glu Thr Ile Pro Val Leu Pro Val His Ser Asn Gly
 65                  70                  75                  80

Ser Pro Glu Pro Gly Gln Pro Val Gln Asn Ala Ile Ser Asp Asp Asp
                 85                  90                  95

Phe Leu Glu Lys Asn Ile Pro Pro Glu Ala Glu Leu Ser Phe Glu
            100                 105                 110

Val Ser Tyr Ser Glu Met Val Thr Glu Ala Leu Lys Arg Asn Lys Leu
            115                 120                 125

Lys Lys Ser Glu Ile Lys Lys Glu Asp Tyr Val Leu Thr Lys Phe Asn
        130                 135                 140

Val Gln Lys Thr Arg Phe Gly Leu Thr Glu Ala Gly Asp Leu Ser Ala
145                 150                 155                 160

Glu Asp Met Lys Lys Ile Arg His Leu Ser Leu Ile Glu Leu Thr Ala
                165                 170                 175

Phe Phe Asp Ala Phe Gly Ile Gln Leu Lys Arg Asn Lys Thr Glu Lys
            180                 185                 190

Val Lys Gly Arg Asp Asn Gly Ile Phe Gly Val Pro Leu Thr Val Leu
        195                 200                 205

Leu Asp Gly Asp Arg Lys Lys Asp Pro Gly Val Lys Val Pro Leu Val
210                 215                 220

Leu Gln Lys Phe Phe Glu Lys Val Glu Glu Ser Gly Leu Glu Ser Glu
225                 230                 235                 240

Gly Ile Phe Arg Leu Ser Gly Cys Thr Ala Lys Val Lys Gln Tyr Arg
                245                 250                 255

Glu Glu Leu Asp Ala Lys Phe Asn Ala Asp Lys Phe Lys Trp Asp Lys
            260                 265                 270

Met Cys His Arg Glu Ala Ala Val Met Leu Lys Ala Phe Phe Arg Glu
        275                 280                 285

Leu Pro Thr Ser Leu Phe Pro Val Glu Tyr Ile Pro Ala Phe Ile Ser
290                 295                 300

Leu Met Glu Arg Gly Pro His Val Lys Val Gln Phe Gln Ala Leu His
305                 310                 315                 320

Leu Met Val Met Ala Leu Pro Asp Ala Asn Arg Asp Ala Ala Gln Ala
                325                 330                 335

Leu Met Thr Phe Phe Asn Lys Val Ile Ala Asn Glu Ser Lys Asn Arg
            340                 345                 350

Met Ser Leu Trp Asn Ile Ser Thr Val Met Ala Pro Asn Leu Phe Phe
        355                 360                 365

Ser Arg Ser Lys His Ser Asp Tyr Glu Glu Leu Leu Leu Ala Asn Thr
        370                 375                 380

Ala Ala His Ile Ile Arg Leu Met Leu Lys Tyr Gln Lys Ile Leu Trp
385                 390                 395                 400

Lys Val Pro Ser Phe Leu Ile Thr Gln Val Arg Arg Met Asn Glu Ala
                405                 410                 415

Thr Met Leu Leu Lys Lys Gln Leu Pro Ser Val Arg Lys Leu Leu Arg
            420                 425                 430

Arg Lys Thr Leu Glu Arg Glu Thr Ala Ser Pro Lys Thr Ser Lys Val
        435                 440                 445

Leu Gln Lys Ser Pro Ser Ala Arg Arg Met Ser Asp Val Pro Glu Gly
        450                 455                 460

Val Ile Arg Val His Ala Pro Leu Leu Ser Lys Val Ser Met Ala Ile
465                 470                 475                 480

Gln Leu Asn Asn Gln Thr Lys Ala Lys Asp Ile Leu Ala Lys Phe Gln
```

```
                    485                 490                 495
Tyr Glu Asn Arg Ile Leu His Trp Gln Arg Ala Ala Leu Ser Phe Leu
            500                 505                 510

Asn Gly Lys Trp Val Lys Glu Arg Glu Ser Thr Glu Thr Asn
            515                 520                 525

Arg Ser Pro Lys His Val Phe Leu Phe Thr Ile Gly Leu Asp Ile Ser
            530                 535                 540

Thr
545

<210> SEQ ID NO 44
<211> LENGTH: 468
<212> TYPE: PRT
<213> ORGANISM: Homo sapiens

<400> SEQUENCE: 44

Met Ala Ala Ser Ser Asn Ser Ser Leu Ser Gly Ser Ser Val Ser Ser
1               5                   10                  15

Asp Ala Glu Glu Tyr Gln Pro Pro Ile Trp Lys Ser Tyr Leu Tyr Gln
            20                  25                  30

Leu Gln Gln Glu Ala Pro Arg Pro Lys Arg Ile Ile Cys Pro Arg Glu
        35                  40                  45

Val Glu Asn Arg Pro Lys Tyr Tyr Gly Arg Glu Phe His Gly Ile Ile
    50                  55                  60

Ser Arg Glu Gln Ala Asp Glu Leu Leu Gly Val Glu Gly Ala Tyr
65                  70                  75                  80

Ile Leu Arg Glu Ser Gln Arg Gln Pro Gly Cys Tyr Thr Leu Ala Leu
                85                  90                  95

Arg Phe Gly Asn Gln Thr Leu Asn Tyr Arg Leu Phe His Asp Gly Lys
            100                 105                 110

His Phe Val Gly Glu Lys Arg Phe Glu Ser Ile His Asp Leu Val Thr
        115                 120                 125

Asp Gly Leu Ile Thr Leu Tyr Ile Glu Thr Lys Ala Ala Glu Tyr Ile
    130                 135                 140

Ser Lys Met Thr Thr Asn Pro Ile Tyr Glu His Ile Gly Tyr Ala Thr
145                 150                 155                 160

Leu Leu Arg Glu Lys Val Ser Arg Arg Leu Ser Arg Ser Lys Asn Glu
                165                 170                 175

Pro Arg Lys Thr Asn Val Thr His Glu Glu His Thr Ala Val Glu Lys
            180                 185                 190

Ile Ser Ser Leu Val Arg Arg Ala Ala Leu Thr His Asn Asp Asn His
        195                 200                 205

Phe Asn Tyr Glu Lys Thr His Asn Phe Lys Val His Thr Phe Arg Gly
    210                 215                 220

Pro His Trp Cys Glu Tyr Cys Ala Asn Phe Met Trp Gly Leu Ile Ala
225                 230                 235                 240

Gln Gly Val Arg Cys Ser Asp Cys Gly Leu Asn Val His Lys Gln Cys
                245                 250                 255

Ser Lys His Val Pro Asn Asp Cys Gln Pro Asp Leu Lys Arg Ile Lys
            260                 265                 270

Lys Val Tyr Cys Cys Asp Leu Thr Thr Leu Val Lys Ala His Asn Thr
        275                 280                 285

Gln Arg Pro Met Val Val Asp Ile Cys Ile Arg Glu Ile Glu Ala Arg
    290                 295                 300
```

```
Gly Leu Lys Ser Glu Gly Leu Tyr Arg Val Ser Gly Phe Thr Glu His
305                 310                 315                 320

Ile Glu Asp Val Lys Met Ala Phe Asp Arg Asp Gly Glu Lys Ala Asp
                325                 330                 335

Ile Ser Ala Asn Val Tyr Pro Asp Ile Asn Ile Ile Thr Gly Ala Leu
                340                 345                 350

Lys Leu Tyr Phe Arg Asp Leu Pro Ile Pro Val Ile Thr Tyr Asp Thr
            355                 360                 365

Tyr Ser Lys Phe Ile Asp Ala Ala Lys Ile Ser Asn Ala Asp Glu Arg
        370                 375                 380

Leu Glu Ala Val His Glu Val Leu Met Leu Pro Pro Ala His Tyr
385                 390                 395                 400

Glu Thr Leu Arg Tyr Leu Met Ile His Leu Lys Lys Val Thr Met Asn
                405                 410                 415

Glu Lys Asp Asn Phe Met Asn Ala Glu Asn Leu Gly Ile Val Phe Gly
                420                 425                 430

Pro Thr Leu Met Arg Pro Pro Glu Asp Ser Thr Leu Thr Leu His
                435                 440                 445

Asp Met Arg Tyr Gln Lys Leu Ile Val Gln Ile Leu Ile Glu Asn Glu
450                 455                 460

Asp Val Leu Phe
465

<210> SEQ ID NO 45
<211> LENGTH: 141
<212> TYPE: PRT
<213> ORGANISM: Homo sapiens

<400> SEQUENCE: 45

Met Ala Gln Tyr Leu Ser Thr Leu Leu Leu Leu Ala Thr Leu Ala
1               5                   10                  15

Val Ala Leu Ala Trp Ser Pro Lys Glu Glu Asp Arg Ile Ile Pro Gly
                20                  25                  30

Gly Ile Tyr Asn Ala Asp Leu Asn Asp Glu Trp Val Gln Arg Ala Leu
            35                  40                  45

His Phe Ala Ile Ser Glu Tyr Asn Lys Ala Thr Lys Asp Asp Tyr Tyr
        50                  55                  60

Arg Arg Pro Leu Arg Val Leu Arg Ala Arg Gln Gln Thr Val Gly Gly
65                  70                  75                  80

Val Asn Tyr Phe Phe Asp Val Glu Val Gly Arg Thr Ile Cys Thr Lys
                85                  90                  95

Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
            115                 120                 125

Asn Arg Arg Ser Leu Val Lys Ser Arg Cys Gln Glu Ser
        130                 135                 140

<210> SEQ ID NO 46
<211> LENGTH: 732
<212> TYPE: PRT
<213> ORGANISM: Homo sapiens

<400> SEQUENCE: 46

Met Ser Glu Thr Ser Arg Thr Ala Phe Gly Gly Arg Arg Ala Val Pro
1               5                   10                  15
```

```
Pro Asn Asn Ser Asn Ala Ala Glu Asp Asp Leu Pro Thr Val Glu Leu
                20                  25                  30
Gln Gly Val Val Pro Arg Gly Val Asn Leu Gln Glu Phe Leu Asn Val
            35                  40                  45
Thr Ser Val His Leu Phe Lys Glu Arg Trp Asp Thr Asn Lys Val Asp
    50                  55                  60
His His Thr Asp Lys Tyr Glu Asn Asn Lys Leu Ile Val Arg Arg Gly
65                  70                  75                  80
Gln Ser Phe Tyr Val Gln Ile Asp Phe Ser Arg Pro Tyr Asp Pro Arg
                85                  90                  95
Arg Asp Leu Phe Arg Val Glu Tyr Val Ile Gly Arg Tyr Pro Gln Glu
            100                 105                 110
Asn Lys Gly Thr Tyr Ile Pro Val Pro Ile Val Ser Glu Leu Gln Ser
        115                 120                 125
Gly Lys Trp Gly Ala Lys Ile Val Met Arg Glu Asp Arg Ser Val Arg
    130                 135                 140
Leu Ser Ile Gln Ser Ser Pro Lys Cys Ile Val Gly Lys Phe Arg Met
145                 150                 155                 160
Tyr Val Ala Val Trp Thr Pro Tyr Gly Val Leu Arg Thr Ser Arg Asn
                165                 170                 175
Pro Glu Thr Asp Thr Tyr Ile Leu Phe Asn Pro Trp Cys Glu Asp Asp
            180                 185                 190
Ala Val Tyr Leu Asp Asn Glu Lys Glu Arg Glu Glu Tyr Val Leu Asn
        195                 200                 205
Asp Ile Gly Val Ile Phe Tyr Gly Glu Val Asn Asp Ile Lys Thr Arg
    210                 215                 220
Ser Trp Ser Tyr Gly Gln Phe Glu Asp Gly Ile Leu Asp Thr Cys Leu
225                 230                 235                 240
Tyr Val Met Asp Arg Ala Gln Met Asp Leu Ser Gly Arg Gly Asn Pro
                245                 250                 255
Ile Lys Val Ser Arg Val Gly Ser Ala Met Val Asn Ala Lys Asp Asp
            260                 265                 270
Glu Gly Val Leu Val Gly Ser Trp Asp Asn Ile Tyr Ala Tyr Gly Val
        275                 280                 285
Pro Pro Ser Ala Trp Thr Gly Ser Val Asp Ile Leu Leu Glu Tyr Arg
    290                 295                 300
Ser Ser Glu Asn Pro Val Arg Tyr Gly Gln Cys Trp Val Phe Ala Gly
305                 310                 315                 320
Val Phe Asn Thr Phe Leu Arg Cys Leu Gly Ile Pro Ala Arg Ile Val
                325                 330                 335
Thr Asn Tyr Phe Ser Ala His Asp Asn Asp Ala Asn Leu Gln Met Asp
            340                 345                 350
Ile Phe Leu Glu Glu Asp Gly Asn Val Asn Ser Lys Leu Thr Lys Asp
        355                 360                 365
Ser Val Trp Asn Tyr His Cys Trp Asn Glu Ala Trp Met Thr Arg Pro
    370                 375                 380
Asp Leu Pro Val Gly Phe Gly Gly Trp Gln Ala Val Asp Ser Thr Pro
385                 390                 395                 400
Gln Glu Asn Ser Asp Gly Met Tyr Arg Cys Gly Pro Ala Ser Val Gln
                405                 410                 415
Ala Ile Lys His Gly His Val Cys Phe Gln Phe Asp Ala Pro Phe Val
            420                 425                 430
Phe Ala Glu Val Asn Ser Asp Leu Ile Tyr Ile Thr Ala Lys Lys Asp
```

435                 440                 445
Gly Thr His Val Val Glu Asn Val Asp Ala Thr His Ile Gly Lys Leu
            450                 455                 460

Ile Val Thr Lys Gln Ile Gly Gly Asp Gly Met Met Asp Ile Thr Asp
465                 470                 475                 480

Thr Tyr Lys Phe Gln Glu Gly Gln Glu Glu Arg Leu Ala Leu Glu
                    485                 490                 495

Thr Ala Leu Met Tyr Gly Ala Lys Lys Pro Leu Asn Thr Glu Gly Val
            500                 505                 510

Met Lys Ser Arg Ser Asn Val Asp Met Asp Phe Glu Val Glu Asn Ala
            515                 520                 525

Val Leu Gly Lys Asp Phe Lys Leu Ser Ile Thr Phe Arg Asn Asn Ser
            530                 535                 540

His Asn Arg Tyr Thr Ile Thr Ala Tyr Leu Ser Ala Asn Ile Thr Phe
545                 550                 555                 560

Tyr Thr Gly Val Pro Lys Ala Glu Phe Lys Lys Glu Thr Phe Asp Val
                    565                 570                 575

Thr Leu Glu Pro Leu Ser Phe Lys Lys Glu Ala Val Leu Ile Gln Ala
            580                 585                 590

Gly Glu Tyr Met Gly Gln Leu Leu Glu Gln Ala Ser Leu His Phe Phe
            595                 600                 605

Val Thr Ala Arg Ile Asn Glu Thr Arg Asp Val Leu Ala Lys Gln Lys
            610                 615                 620

Ser Thr Val Leu Thr Ile Pro Glu Ile Ile Lys Val Arg Gly Thr
625                 630                 635                 640

Gln Val Val Gly Ser Asp Met Thr Val Thr Val Glu Phe Thr Asn Pro
                    645                 650                 655

Leu Lys Glu Thr Leu Arg Asn Val Trp Val His Leu Asp Gly Pro Gly
            660                 665                 670

Val Thr Arg Pro Met Lys Lys Met Phe Arg Glu Ile Arg Pro Asn Ser
            675                 680                 685

Thr Val Gln Trp Glu Glu Val Cys Arg Pro Trp Val Ser Gly His Arg
            690                 695                 700

Lys Leu Ile Ala Ser Met Ser Ser Asp Ser Leu Arg His Val Tyr Gly
705                 710                 715                 720

Glu Leu Asp Val Gln Ile Gln Arg Arg Pro Ser Met
                    725                 730

<210> SEQ ID NO 47
<211> LENGTH: 476
<212> TYPE: PRT
<213> ORGANISM: Homo sapiens

<400> SEQUENCE: 47

Met Val Gly Ala Met Trp Lys Val Ile Val Ser Leu Val Leu Leu Met
1                   5                   10                  15

Pro Gly Pro Cys Asp Gly Leu Phe Arg Ser Leu Tyr Arg Ser Val Ser
                    20                  25                  30

Met Pro Pro Lys Gly Asp Ser Gly Gln Pro Leu Phe Leu Thr Pro Tyr
            35                  40                  45

Ile Glu Ala Gly Lys Ile Gln Lys Gly Arg Glu Leu Ser Leu Val Gly
            50                  55                  60

Pro Phe Pro Gly Leu Asn Met Lys Ser Tyr Ala Gly Phe Leu Thr Val
65                  70                  75                  80

Asn Lys Thr Tyr Asn Ser Asn Leu Phe Phe Trp Phe Pro Ala Gln
            85                  90                  95
Ile Gln Pro Glu Asp Ala Pro Val Val Leu Trp Leu Gln Gly Gly Pro
    100                 105                 110
Gly Gly Ser Ser Met Phe Gly Leu Phe Val Glu His Gly Pro Tyr Val
        115                 120                 125
Val Thr Ser Asn Met Thr Leu Arg Asp Arg Asp Phe Pro Trp Thr Thr
130                 135                 140
Thr Leu Ser Met Leu Tyr Ile Asp Asn Pro Val Gly Thr Gly Phe Ser
145                 150                 155                 160
Phe Thr Asp Asp Thr His Gly Tyr Ala Val Asn Glu Asp Asp Val Ala
                165                 170                 175
Arg Asp Leu Tyr Ser Ala Leu Ile Gln Phe Phe Gln Ile Phe Pro Glu
            180                 185                 190
Tyr Lys Asn Asn Asp Phe Tyr Val Thr Gly Glu Ser Tyr Ala Gly Lys
        195                 200                 205
Tyr Val Pro Ala Ile Ala His Leu Ile His Ser Leu Asn Pro Val Arg
    210                 215                 220
Glu Val Lys Ile Asn Leu Asn Gly Ile Ala Ile Gly Asp Gly Tyr Ser
225                 230                 235                 240
Asp Pro Glu Ser Ile Ile Gly Gly Tyr Ala Glu Phe Leu Tyr Gln Ile
                245                 250                 255
Gly Leu Leu Asp Glu Lys Gln Lys Lys Tyr Phe Gln Lys Gln Cys His
            260                 265                 270
Glu Cys Ile Glu His Ile Arg Lys Gln Asn Trp Phe Glu Ala Phe Glu
        275                 280                 285
Ile Leu Asp Lys Leu Leu Asp Gly Asp Leu Thr Ser Asp Pro Ser Tyr
    290                 295                 300
Phe Gln Asn Val Thr Gly Cys Ser Asn Tyr Tyr Asn Phe Leu Arg Cys
305                 310                 315                 320
Thr Glu Pro Glu Asp Gln Leu Tyr Tyr Val Lys Phe Leu Ser Leu Pro
                325                 330                 335
Glu Val Arg Gln Ala Ile His Val Gly Asn Gln Thr Phe Asn Asp Gly
            340                 345                 350
Thr Ile Val Glu Lys Tyr Leu Arg Glu Asp Thr Val Gln Ser Val Lys
        355                 360                 365
Pro Trp Leu Thr Glu Ile Met Asn Asn Tyr Lys Val Leu Ile Tyr Asn
    370                 375                 380
Gly Gln Leu Asp Ile Ile Val Ala Ala Ala Leu Thr Glu Arg Ser Leu
385                 390                 395                 400
Met Gly Met Asp Trp Lys Gly Ser Gln Glu Tyr Lys Lys Ala Glu Lys
                405                 410                 415
Lys Val Trp Lys Ile Phe Lys Ser Asp Ser Glu Val Ala Gly Tyr Ile
            420                 425                 430
Arg Gln Ala Gly Asp Phe His Gln Val Ile Ile Arg Gly Gly His His
        435                 440                 445
Ile Leu Pro Tyr Asp Gln Pro Leu Arg Ala Phe Asp Met Ile Asn Arg
    450                 455                 460
Phe Ile Tyr Gly Lys Gly Trp Asp Pro Tyr Val Gly
465                 470                 475

<210> SEQ ID NO 48
<211> LENGTH: 1011
<212> TYPE: PRT

<213> ORGANISM: Homo sapiens

<400> SEQUENCE: 48

```
Met Arg Val Phe Leu Cys Ala Tyr Ile Leu Leu Leu Met Val Ser
1               5                   10                  15

Gln Leu Arg Ala Val Ser Phe Pro Glu Asp Asp Glu Pro Leu Asn Thr
            20                  25                  30

Val Asp Tyr His Tyr Ser Arg Gln Tyr Pro Val Phe Arg Gly Arg Pro
            35                  40                  45

Ser Gly Asn Glu Ser Gln His Arg Leu Asp Phe Gln Leu Met Leu Lys
        50                  55                  60

Ile Arg Asp Thr Leu Tyr Ile Ala Gly Arg Asp Gln Val Tyr Thr Val
65                  70                  75                  80

Asn Leu Asn Glu Met Pro Lys Thr Glu Val Ile Pro Asn Lys Lys Leu
                85                  90                  95

Thr Trp Arg Ser Arg Gln Gln Asp Arg Glu Asn Cys Ala Met Lys Gly
            100                 105                 110

Lys His Lys Asp Glu Cys His Asn Phe Ile Lys Val Phe Val Pro Arg
        115                 120                 125

Asn Asp Glu Met Val Phe Val Cys Gly Thr Asn Ala Phe Asn Pro Met
130                 135                 140

Cys Arg Tyr Tyr Arg Leu Ser Thr Leu Glu Tyr Asp Gly Glu Glu Ile
145                 150                 155                 160

Ser Gly Leu Ala Arg Cys Pro Phe Asp Ala Arg Gln Thr Asn Val Ala
                165                 170                 175

Leu Phe Ala Asp Gly Lys Leu Tyr Ser Ala Thr Val Ala Asp Phe Leu
            180                 185                 190

Ala Ser Asp Ala Val Ile Tyr Arg Ser Met Gly Asp Gly Ser Ala Leu
        195                 200                 205

Arg Thr Ile Lys Tyr Asp Ser Lys Trp Ile Lys Glu Pro His Phe Leu
210                 215                 220

His Ala Ile Glu Tyr Gly Asn Tyr Val Tyr Phe Phe Phe Arg Glu Ile
225                 230                 235                 240

Ala Val Glu His Asn Asn Leu Gly Lys Ala Val Tyr Ser Arg Val Ala
                245                 250                 255

Arg Ile Cys Lys Asn Asp Met Gly Gly Ser Gln Arg Val Leu Glu Lys
            260                 265                 270

His Trp Thr Ser Phe Leu Lys Ala Arg Leu Asn Cys Ser Val Pro Gly
        275                 280                 285

Asp Ser Phe Phe Tyr Phe Asp Val Leu Gln Ser Ile Thr Asp Ile Ile
290                 295                 300

Gln Ile Asn Gly Ile Pro Thr Val Val Gly Val Phe Thr Thr Gln Leu
305                 310                 315                 320

Asn Ser Ile Pro Gly Ser Ala Val Cys Ala Phe Ser Met Asp Asp Ile
                325                 330                 335

Glu Lys Val Phe Lys Gly Arg Phe Lys Glu Gln Lys Thr Pro Asp Ser
            340                 345                 350

Val Trp Thr Ala Val Pro Glu Asp Lys Val Pro Lys Pro Arg Pro Gly
        355                 360                 365

Cys Cys Ala Lys His Gly Leu Ala Glu Ala Tyr Lys Thr Ser Ile Asp
370                 375                 380

Phe Pro Asp Glu Thr Leu Ser Phe Ile Lys Ser His Pro Leu Met Asp
385                 390                 395                 400
```

```
Ser Ala Val Pro Pro Ile Ala Asp Glu Pro Trp Phe Thr Lys Thr Arg
                405                 410                 415
Val Arg Tyr Arg Leu Thr Ala Ile Ser Val Asp His Ser Ala Gly Pro
            420                 425                 430
Tyr Gln Asn Tyr Thr Val Ile Phe Val Gly Ser Glu Ala Gly Met Val
        435                 440                 445
Leu Lys Val Leu Ala Lys Thr Ser Pro Phe Ser Leu Asn Asp Ser Val
    450                 455                 460
Leu Leu Glu Glu Ile Glu Ala Tyr Asn His Ala Lys Cys Ser Ala Glu
465                 470                 475                 480
Asn Glu Glu Asp Lys Lys Val Ile Ser Leu Gln Leu Asp Lys Asp His
                485                 490                 495
His Ala Leu Tyr Val Ala Phe Ser Ser Cys Ile Ile Arg Ile Pro Leu
            500                 505                 510
Ser Arg Cys Glu Arg Tyr Gly Ser Cys Lys Lys Ser Cys Ile Ala Ser
        515                 520                 525
Arg Asp Pro Tyr Cys Gly Trp Leu Ser Gln Gly Ser Cys Gly Arg Val
    530                 535                 540
Thr Pro Gly Met Leu Leu Thr Glu Asp Phe Phe Ala Phe His Asn
545                 550                 555                 560
His Ser Ala Glu Gly Tyr Glu Gln Asp Thr Glu Phe Gly Asn Thr Ala
                565                 570                 575
His Leu Gly Asp Cys His Gly Val Arg Trp Glu Val Gln Ser Gly Glu
            580                 585                 590
Ser Asn Gln Met Val His Met Asn Val Leu Ile Thr Cys Val Phe Ala
        595                 600                 605
Ala Phe Val Leu Gly Ala Phe Ile Ala Gly Val Ala Val Tyr Cys Tyr
    610                 615                 620
Arg Asp Met Phe Val Arg Lys Asn Arg Lys Ile His Lys Asp Ala Glu
625                 630                 635                 640
Ser Ala Gln Ser Cys Thr Asp Ser Ser Gly Ser Phe Ala Lys Leu Asn
                645                 650                 655
Gly Leu Phe Asp Ser Pro Val Lys Glu Tyr Gln Gln Asn Ile Asp Ser
            660                 665                 670
Pro Lys Leu Tyr Ser Asn Leu Leu Thr Ser Arg Lys Glu Leu Pro Pro
        675                 680                 685
Asn Gly Asp Thr Lys Ser Met Val Met Asp His Arg Gly Gln Pro Pro
    690                 695                 700
Glu Leu Ala Ala Leu Pro Thr Pro Glu Ser Thr Pro Val Leu His Gln
705                 710                 715                 720
Lys Thr Leu Gln Ala Met Lys Ser His Ser Glu Lys Ala His Gly His
                725                 730                 735
Gly Ala Ser Arg Lys Glu Thr Pro Gln Phe Phe Pro Ser Ser Pro Pro
            740                 745                 750
Pro His Ser Pro Leu Ser His Gly His Ile Pro Ser Ala Ile Val Leu
        755                 760                 765
Pro Asn Ala Thr His Asp Tyr Asn Thr Ser Phe Ser Asn Ser Asn Ala
    770                 775                 780
His Lys Ala Glu Lys Lys Leu Gln Asn Ile Asp His Pro Leu Thr Lys
785                 790                 795                 800
Ser Ser Ser Lys Arg Asp His Arg Arg Ser Val Asp Ser Arg Asn Thr
                805                 810                 815
Leu Asn Asp Leu Leu Lys His Leu Asn Asp Pro Asn Ser Asn Pro Lys
```

```
                     820                 825                 830
Ala Ile Met Gly Asp Ile Gln Met Ala His Gln Asn Leu Met Leu Asp
                835                 840                 845

Pro Met Gly Ser Met Ser Glu Val Pro Pro Lys Val Pro Asn Arg Glu
        850                 855                 860

Ala Ser Leu Tyr Ser Pro Ser Thr Leu Pro Arg Asn Ser Pro Thr
865                 870                 875                 880

Lys Arg Val Asp Val Pro Thr Thr Pro Gly Val Pro Met Thr Ser Leu
                885                 890                 895

Glu Arg Gln Arg Gly Tyr His Lys Asn Ser Ser Gln Arg His Ser Ile
        900                 905                 910

Ser Ala Met Pro Lys Asn Leu Asn Ser Pro Asn Gly Val Leu Leu Ser
        915                 920                 925

Arg Gln Pro Ser Met Asn Arg Gly Gly Tyr Met Pro Thr Pro Thr Gly
        930                 935                 940

Ala Lys Val Asp Tyr Ile Gln Gly Thr Pro Val Ser Val His Leu Gln
945                 950                 955                 960

Pro Ser Leu Ser Arg Gln Ser Ser Tyr Thr Ser Asn Gly Thr Leu Pro
                965                 970                 975

Arg Thr Gly Leu Lys Arg Thr Pro Ser Leu Lys Pro Asp Val Pro Pro
        980                 985                 990

Lys Pro Ser Phe Val Pro Gln Thr Pro Ser Val Arg Pro Leu Asn Lys
        995                 1000                1005

Tyr Thr Tyr
  1010

<210> SEQ ID NO 49
<211> LENGTH: 218
<212> TYPE: PRT
<213> ORGANISM: Homo sapiens

<400> SEQUENCE: 49

Met Ala Glu Gly Ser Arg Thr Gln Ala Pro Gly Lys Gly Pro Pro Leu
1               5                   10                  15

Ser Ile Gln Phe Leu Arg Ala Gln Tyr Glu Gly Leu Lys Arg Gln Gln
            20                  25                  30

Arg Thr Gln Ala His Leu Leu Val Leu Pro Lys Gly Gly Asn Thr Pro
        35                  40                  45

Ala Pro Ala Glu Ser Met Val Asn Ala Val Trp Ile Asn Lys Glu Arg
    50                  55                  60

Arg Ser Ser Leu Ser Leu Glu Glu Ala Asp Ser Glu Val Glu Gly Arg
65                  70                  75                  80

Leu Glu Glu Ala Ala Gln Gly Cys Leu Gln Ala Pro Lys Ser Pro Trp
                85                  90                  95

His Thr His Leu Glu Met His Cys Leu Val Gln Thr Ser Pro Gln Asp
            100                 105                 110

Thr Ser His Gln Val His His Arg Gly Lys Leu Val Gly Ser Asp Gln
        115                 120                 125

Arg Leu Pro Pro Glu Gly Asp Thr His Leu Phe Glu Thr Asn Gln Met
    130                 135                 140

Thr Gln Gln Gly Thr Gly Ile Pro Glu Ala Ala Gln Leu Pro Cys Gln
145                 150                 155                 160

Val Gly Asn Thr Gln Thr Lys Ala Val Glu Ser Gly Leu Lys Phe Ser
                165                 170                 175
```

```
Thr Gln Cys Pro Leu Ser Ile Lys Asn Pro His Arg Ser Gly Lys Pro
                180                 185                 190

Ala Tyr Tyr Pro Phe Pro Gln Arg Lys Thr Pro Arg Ile Ser Gln Ala
            195                 200                 205

Ala Arg Asn Leu Gly Leu Tyr Gly Ser Ala
        210                 215
```

<210> SEQ ID NO 50
<211> LENGTH: 709
<212> TYPE: PRT
<213> ORGANISM: Homo sapiens

<400> SEQUENCE: 50

```
Met Glu Ser Met Gly Met Val Tyr Ser Val Pro Ser Ser Cys Asn Gly
1               5                   10                  15

Pro Thr Glu Ser Thr Phe Ser Thr Ser Trp Lys Gly Asp Ala Phe Thr
            20                  25                  30

Tyr Met Thr Pro Ser Ala Thr Ser Gln Ser Asn Gln Val Asn Glu Asn
            35                  40                  45

Gly Lys Asn Pro Ser Cys Gly Asn Ser Trp Val Ser Leu Asn Lys Val
        50                  55                  60

Pro Pro Leu Val Pro Lys Glu Ala Ala Thr Leu Leu Val Ala Arg Asp
65                  70                  75                  80

Asn Pro Ala Gly Cys Ser Gly Ser Ala Gly Tyr Pro Glu Arg Leu Ile
                85                  90                  95

Gln Gln Arg His Met Pro Glu Arg Pro Ser Lys Ile Gly Leu Leu Thr
            100                 105                 110

Ser Gly Thr Ser Arg Leu Glu Thr Gly Pro Gly Gly Ala Ser Arg Phe
        115                 120                 125

Arg Glu Arg Ser Leu Ser Val Pro Thr Asp Ser Gly Thr Thr Asp Val
130                 135                 140

Asp Tyr Asp Glu Glu Gln Lys Ala Asn Glu Ala Cys Ala Leu Pro Phe
145                 150                 155                 160

Ala Ser Thr Ser Ser Glu Gly Ser Asn Ser Ala Asp Asn Ile Ala Ser
                165                 170                 175

Leu Ser Ala Gln Gln Glu Ala Gln His Arg Arg Gln Arg Ser Lys Ser
            180                 185                 190

Ile Ser Leu Arg Lys Ala Lys Lys Pro Ser Pro Thr Arg Ser
        195                 200                 205

Val Ser Leu Val Lys Asp Glu Pro Gly Leu Leu Pro Glu Gly Gly Ser
210                 215                 220

Ala Leu Pro Lys Asp Gln Arg Pro Lys Ser Leu Cys Leu Ser Leu Glu
225                 230                 235                 240

His Gln Gly His His Ser Ser Pro Asp Ala Gln Gly His Pro Ala
                245                 250                 255

Ile Pro Asn His Lys Asp Pro Glu Ser Thr Gln Phe Ser His His Trp
            260                 265                 270

Tyr Leu Thr Asp Trp Lys Ser Gly Asp Thr Tyr Gln Ser Leu Ser Ser
        275                 280                 285

Ser Ser Thr Ala Thr Gly Thr Thr Val Ile Glu Cys Thr Gln Val Gln
        290                 295                 300

Gly Ser Ser Glu Ser Leu Ala Ser Pro Ser Thr Ser Arg Ala Thr Thr
305                 310                 315                 320

Pro Ser Gln Leu Ser Ile Glu Val Glu Ala Arg Glu Ile Ser Ser Pro
                325                 330                 335
```

Gly Arg Pro Pro Gly Leu Met Ser Pro Ser Ser Gly Tyr Ser Ser Gln
            340                 345                 350

Ser Glu Thr Pro Thr Pro Thr Val Ser Met Ser Leu Thr Leu Gly His
        355                 360                 365

Leu Pro Pro Pro Ser Ser Val Arg Val Arg Pro Val Val Pro Glu
370                 375                 380

Arg Lys Ser Ser Leu Pro Pro Thr Ser Pro Met Glu Lys Phe Pro Lys
385                 390                 395                 400

Ser Arg Leu Ser Phe Asp Leu Pro Leu Thr Ser Ser Pro Asn Leu Asp
                405                 410                 415

Leu Ser Gly Met Ser Ile Ser Ile Arg Ser Lys Thr Lys Val Ser Arg
            420                 425                 430

His His Ser Glu Thr Asn Phe Gly Val Lys Leu Ala Gln Lys Thr Asn
        435                 440                 445

Pro Asn Gln Pro Ile Met Pro Met Val Thr Gln Ser Asp Leu Arg Ser
    450                 455                 460

Val Arg Leu Arg Ser Val Ser Lys Ser Glu Pro Glu Asp Asp Ile Glu
465                 470                 475                 480

Ser Pro Glu Tyr Ala Glu Glu Pro Arg Ala Glu Glu Val Phe Thr Leu
                485                 490                 495

Pro Glu Arg Lys Thr Lys Pro Pro Val Ala Glu Lys Pro Pro Val Ala
            500                 505                 510

Arg Arg Pro Pro Ser Leu Val His Lys Pro Pro Ser Val Pro Glu Glu
        515                 520                 525

Tyr Ala Leu Thr Ser Pro Thr Leu Ala Met Pro Pro Arg Ser Ser Ile
    530                 535                 540

Gln His Ala Arg Pro Leu Pro Gln Asp Ser Tyr Thr Val Val Arg Lys
545                 550                 555                 560

Pro Lys Pro Ser Ser Phe Pro Asp Gly Arg Ser Pro Gly Glu Ser Thr
                565                 570                 575

Ala Pro Ser Ser Leu Val Phe Thr Pro Phe Ala Ser Ser Ser Asp Ala
            580                 585                 590

Phe Phe Ser Gly Thr Gln Gln Pro Pro Gln Gly Ser Val Glu Asp Glu
        595                 600                 605

Gly Pro Lys Val Arg Val Leu Pro Glu Arg Ile Ser Leu Gln Ser Gln
    610                 615                 620

Glu Glu Ala Glu Lys Lys Lys Gly Lys Ile Pro Pro Pro Val Pro Lys
625                 630                 635                 640

Lys Pro Ser Val Leu Tyr Leu Pro Leu Thr Ser Pro Thr Ala Gln Met
                645                 650                 655

Glu Ala Tyr Val Ala Glu Pro Arg Leu Pro Leu Ser Pro Ile Ile Thr
            660                 665                 670

Leu Glu Glu Asp Thr Lys Cys Pro Ala Thr Gly Asp Asp Leu Gln Ser
        675                 680                 685

Leu Gly Gln Arg Val Thr Ser Thr Pro Gln Ala Asp Ser Glu Arg Glu
    690                 695                 700

Ala Ser Pro Leu Gly
705

<210> SEQ ID NO 51
<211> LENGTH: 684
<212> TYPE: PRT
<213> ORGANISM: Homo sapiens

```
<400> SEQUENCE: 51

Met Ala Ser Gly Arg Gly Trp Asp Ser His Glu Asp Leu
1               5                   10                  15

Pro Val Tyr Leu Ala Arg Pro Gly Thr Thr Asp Gln Val Pro Arg Gln
                20                  25                  30

Lys Tyr Gly Gly Met Phe Cys Asn Val Glu Gly Ala Phe Glu Ser Lys
            35                  40                  45

Thr Leu Asp Phe Asp Ala Leu Ser Val Gly Gln Arg Gly Ala Lys Thr
        50                  55                  60

Pro Arg Ser Gly Gln Gly Ser Asp Arg Gly Ser Gly Ser Arg Pro Gly
65                  70                  75                  80

Ile Glu Gly Asp Thr Pro Arg Arg Gly Gln Gly Arg Glu Glu Ser Arg
                    85                  90                  95

Glu Pro Ala Pro Ala Ser Pro Ala Pro Ala Gly Val Glu Ile Arg Ser
                100                 105                 110

Ala Thr Gly Lys Glu Val Leu Gln Asn Leu Gly Pro Lys Asp Lys Ser
            115                 120                 125

Asp Arg Leu Leu Ile Lys Gly Arg Ile Val Asn Asp Asp Gln Ser
        130                 135                 140

Phe Tyr Ala Asp Ile Tyr Met Glu Asp Gly Leu Ile Lys Gln Ile Gly
145                 150                 155                 160

Asp Asn Leu Ile Val Pro Gly Gly Val Lys Thr Ile Glu Ala Asn Gly
                165                 170                 175

Lys Met Val Ile Pro Gly Gly Ile Asp Val His Thr His Phe Gln Met
            180                 185                 190

Pro Tyr Lys Gly Met Thr Thr Val Asp Asp Phe Phe Gln Gly Thr Lys
        195                 200                 205

Ala Ala Leu Ala Gly Gly Thr Thr Met Ile Ile Asp His Val Val Pro
    210                 215                 220

Glu Pro Glu Ser Ser Leu Thr Glu Ala Tyr Glu Lys Trp Arg Glu Trp
225                 230                 235                 240

Ala Asp Gly Lys Ser Cys Cys Asp Tyr Ala Leu His Val Asp Ile Thr
                245                 250                 255

His Trp Asn Asp Ser Val Lys Gln Glu Val Gln Asn Leu Ile Lys Asp
            260                 265                 270

Lys Gly Val Asn Ser Phe Met Val Tyr Met Ala Tyr Lys Asp Leu Tyr
        275                 280                 285

Gln Val Ser Asn Thr Glu Leu Tyr Glu Ile Phe Thr Cys Leu Gly Glu
    290                 295                 300

Leu Gly Ala Ile Ala Gln Val His Ala Glu Asn Gly Asp Ile Ile Ala
305                 310                 315                 320

Gln Glu Gln Thr Arg Met Leu Lys Met Gly Ile Thr Gly Pro Glu Gly
                325                 330                 335

His Val Leu Ser Arg Pro Glu Glu Leu Glu Ala Glu Ala Val Phe Arg
            340                 345                 350

Ala Ile Thr Ile Ala Ser Gln Thr Asn Cys Pro Leu Tyr Val Thr Lys
        355                 360                 365

Val Met Ser Lys Ser Ala Ala Asp Leu Ile Ser Gln Ala Arg Lys Lys
    370                 375                 380

Gly Asn Val Val Phe Gly Glu Pro Ile Thr Ala Ser Leu Gly Ile Asp
385                 390                 395                 400

Gly Thr His Tyr Trp Ser Lys Asn Trp Ala Lys Ala Ala Ala Phe Val
                405                 410                 415
```

```
Thr Ser Pro Pro Leu Ser Pro Asp Pro Thr Thr Pro Asp Tyr Ile Asn
            420                 425                 430

Ser Leu Leu Ala Ser Gly Asp Leu Gln Leu Ser Gly Ser Ala His Cys
            435                 440                 445

Thr Phe Ser Thr Ala Gln Lys Ala Ile Gly Lys Asp Asn Phe Thr Ala
    450                 455                 460

Ile Pro Glu Gly Thr Asn Gly Val Glu Arg Met Ser Val Ile Trp
465                 470                 475                 480

Asp Lys Ala Val Ala Thr Gly Lys Met Asp Glu Asn Gln Phe Val Ala
                485                 490                 495

Val Thr Ser Thr Asn Ala Ala Lys Ile Phe Asn Leu Tyr Pro Arg Lys
            500                 505                 510

Gly Arg Ile Ser Val Gly Ser Asp Ser Asp Leu Val Ile Trp Asp Pro
            515                 520                 525

Asp Ala Val Lys Ile Val Ser Ala Lys Asn His Gln Ser Ala Ala Glu
            530                 535                 540

Tyr Asn Ile Phe Glu Gly Met Glu Leu Arg Gly Ala Pro Leu Val Val
545                 550                 555                 560

Ile Cys Gln Gly Lys Ile Met Leu Glu Asp Gly Asn Leu His Val Thr
                565                 570                 575

Gln Gly Ala Gly Arg Phe Ile Pro Cys Ser Pro Phe Ser Asp Tyr Val
            580                 585                 590

Tyr Lys Arg Ile Lys Ala Arg Arg Lys Met Ala Asp Leu His Ala Val
            595                 600                 605

Pro Arg Gly Met Tyr Asp Gly Pro Val Phe Asp Leu Thr Thr Thr Pro
            610                 615                 620

Lys Gly Gly Thr Pro Ala Gly Ser Ala Arg Gly Ser Pro Thr Arg Pro
625                 630                 635                 640

Asn Pro Pro Val Arg Asn Leu His Gln Ser Gly Phe Ser Leu Ser Gly
                645                 650                 655

Thr Gln Val Asp Glu Gly Val Arg Ser Ala Ser Lys Arg Ile Val Ala
            660                 665                 670

Pro Pro Gly Gly Arg Ser Asn Ile Thr Ser Leu Ser
            675                 680

<210> SEQ ID NO 52
<211> LENGTH: 1069
<212> TYPE: PRT
<213> ORGANISM: Homo sapiens

<400> SEQUENCE: 52

Met Leu Arg Met Arg Thr Ala Gly Trp Ala Gly Trp Cys Leu Gly
1               5                   10                  15

Cys Cys Leu Leu Leu Pro Leu Ser Leu Ser Leu Ala Ala Lys Gln
                20                  25                  30

Leu Leu Arg Tyr Arg Leu Ala Glu Glu Gly Pro Ala Asp Val Arg Ile
            35                  40                  45

Gly Asn Val Ala Ser Asp Leu Gly Ile Val Thr Gly Ser Gly Glu Val
            50                  55                  60

Thr Phe Ser Leu Glu Ser Gly Ser Glu Tyr Leu Lys Ile Asp Asn Leu
65                  70                  75                  80

Thr Gly Glu Leu Ser Thr Ser Glu Arg Arg Ile Asp Arg Glu Lys Leu
                85                  90                  95

Pro Gln Cys Gln Met Ile Phe Asp Glu Asn Glu Cys Phe Leu Asp Phe
```

```
                100                 105                 110
Glu Val Ser Val Ile Gly Pro Ser Gln Ser Trp Val Asp Leu Phe Glu
            115                 120                 125

Gly Gln Val Ile Val Leu Asp Ile Asn Asp Asn Thr Pro Thr Phe Pro
        130                 135                 140

Ser Pro Val Leu Thr Leu Thr Val Glu Glu Asn Arg Pro Val Gly Thr
145                 150                 155                 160

Leu Tyr Leu Leu Pro Thr Ala Thr Asp Arg Asp Phe Gly Arg Asn Gly
                165                 170                 175

Ile Glu Arg Tyr Glu Leu Leu Gln Pro Gly Gly Gly Gly Ser Gly
            180                 185                 190

Gly Glu Ser Arg Arg Ala Gly Ala Asp Ser Ala Pro Tyr Pro Gly
        195                 200                 205

Gly Gly Gly Asn Gly Ala Ser Gly Gly Gly Ser Gly Ser Lys Arg
        210                 215                 220

Arg Leu Asp Ala Ser Glu Gly Gly Gly Thr Asn Pro Gly Gly Arg
225                 230                 235                 240

Ser Ser Val Phe Glu Leu Gln Val Ala Asp Thr Pro Asp Gly Glu Lys
                245                 250                 255

Gln Pro Gln Leu Ile Val Lys Gly Ala Leu Asp Arg Glu Gln Arg Asp
                260                 265                 270

Ser Tyr Glu Leu Thr Leu Arg Val Arg Asp Gly Gly Asp Pro Pro Arg
        275                 280                 285

Ser Ser Gln Ala Ile Leu Arg Val Leu Ile Thr Asp Val Asn Asp Asn
        290                 295                 300

Ser Pro Arg Phe Glu Lys Ser Val Tyr Glu Ala Asp Leu Ala Glu Asn
305                 310                 315                 320

Ser Ala Pro Gly Thr Pro Ile Leu Gln Leu Arg Ala Ala Asp Leu Asp
                325                 330                 335

Val Gly Val Asn Gly Gln Ile Glu Tyr Val Phe Gly Ala Ala Thr Glu
            340                 345                 350

Ser Val Arg Arg Leu Leu Arg Leu Asp Glu Thr Ser Gly Trp Leu Ser
        355                 360                 365

Val Leu His Arg Ile Asp Arg Glu Glu Val Asn Gln Leu Arg Phe Thr
        370                 375                 380

Val Met Ala Arg Asp Arg Gly Gln Pro Pro Lys Thr Asp Lys Ala Thr
385                 390                 395                 400

Val Val Leu Asn Ile Lys Asp Glu Asn Asp Asn Val Pro Ser Ile Glu
                405                 410                 415

Ile Arg Lys Ile Gly Arg Ile Pro Leu Lys Asp Gly Val Ala Asn Val
                420                 425                 430

Ala Glu Asp Val Leu Val Asp Thr Pro Ile Ala Leu Val Gln Val Ser
            435                 440                 445

Asp Arg Asp Gln Gly Glu Asn Gly Val Val Thr Cys Thr Val Val Gly
        450                 455                 460

Asp Val Pro Phe Gln Leu Lys Pro Ala Ser Asp Thr Glu Gly Asp Gln
465                 470                 475                 480

Asn Lys Lys Lys Tyr Phe Leu His Thr Ser Thr Pro Leu Asp Tyr Glu
                485                 490                 495

Ala Thr Arg Glu Phe Asn Val Val Ile Val Ala Val Asp Ser Gly Ser
            500                 505                 510

Pro Ser Leu Ser Ser Asn Asn Ser Leu Ile Val Lys Val Gly Asp Thr
        515                 520                 525
```

```
Asn Asp Asn Pro Pro Met Phe Gly Gln Ser Val Val Glu Val Tyr Phe
    530                 535                 540

Pro Glu Asn Asn Ile Pro Gly Glu Arg Val Ala Thr Val Leu Ala Thr
545                 550                 555                 560

Asp Ala Asp Ser Gly Lys Asn Ala Glu Ile Ala Tyr Ser Leu Asp Ser
                565                 570                 575

Ser Val Met Gly Ile Phe Ala Ile Asp Pro Asp Ser Gly Asp Ile Leu
            580                 585                 590

Val Asn Thr Val Leu Asp Arg Glu Gln Thr Asp Arg Tyr Glu Phe Lys
        595                 600                 605

Val Asn Ala Lys Asp Lys Gly Ile Pro Val Leu Gln Gly Ser Thr Thr
    610                 615                 620

Val Ile Val Gln Val Ala Asp Lys Asn Asp Asn Asp Pro Lys Phe Met
625                 630                 635                 640

Gln Asp Val Phe Thr Phe Tyr Val Lys Glu Asn Leu Gln Pro Asn Ser
                645                 650                 655

Pro Val Gly Met Val Thr Val Met Asp Ala Asp Lys Gly Arg Asn Ala
            660                 665                 670

Glu Met Ser Leu Tyr Ile Glu Glu Asn Asn Ile Phe Ser Ile Glu
        675                 680                 685

Asn Asp Thr Gly Thr Ile Tyr Ser Thr Met Ser Phe Asp Arg Glu His
    690                 695                 700

Gln Thr Thr Tyr Thr Phe Arg Val Lys Ala Val Asp Gly Gly Asp Pro
705                 710                 715                 720

Pro Arg Ser Ala Thr Ala Thr Val Ser Leu Phe Val Met Asp Glu Asn
                725                 730                 735

Asp Asn Ala Pro Thr Val Thr Leu Pro Lys Asn Ile Ser Tyr Thr Leu
            740                 745                 750

Leu Pro Pro Ser Ser Asn Val Arg Thr Val Val Ala Thr Val Leu Ala
        755                 760                 765

Thr Asp Ser Asp Asp Gly Ile Asn Ala Asp Leu Asn Tyr Ser Ile Val
    770                 775                 780

Gly Gly Asn Pro Phe Lys Leu Phe Glu Ile Asp Pro Thr Ser Gly Val
785                 790                 795                 800

Val Ser Leu Val Gly Lys Leu Thr Gln Lys His Tyr Gly Leu His Arg
                805                 810                 815

Leu Val Val Gln Val Asn Asp Ser Gly Gln Pro Ser Gln Ser Thr Thr
            820                 825                 830

Thr Leu Val His Val Phe Val Asn Glu Ser Val Ser Asn Ala Thr Ala
        835                 840                 845

Ile Asp Ser Gln Ile Ala Arg Ser Leu His Ile Pro Leu Thr Gln Asp
    850                 855                 860

Ile Ala Gly Asp Pro Ser Tyr Glu Ile Ser Lys Gln Arg Leu Ser Ile
865                 870                 875                 880

Val Ile Gly Val Val Ala Gly Ile Met Thr Val Ile Leu Ile Ile Leu
                885                 890                 895

Ile Val Val Met Ala Arg Tyr Cys Arg Ser Lys Asn Lys Asn Gly Tyr
            900                 905                 910

Glu Ala Gly Lys Lys Asp His Glu Asp Phe Phe Thr Pro Gln Gln His
        915                 920                 925

Asp Lys Ser Lys Lys Pro Lys Lys Asp Lys Lys Asn Lys Ser Lys
    930                 935                 940
```

```
Gln Pro Leu Tyr Ser Ser Ile Val Thr Val Glu Ala Ser Lys Pro Asn
945                 950                 955                 960

Gly Gln Arg Tyr Asp Ser Val Asn Glu Lys Leu Ser Asp Ser Pro Ser
            965                 970                 975

Met Gly Arg Tyr Arg Ser Val Asn Gly Gly Pro Gly Ser Pro Asp Leu
            980                 985                 990

Ala Arg His Tyr Lys Ser Ser Pro Leu Pro Thr Val Gln Leu His
            995                 1000                1005

Pro Gln Ser Pro Thr Ala Gly Lys Lys His Gln Ala Val Gln Asp Leu
    1010                1015                1020

Pro Pro Ala Asn Thr Phe Val Gly Ala Gly Asp Asn Ile Ser Ile Gly
1025                1030                1035                1040

Ser Asp His Cys Ser Glu Tyr Ser Cys Gln Thr Asn Asn Lys Tyr Ser
            1045                1050                1055

Lys Gln Met Arg Leu His Pro Tyr Ile Thr Val Phe Gly
            1060                1065

<210> SEQ ID NO 53
<211> LENGTH: 345
<212> TYPE: PRT
<213> ORGANISM: Homo sapiens

<400> SEQUENCE: 53

Met Glu Glu Lys Tyr Leu Pro Glu Leu Met Ala Glu Lys Asp Ser Leu
1               5                   10                  15

Asp Pro Ser Phe Thr His Ala Leu Arg Leu Val Asn Gln Glu Ile Glu
            20                  25                  30

Lys Phe Gln Lys Gly Glu Gly Lys Glu Glu Lys Tyr Ile Asp Val Val
        35                  40                  45

Ile Asn Lys Asn Met Lys Leu Gly Gln Lys Val Leu Ile Pro Val Lys
    50                  55                  60

Gln Phe Pro Lys Phe Asn Phe Val Gly Lys Leu Leu Gly Pro Arg Gly
65                  70                  75                  80

Asn Ser Leu Lys Arg Leu Gln Glu Glu Thr Leu Thr Lys Met Ser Ile
            85                  90                  95

Leu Gly Lys Gly Ser Met Arg Asp Lys Ala Lys Glu Glu Glu Leu Arg
            100                 105                 110

Lys Ser Gly Glu Ala Lys Tyr Phe His Leu Asn Asp Asp Leu His Val
        115                 120                 125

Leu Ile Glu Val Phe Ala Pro Pro Ala Glu Ala Tyr Ala Arg Met Gly
    130                 135                 140

His Ala Leu Glu Glu Ile Lys Lys Phe Leu Ile Pro Asp Tyr Asn Asp
145                 150                 155                 160

Glu Ile Arg Gln Ala Gln Leu Gln Glu Leu Thr Tyr Leu Asn Gly Gly
            165                 170                 175

Ser Glu Asn Ala Asp Val Pro Val Val Arg Gly Lys Pro Thr Leu Arg
            180                 185                 190

Thr Arg Gly Val Pro Ala Pro Ala Ile Thr Arg Gly Arg Gly Gly Val
        195                 200                 205

Thr Ala Arg Pro Val Gly Val Val Pro Arg Gly Thr Pro Thr Pro
    210                 215                 220

Arg Gly Val Leu Ser Thr Arg Gly Pro Val Ser Arg Gly Arg Gly Leu
225                 230                 235                 240

Leu Thr Pro Arg Ala Arg Gly Val Pro Pro Thr Gly Tyr Arg Pro Pro
            245                 250                 255
```

```
Pro Pro Pro Pro Thr Gln Glu Thr Tyr Gly Glu Tyr Asp Tyr Asp Asp
            260                 265                 270

Gly Tyr Gly Thr Ala Tyr Asp Glu Gln Ser Tyr Asp Ser Tyr Asp Asn
        275                 280                 285

Ser Tyr Ser Thr Pro Ala Gln Ser Gly Ala Asp Tyr Tyr Asp Tyr Gly
    290                 295                 300

His Gly Leu Ser Glu Glu Thr Tyr Asp Ser Tyr Gly Gln Glu Glu Trp
305                 310                 315                 320

Thr Asn Ser Arg His Lys Ala Pro Ser Ala Arg Thr Ala Lys Gly Val
                325                 330                 335

Tyr Arg Asp Gln Pro Tyr Gly Arg Tyr
            340                 345

<210> SEQ ID NO 54
<211> LENGTH: 142
<212> TYPE: PRT
<213> ORGANISM: Homo sapiens

<400> SEQUENCE: 54

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 55
<211> LENGTH: 296
<212> TYPE: PRT
<213> ORGANISM: Homo sapiens

<400> SEQUENCE: 55

Met Thr Lys Thr Ala Leu Leu Lys Leu Phe Val Ala Ile Val Ile Thr
1               5                   10                  15

Phe Ile Leu Ile Leu Pro Glu Tyr Phe Lys Thr Pro Lys Glu Arg Thr
            20                  25                  30

Leu Glu Leu Ser Cys Leu Glu Val Cys Leu Gln Ser Asn Phe Thr Tyr
        35                  40                  45

Ser Leu Ser Ser Leu Asn Phe Ser Phe Val Thr Phe Leu Gln Pro Val
    50                  55                  60

Arg Glu Thr Gln Ile Ile Met Arg Ile Phe Leu Asn Pro Ser Asn Phe
65                  70                  75                  80

Arg Asn Phe Thr Arg Thr Cys Gln Asp Ile Thr Gly Glu Phe Lys Met
                85                  90                  95
```

```
Cys Ser Ser Cys Leu Val Cys Glu Pro Lys Gly Asn Met Asp Phe Ile
                100                 105                 110

Ser Gln Glu Gln Thr Ser Lys Val Leu Ile Arg Arg Gly Ser Met Glu
            115                 120                 125

Val Lys Ala Asn Asp Phe His Ser Pro Cys Gln His Phe Asn Phe Ser
130                 135                 140

Val Ala Pro Leu Val Asp His Leu Glu Glu Tyr Asn Thr Thr Cys His
145                 150                 155                 160

Leu Lys Asn His Thr Gly Arg Ser Thr Ile Met Glu Asp Glu Pro Ser
                165                 170                 175

Lys Glu Lys Ser Ile Asn Tyr Thr Cys Arg Ile Met Glu Tyr Pro Asn
            180                 185                 190

Asp Cys Ile His Ile Ser Leu His Leu Glu Met Asp Ile Lys Asn Ile
        195                 200                 205

Thr Cys Ser Met Lys Ile Thr Trp Tyr Ile Leu Val Leu Leu Val Phe
    210                 215                 220

Ile Phe Leu Ile Ile Leu Thr Ile Arg Lys Ile Leu Glu Gly Gln Arg
225                 230                 235                 240

Arg Val Gln Lys Trp Gln Ser His Arg Asp Lys Pro Thr Ser Val Leu
                245                 250                 255

Leu Arg Gly Ser Asp Ser Glu Lys Leu Arg Ala Leu Asn Val Gln Val
            260                 265                 270

Leu Ser Ala Glu Thr Thr Gln Arg Leu Pro Leu Asp Gln Val Gln Glu
        275                 280                 285

Val Leu Pro Pro Ile Pro Glu Leu
    290                 295

<210> SEQ ID NO 56
<211> LENGTH: 141
<212> TYPE: PRT
<213> ORGANISM: Homo sapiens

<400> SEQUENCE: 56

Met Ala Arg Pro Leu Cys Thr Leu Leu Leu Met Ala Thr Leu Ala
1               5                   10                  15

Gly Ala Leu Ala Ser Ser Lys Glu Glu Asn Arg Ile Ile Pro Gly
                20                  25                  30

Gly Ile Tyr Asp Ala Asp Leu Asn Asp Glu Trp Val Gln Arg Ala Leu
            35                  40                  45

His Phe Ala Ile Ser Glu Tyr Asn Lys Ala Thr Glu Asp Glu Tyr Tyr
    50                  55                  60

Arg Arg Pro Leu Gln Val Leu Arg Ala Arg Glu Gln Thr Phe Gly Gly
65                  70                  75                  80

Val Asn Tyr Phe Phe Asp Val Glu Val Gly Arg Thr Ile Cys Thr Lys
                85                  90                  95

Ser Gln Pro Asn Leu Asp Thr Cys Ala Phe His Glu Gln Pro Glu Leu
            100                 105                 110

Gln Lys Lys Gln Leu Cys Ser Phe Glu Ile Tyr Glu Val Pro Trp Glu
        115                 120                 125

Asp Arg Met Ser Leu Val Asn Ser Arg Cys Gln Glu Ala
    130                 135                 140

<210> SEQ ID NO 57
<211> LENGTH: 80
<212> TYPE: PRT
```

<213> ORGANISM: Homo sapiens

<400> SEQUENCE: 57

Met Gly Arg Ala Met Val Ala Arg Leu Gly Leu Gly Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80

<210> SEQ ID NO 58
<211> LENGTH: 268
<212> TYPE: PRT
<213> ORGANISM: Homo sapiens

<400> SEQUENCE: 58

Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ala Ser Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
    130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
            260                 265

<210> SEQ ID NO 59
<211> LENGTH: 579
<212> TYPE: PRT
<213> ORGANISM: Homo sapiens

<400> SEQUENCE: 59

Met Leu Arg Ser Gly Pro Ala Ser Gly Pro Ser Val Pro Thr Gly Arg
1               5                   10                  15

Ala Met Pro Ser Arg Arg Val Ala Arg Pro Ala Ala Pro Glu Leu
            20                  25                  30

Gly Ala Leu Gly Ser Pro Asp Leu Ser Ser Leu Ser Leu Ala Val Ser
            35                  40                  45

Arg Ser Thr Asp Glu Leu Glu Ile Ile Asp Glu Tyr Ile Lys Glu Asn
50                  55                  60

Gly Phe Gly Leu Asp Gly Gly Gln Pro Gly Pro Gly Glu Gly Leu Pro
65                  70                  75                  80

Arg Leu Val Ser Arg Gly Ala Ala Ser Leu Ser Thr Val Thr Leu Gly
                85                  90                  95

Pro Val Ala Pro Pro Ala Thr Pro Pro Trp Gly Cys Pro Leu Gly
            100                 105                 110

Arg Leu Val Ser Pro Ala Pro Gly Pro Gly Pro Gln Pro His Leu Val
            115                 120                 125

Ile Thr Glu Gln Pro Lys Gln Arg Gly Met Arg Phe Arg Tyr Glu Cys
130                 135                 140

Glu Gly Arg Ser Ala Gly Ser Ile Leu Gly Glu Ser Ser Thr Glu Ala
145                 150                 155                 160

Ser Lys Thr Leu Pro Ala Ile Glu Leu Arg Asp Cys Gly Gly Leu Arg
                165                 170                 175

Glu Val Glu Val Thr Ala Cys Leu Val Trp Lys Asp Trp Pro His Arg
            180                 185                 190

Val His Pro His Ser Leu Val Gly Lys Asp Cys Thr Asp Gly Ile Cys
            195                 200                 205

Arg Val Arg Leu Arg Pro His Val Ser Pro Arg His Ser Phe Asn Asn
210                 215                 220

Leu Gly Ile Gln Cys Val Arg Lys Lys Glu Ile Glu Ala Ala Ile Glu
225                 230                 235                 240

Arg Lys Ile Gln Leu Gly Ile Asp Pro Tyr Asn Ala Gly Ser Leu Lys
                245                 250                 255

Asn His Gln Glu Val Asp Met Asn Val Val Arg Ile Cys Phe Gln Ala
            260                 265                 270

Ser Tyr Arg Asp Gln Gln Gly Gln Met Arg Arg Met Asp Pro Val Leu
            275                 280                 285

Ser Glu Pro Val Tyr Asp Lys Lys Ser Thr Asn Thr Ser Glu Leu Arg
290                 295                 300

Ile Cys Arg Ile Asn Lys Glu Ser Gly Pro Cys Thr Gly Gly Glu Glu
305                 310                 315                 320

Leu Tyr Leu Leu Cys Asp Lys Val Gln Lys Glu Asp Ile Ser Val Val
                325                 330                 335

Phe Ser Arg Ala Ser Trp Glu Gly Arg Ala Asp Phe Ser Gln Ala Asp
            340                 345                 350

Val His Arg Gln Ile Ala Ile Val Phe Lys Thr Pro Pro Tyr Glu Asp
            355                 360                 365

Leu Glu Ile Val Glu Pro Val Thr Val Asn Val Phe Leu Gln Arg Leu
370                 375                 380

```
Thr Asp Gly Val Cys Ser Glu Pro Leu Pro Phe Thr Tyr Leu Pro Arg
385                 390                 395                 400

Asp His Asp Ser Tyr Gly Val Asp Lys Lys Arg Lys Arg Gly Met Pro
            405                 410                 415

Asp Val Leu Gly Glu Leu Asn Ser Ser Asp Pro His Gly Ile Glu Ser
            420                 425                 430

Lys Arg Lys Lys Lys Pro Ala Ile Leu Asp His Phe Leu Pro Asn
        435                 440                 445

His Gly Ser Gly Pro Phe Leu Pro Pro Ser Ala Leu Leu Pro Asp Pro
    450                 455                 460

Asp Phe Phe Ser Gly Thr Val Ser Leu Pro Gly Leu Glu Pro Pro Gly
465                 470                 475                 480

Gly Pro Asp Leu Leu Asp Asp Gly Phe Ala Tyr Asp Pro Thr Ala Pro
            485                 490                 495

Thr Leu Phe Thr Met Leu Asp Leu Leu Pro Ala Pro Pro His Ala
            500                 505                 510

Ser Ala Val Val Cys Ser Gly Gly Ala Gly Ala Val Val Gly Glu Thr
            515                 520                 525

Pro Gly Pro Glu Pro Leu Thr Leu Asp Ser Tyr Gln Ala Pro Gly Pro
530                 535                 540

Gly Asp Gly Gly Thr Ala Ser Leu Val Gly Ser Asn Met Phe Pro Asn
545                 550                 555                 560

His Tyr Arg Glu Ala Ala Phe Gly Gly Gly Leu Leu Ser Pro Gly Pro
                565                 570                 575

Glu Ala Thr

<210> SEQ ID NO 60
<211> LENGTH: 9
<212> TYPE: DNA
<213> ORGANISM: Artificial Sequence
<220> FEATURE:
<223> OTHER INFORMATION: A synthetic oligonucleotide sequence

<400> SEQUENCE: 60 uucaagaga                                                                9

<210> SEQ ID NO 61
<211> LENGTH: 750
<212> TYPE: DNA
<213> ORGANISM: Homo sapiens

<400> SEQUENCE: 61
tgcctccaga aagggttgag aagataatgg atcagattga aaagtacatc atgactcatc     60
tctgtaaata tgcgttctgt ccagaacccc agtgagcctg gaagactggg tgctatggga    120
aatgtcatca atccaatgct agtgaaagat gtgactgggg aatgctgaaa atgcgcacc    180
cctgggagga atgaggaaag atgacatcca ctgacttgtt atttttttga gaaggagtct    240
tgctctgttg cccaggctgg agtgtggtgg cacgatctcg gctcactgat gatgagaaga    300
aagatcttgc cattcaaaag aggatcagag tggaagcttc tctgtggtgt cagaaagacg    360
aggaatgtgg tgacctcacc tatccatctc cctcaaggca gcttttgacc tgaactggtt    420
atttcctact tgcctcctgg agttgctaat aaaataaaca ctaaagcttc gcagtttcta    480
aaaagaccat gaagccctga gagtaatgaa aaggttcctg aaattgaggt cactgtggaa    540
ggagaatcta atgcctgatg atctgtcact atctcccatc accccagat gggaccatct    600
agttgcagga aagaaggtc aagactccca gtcattctac attatgcctc agccaagatg    660
```

```
tctcacccca ctctctctga tgcaacaaga agcccctgga gaacgtttca gtcccatttt    720
gtacttctgt catgtgctca tcacagtctg                                     750
```

TARGETING CHROMOSOMAL INSTABILITY AND DOWNSTREAM CYTOSOLIC DNA SIGNALING FOR CANCER TREATMENT

PRIORITY CLAIM TO RELATED APPLICATIONS

This application is a U.S. national stage filing under 35 U.S.C. § 371 from International Application No. PCT/US2018/041480, filed on 10 Jul. 2018, and published as WO2019/014246 on 17 Jan. 2019, which claims the benefit of priority to the filing date of U.S. Provisional Application Ser. No. 62/530,661, filed Jul. 10, 2017, the contents of which are specifically incorporated by reverence herein in their entirety.

FEDERAL FUNDING

This invention was made with government support under grant number CA197588 awarded by the National Institutes of Health and grant number W81XWH-16-1-0315 awarded by the ARMY/MRMC. The government has certain rights in the invention.

BACKGROUND

Cancer is an uncontrolled growth of abnormal cells in various parts of the body. Presently cancer may be treated by surgery, radiotherapy, chemotherapy, immunotherapy, etc., with varying degrees of success. However, surgical therapy cannot completely remove extensively metastasized tumor cells. Radiotherapy and chemotherapy do not have sufficient selectivity to kill cancer cells in the presence of rapidly proliferating normal cells. Immunotherapy is largely limited to the use of cytokines or therapeutic cancer vaccines. Cytokines may cause serious toxicity and continuous use of vaccines may lead to immune tolerance.

SUMMARY

Previously, one of the major concerns regarding cytosolic DNA was that it induces immune responses. However, as described herein, chromosomal instability can generate cytosolic DNA, which increases the incidence and potential for metastasis of cancer cells. As further illustrated herein, chromosomal instabilities such as chromosomal missegregation, and micronuclei can also increase the incidence and potential for metastasis of cancer cells.

Methods compositions described are useful for treatment of patients with increased levels of chromosomal instability, increased levels of cytosolic DNA, chromosomal missegregation, or a combination thereof. The compositions and methods can also reduce and/or inhibit metastasis, cancer drug resistance, or combinations thereof. In some cases, the compositions and methods are useful for modulating kinesin-13 expression, and the compositions and methods can reduce chromosomal instability.

For example, methods and compositions are described herein that can increase the expression and/or activity of kinesin-13 proteins such as Kif2b, MCAK/Kif2c, or KIF13A in cells. In some cases, the methods and compositions can increase the expression and/or activity of ABCC4, ABCG2. The methods can also include inhibiting STING, cGAS, NF-κB transcription factor p52, NF-κB transcription factor RelB, ENPP1, LTβR, BAFFR, CD40, RANK, FN14, NIK (MAP3K14), MST1, or any combination thereof in a mammalian cell. Such compositions and methods are useful for treating and inhibiting the progression of cancer, including the development and progression of metastatic cancer.

Other methods are described herein that include assays for the design and development of new compounds that are useful for treatment of cancer, including metastatic cancer.

BRIEF DESCRIPTION OF THE FIGURES

FIGS. 1A-1M illustrates that chromosomal aberrations are prevalent in human metastases. FIG. 1A graphically illustrates the Weighted Genomic Instability Index (wGII) of matched primary tumors (P) and brain metastases (M), where n=61 primary tumors-metastasis matched pairs, boxes span the $25^{th}$-$75^{th}$ percentiles, bars span $10^{th}$-$90^{th}$ percentile, and significance was tested using Wilcoxon matched-pairs signed rank test. RCC, renal cell carcinoma. FIG. 1B-1 graphically illustrates differences in wGII between metastases and matched primary breast tumors. FIG. 1B-2 graphically illustrates differences in wGII between metastases and matched primary lung tumors. FIG. 1B-3 graphically illustrates differences in wGII between metastases and matched renal cell carcinoma primary tumors. FIG. 1B-4 graphically illustrates differences in wGII between metastases and matched primary tumors. FIG. 1C graphically illustrates the number of clones (based on karyotypes) in primary (P) breast tumors (n=637) or metastases (M, n=131) found in the Mitelman Database. FIG. 1D graphically illustrates the Log 2 of the number of chromosomes per clone found in primary breast tumors (n=983 clones) or metastases (n=186 clones). FIG. 1E graphically illustrates the number of chromosomal aberrations per clone found in primary breast tumors (n=983 clones) or metastases (n=186 clones). In FIGS. 1C-1E the boxes span the $25^{th}$-$75^{th}$ percentiles, bars span $10^{th}$-$90^{th}$ percentile, significance tested using two-tailed Mann Whitney test. FIG. 1F shows images of formalin-fixed paraffin-embedded head and neck squamous cell carcinoma cells undergoing anaphase. Arrows point examples of chromosome missegregation, scale bar 5-μm. FIG. 1G graphically illustrates the percentage of anaphase cells exhibiting evidence of chromosome missegregation in tumors from patients with (N+, n=22 patients) or without (N−, n=18 patients) clinically detectable lymph node metastases. Boxes span the $25^{th}$-$75^{th}$ percentiles, bars span $10^{th}$-$90^{th}$ percentile, significance tested using two-tailed Mann Whitney test. FIG. 1H graphically illustrates the weighted genomic instability index (wGII) of brain metastases as a function of the wGII of the matched primary tumor. The red line represents linear regression. FIG. 1I graphically illustrates the number of chromosome aberrations per clone as a function of the total number of chromosomes in a given clone in samples derived from primary and metastatic breast cancer and depicted in FIGS. 1D-1E, data points represent average±SD. FIG. 1J graphically illustrates the percentage of N− or N+ patients as a function of chromosome missegregation frequency (n=20 patients for CIN-low and CIN-high), significance tested using Fisher Exact test. FIG. 1K graphically illustrates cell confluence as a function of time of MDA-MB-231 cells that express various kinesin-13 proteins. The data points represent average±SD, n=4 experiments. FIG. 1L shows immunoblots of cells expressing various GFP-tagged kinesin-13 proteins stained using anti-GFP antibody, β-actin used as a loading control. FIG. 1M shows cells expressing MCAK and dnMCAK stained for microtubules (DM1A), centrosomes (pericentrin) and DNA (DAPI), scale bar 5-μm.

FIGS. 2A-2J illustrate that chromosomal instability (CIN) is a driver of metastasis. FIG. 2A illustrates anaphase cells stained for anti-centromere protein (ACA) and DNA (DAPI), scale bar, 5-μm. FIG. 2B-1 graphically illustrates the percentage of MDA-MB-231 anaphase cells exhibiting evidence of chromosome missegregation in control cells or cells expressing kinesin-13 proteins, bars represent mean±SD, n=150 cells, 3 experiments, significance tested using two-tailed t-test. FIG. 2B-2 graphically illustrates the percentage of anaphase H2030 cells exhibiting evidence of chromosome missegregation in control cells or cells expressing kinesin-13 proteins, bars represent mean±SD, n=150 cells, 3 experiments, significance tested using two-tailed t-test. FIG. 2C graphically illustrates photon flux (p/s) of whole animals imaged 5 weeks after intracardiac injection with MDA-MB-231 cells expressing different kinesin-13 proteins. Significance tested using two-sided Mann Whitney test, n=7-14 mice per group, 4 independent experiments. FIG. 2D illustrates images of photon flux (p/s) of whole animals imaged 5 weeks after intracardiac injection with MDA-MB-231 cells expressing different kinesin-13 proteins. FIG. 2E graphically illustrates the disease-specific survival of mice injected with MDA-MB-231 cells with various levels of chromosomal instability: CIN-high (dnMCAK; left-most graph showing least survival over time), CIN-medium (control, Kif2a, or tubulin; middle graph showing middle levels of survival over time), or CIN-low (MCAK or Kif2b; right-most graph showing most survival over time), n=10 mice for CIN-high, 23 mice for CIN-medium, and 20 mice for CIN-low, pairwise significance tested with log-rank test. FIG. 2F-1 shows representative karyotypes (DAPI607 banding) from parental MDA-MB-231 cell #2 that were allowed to divide for 30 days. FIG. 2F-2 shows representative karyotypes (DAPI607 banding) from parental MDA-MB-231 cell #4 that were allowed to divide for 30 days. FIG. 2G shows representative karyotypes (DAPI607 banding) of a cell derived from a single MCAK expressing cell that was allowed to divide for 30 days. FIG. 2H shows representative karyotypes (DAPI607 banding) of a cell derived from a single Kif2a expressing cell that was allowed to divide for 30 days. FIG. 2I graphically illustrates the number of non-clonal (present in <25% of the cells in a single clone) neochromosomes in CIN-low (MCAK; left bar for each chromosome) or CIN-medium/high (control, Kif2a, dnMCAK; right bar for each chromosome) MDA-MB-231 cells. 'Mar' denotes structurally abnormal chromosomes that cannot be unambiguously identified by conventional banding, bars represent mean±SD, n=140 cells from 7 clonal populations, significance tested using two-way ANOVA test. FIG. 2J shows examples of chromosomes taken from 6 distinct cells belonging to the same clonal population—derived from a single Kif2a-expressing cell—showing convergent translocations involving chromosome 22 with other distinct chromosomes.

FIGS. 3A-3M illustrates opposing roles for chromosomal instability (CIN) in primary tumors and metastases. FIG. 3A is a schematic illustrating the method of collection for samples shown in FIGS. 3B-3E, where in the original the colors of the cells in the schematic matches the color of the bars in FIGS. 3B-3E. FIG. 3B-1 graphically illustrates the percentage of anaphase cells arising from metastasis-competent patient-derived xenografts (PDX) belonging to the ER breast cancer subtype, to illustrate evidence of chromosome missegregation in first-passage cells derived from primary tumors, and from liver metastases. FIG. 3B-2 graphically illustrates the percentage of anaphase cells arising from metastasis-competent patient-derived xenografts (PDX) belonging to the TNBC breast cancer subtype, to illustrate evidence of chromosome missegregation in first-passage cells derived from primary tumors, and from liver metastases. FIG. 3C graphically illustrates the percentage of anaphase cells arising from CIN-low cells, to illustrate evidence of chromosome missegregation in injected cells, first-passage cells derived from primary tumors, spontaneous metastases arising from primary tumors in the same animal, and metastases obtained from direct intracardiac implantation. FIG. 3D graphically illustrates the percentage of anaphase cells arising from CIN-medium (Kif2a) cells, to illustrate evidence of chromosome missegregation in injected cells, first-passage cells derived from primary tumors, spontaneous metastases arising from primary tumors in the same animal, and metastases obtained from direct intracardiac implantation. FIG. 3E graphically illustrates the percentage of anaphase cells arising from CIN-high (dnMCAK) cells, to illustrate evidence of chromosome missegregation in injected cells, first-passage cells derived from primary tumors, spontaneous metastases arising from primary tumors in the same animal, and metastases obtained from direct intracardiac implantation. For FIGS. 2B-2E the bars represent mean±SD, n=150 cells, 3 independent experiments, * $p<0.05$ and denotes samples with higher missegregation rates than the injected lines, #$p<0.05$ and denotes samples with lower missegregation rates than the injected lines, ** $p<0.05$ and it denotes significant differences between metastases and matched primary tumors from the same animals, two-tailed t-test. ST met, soft tissue metastasis. FIG. 3F shows a Volcano plot illustrating changes in differentially expressed genes between CIN-low (MCAK and Kif2b) and CIN-medium/high (control, Kif2a, and dnMCAK) MDA-MB-231 cells. Data points in the right upper area (Log 2 of greater than 2.6) correspond to genes subsequently used for determining the chromosomal instability (CIN) signature. FIG. 3G is an enrichment plot for TAVAZOIE_METASTASIS gene set. FIG. 3H shows a distant metastasis-free survival (DMFS) plot of patients with high (CIN-High; lower graph line) or low (CIN-Low; upper graph line) expression of the CIN signature genes in a meta-analysis of patients. FIG. 3I shows a distant metastasis-free survival (DMFS) plot of patients with high (CIN-High; lower graph line) or low (CIN-Low; upper graph line) expression of the CIN signature genes in a validation cohort of 171 patients. As noted in Example 1, the CIN signature genes include PELI2, BMP2, SHH, TNS4, RAB3B, ROBO1, ARHGAP28, CHN2, CST1, F13A1, CPVL, SEMA6D, NHSL2, GTF2IP7, DPYSL3, PCDH7, KHDRBS3, TRAC, TMEM156, CST4, CD24, FGF5, NTN4. FIGS. 3J-3M illustrate that chromosomal instability promotes formation and maintenance of metastasis. FIG. 3J-1 graphically illustrates a normalized photon flux plot over time of whole animals injected with MDA-MB-231 cells expressing kinesin-13 proteins Bars represent mean±s.e.m. n=7-14 mice per group. FIG. 3J-2 shows images of a mouse injected with MDA-MB-231 cells expressing dnMCAK where disease burden was tracked using bioluminescence. FIG. 3J-3 shows images of a mouse injected with MDA-MB-231 cells expressing Kif2b where disease burden was tracked using BLI. FIG. 3K illustrates photon flux (p/s) of whole animals imaged 5 weeks after intracardiac injection with control or MCAK expressing H2030 cells. Significance tested using two-sided Mann Whitney test, n=10 mice in the MCAK group and 5 mice in the control group. FIG. 3L shows representative BLI images of mice orthotopically transplanted with MDA-MB-231 cells before (Day 33) and after (Day 90) tumor excision. Metastasis can be detected in the mouse transplanted with dnMCAK expressing cells at day 90. FIG. 3M shows a distant metastasis-free survival (DMFS) of mice orthotopically transplanted with MDA-MB-231 cells with various levels of chromosomal instability. As illustrated the animals that received CIN-low cells all survived (top graph line), while most of the animals that received CIN-medium cells survived (middle graph line), but most animals that received CIN-high cells did not survive (bottom graph line), n=5-9 mice group, pairwise significance tested with log-rank test.

FIG. 4A shows a gene expression heat map of 6,821 cells (columns) and genes involved in epithelial-to-mesenchymal transition (EMT, rows). Black rectangle denotes a gene-cell cluster enriched for mesenchymal traits. FIG. 4B shows a t-stochastic neighbor embedding (tSNE) projection of 6,821 MCAK, Kif2b, and dnMCAK expressing cells with 12 subpopulations identified using unsupervised K-nearest neighbor graph theory. Heatmap shows normalized enrichment score (NES) for gene sets with FDRq<0.05 inferred from gene set enrichment analysis of differentially expressed genes of each subpopulation. FIG. 4C shows representative images of cells expressing MCAK or dnMCAK stained for β-actin, Vimentin, and DNA scale bar 50-μm. FIG. 4D shows representative images of cells which invaded through a collagen membrane within 18 hours of culture. FIG. 4E graphically illustrates the numbers of cells which invaded through a collagen membrane within 18 hours of culture (see FIG. 4D). Bars represent mean±s.e.m., * p<0.05. ** p<0.01, two-sided Mann Whitney test, n=10 high-power fields, 2 independent experiments. FIG. 4F shows a principle component analysis (PCA) plot of MDA-MB-231 cells expressing different kinesin-13 proteins based on bulk RNA expression data. FIG. 4G shows results of a gene set enrichment analysis (GSEA) of HALLMARK gene sets highly enriched in CIN-medium/high (control, Kif2a, and dnMCAK) compared with CIN-low cells (MCAK and Kif2b). FIG. 4H shows a plot of normalized enrichment score versus False Discovery Rate (FDR).

FIGS. 5A-5I illustrate cell-intrinsic inflammation from cytosolic DNA in chromosomally unstable cells. FIG. 5A shows a gene-gene correlation heat-map showing expression modules and the HALLMARKS gene sets most significantly correlated with Module 2. NES, normalized enrichment score. FIG. 5B shows a tSNE projection (above) of 6,821 MCAK, Kif2b, and dnMCAK expressing cells labeled either with their kinesin-13 expression status or expression level of key gene signatures. Single-cell correlation plots between key gene signatures are shown below. FIG. 5C-1 shows a representative image of a micronucleus near a primary nucleus in a cell stained with ACA and DAPI, scale bar 5-μm. FIG. 5C-2 graphically illustrates the percentage of micronuclei in MDA-MB-231 cells that express various kinesin-13 proteins. FIG. 5C-3 graphically illustrates the percentage of micronuclei in H2030 cells that express various kinesin-13 proteins. The boxes in FIGS. 5C-2 and 5C-3 span the median and inter-quartile range, bars span the $5^{th}$-$9^{th}$ percentile, n=638-1127 cells, 10 high-power fields, 3 independent experiments, significance tested using two-sided Mann Whitney test. FIG. 5D graphically illustrates the percentage of micronuclei in cells derived from primary tumors and metastases previously depicted in FIGS. 3C-3E. Bars represent median and inter-quartile range, n=10 primary tumors and 28 metastases, 500-1500 cells/sample, significance tested using two-sided Mann Whitney test. FIG. 5E graphically illustrates a correlation between the percentage of cells exhibiting evidence of chromosome missegregation and percentage of micronuclei in all injected cell lines as well as cells derived from primary tumors and metastases. FIG. 5F shows MCAK and dnMCAK expressing cells stained for DNA (DAPI), cytosolic double-stranded DNA (using anti-dsDNA antibody), or single-stranded DNA (using anti-ssDNA antibody), scale bar 20-μm. FIG. 5G graphically illustrates normalized cytosolic-to-nuclear DNA ratios in CIN-medium/high and CIN-low MDA-MB-231 and H2030 cells. Bars represent mean±SD, significance tested using two-sided Mann Whitney test. FIG. 5H shows cells stained for DNA (DAPI), cytosolic DNA (dsDNA), or Dnase2 (RFP reporter), scale bar 10-μm, arrows denote Dnase2 expressing cells. FIG. 5I shows cells stained for DNA (DAPI), cytosolic DNA (dsDNA), or mCherry-Lamin B2, scale bar 10-μm, arrows denote mCherry-Lamin B2 expressing cells.

FIGS. 6A-6J illustrate metastasis from cellular responses to cytosolic DNA. FIG. 6A shows a cell stained using DAPI (DNA), cytosolic DNA (dsDNA), or anti-cGAS antibody, scale bar 5-μm. FIG. 6B graphically illustrates the percentages of micronuclei with (cGAS+) or without (cGAS−) cGAS localization in cells expressing kinesin-13 proteins (or Lamin B2 and dnMCAK), n=400 cells, 4 experiments, significance tested using two-sided Mann Whitney test. FIG. 6C shows immunoblots of lysates from cells expressing different kinesin-13 proteins or STING shRNA (dnMCAK), β-actin used as a loading control. FIG. 6D illustrates normalized ratios of phosphorylated p100-to-total p100 (above) and p52-to-p100 (below) protein levels from CIN-med/high cells (Control, Kif2a, and dnMCAK), CIN-low cells (Kif2b and MCAK) or STING-depleted dnMCAK expressing cells (STING shRNA). Bars represent mean±s.e.m., * p<0.05,  p<0.01, two-tailed Mann-Whitney test, n=4 biological replicates. FIG. 6E shows MCAK, dnMCAK expressing cells, and cells expressing control or STING shRNA, stained for RelB and DNA (DAPI), arrows point to RelB-positive nuclei, scale bar 20-μm. FIG. 6F graphically illustrates the average z-normalized expression of CIN-responsive noncanonical NF-κB target genes in breast cancer patents with low (<$30^{th}$ percentile) or high (>$30^{th}$ percentile) chromosomal instability gene expression signature, boxes span interquartile range, bars span $10^{th}$-$90^{th}$ percentile, significance tested using two-sided Mann Whitney test. FIG. 6G-1 graphically illustrates the photon flux (p/s) of whole animals imaged 5 weeks after intracardiac injection with cells expressing control shRNA or STING shRNA. Significance tested using two-sided Mann Whitney test, n=9 mice in the control group and 16 mice in the STING shRNA group. FIG. 6G-2 shows whole animals imaged 5 weeks after intracardiac injection with cells expressing control shRNA or STING shRNA. FIG. 6H graphically illustrates the number of cells expressing shRNA targeting genes in the DNA sensing or noncanonical NF-κB pathways which invaded through a collagen membrane within 24 hours of culture. Bars represent mean±s.e.m.,  p<0.0001, two-sided Mann Whitney test, n=10 high-power fields, 2 experiments. FIGS. 6I-6J illustrate single-cell sequencing and population detection. FIG. 6I illustrates the cellular composition of every subpopulation presented in FIG. 4B. FIG. 6J shows violin plots illustrating expression of key metastasis and invasion genes in a subpopulation of cells enriched for epithelial-to-mesenchymal transition (EMT) and chromosomal instability genes (subpopulation 'M') compared with the remaining subpopulations, subpopulations were identified using unsupervised K-nearest neighbor graph theory.

FIG. 7A-7F illustrate that chromosomal instability promotes a viral-like immune response that promotes metastasis yet at the same time recruits a large amount of an immune infiltrate. FIG. 7A shows that chromosomal instability promotes a viral-like immune response that promotes a large amount of an immune infiltrate. FIG. 7B is a schematic diagram illustrating that chromosomal instability (CIN) is linked to metastasis and tumor immune infiltrate through tumor-cell intrinsic inflammatory response to cytosolic DNA. FIG. 7C-1 shows representative phase contrast images of cells in the wound area, 36-hours after wound creation. FIG. 7C-2 graphically illustrates the length-to-width ratio of cells expressing different kinesin-13 proteins. For FIGS. 7C-1 and 7C-2, the bars span the interquartile range, n=100 cells, 2 experiments. ** p<0.0001, Mann Whitney test. FIG. 7D-1 shows representative cells that express MCAK (CIN-low) stained with β-catenin or DNA (DAPI), scale bar 30-μm. FIG. 7D-2 shows representative cells that express dnMCAK (CIN-high) stained with β-catenin or DNA (DAPI), scale bar 30-μm. FIG. 7E-1 shows phase-contrast images of a wound-healing assay of cells expressing kinesin-13 proteins, scale bar 800-μm. FIG. 7E-2 graphically illustrates the wound area (normalized to the 0 h time point) 24 h and 45 h after wound creation. * p<0.05, two-tailed t-test. FIG. 7F-1 shows images of cells which invaded through a polycarbonate membrane containing 8-μm pores within 18 hours of culture. FIG. 7F-2 graphically illustrates the normalized optical density (O.D.) of cells scraped from the bottom of the membrane, bars represent mean±s.e.m., * p<0.05, two-sided t-test, n=3 experiments.

FIG. 8A graphically illustrate the percentage of micronuclei in CIN-low samples depicted in FIG. 3C. FIG. 8B graphically illustrate the percentage of micronuclei in CIN-low samples depicted in FIG. 3D. FIG. 8C graphically illustrate the percentage of micronuclei in CIN-low samples depicted in FIG. 3E. For FIGS. 8A-8C: injected cells, first-passage cells derived from primary tumors, or metastases (some spontaneous metastases arising from primary tumors, some metastases obtained from direct intracardiac implantation). Bars represent mean±s.e.m., n=10 high-power fields encompassing 500-1500 cells/sample, 3 experiments, * p<0.05 and denotes samples with higher missegregation rates than the injected lines, #p<0.05 and denotes samples with lower missegregation rates than the injected lines, * p<0.05 and it denotes significant differences between metastases and matched primary tumors from the same animals, two-tailed t-test.

FIG. 9A graphically illustrates disease-specific survival of mice injected with dnMCAK expressing cells co-expressing either control shRNA or STING shRNA n=9 mice in the control group and 16 mice in the STING shRNA group, significance tested with log-rank test. As shown, reducing STING expression by expression of STING shRNA increases the survival of dnMCAK expressing cells. FIG. 9B graphically illustrates distant metastasis-free survival (DMFS) over time of breast cancer patients expressing high and lower levels of regulators of noncanonical NF-κB (where NFKB2, RelB, MAP3K14 positively regulate NF-κB, and TRAF2, TRAF3, BIRC2, BIRC3 negatively regulate NF-κB). As shown, expression of lower levels of such regulators of noncanonical NF-κB improves survival. FIG. 9C graphically illustrates distant metastasis-free survival (DMFS) over time of breast cancer patients expressing high and lower levels of CIN-responsive non-canonical NF-κB targets (where PPARG, DDIT3, NUPR1, RAB3B, IGFBP4, LRRC8C, TCP11 L2, MAFK, NRG1, F2R, KRT19, CTGF, ZFC3H1 positively regulate, and MACROD1, GSTA4, SCN9A, BDNF, LACTB negatively regulate CIN-responsive non-canonical NF-κB targets). As shown, down regulation of such CIN-responsive non-canonical NF-κB targets improves survival. FIG. 9D graphically illustrates distant metastasis-free survival (DMFS) over time of breast cancer patients expressing high and lower levels of regulators of canonical NF-κB (NFKB1, RelA, TRAF1, TRAF4, TRAF5, TRAF6). As shown, increased expression of such regulators of canonical NF-κB improves survival. FIG. 9E graphically illustrates distant metastasis-free survival (DMFS) over time of breast cancer patients expressing high and lower levels of regulators of interferon signaling (IRF1, IRF3, IRF7, TBK1). As shown, increased expression of such regulators of interferon signaling improves survival. FIG. 9F graphically illustrates relapse-free survival (RFS) over time of breast cancer patients expressing high and lower levels of regulators of noncanonical NF-κB. As shown, expression of lower levels of regulators of noncanonical NF-κB improves survival. FIG. 9G graphically illustrates relapse-free survival (RFS) over time of breast cancer patients expressing high and lower levels of CIN-responsive non-canonical NF-κB targets. As shown expression of slightly higher levels of CIN-responsive non-canonical NF-κB targets improves survival somewhat. FIG. 9H graphically illustrates relapse-free survival (RFS) over time of breast cancer patients expressing high and lower levels of regulators of canonical NF-κB. As illustrated, increased expression of regulators of canonical NF-κB improves survival. FIG. 9I graphically illustrates relapse-free survival (RFS) over time of breast cancer patients expressing high and lower levels of regulators of interferon signaling. As illustrated, increased expression of regulators of interferon signaling improves survival. FIG. 9J graphically illustrates progression-free survival (PFS) over time of lung cancer patients expressing high and lower levels of regulators of noncanonical NF-κB. As illustrated, reduced expression of regulators of noncanonical NF-κB improves survival. FIG. 9K graphically illustrates progression-free survival (PFS) over time of lung cancer patients expressing high and lower levels of CIN-responsive non-canonical NF-κB targets. As illustrated, reduced expression of CIN-responsive non-canonical NF-κB targets improves survival. FIG. 9L graphically illustrates progression-free survival (PFS) over time of lung cancer patients expressing high and lower levels of regulators of canonical NF-κB. As illustrated, increased expression of regulators of canonical NF-κB improves survival. FIG. 9M graphically illustrates progression-free survival (PFS) over time of lung cancer patients expressing high and lower levels of regulators of interferon signaling. As illustrated, increased expression of regulators of interferon signaling improves survival.

FIG. 10A illustrates the cGAMP transitions that can be detected by LC-MS. FIG. 10B graphically illustrates quantification of cGAMP in chromosomally unstable urine triple-negative breast cancer cells (4T1) using targeted LC-MS metabolomics. As illustrated, knockdown of cGAS in 4T1 cells reduces the abundance of cGAMP.

DETAILED DESCRIPTION

Figure 1D:
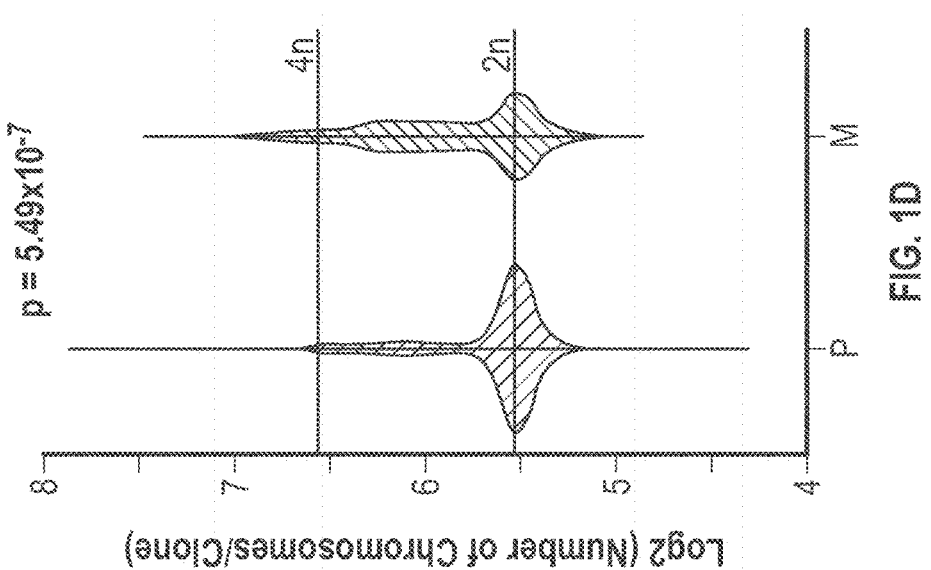

As illustrated herein, human metastases are significantly more chromosomally unstable compared with their primary tumor counterparts. More specifically, ongoing chromosome segregation errors, as well as the presence of micronuclei or cytosolic DNA, are predictive of metastasis as increasing chromosome segregation errors enriches for metastasis-initiating tumor cell subpopulations. Conversely, reduction in chromosomal instability leads to durable suppression of metastatic outbreaks even in highly aneuploid—yet stable—cells. The methods and compositions described herein are useful for detecting, monitoring, and treating such chromosomal instabilities and metastatic cancers.

Detection and Monitoring of Cancer

As illustrated herein, chromosomal instability is a marker indicating that a subject has cancer and chromosomal instability is especially useful for predicting, detecting and monitoring metastatic cancer. A large percentage (60-80%) of human solid tumors contain chromosomal instability. Hence, methods for diagnosing cancer, especially metastatic cancer, are described herein. Such methods are surprisingly effective at predicting, detecting, monitoring and treating cancer, including metastatic cancer. The methods of treatment described herein can be paired with the methods for predicting, detecting and monitoring metastatic cancer.

For example, one method for predicting, detecting and monitoring cancer (including metastatic cancer) can include obtaining a sample from a subject; and detecting and/or quantifying whether cells within the sample exhibit chromosomal instability. The methods can also include treating the subject when chromosomal instability is detected in the subject's sample.

For example, one method includes initiating treatment or modifying treatment of a subject having cells or tissues that have detectable levels of chromosomal instability, where the treatment includes administration of an agent that can reduce the incidence or progression of metastatic cancer.

As used herein, "obtaining a test sample" involves removing a sample of tissue or fluid from a patient, receiving a sample of tissue or fluid from a patient, receiving a patient's tissue or fluid sample from a physician, receiving a patient's tissue or fluid sample via mail delivery and/or removing a patient's tissue or fluid sample from a storage apparatus (e.g., a refrigerator or freezer) or a facility. Thus, obtaining a test sample can involve removal or receipt of the test sample directly from the patient, but obtaining a test sample can also include receipt of a test sample indirectly from a medical worker, from a storage apparatus/facility, from a mail delivery service after transportation from a medical facility, and any combination thereof. The test sample can therefore originate in one location, and be transported to another location where it is received and tested. Any of these activities or combinations of activities involves "obtaining a test sample." The test sample can be body fluid or a tissue sample. For example, the test sample can be a cell sample that is suspected of containing cancer cells. The sample can include cells and/or tissues from one or more primary tumors, tumor cells derived from primary tumors, tumor cells purified from the circulation, metastatic cell samples, or cells derived from metastatic tumors. Samples can include cells from established metastases, for example because increased chromosomal instability is a marker for a more aggressive disease. For example, the sample can be a tissue biopsy of breast or lung tissues (or of any of the tissue types mentioned herein). In another example, when detecting some cancer markers (e.g. cGAMP levels) to predict, detect, or monitor cancer (especially metastatic cancer), the sample can be a bodily fluid such as blood, serum, plasma, urine, ascites fluid, lymph fluid, or a combination thereof.

As used herein detecting and/or quantifying whether cells within the sample exhibit chromosomal instability can include detecting and/or quantifying micronuclei, chromosomal missegregation, or cytosolic chromosomal DNA in cells of sample. Detecting and/or quantifying micronuclei, chromosomal missegregation, cytosolic DNA, or a combination thereof can be done, for example, by examining cell chromosomes through a microscope, and counting the number(s) of micronuclei, chromosomal missegregations, cytosolic DNA, or a combination thereof.

In some cases, the cell samples can be fixed and/or lysed. Anaphase cells can be selected for analysis. Chromosomes can in some cases be treated with a protease (e.g., trypsin), for example, to improve visualization. In some cases, the chromosomes can be stained with a dye or a labeled antibody that facilitates visualization of chromosomes or DNA. Examples of dyes that can be used include Hematoxylin and Eosin (H&E) stain, 4',6-diamidino-2-phenylindole (DAPI) stain, quinacrine stain, Giemsa stain, and other chromosomal or DNA stains.

Cancer, especially metastatic cancer, can be predicted, detected, or undergoing progression, for example, when at least 10%, or at least 11%, or at least 12%, or at least 13%, or at least 14%, or at least 15% of chromosomes exhibit missegregations. In some cases, cancer, especially metastatic cancer, can be predicted, detected, or undergoing progression when about 15-20% of chromosomes exhibit missegregations.

Micronuclei can be easier to identify than chromosomal missegregations. Cancer, especially metastatic cancer, can be predicted, detected, or can be undergoing progression, for example, when at least 3%, at least 4% or at least 5% of cells exhibit micronuclei. In some cases, cancer, especially metastatic cancer, can be predicted, detected, or undergoing progression when about 5% to 8% of cells exhibit micronuclei.

In some cases, any amount of cytosolic DNA is indicative of cancer. Cytosolic DNA can be detected by DNA (staining) in the cytosol (rather than in nuclei). To detect cytosolic DNA any convenient DNA stain can be used. For example, a stain for double-stranded DNA can be used for detecting and quantifying cytosolic DNA. Cancer, especially metastatic cancer, can be predicted, can be detected, or can be undergoing progression, for example, when a 1-fold to 2-fold increase in staining intensity within the cytosol is observed compared to a normal non-cancer tissue. The normal, non-cancerous tissue used for comparison can be from the same patient or it can be a reference tissue derived from normal tissue samples.

An assay for detecting and quantifying cyclic guanosine monophosphate-adenosine monophosphate (cGAMP) is described herein and can be used to identify patients with cancer, including metastatic cancer. For example, total cGAMP concentration in a sample can be used as a marker for metastasis, by comparing the cGAMP levels in the sample compared to a reference normal tissue or adjacent normal tissue taken from the same patient. Increases in cGAMP of 10%, or 20%, or 30%, or 50%, or 70%, or 80%, or 90% can identify a patient who has or will develop cancer, including metastatic cancer. In some cases, increases in cGAMP at 1-fold to 2-fold over normal can identify a patient who has or will develop cancer, including metastatic cancer. Increased cGAMP concentrations in pre-therapy and shortly post therapy samples is a marker for tumor response. An increase of an additional 1-fold to 2-fold change in cGAMP levels is an indication of tumor response.

A method is described herein for diagnosing metastatic disease in patients using cGAMP as a novel metabolite biomarker for CIN driven cancers and metastatic disease. Measurements of cGAMP can serve as a clinical modality to accurately and specifically identify patients with metastatic disease. Measurement of cGAMP in patient samples (tumor, non-cancerous tissues, blood, serum, urine, and plasma), and the relative presence or absence of cGAMP therein, may also provide information that clinicians can correlate with a probable diagnosis of cancer aggressiveness or metastatic disease, as well as a negative diagnosis (e.g., normal or lack of disease).

In addition, a method is described herein for monitoring patient response to treatment based on determining the levels of cGAMP over time and establishing a cGAMP profile. Such a method can include generating a cGAMP profile in a subject, comprising of obtaining a sample from the subject; using liquid chromatography and/or mass spectroscopy to measure the level of cGAMP; and based on the comparison, generating a prolife that indicates whether the subject has metastatic disease. The reference profile can be obtained from a population of healthy control subjects without metastatic disease, population of subjects having localized cancerous disease, and a population of subjects having metastatic disease.

The cGAMP concentrations or amounts measured in a sample can be compared to normal reference values from a normal tissue (not necessarily from the same patient) or, if available to cGAMP levels in adjacent normal tissues. For example, in the case of a patient with mastectomy after the diagnosis or breast cancer, measurement of cGAMP levels in a sample of the normal breast (not involved with cancer) can be used as a reference or control value. Alternatively, for patients in which normal tissue is unavailable, a reference banked normal tissue from non-cancerous breasts for example can be used as a reference or control.

Once a profile is established, cGAMP levels can be used as a point of reference to compare and characterize unknown samples and samples for which further information is sought. For example, a decreased level of cGAMP (at least 10% or more, or a decrease of greater than 1-fold, 2-fold or more relative to a baseline) relative to a control (e.g., a sample taken from a subject at an earlier point in time or mean cGAMP levels determined from a population profile mentioned above) may indicate a positive treatment outcome. However, an increased level of cGAMP (at least 10% or more, or an increase greater than 1-fold) can indicate the presence or likelihood of metastatic disease and poor treatment outcome.

The determination of metastatic disease is based on the measured level of cGAMP as compared to a reference control level or a personalized longitudinal time points. The control level is indicative of the level of the one in a control subject who does not have metastatic disease, or before and after treatment.

In both aforementioned embodiments, measuring the level of cGAMP as a biomarker can include using liquid chromatography-mass spectrometry (LC-MS).

In brief, samples are collected from urine, blood, plasma, serum and cerebrospinal fluid. In certain embodiments, the sample also comprises of tumor cells or normal tissue cells adjacent to a tumor. Once collected, the sample is processed as described herein. Non-limiting, exemplary processing steps for use in embodiments of the invention include extraction of organic acids, column purification (e.g., anion exchange purification), chromatography (e.g., size-exclusion chromatography), centrifugation, and alcohol treatment (e.g. methanol or ethanol).

For example, cells from a cell sample can be washed and then frozen on liquid nitrogen to preserve metabolic state of the cells. Cells can then be collected/scraped into cold methanol (−80° C.). Methanolic metabolite extracts can then purified by Solid Phase Extraction (SPE) using HyperSep aminopropyl solid phase columns as described by Collins et al. (Cell Host & Microbe 17(6): 820-828 (2015)). Effluents can be dried and reconstituted in 70% acetonitrile in ddH$_2$O. The reconstituted effluents can be analyzed by LC-MS/MS analysis.

In some cases, serum or media can be evaluated for cGAMP concentrations or amounts. To detect/quantify secreted cGAMP in culture media, aliquots of conditioned media can be collected, mixed 80:20 with methanol, and centrifuged at 3,000 rpm for 20 minutes at 4 degrees Celsius. The resulting supernatant can be collected and stored at −80 degrees Celsius prior to LC-MS/MS to assess cGAMP levels.

To measure whole-cell associated metabolites, media can be aspirated and cells can be harvested, e.g., at a non-confluent density.

A variety of different liquid chromatography (LC) separation methods can be used.

Each method can be coupled by negative electrospray ionization (ESI, −3.0 kV) to triple-quadrupole mass spectrometers operating in multiple reaction monitoring (MRM) mode, with MS parameters optimized on infused metabolite standard solutions.

Methods are also described herein that identify ongoing breast cancer metastasis and/or patients who will undergo or survive breast cancer metastasis. Decreased expression of one or more of the following genes in a test sample can identify ongoing breast cancer metastasis and/or patients who will undergo breast cancer metastasis: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, FGF5 or NTN.

As described herein, elevated expression of these genes PREDICTS increased distant-metastasis free survival in breast cancer. Elevated expression of the following genes is referred to as the chromosomal instability (CIN) signature: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, FGF5, and NTN4. Hence, methods are also described herein that identify patients who can have metastasis free survival where the method involves quantifying expression of one or more of PELI2, BMP2, SHH, TNS4, RAB3B, ROBO1, ARHGAP28, CHN2, CST1, F3A1, CPVL, SEMA6D, C9orf152, NHSL2, GTF2IP7, DPYSL3, PCDH7, KHDRBS3, TRAC, TMEM156, CST4, CD24, or FGF5 gene in a patient sample to obtain a measured quantified expression level for one or more of these genes of the patient. In some cases, this method can involve measuring expression levels of these genes but no other genes.

Microarray gene expression datasets deposited in the KM-Plotter database (see website at www.kmplot.com) were evaluated as described herein. The following microarray probes were used for each gene (please note that some genes have multiple names and alternate names could be listed below): 219132_at (PELI2), 205289_at (BMP2), 207586_at (SHH), 230398_at (TNS4), 227123_at (RAB3B), 213194_at (ROBO1), 227911_at (ARHGAP28), 213385_at (CHN2), 206224_at (CST1), 203305_at (F3A1), 208146_s_at (CPVL), 226492_at (SEMA6D), 201431_s_at (DPYSL3), 228640_at (PCDH7), 209781_sat (etoile), 210972_x_at (TRA@), 220169_at (TMEM156), 206994_at (CST4), 266_s_at (CD24), 210311_at (FGF5), 200948_at (MLF2). A cutoff value of 36 percentile was used such that the patients with cumulative expression of the genes above that which were in the bottom 36-percentile had higher metastasis-free survival.

In the second data set, publicly deposited gene expression data derived from next-gen sequencing was used and the median expression values were used as a cutoff value to identify patients with improved survival. Those having expression values greater than the median expression values of PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, an FGF5 had improved survival. Thus, expression levels of each of these genes can be quantified in a patient sample and these quantified expression level can be compared to median reference expression levels for each of these genes. Such median reference expression levels for each of these genes can be the median expression of each of these genes in samples from a series of patients with metastatic cancer.

The sample tested can be from a patient with breast cancer, for example, a patient without detectable metastatic breast cancer, or one without significant metastatic breast cancer. Similarly, the median reference expression levels can be obtained from a series of samples from patients with ongoing metastatic breast cancer.

In this type of analysis, it is typical to use cutoff values ranging from the 25-percentile to the 75-percentile depending on the patient population and assay used.

Similar results obtained using the first and second methods.

Hence, a method is described herein to identify patients with improved survival. The method can include collecting samples from patients with a primary cancer type (e.g., primary breast cancer); RNA purification and preparation according to standard protocols for NextGen sequencing (see, e.g., website at qiagen.com/us/shop/sample-technologies/rna/total-rna/measy-mini-kit/#orderinginformation); determining the relative or absolute RNA expression levels using RT-PCR, NextGen sequencing or microarray method; summing up the expression values of the 23 genes; determining in this cohort the best cutoff to predict distant metastasis-free survival (DMFS); using this as an absolute cutoff for subsequent patients. Note in some cases a normal tissue reference control can be used for optimal calibration (e.g. breast tissue for breast cancer, normal pancreas for pancreatic cancer etc.).

The measured quantified expression level(s) so obtained can be compared to a control, for example, a median or mean expression level of one or more corresponding PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5 gene in a set of patients with ongoing breast cancer metastasis. A patient can have metastasis free survival when the measured quantified expression level(s) are greater than the control level. For example, such a patient with increased metastasis free survival when the measured quantified expression level(s) are greater than the control level, can survive for at least 5 months, at least 10 months, at least 12 months, at least 15 months, at least 20 months, at least 25 months, at least 50 months, or at least 100 months more than a control set of patients with ongoing breast cancer metastasis.

In some cases, the decreased or increased expression can be of two or more, or three or more, or four or more, or five or more, or six or more, or seven or more, or eight or more, or nine or more, ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more of these genes. As used herein, decreased or increased expression of these genes can be at least a 10%, or 20% or 30%, or 40%, or 50%, or 60%, or 75%, or 100% decrease or increase in expression of the foregoing genes compared to a control. Such a decrease or increase of expression of these genes can also be at least a 1.2-fold, or 1.5-fold, or 2-fold, or 3-fold, or 5-fold, or 7-fold, or 10-fold increase compared to a control. Such a control can be healthy or non-cancerous tissue sample. In other cases, the control can be a cancerous or metastatic tissue.

Treatment Methods

Surprisingly, the pro-metastatic phenotype imparted by chromosomal instability is driven by a tumor cell-intrinsic inflammatory response to cytosolic double-stranded DNA (dsDNA). Sensing of cytosolic DNA by cyclic GMP-AMP synthase (cGAS), and its downstream effector STING, activates the noncanonical NF-κB pathway and drives invasion and metastasis in a tumor cell-autonomous manner. This unexpected link between chromosomal instability and innate cellular inflammation offers new avenues for therapeutic intervention in genomically unstable tumors. Hence, the treatment methods described herein can include methods for identifying whether cells in a patent sample exhibit increased levels of cytosolic DNA, micronuclei, chromosomal missegregation, or a combination thereof. As described herein, increased levels of cGAMP are also indicative of cancer, especially metastatic cancer. Patients with increased levels of cytosolic DNA, micronuclei, chromosomal missegregation, or a combination thereof can then be treated as described herein or by a variety of other treatment methods.

For example, one method can include administering a metastatic chemotherapeutic agent to a patient with a cell sample or bodily fluid sample:

a. having at least 10%, or at least 11%, or at least 12%, or at least 13%, or at least 14%, or at least 15% detectable chromosomal missegregations within one or cells of the cell sample;

b. having at least 3%, at least 4% or at least 5% of cells detectable micronuclei within one or cells of the cell sample;

c. having detectable cytosolic double-stranded DNA within one or cells of the cell sample; or d. having at least 10%, or 20%, or 30%, or 50%, or 70%, or 80%, or 90% greater concentration or amount of cGAMP in the cell sample or bodily fluid sample;

to thereby treat metastatic cancer in the patient.

A variety of chemotherapeutic agents can be employed. Methods described herein can, for example, include administering kinesin-13 proteins such as Kif2b, MCAK/Kif2c, and/or KIF13A and, optionally, administering ABCC4 and/or ABCG2 proteins. Methods described herein can include expression of kinesin-13 proteins such as Kif2b, MCAK/Kif2c, and/or KIF13A in a transgene or vector, and, optionally, expression of ABCC4 and/or ABCG2 in a transgene or vector. The methods can also include inhibiting STING, cGAS, NF-κB transcription factor p52, NF-κB transcription factor RelB, ENPP1, LTβR, BAFFR, CD40, RANK, FN14, NIK (MAP3K14), MST1, or any combination thereof.

For example, methods and compositions are described herein that involve increased expression and/or activity of kinesin-13 proteins such as Kif2b, MCAK/Kif2c, or KIF13A in cells. Such methods and compositions are useful for treating cancer. The methods and compositions can include increased expression and/or activity of ABCC4, ABCG2, or a combination thereof. Agonists of such kinesin-13 proteins, ABCC4 proteins, ABCG2 proteins, or a combination thereof ca be used to increase the activity of these proteins.

The methods and compositions described herein can also include inhibiting STING, cGAS, NF-κB transcription factor p52, NF-κB transcription factor RelB, ENPP1, LTβR, BAFFR, CD40, RANK, FN14, NIK (MAP3K14), MST1, or any combination thereof in a mammalian cell. The cells can be in vitro (e.g., in culture) or in vivo (e.g., within a subject animal).

Compositions and methods described herein can include use of kinesin-13 proteins such as Kif2b, MCAK/Kif2c, and/or KIF13A proteins. The compositions and methods can also include use of kinesin-13 nucleic acids encoding kinesin-13 such as Kif2b, MCAK/Kif2c, KIF13A, or a combination thereof. The compositions and methods can also include one or inhibitors of STING, cGAS, NF-κB transcription factor p52, NF-κB transcription factor RelB, ENPP1, LTβR, BAFFR, CD40, RANK, FN14, NIK (MAP3K14), MST1, or a combination thereof. Examples of such inhibitors include antibodies or inhibitory nucleic acids (e.g., in a carrier or expressed from an expression vector). Such compositions and methods are useful for treating and inhibiting the development of cancer, including metastatic cancer.

As described herein increased activity and/or levels of kinesin-13 proteins such as Kif2b, MCAK/Kif2c, and/or KIF13A, as well as increased activity and/or levels of ABCC4 and/or ABCG2 can reduce the incidence and/or progression of cancer, including metastatic cancer. Reducing expression of STING, cGAS, NF-κB transcription factor p52, NF-κB transcription factor RelB, ENPP1, LTβR, BAFFR, CD40, RANK, FN14, NIK (MAP3K14), MST1, or any combination thereof can also reduce the incidence and/or progression of cancer, including metastatic cancer.

Sequences for kinesin-13 proteins and nucleic acids such as Kif2b, MCAK/Kif2c, and KIF13A, as well as ABCC4, ABCG2 proteins and nucleic acids, and sequences for STING, cGAS, NF-κB transcription factor p52, and NF-κB transcription factor RelB, ENPP1, LTβR, BAFFR, CD40, RANK, FN14, NIK (MAP3K14), and MST1 are available, for example, from the database maintained by the National Center for Biotechnology Information (NCBI) data at ncbi.nlm.nih.gov.

For example, one kinesin-13 protein is the a Kif2b protein, which can have the following human sequence (SEQ ID NO:1; NCBI accession number NP_115948).

```
  1 MASQFCLPES PCLSPLKPLK PHFGDIQEGI YVAIQRSDKR
 41 IHLAVVTEIN RENYWVTVEW VEKAVKKGKK IDLETILLLN
 81 PALDSAEHPM PPPPLSPLAL APSSAIRDQR TATKWVAMIP
121 QKNQTASGDS LDVRVPSKPC LMKQKKSPCL WEIQKLQEQR
161 EKRRRLQQEI RARRALDVNT RNPNYEIMHM IEEYRRHLDS
201 SKISVLEPPQ EHRICVCVRK RPLNQRETTL KDLDIITVPS
241 DNVVMVHESK QKVDLTRYLQ NQTFCFDHAF DDKASNELVY
231 QFTAQPLVES IFRKGMATCF AYGQTGSGKT YTMGGDFSGT
321 AQDCSKGIYA LVAQDVFLLL RNSTYEKLDL KVYGTFFEIY
361 GGKVYDLLNW KKKLQVLEDG NQQIQVVGLQ EKEVCCVEEV
401 LNLVEIGNSC RTSRQTPVNA HSSRSHAVFQ IILKSCRIMH
441 GKFSLVDLAG NERCADTTKA SRKRQLEGAE INKSLLALKE
481 CILALCQNKP HTPFRASKLT LVLRDSFIGQ NSSTCMIATI
521 SPGMTSCENT LNTLRYANRV KKLNVDVRPY HRGHYPIGHE
561 APRMLKSHIG NSEMSLQRDE FIKIPYVQSE EQKEIEEVET
601 LPTLLGKDTT ISGKGSSQWL ENIQERAGGV HHDIDFCIAR
641 SLSILEQKID ALTEIQKKLK LLLADLHVKS KVE
```

A cDNA sequence that encodes the SEQ ID NO:1 human Kif2b protein is shown below as SEQ ID NO:2 (NCBI accession number NM_032559).

```
   1 GTAGTGGCCC CAGTCCGGGC CCCGGCGCGC TAGGCTCACA
  41 AAGGCAGGCA CAGACTGCAA CCCTGCTCAG TGCTCCGGGC
  81 GCTTCAGGCT GGCTTGGGTC CTGCTGCTCC AACCCCAAGG
 121 GCCCTGGAGC GCTCCCTGAT ACCTCCATCA CTCACCATGG
 161 CCAGCCAGTT CTGCCTCCCT GAATCCCCAT GTCTCTCGCC
 201 CCTGAAACCC TTGAAGCCAC ATTTCGGAGA CATCCAAGAG
 241 GGCATCTACG TGGCGATCCA GCGCAGTGAC AAGCGGATCC
 281 ACCTCGCTGT GGTCACGGAG ATCAACAGAG AAAACTATTG
 321 GGTCACGGTA GAGTGGGTGG AGAAAGCAGT CAAAAAGGC
 361 AAGAAGATTG ACCTGGAGAC CATACTCCTG CTGAATCCAG
 401 CTCTGGACTC TGCTGAACAC CCCATGCCGC CCCCGCCCTT
 441 ATCCCCCTTG GCTCTGGCGC CCTCTTCGGC CATCAGGGAC
 481 CAGCGTACCG CCACGAAATG GGTTGCGATG ATCCCCCAGA
 521 AAAACCAAAC AGCCTCAGGG GACAGCCTGG ATGTGAGGGT
 561 CCCCACCAAA CCTTGTCTGA TGAAGCAGAA AAAGTCTCCC
 601 TGCCTCTGGG AAATCCAGAA ACTGCAGGAC CAGCGCCAAA
 641 AGCGCAGGCC GCTGCAGCAG GAGATCCGAG CTAGACGCGC
 681 CCTCGATGTC AATACCAGAA ACCCCAACTA CGAAATCATC
 721 CACATGATCG AAGAGTATCG CAGGCACCTG GACACCACCA
 761 AGATCTCAGT CCTGGACCCC CCGCAAGAAC ATCGCATCTG
 801 CGTCTGCGTG AGGAAGCGGC CTCTCAACCA GCGAGAGACA
 841 ACCTTAAAGG ACCTGGATAT CATCACCGTC CCCTCGGACA
 881 ATGTGGTTAT GGTGCATGAG TCCAAGCAAA AGGTGGACCT
 921 CACTCGCTAC CTGCAGAACC AGACCTTCTG CTTCGACCAT
 961 GCCTTCGATG ACAAAGCCTC CAACGAGTTG GTGTACCAGT
1001 TCACCGCCCA GCCACTGGTG GAGTCCATCT TCCGCAAGGG
1041 CATGGCCACC TGCTTTGCCT ATGGGCAGAC GGGAAGTGGG
1081 AAGACGTACA CCATGGGTGG AGACTTTTCA GGAACGGCCC
1121 AAGATTGTTC TAAGGGCATT TATGCTCTGG TGGCACAGGA
```

-continued

```
1161 TGTCTTTCTC CTGCTCAGAA ACTCCACATA TGAGAAGCTG
1201 GACCTCAAAG TCTATGGGAC ATTTTTTGAG ATTTATGGGG
1241 GCAAGGTGTA TGATTTGTTG AACTGGAAGA AGAAGCTGCA
1281 AGTCCTTGAG GATGGCAATC AGCAAATCCA AGTGGTCGGG
1321 CTGCAGGAGA AGAGGTGTG TTGTGTGGAG GAAGTGCTGA
1361 ACCTGGTGGA AATAGGGAAT AGCTGTCGGA CTTCCAGGCA
1401 AACACCTGTC AACGCTCACT CATCCAGGAG CCATGCAGTG
1441 TTCCAGATCA TCCTGAAGTC AGGACGGATA ATGCATGGCA
1481 AGTTTTCCCT CCTTGATTTA GCTGGGAATG AAAGAGGAGC
1521 AGATACAACC AACCCCACCC CGAAAACCCA GCTCGAAGGC
1561 GCAGAGATTA ACAAGACTCT TCTACCCCTC AAAGAATCTA
1601 TTCTGGCTTT CGCTCAGAAC AAGCCTCACA CCCCATTCAG
1641 AGCCAGCAAA CTCACACTGG TGCTCCGGGA CTCCTTTATA
1681 GGCCAGAACT CCTCCACTTG CATGATTGCT ACCATCTCTC
1721 CGGGGATGAC CTCTTGTGAA AACACTCTCA ACACTTTAAG
1761 ATATGCAAAC AGAGTAAAAA AATTAAATGT AGATGTAAGG
1801 CCCTACCATC GTGGCCACTA TCCGATTGGA CATGAGGCAC
1841 CAAGGATGTT AAAAAGTCAC ATCGGAAATT CAGAAATGTC
1881 CCTTCAGAGG GATGAATTTA TTAAAATACC TTATGTACAG
1921 AGTGAGGAGC AGAAAGAGAT TGAAGAGGTT GAAACATTAC
1961 CCACTCTGTT AGGGAAGGAT ACCACAATTT CAGGGAAGGG
2001 ATCTAGCCAA TGGCTGGAAA ACATCCAGGA GAGAGCTGGT
2041 GGAGTACACC ATGATATTGA TTTTTGCATT GCCCGGTCTT
2081 TGTCCATTTT GGAGCAGAAA ATTGATGCTC TGACCGAGAT
2121 CCAAAAGAAA CTGAAATTAT TACTAGCTGA CCTCCACGTG
2161 AAGAGCAAGG TAGAGTGAAG CCAATGGCGA GAGATCAGGT
2201 CCGAAATGCT GCATTGCTGC AGTTTCCACC ACTCTTATAC
2241 AGGAAAACTG TCCAAATTAT CTAAAGATCC TCCTGAGAAG
2281 CTTAAAACAT CTTAAAATAC ACTGATGGGA ACATGCTCT
2321 TTCTTCTGCC TCTGT
```

A kinesin-13 protein is the MCAK/Kif2c protein, which can have the following human sequence (SEQ ID NO:3; NCBI accession number BAG50306.1).

```
  1 MAMDSSLQAR LFPGLAIKIQ RSNGLIHSAN VRTVNLEKSC
 41 VSVEWAEGGA TKGKEIDFDD VAAINPELLQ LLPLHPKDNL
 81 PLQENVTIQK QKRRSVNSKI PAPKESLRSR STRMSTVSEL
121 RITAQENDME VELPAAANSR KQFSVPPAPT RPSCPAVAEI
161 PLRMVSEEME EQVHSIRGSS SANPVNSVRR KSCLVREVEK
201 MKNKREEKKA QNSEMRMKRA QEYDSSFPNW EFARMIKEFR
241 ATLECHPLTM TDPIEEHRIC VCVRKRPLNK QELAKKEIDV
281 ISIPSKCLLL VHEPKLKVDL TKYLENQAFC FDFAFDETAS
321 NEVVYRFTAR PLVQTIFEGG KATCFAYGQT GSGKTHTMGG
361 DLSGKAQNAS KGIYAMASRD VFLLKNOPCY RKLGLEVYVT
401 FFEIYNGKLF DLLNKKAKLR VLEDGKQQWQ VVGLQEHLVN
441 SADDVIKMLD MGSACRTSGQ TFANSNSSRS HACFQIILRA
481 KGRMHGKFSL VDLAGNERGA DTSSADRQTR MEGAEINKSL
521 LALKECIRAL GQNKAHTPFR ESKLTQVLRD SFIGENSRTC
561 MIATISPGIS SCEYTLNTLR YADRVKELSP HSGPSGEQLI
601 QMETEEMEAC SNGALIPGNL SKEEEELSSQ MSSFNEAMTQ
641 IRELEEKAME ELKEIIQQGP DWLELSEMTE QPDYDLETFV
681 NKAESALAQQ AKHFSALRDV IKALRLAMQL EEQASRQISS
721 KKRPQ
```

A cDNA sequence that encodes the SEQ ID NO:3 human MCAK/Kif2c protein is shown below as SEQ ID NO:4 (NCBI accession number AB264115.1).

```
   1 ACGCTTGCGC GCGGGATTTA AACTGCGGCG GTTTACGCGG
  41 CGTTAAGACT TCGTAGGGTT AGCGAAATTG AGGTTTCTTG
  81 GTATTGCGCG TTTCTCTTCC TTGCTGACTC TCCGAATGGC
 121 CATGGACTCC TCGCTTCAGG CCCGCCTGTT TCCCGGTCTC
 161 GCTATCAAGA TCCAACGCAG TAATGGTTTA ATTCACAGTG
 201 CCAATGTAAC GACTGTGAAC TTGGAGAAAT CCTGTGTTTC
 241 AGTGGAATGG CAGAAGGAG GTGCCACAAA GGGCAAAGAG
 281 ATTGATTTTG ATGATGTGGC TGCAATAAAC CCAGAACTCT
 321 TACAGCTTCT TCCCTTACAT CCGAAGGACA ATCTGCCCTT
 361 GCAGGAAAAT GTAACAATCC AGAAACAAAA ACGGAGATCC
 401 GTCAACTCCA AAATTCCTGC TCCAAAAGAA AGTCTTCGAA
 441 GCCGCTCCAC TCGCATGTCC ACTGTCTCAG AGCTTCGCAT
 481 CACGGCTCAG GAGAATGACA TGGAGGTGGA GCTGCCTGCA
 521 GCTGCAAACT CCCGCAAGCA GTTTTCAGTT CCTCCTGCCC
 561 CCACTAGGCC TTCCTGCCCT GCAGTGGCTG AAATACCATT
 601 GAGGATGGTC AGCGAGGAGA TGGAAGAGCA AGTCCATTCC
 641 ATCCGTGGCA GCTCTTCTGC AAACCCTGTG AACTCAGTTC
 681 GGAGGAAATC ATGTCTTGTG AAGGAAGTGG AAAAAATGAA
 721 GAACAAGCGA AAGAGAAGA AGGCCCAGAA CTCTGAAATG
 761 AGAATGAAGA GAGCTCAGGA GTATGACAGT AGTTTTCCAA
 801 ACTGGGAATT TGCCCCAATC ATTAAAGAAT TCGGGCTAC
 841 TTTGGAATGT CATCCACTTA CTATGACTGA TCCTATCGAA
 881 GAGCACAGAA TATGTGTCTG TGTTAGGAAA CGCCCACTGA
 921 ATAAGCAAGA ATTGGCCAAG AAAGAAATTG ATGTGATTTC
 961 CATTCCTAGC AAGTGTCTCC TCTTGGTACA TGAACCCAAG
1001 TTGAAAGTGG ACTTAACAAA GTATCTGGAC AACCAAGCAT
```

```
1041 TCTGCTTTGA CTTTGCATTT GATGAAACAG CTTCGAATGA
1081 AGTTGTCTAC AGGTTCACAC CAAGGCCACT GGTACAGACA
1121 ATCTTTGAAG GTGGAAAAGC AACTTGTTTT GCATATGGCC
1161 AGACAGGAAG TGGCAAGACA CATACTATGG GCGGAGACCT
1201 CTCTGGGAAA GCCCAGAATG CATCCAAAGG GATCTATGCC
1241 ATGGCCTCCC GGGACGTCTT CCTCCTGAAG AATCAACCCT
1281 GCTACCGGAA GTTGGGCCTG GAAGTCTATG TGACATTCTT
1321 CGAGATCTAC AATGGGAAGC TGTTTGACCT GCTCAACAAG
1361 AAGGCCAAGC TGCGCGTGCT GGAGGACGCC AAGCAACAGG
1401 TGCAAGTGGT GGGGCTGCAG GAGCATCTGG TTAACTCTGC
1441 TGATGATGTC ATCAAGATGC TCGACATGCG CAGCGCCTGC
1481 AGAACCTCTG GCAGACATT TGCCAACTCC AATTCCTCCC
1521 GCTCCCACGC GTGCTTCCAA ATTATTCTTC GAGCTAAAGG
1561 GAGAATGCAT GGCAAGTTCT CTTTGGTAGA TCTGGCAGGG
1601 AATGAGCGAG GCGCAGACAC TTCCAGTGCT GACCGCCAGA
1641 CCCGCATGGA GGGCGCAGAA ATCAACAAGA GTCTCTTAGC
1631 CCTGAAGGAG TGCATCACCG CCCTGGGACA GAACAAGGCT
1721 CACACCCCGT TCCGTGAGAG CAAGCTGACA CAGGTGCTGA
1761 GGGACTCCTT CATTGGGGAA AACTCTAGGA CTTGCATGAT
1801 TGCCACGATC TCACCAGGCA TAAGCTCCTG TGAATATACT
1841 TTAAACACCC TGAGATATGC AGACAGGGTC AAGGAGCTGA
1881 GCCCCACAG TGGGCCCAGT GGAGAGCAGT TGATTCAAAT
1921 GGAAACAGAA GAGATGGAAG CCTGCTCTAA CGGGGCGCTG
1961 ATTCCAGGCA ATTTATCCAA GGAAGAGGAG GAAGTGTCTT
2001 CCCAGATGTC CAGCTTTAAC GAAGCCATGA CTCAGATCAG
2041 GGAGCTGGAG GAGAAGGCTA TGGAAGAGCT CAAGGAGATC
2081 ATACAGCAAG GACCAGACTG GCTTGAGCTC TCTGAGATGA
2121 CCGAGCAGCC AGACTATGAC CTGGAGACCT TTGTGAACAA
2161 AGCGGAATCT GCTCTGGCCC AGCAAGCCAA GCATTTCTCA
2201 GCCCTGCGAG ATGTCATCAA GGCCTTAGGC CTGGCCATGC
2241 AGCTGGAAGA GCAGGCTAGC AGACAAATAA GCAGCAAGAA
2281 ACGGCCCCAG TGACGACTGC AAATAAAAAT CTGTTTGGTT
2321 TGACACCCAG CCTCTTCCCT GGCCCTCCCC AGAGAACTTT
2361 GGGTACCTGG TGGGTCTAGG CAGGGTCTGA GCTGGGACAG
2401 GTTCTGGTAA ATGCCAAGTA TGGGGCATC TGGGCCCAGG
2441 GCAGCTGGGG AGGGGGTCAG AGTCACATGG ACACTCCTT
2481 TTCTGTTCCT CAGTTGTCGC CCTCACGAGA GGAAGGAGCT
2521 CTTAGTTACC CTTTTGTGTT GCCTTCTTT CCATCAAGGG
2561 GAATGTTCTC AGCATAGAGC TTTCTCCGCA GCATCCTGCC
2601 TGCGTGGACT GGCTGCTAAT GGAGAGCTCC CTGGGGTTGT
2641 CCTGGCTCTG GGGAGAGAGA CGGAGCCTTT AGTACAGCTA
2681 TCTGCTGGCT CTAAACCTTC TACGCCTTTG GGCCGAGCAC
2721 TGAATGTCTT GTACTTTAAA AAAATGTTTC TGAGACCTCT
2761 TTCTACTTTA CTGTCTCCCT AGAGTCCTAG AGGATCCCTA
2801 CTGTTTTCTG TTTTATGTGT TTATACATTG TATGTAACAA
2841 TAAAGAGAAA AATAAAAAA AAAAAAAAAA AAAAAAAAA
2881 AAAAAA
```

Another kinesin-13 protein is the KIF13A protein, which can have the following human sequence (SEQ ID NO:5; NCBI accession number NP_071396.4).

```
  1 MSDTKVKVAV RVRPMNRREL ELNTKCVVEM EGNQTVLHPP
 41 PSNTKQGERK PPKVFAFDYC FWSMDESNTT KYAGQEVVFK
 81 CLGEGILEKA FQGYNACIFA YGQTGSGKSF SMMGHAEQLG
121 LIPRLCCALF KRISLEQNES QTFKVEVSYM EIYNEKVRDL
161 LDPKGSRQSL KVREHKVLGP YVDGLSQLAV TSFEDIESLM
201 SEGNKSRTVA ATNMNEESSR SHAVFNIIIT QTLYDLQSGN
241 SGEKVSKVSL VDLAGSERVS KTGAAGERLK EGSNINKSLT
281 TLGLVISSLA DQAAGKGKSK FVPYRDSVLT WLLKDNLGGN
321 SQTSMIATIS PAADNYEETL STLRYADRAK RIVNHAVVNE
361 DPNAKVIREL REEVEKLREQ LSQAEAMKAP ELEKKLEESE
401 KLIKELTVTW EEKLRKTEEI AQERQRQLES MGISLEMSGI
441 KVGDDKCYLV NLNADPALNE LLVYYLKDHT RVGADTSQDI
481 QLFGIGIQPQ HCEIDIASDG DVILTPKENA RSCVNGTLVC
521 STTQLWHGDR ILWGNNHFFR INLPKRKRRD WLKDFEKETG
561 PPEHDLDAAS EASSEPDYNY EFAQMEVIMK TLNSNDPVQN
601 VVQVLEKQYL EEKRSALEEQ RLMYERELEQ LRQQLSPDRQ
641 PQSSGPDRLA YSSQTAQQKV TQWAEERDEL FRQSLAKLRE
681 QLVKANTLVR EANFLAEEMS KLTDYQVTLQ IPAANLSANR
721 KRGAIVSEPA IQVRRKGKST QVWTIEKLEN KLIDMRDLYQ
761 EWKEKVPEAK RLYGKRGDPF YEAQENHNLI GVANVFLECL
801 FCDVKLQYAV PIISQQGEVA GRLHVEVMRV TGAVPERVVE
841 DDSSENSSES GSLEVVDSSG EIIHRVKKLT CRVKIKEATG
881 LPINLSNFVF CQYTFWDQCE STVAAPVVDP EVPSPQSKDA
921 QYTVTFSHCK DYVVNVTEEF LEFISDGALA IEVWGHRCAG
961 NGSSIWEVDS LHAKTRTLHD RWNEVTRRIE MWISILELNE
1001 LGEYAAVELH QAKDVNTGGI FQLRQGHSRR VQVTVKPVQH
1041 SGTLPLMVEA ILSVSIGCVT ARSTKLQRGL DSYQRDDEDG
1081 DDMDSYQEED LNCVRERWSD ALIKRREYLD EQIKKVSNKT
1121 EKTEDDVERE AQLVEQWVGLTEERNAVLVP APGSGIPGAP
1161 ADWIPPPGME THIPVLFLDL NADDLSANEQ LVGPHASCVN
1201 SILPKEHGSQ FFYLPIIKHS DDEVSATASW DSSVHDSVHL
```

```
1241  NRVTPQNERI YLIVKTTVQL SHPAAMELVL RKRIAANIYN
1281  KQSFTQSLKR RISLKNIFYS CGVTYEIVSN IPKATEEIED
1321  RETTALLAAR SENEGTSDGE TYIEKYTRGV LQVENILSLE
1361  RLRQAVTVKE ALSTKARHIR RSLSTPNVHN VSSSRPDLSG
1401  FDEDDKGWPE NQLDMSDYSS SYQDVACYGT LPRDSPRRNK
1441  EGCTSETPHA LTVSPFKAFS PQPPKFFKPL MPVKEEHKKR
1481  IALEARPLLS QESMPPPQAH NPGCIVPSGS NGSSMPVEHN
1521  SKREKKIDSE EEENELEAIN RKLISSQPYV PVEFADFSVY
1561  NASLENREWF SSKVDLSNSR VLEKEVSRSP TTSSITSGYF
1601  SHSASNATLS DMVVPSSDSS DQLAIQTKDA DSTEHSTPSL
1641  VHDFRPSSNK ELTEVEKGLV KDKIIVVPLK ENSALAKGSP
1681  SSQSIPEKNS KSLCRTGSCS ELDACPSKIS QPARGFCPRE
1721  VTVEHTTNIL EDHSFTEFMG VSEGKDFDGL TDSSAGELSS
1761  RRSLPNKTGG KTVSDGLHHP SQLHSKLEND QVIIPEAAFW
1801  VLCCQ
```

A cDNA sequence that encodes the SEQ ID NO:5 human KIF13A protein is shown below as SEQ ID NO:6 (NCBI accession number NM_022113.5).

```
   1  CGGGATGGCC CGCGCGCCTC GGCGCTGCCT CTCGGAGCTC
  41  ACGGCGGAGC GGCGGCGGCC GCGCTCGAGG GGCGCGCGGC
  81  TGCAGCGGCG GCGGCGCCGC GCGTGAGGGG CCGCCTAAGG
 121  CCGAGCGGGC GCGGCGAGCG GCCGGGCGAG CGCAGCCAAC
 161  ATGTCGGATA CCAAGGTAAA AGTTGCCGTC CGGGTCCGGC
 201  CCATGAACCG ACGAGAACTG GAACTGAACA CCAAGTGCGT
 241  GGTGGAGATG GAAGGGAATC AAACGGTCCT GCACCCTCCT
 281  CCTTCTAACA CCAAACAGGG AGAAAGGAAA CCTCCCAAGG
 321  TATTTGCCTT TGATTATTGC TTTTGGTCCA TGGATGAATC
 361  TAACACTACA AAATACGCTG GTCAAGAAGT GGTTTTCAAG
 401  TGCCTTGGGG AAGGAATTCT TGAAAAAGCC TTTCAGGGGT
 441  ATAATGCGTG TATTTTTGCA TATGGACAGA CAGGTTCGGG
 481  AAAATCCTTT TCCATGATGG GCCATGCTGA GCAGGTGGGC
 521  CTTATTCCAA GGCTCTGCTG TGCTTTATTT AAAAGGATCT
 561  CTTTGGAGCA AAATGAGTCA CAGACCTTTA AGTTGAAGT
 601  GTCCTATATG GAAATTTATA ATGAGAAAGT TCGGGATCTT
 641  TTAGACCCCA AAGGGAGTAG ACAGTCTCTT AAAGTTCGAG
 681  AACATAAAGT TTTGGGACCA TATGTAGATG GTTTATCTCA
 721  ACTAGCTGTC ACTAGTTTTG AGGATATTGA GTCATTGATG
 761  TCTGAGGGAA ATAAGTCTCG AACGGTAGCT GCTACCAACA
 801  TGAACGAAGA AAGCAGCCGC TCCCATGCTG TGTTCAACAT
 841  CATAATCACA CAGACACTTT ATGACCTGCA GTCTGGGAAT
 881  TCCGGGGAGA AAGTCAGTAA GGTCAGCTTG GTAGACCTGG
 921  CGGGTAGCGA AAGAGTATCT AAAACAGGAG CTGCAGGAGA
 961  CCGACTGAAA GAAGGCAGCA ACATTAACAA ATCGCTTACA
1001  ACCTTCGGGT TGGTTATATC ATCACTGGCT GACCAGGCAG
1041  CTGGCAAGGG TAAAAGCAAA TTTGTGCCTT ATCGAGATTC
1081  AGTCCTCACT TGGCTGCTTA AGGACAACTT GGGGGGCAAC
1121  AGCCAAACCT CTATGATAGC CACAATCAGC CCAGCCGCAG
1161  ACAACTATGA AGAGAGCCTC TCCACATTAA GATATGCAGA
1201  CCGAGCCAAA AGGATTGTGA ACCATGCTGT TGTGAATGAG
1241  GACCCCAACG CAAAAGTGAT CCGAGAACTG CGGGAGGAAG
1281  TCGAGAAAGT GAGAGAGCAG CTCTCTCAGG CAGAGGCCAT
1321  GAAGGCCCCT GAACTGAAGG AGAAGCTCGA AGAGTCTGAA
1361  AAGCTGATAA AGAACTAAC AGTGACTTGG GAAGAGAAGC
1401  TGAGAAAAAC AGAAGAGATA GCACAGGAAA GACAACGACA
1441  AGTTGAAAGC ATGGGGATTT CCCTGGAGAT GTCCGGTATC
1481  AAGGTGGGGG ATGACAAATG CTACTTAGTC AATCTGAATG
1521  CAGACCCTGC TCTTAACGAA CTTCTGGTTT ATTATTTAAA
1561  GGATCACACC AGGGTGGGTG CAGATACCTC TCAAGATATC
1601  CAGCTTTTTG GCATAGGAAT TCAGCCTCAG CACTGTGAGA
1641  TTGACATTGC ATCTGATGGA GACGTCACTC TCACTCCAAA
1681  AGAAAATGCA AGGTCCTGTG TGAACGGCAC CCTTGTGTGC
1721  AGTACCACCC AGCTGTGGCA TGGTGACCGA ATCCTATGGG
1761  GAAATAATCA CTTTTTTAGA ATAAACTTAC CTAAGAGGAA
1801  ACGTCGAGAT TGGTTGAAAG ACTTTGAAAA AGAAACGGGC
1841  CCGCCAGAGC ATGACCTGGA TGCAGCCAGT GAGGCTTCCT
1881  CTGAACCAGA CTATAACTAT GAATTTGCAC AGATGGAAGT
1921  TATCATGAAA ACCCTGAATA GTAATGACCC AGTTCAAAAT
1961  GTGGTTCAGG TCCTGGAGAA ACAATACCTA AAGAAAAGA
2001  GAAGTGCCCT AGAGGAGCAG CGGCTCATGT ATGAGCGGGA
2041  ACTGGAGCAA CTCCGCCAGC AGCTCTCCCC CGACAGGCAG
2081  CCACAGAGTA GCGGCCCTGA CCGCCTGGCC TACAGCAGCC
2121  AGACACCGCA CCAGAAGGTG ACCCAGTGGG CAGAAGAGAG
2161  GGATGAACTC TTCCGACAAA GCCTGGCAAA ACTGCGAGAG
2201  CAGCTGGTTA AGCTAATAC CTTGGTGAGG GAAGCAAACT
2241  TCCTGGCTGA GGAAATGAGC AAACTCACCG ATTACCAAGT
2281  GACTCTTCAG ATCCCTGCTG CAAACCTCAG TGCCAATAGG
2321  AAGAGAGGTG CAATAGTGAG TGAACCAGCT ATCCAAGTGA
2361  GGAGGAAAGG AAAGAGCACC CAAGTGTGGA CCATTGAGAA
2401  GCTGGAGAAT AAATTAATTG ACATGAGAGA CCTTTACCAA
2441  GAATGGAAGG AAAAAGTTCC TGAGGCAAAG AGACTCTACG
2481  GAAAACGAGG TGACCCTTTC TATGAAGCCC AAGAAAATCA
```

```
2521 CAACCTCATC GGGGTGGCGA ATGTATTCTT GGAATGCCTC
2561 TTCTGTGATG TGAAACTTCA GTATGCAGTC CCTATCATCA
2601 GCCAGCAGGG GGAGGTTGCA GGGCGTCTCC ACGTGGAAGT
2641 GATGCGTGTT ACAGGAGCTG TTCCAGAGCG TGTGGTGGAG
2681 GATGACTCTT CGGAGAATTC CAGTGAAAGT GGGAGCCTTG
2721 AAGTCGTAGA CAGCAGCGGG GAAATCATTC ACCGAGTCAA
2761 AAAGCTGACA TGTCGGGTAA AAATTAAAGA AGCAACGGGG
2801 CTGCCCTTAA ACCTCTCAAA TTTTGTCTTC TGTCAATACA
2841 CATTCTGGGA CCAGTGTGAG TCTACGGTGG CTGCCCCGGT
2881 GGTGGACCCC GAGGTGCCTT CACCACAGTC CAAGGATGCC
2921 CAGTACACAG TGACCTTCTC CCACTGTAAG GACTATGTGG
2961 TGAATGTAAC AGAAGAATTT CTGGAGTTCA TTTCAGATGG
3001 AGCACTGGCC ATTGAAGTAT GGGGCCACCG GTGTGCTGGA
3041 AATGGCAGCT CCATCTGGGA GGTCGATTCT CTTCATGCTA
3081 AGACAAGAAC ACTGCATGAC AGGTGGAATG AAGTAACGCG
3121 AAGAATAGAA ATGTGGATCT CCATATTAGA ATTGAATGAG
3161 TTAGGAGAGT ATGCTGCAGT GGAACTTCAT CAGGCAAAAG
3201 ATGTCAACAC AGGAGGCATC TTTCAACTTA GACAGGGTCA
3241 TTCCCGTAGA GTACAAGTCA CGGTGAAACC TGTGCAGCAT
3281 TCAGGGACAC TGCCACTTAT GGTTGAAGCC ATCCTGTCAG
3321 TATCCATCGG CTGTGTAACT GCCAGGTCCA CCAAACTCCA
3361 AAGAGGGCTG GACAGTTACC AGAGAGATGA TGAGGATGGT
3401 GATGATATGG ATAGTTATCA GGAAGAAGAC TTAAACTGCG
3441 TAAGGGAGAG GTGGTCAGAT GCACTCATTA AACGACGAGA
3481 ATACCTGGAT GAACAGATAA AAAAGTCAG CAATAAAACA
3521 GAGAAAACAG AGGACGATGT GGAGCGGGAA GCCCAGCTTG
3561 TGGAGCAGTG GGTAGGGCTG ACTGAGGAAA GGAATGCTGT
3601 GCTGGTGCCA GCCCCAGGCA GTGGGATTCC TGGGGCACCT
3641 GCCGACTGGA TCCCACCTCC TGGAATGGAA ACCCACATAC
3681 CAGTTCTCTT CCTCGATTTG AATGCGGATG ACCTCAGTGC
3721 CAATGAGCAG CTTGTTGGCC CCCATGCATC CGGCGTGAAC
3761 TCCATCCTGC CAAGGAGCA TGGCAGCCAG TTTTTCTACC
3801 TGCCCATCAT AAAGCACAGT GATGATGAGG TTTCAGCCAC
3841 AGCCTCTTGG GATTCCTCGG TGCATGATTC TGTTCACTTG
3881 AATAGGGTCA CACCACAGAA TGAAAGGATT TACCTAATTG
3921 TGAAACCAC AGTTCAACTC AGCCACCCTG CTGCTATGGA
3961 GTTAGTATTA CGAAAACGAA TTGCAGCCAA TATTTACAAC
4001 AAACAGAGTT TCACGCAGAG TTTGAAGAGG AGAATATCCC
4041 TGAAAATAT ATTTTATTCC TGTGGTGTAA CCTATGAAAT
4081 AGTATCCAAT ATACCAAAGG CAACTGAGGA GATAGAGGAC
4121 CGGGAAACGC TGGCTCTCCT GGCAGCAAGG AGTGAAAACG
4161 AAGGCACATC AGATGGGGAG ACGTACATTG AGAAGTACAC
4201 TCGAGGCGTC CTGCAGGTGG AAAACATTCT GAGTCTTGAA
4241 CGGCTCCGGC AGGCCGTCAC AGTCAAAGAA GCACTTTCCA
4281 CCAAAGCCCG GCACATTCGG AGGAGCCTCA GTACACCAAA
4321 TGTTCATAAT GTCTCTTCCA GCCGACCGGA CCTTTCTGGC
4361 TTTGATGAAG ATGACAAGGG TTGGCCAGAG AACCAGTTGG
4401 ACATGTCTGA CTATAGCTCC AGTTACCAAG ATGTAGCATG
4441 TTATGGAACT TTACCCAGGG ATTCTCCTCG AAGGAATAAA
4481 GAAGGTTGTA CATCAGAGAC TCCTCATGCC TTAACCGTCA
4521 GCCCTTTTAA AGCATTCTCT CCTCAGCCAG CAAAGTTTTT
4561 CAAGCCCCTA ATGCCTGTAA AGAGGAGCA TAAGAAAAGG
4601 ATAGCCCTGG AAGCAAGGCC TCTTCTAAGC CAGGAGAGCA
4641 TGCCTCCACC TCAGGCACAT AACCCTGGCT GCATTGTACC
4681 CTCAGGAAGC AATGGCAGCA GCATGCCAGT AGAACACAAT
4721 AGCAAACGTG AGAAGAAGAT TGACTCTGAG GAGGAAGAAA
4761 ATGAGCTGGA AGCTATTAAC AGGAAGCTAA TAAGTTCACA
4801 GCCTTATGTA CCTGTGGAGT TTGCTGACTT CAGTGTTTAC
4841 AATGCCAGCT GGAGAACAG GGAATGGTTT TCCTCTAAAG
4881 TAGATCTGTC AAAACTCACGG GTCTTGGAGA AAGAAGTGTC
4921 CCGTAGCCCT ACCACCAGCA GTATTACCAG TGGCTACTTT
4961 TCCCACAGTG CCTCCAATGC CACCCTGTCT GACATGGTGG
5001 TCCCTTCTAG TGACAGCTCA GACCAGCTGG CCATTCAGAC
5041 GAAGGATGCA GACTCCACCG AGCACTCCAC ACCATCGCTT
5081 GTGCATGATT TCAGGCCGTC CTCAAACAAA GAGTTGACAG
5121 AAGTCGAAAA AGGCTTGGTA AAGGACAAGA TAATTGTGGT
5161 GCCACTCAAG GAAAACAGTG CCTTAGCCAA AGGGAGCCCA
5201 TCATCCCAGA GCATCCCTGA GAAAAACTCC AAATCACTGT
5241 GCAGGACTGG CTCATGTTCA GAACTAGATG CCTGCCCCAG
5281 CAAAATTAGC CAGCCAGCCA GGGGATTCTG CCCCAGGGAG
5321 GTGACGGTAG AACACACCAC CAACATCCTT GAAGACCATT
5361 CTTTCACAGA ATTTATGGGA GTGTCAGAGG GAAAAGATTT
5401 TGATGGTTTG ACAGATTCTT CTGCTGGAGA GCTTTCCAGT
5441 AGGAGGAGTC TACCAAATAA AACAGGCGGC AAGACTGTCT
5481 CCGATGGGCT CCACCACCCC AGCCAGCTGC ATTCCAAGTT
5521 AGAGAATGAC CAGGTAATAA TTCCAGAGGC AGCCTTTTGG
5561 GTTCTYTGCT GTCAATGAGT ATGTCTAACT GTATGTCAAC
5601 CCCAGAGGCC CTTCACCGCA CAACTTGGT AGGAAAGATT
5641 CATCCAGTTG TTTGTGACAG CAAAGATGAG CCCACAGAGA
5681 AGGAGGCTCA CTTCCTGCAC AGCTGTCTCT GTCGGAGAGC
5721 AAGTCTGTTT TGGGAACTAG AACGCAATTG TGAAATTATA
```

```
5761 AGACCAGTGG ATTTTTTTAC CTGGCACATG GGTTGGTGTT
5801 GAATGAAGTG TTCAGATGGA TAAGGATCAA TCTCATATTC
5841 ATTCCCTGGG ATGTTTAGTT ACCAGTTTTC CCAAAGTGTT
5881 CTGGTAGCAT CTACCATATT TCATCAAATC TGTGATTCCT
5921 TTGATTATTA TATGAACCAT TATTTTATGT ATCATTAAGA
5961 AAAAATACTG CCAATTAAAC TCTGTCATAT CAACAAAAAA
6001 AAAAA
```

An example sequence for a human MCAK protein is shown below as SEQ ID NO:7; NCBI accession number NP_006836.2).

```
  1 MAMDSSLQAR LFPGLAIKIQ RSNGLIHSAN VRTVNLEKSC
 41 VSVEWAEGGA TKGKEIDFDD VAAINPELLQ LLPLHPKDNL
 81 PLQENVTIQK QKRRSVNSKI PAPKESLRSR STRMSTVSEL
121 RITAQENDME VELPAAANSR KQFSVPPAPT RPSCPAVAEI
161 PLRMVSEEME EQVHSIRGSS SANPVNSVRR KSCLVKEVEK
201 MKNKREEKKA QNSEMRMKRA QEYDSSFPNW EFARMIKEFR
241 ATLECHPLTM TDPIEEHRIC VCVRKRPLNK QELAKKEIDV
231 ISIPSKCLLL VHEPKLKVDL TKYLENQAFC FDFAFDETAS
321 NEVVYRFTAR PLVQTIFEGG KATCFAYGQT GSGKTHTMGG
361 DLSGKAQNAS KGIYAMASRD VFLLKNQPCY RKLGLEVYVT
401 FFEIYNGKLF DLLNKKAKLR VLEDGKQQVQ VVGLQEHLVN
441 SADDVIKMID MGSACRTSGQ TFANSNSSRS HACFQIILRA
431 KGRMHGKFSL VDLAGNERGA DTSSADRQTR MEGAEINKSL
521 LALKECIRAL GQNKAHTPFR ESKLTQVLRD SFIGENSRTC
561 MIATISPGIS SCEYTLNTLR YADRVKELSP HSGPSGEQLI
601 QMETEEMEAC SNGALIPGNL SKEEEELSSQ MSSFNEAMTQ
641 IRELEEKAME ELKEIIQQGP DWLELSEMTE QPDYDLETFV
681 NKAESALAQQ AKHFSALRDV IKALRLAMQL EEQASRQISS
721 KKRPQ
```

A cDNA sequence that encodes the SEQ ID NO:7 human MCAK protein is shown below as SEQ ID NO:8 (NCBI accession number NM 0068453).

```
   1 ACGCTTGCGC GCGGGATTTA AACTGCGGCG GTTTACGCGG
  41 CGTTAAGACT TCGTAGGGTT AGCGAAATTG AGGTTTCTTG
  81 GTATTGCGCG TTTCTCTTCC TTGCTGACTC TCCGAATGGC
 121 CATGGACTCG TCGCTTCAGG CCCGCCTGTT TCCCGGTCTC
 161 GCTATCAAGA TCCAACGCAG TAATGGTTTA ATTCACAGTG
 201 CCAATGTAAG GACTGTGAAC TTGGAGAAAT CCTGTGTTTC
 241 AGTGGAATGG GCAGAAGGAG GTGCCACAAA GGGCAAAGAG
 281 ATTGATTTTG ATGATGTGGC TGCAATAAAC CCAGAACTCT
 321 TACAGCTTCT TCCCTTACAT CCGAAGGACA ATCTGCCCTT
 361 GCAGGAAAAT GTAACAATCC AGAAACAAAA ACGGAGATCC
 401 GTCAACTCCA AAATTCCTGC TCCAAAAGAA AGTCTTCGAA
 441 GCCGCTCCAC TCGCATGTCC ACTGTCTCAG AGCTTCGCAT
 481 CACGGCTCAG GAGAATGACA TGGAGGTGGA GCTGCCTGCA
 521 GCTGCAAACT CCCGCAAGCA GTTTTCAGTT CCTCCTGCCC
 561 CCACTAGGCC TTCCTGCCCT GCAGTGGCTG AAATACCATT
 601 GAGGATGGTC AGCGAGGAGA TGGAAGAGCA GTCCATTCC
 641 ATCCGAGGCA GCTCTTCTGC AAACCCTGTG AACTCAGTTC
 681 GGAGGAAATC ATGTCTTGTG AAGGAAGTGG AAAAAATGAA
 721 GAACAAGCGA AAGAGAAGA AGGCCCAGAA CTCTGAAATG
 761 AGAATGAAGA GAGCTCAGGA GTATGACAGT AGTTTTCCAA
 801 ACTGGGAATT TGCCCGAATG ATTAAAGAAT TTCGGGCTAC
 841 TTTGGAATGT CATCCACTTA CTATGACTGA TCCTATCGAA
 881 GAGCACAGAA TATGTGTCTG TGTTAGGAAA CGCCCACTGA
 921 ATAAGCAAGA ATTGGCCAAG AAAGAAATTG ATGTGATTTC
 961 CATTCCTAGC AAGTGTCTCC TCTTGGTACA TGAACCCAAG
1001 TTGAAAGTGG ACTTAACAAA GTATCTGGAG AACCAAGCAT
1041 TCTGCTTTGA CTTTGCATTT GATGAAACAG CTTCGAATGA
1081 AGTTGTCTAC AGGTTCACAG CAAGGCCACT GGTACAGACA
1121 ATCTTTGAAG GTGGAAAAGC AACTTGTTTT GCATATGGCC
1161 AGACAGGAAG TGGCAAGACA CATACTATGG GCGGAGACCT
1201 CTCTGGGAAA GCCCAGAATG CATCCAAAGG GATCTATGCC
1241 ATGGCCTCCC GGGACGTCTT CCTCCTGAAG AATCAACCCT
1281 GCTACCGGAA GTTGGGCCTG GAAGTCTATG TGACATTCTT
1321 CGAGATCTAC AATGGGAAGC TGTTTGACCT GCTCAACAAG
1361 AAGCCCAAGC TGCGCGTGCT GGAGGACGGC AAGCAACAGG
1401 TGCAAGTGGT GGGGCTGCAG GAGCATCTGG TTAACTCTGC
1441 TGATGATGTC ATCAAGATGA TCGACATGGG CAGCGCCTGC
1481 AGAACCTCTG GCAGACATT TGCCAACTCC AATTCCTCCC
1521 GCTCCCACGC GTGCTTCCAA ATTATTCTTC GAGCTAAAGG
1561 GAGAATGCAT GGCAAGTTCT CTTTGGTAGA CTGGCAGGG
1601 AATGAGCGAG GCGCGGACAC TTCCAGTGCT GACCGGCAGA
1641 CCCGCATGGA GGGCGCAGAA ATCAACAAGA GTCTCTTAGC
1681 CCTGAAGGAG TGCATCAGGG CCCTGGGACA GAACAAGGCT
1721 CACACCCCGT TCCGTGAGAG CAAGCTGACA CAGGTGCTGA
1761 GGGACTCCTT CATTGGGGAG AACTCTAGGA CTTGCATGAT
1801 TGCCACGATC TCACCAGGCA TAAGCTCCTG TGAATATACT
1841 TTAAACACCC TGAGATATGC AGACAGGGTC AAGGAGCTGA
1881 GCCCCCACAG TGGGCCCAGT GGAGAGCAGT TGATTCAAAT
1921 GGAAACAGAA GAGATGGAAG CCTGCTCTAA CGGGGCGCTG
```

-continued

```
1961 ATTCCAGGCA ATTTATCCAA GGAAGAGGAG GAACTGTCTT
2001 CCCAGATGTC CAGCTTTAAC GAAGCCATGA CTCAGATCAG
2041 GGAGCTGGAG GAGAAGGCTA TGGAAGAGCT CAAGGAGATC
2081 ATACAGCAAG ACCAGACTGC GCTTGAGCTC TCTGAGATGA
2121 CCGAGCAGCC AGACTATGAC CTGGAGACCT TTGTGAACAA
2161 AGCGGAATCT GCTCTGGCCC AGCAAGCCAA GCATTTCTCA
2201 GCCCTGCGAG ATGTCATCAA GGCCTTGCGC CTGGCCATGC
2241 AGCTGGAAGA GCAGGCTAGC AGACAAATAA GCAGCAAGAA
2281 ACGGCCCCAG TGACGACTGC AAATAAAAAT CTGTTTGGTT
2321 TGACACCCAG CCTCTTCCCT GGCCCTCCCC AGAGAACTTT
2361 GGGTACCTGG TGGGTCTAGG CAGGGTCTGA GCTGGGACAG
2401 GTTCTGGTAA ATGCCAAGTA TGGGGGCATC TGGGCCCAGG
2441 GCAGCTGGGG AGGGGGTCAG AGTGACATGG ACACTCCTT
2481 TTCTGTTCCT CAGTTGTCGC CCTCACGAGA GGAAGGAGCT
2521 CTTAGTTACC CTTTTGTGTT GCCCTTCTTT CCATCAAGGG
2561 GAATGTTCTC AGCATAGACC TTTCTCCGCA GCATCCTGCC
2601 TGCGTGGACT GGCTGCTAAT GGAGAGCTCC CTGGGGTTGT
2641 CCTGGCTCTG GGGAGAGAGA CGGAGCCTTT AGTACAGCTA
2681 TCTGCTGGCT CTAAACCTTC TACGCCTTTG GGCCGAGCAC
2721 TGAATGTCTT GTACTTTAAA AAAATGTTTC TGAGACCTCT
2761 TTCTACTTTA CTGTCTCCCT AGAGATCCTA GAGGATCCCT
2801 ACTGTTTTCT GTTTTATGTG TTTATACATT GTATGTAACA
2841 ATAAAGAAA AAAATAAATC AGCTGTTTAA GTGTGTGGAA
2881 AAAAAAAAAA AAAAAA
```

An example sequence for a human ABCC4 protein is shown below as SEQ ID NO:9; NCBI accession number AAH41560.1).

```
  1 MLPVYQEVKP NPLQDANLCS RVFFWWLNPL FKIGHKRRLE
 41 EDDMYSVLPE DRSQHLGEEL QGFWDKEVLR AENDAQKPSL
 81 TRAIIKCYWK SYLVLGIFTL IEESAKVIQP IFLGKIINYF
121 ENYDPMDSVA LNTAYAYATV LTFCTLILAI LHHLYFYHVQ
161 CAGMRLRVAM CHMIYRKALR LSNMAMGKTT TGQIVNLLSN
201 DVNKFDQVTV FLHFLWAGPL QAIAVTALLW MEIGISCLAG
241 MAVLIILLPL QSCFGKLFSS LRSKTATFTD ARIRTMNEVI
281 TGIRIIKMYA WEKSFSNLIT NLRKKEISKI LRSSCLRGMN
321 LASFFSASKI IVFVTFTTYV LLGSVITASR VFVAVTLYGA
361 VRLTVKLFFP SAIERVSEAI VSIRRIQTFL LLDEISQRNR
401 QLPSDGKKMV HVQDFTAFWD KASETPTLQG LSFTVRPGEL
441 LAVVGPVGAG KSSLLSAVLG ELAPSHGLVS VHGRIAYVSQ
481 QPWVFSGTLR SNILFGKKYE KERYEKVIKA CALKKDLQLL
521 EDGDLTVIGD RGTTLSGGQK ARVNLARAVY QDADIYLLDD
561 PLSAVDAEVS RHLFELCICQ ILHEKITILV THQLQYLKAA
601 SQILILKDGK MVQKGTYTEF LKSGIDFGSL LKKDNEESEQ
641 PPVPGTPTLR NRTFSESSVW SQQSSRPSLK DGALESQDTE
681 NVPVTLSEEN RSEGKVGFQA YKNYFRAGAH WIVFIFLILL
721 NTAAQVAYVL QDWWLSYWAN KQSMLNVTVN GGGNVTEKLD
761 LNWYLGIYSG LTVATVLFGI ARSLLVFYVL VNSSQTLHNK
801 MFESILKAPV LFFDRNPIGR ILNRFSKDIG HLDDLLPLTF
841 LDFIQRWDLA VLSWLVSNS
```

A cDNA sequence that encodes the SEQ ID NO:9 human ABCC4 protein is shown below as SEQ ID NO:10 (NCBI accession number BC041560.1).

```
   1 GGCCGGAGCC CCAGCATCCC TGCTTGAGGT CCAGGAGCGG
  41 AGCCCGCGGC CACCGCCGCC TGATCAGCGC GACCCCGGCC
  81 CGCGCCCGCC CCGCCCGGCA AGATGCTGCC CGTGTACCAG
 121 GAGGTGAAGC CCAACCCGCT GCAGGACGCG AACCTCTGCT
 161 CACGCGTGTT CTTCTGGTGG CTCAATCCCT TGTTTAAAAT
 201 TGGCCATAAA CGGAGATTAG AGGAAGATGA TATGTATTCA
 241 GTGCTGCCAG AAGACCGCTC ACAGCACCTT GGAGAGGAGT
 281 TGCAAGGGTT CTGGGATAAA GAAGTTTTAA GAGCTGAGAA
 321 TGACGCACAG AAGCCTTCTT TAACAAGAGC AATCATAAAG
 361 TGTTACTGGA AATCTTATTT AGTTTTGGGA ATTTTTACGT
 401 TAATTGAGGA AAGTGCCAAA GTAATCCAGC CCATATTTTT
 441 GGGAAAAATT ATTAATTATT TTGAAAATTA TGATCCCATG
 481 GATTCTGTGG CTTTGAACAC AGCGTACGCC TATGCCACGG
 521 TGCTGACTTT TTGCACGCTC ATTTTGGCTA TACTGCATCA
 561 CTTATATTTT TATCACGTTC AGTGTGCTGG GATGAGGTTA
 601 CGAGTAGCCA TGTGCCATAT GATTTATCGG AAGGCACTTC
 641 GTCTTAGTAA CATGGCCATG GGGAAGACAA CCACAGGCCA
 681 GATAGTCAAT CTGCTGTCCA ATGATGTGAA CAAGTTTGAT
 721 CAGGTGACAG TGTTCTTACA CTTCCTGTGG GCAGGACCAC
 761 TGCAGGCGAT CGCACTGACT GCCCTACTCT GGATGGAGAT
 801 AGGAATATCG TGCCTTGCTG GGATGGCAGT TCTAATCATT
 841 CTCCTGCCCT TGCAAAGCTG TTTTGGGAAG TTGTTCTCAT
 881 CACTGAGGAG TAAAACTGCA ACTTTCACGG ATGCCAGGAT
 921 CAGGACCATG AATGAAGTTA TAACTGGTAT AAGGATAATA
 961 AAAATGTACG CCTGGGAAAA GTCATTTTCA AATCTTATTA
1001 CCAATTTGAG AAAGAAGGAG ATTTCCAAGA TTCTGAGAAG
1041 TTCCTGCCTC AGGGGGATGA ATTTGGCTTC GTTTTTCAGT
1081 GCAAGCAAAA TCATCGTGTT TGTGACCTTC ACCACCTACG
1121 TGCTCCTCGG CAGTGTGATC ACAGCCAGCC GCGTGTTCGT
```

-continued

```
1161 GGCAGTGACG CTGTATGGGG CTGTGCGGCT GACGGTTACC
1201 CTCTTCTTCC CCTCAGCCAT TGAGAGGGTG TCAGAGGCAA
1241 TCGTCAGCAT CCGAAGAATC CAGACCTTTT TGCTACTTGA
1281 TGAGATATCA CAGCGCAACC GTCAGCTGCC GTCAGATGGT
1321 AAAAGATGG TGCATGTGCA GGATTTTACT GCTTTTTGGG
1361 ATAAGGCATC AGAGACCCCA ACTCTACAAG GCCTTTCCTT
1401 TACTGTCAGA CCTGGCGAAT TGTTAGCTGT GGTCGGCCCC
1441 GTGGGAGCAG GGAAGTCATC ACTGTTAAGT GCCGTGCTCG
1481 GGGAATTGGC CCCAAGTCAC GGGCTGGTCA GCGTGCATGG
1521 AAGAATTGCC TATGTGTCTC AGCAGCCCTG GGTGTTCTCG
1561 GGAACTCTGA GGAGTAATAT TTTATTTGGG AAGAAATACG
1601 AAAAGGAACG ATATGAAAAA GTCATAAAGG CTTGTGCTCT
1641 GAAAAAGGAT TTACAGCTGT TGGAGGATGG TGATCTGACT
1681 GTGATAGGAG ATCGGGGAAC CACGCTGAGT GGAGGGCAGA
1721 AAGCACGGGT AAACCTTGCA AGAGCAGTGT ATCAAGATGC
1761 TGACATCTAT CTCCTGGACG ATCCTCTCAG TGCAGTAGAT
1801 GCGGAAGTTA GCAGACACTT GTTCGAACTG TGTATTTGTC
1841 AAATTTTGCA TGAGAAGATC ACAATTTTAG TGACTCATCA
1881 GTTGCAGTAC CTCAAAGCTG CAAGTCAGAT TCTGATATTG
1921 AAAGATGGTA AAATGGTGCA GAAGGGGACT TACACTGAGT
1961 TCCTAAAATC TGGTATAGAT TTTGGCTCCC TTTTAAAGAA
2001 GGATAATGAG GAAAGTGAAC AACCTCCAGT TCCAGGAACT
2041 CCCACACTAA GGAATCGTAC CTTCTCAGAG TCTTCGGTTT
2081 GGTCTCAACA ATCTTCTAGA CCCTCCTTGA AAGATGGTGC
2121 TCTGGAGAGC CAAGATACAG AGAATGTCCC AGTTACACTA
2161 TCAGAGGAGA ACCGTTCTGA AGGAAAAGTT GGTTTTCAGG
2201 CCTATAAGAA TTACTTCAGA GCTGGTGCTC ACTGGATTGT
2241 CTTCATTTTC CTTATTCTCC TAAACACTGC AGCTCAGGTT
2281 GCCTATGTGC TTCAAGATTG GTGGCTTTCA TACTGGGCAA
2321 ACAAACAAAG TATGCTAAAT GTCACTGTAA ATGGAGGAGG
2361 AAATGTAACC GAGAAGCTAG ATCTTAACTG GTACTTAGGA
2401 ATTTATTCAG CTTTAACTGT AGCTACCGTT CTTTTTGGCA
2441 TAGCAAGATC TCTATTGGTA TTCTACGTCC TTGTTAACTC
2481 TTCACAAACT TTGCACAACA AAATGTTTGA GTCAATTCTG
2521 AAAGCTCCGG TATTATTCTT TGATAGAAAT CCAATAGGAA
2561 GAATTTTAAA TCGTTTCTCC AAAGACATTG ACACTTGGA
2601 TGATTTGCTG CCGCTGACCT TTTAGATTT CATCCAGAGA
2641 TGGGATCTCG CTGTGTTGTC CTGGCTGGTC TCAAACTCCT
2681 AGGCTCAAGC AATCCTCCTC CCTCCTCAAG CAAACCTCAG
2721 TGCTGGGATT ATAGGCATGA GCCACTGTAC CTGGCTAAAT
2761 GTTGTTTTTT TGATATTCAA TTTTTGTTTA TAGAATTTTC
2801 ATTTGTTTTG CTCTTATACT TTTCATCTTT TTATGTTTAT
2841 TGACCAATTA AATATCATTT GGGTAACCAC CTAAAAAAAA
2881 AAAAAAAAAA
```

An example sequence for a human ABCG2 protein is shown below as SEQ ID NO:11; NCBI accession number AAG52982.1).

```
  1 MSSSNVEVFI PVSQGNTNGF PATASNDLKA FTEGAVLSFH
 41 NICYRVKLKS GFLPCRKPVE KEILSNINGI MKPGLNAILG
 81 PTGGGKSSLL DVLAARKDPS GLSGDVLING APRPANFKCN
121 SGYVVQDDVV MGTLTVRENL QFSAALRLAT TMTNHEKNER
161 INRVIQELGL DKVADSKVGT QFIRGVSGGE RKRTSIGMEL
201 ITDPSILFLD EPTTGLDSST ANAVLLLLKR MSKQCRTIIF
241 SIHQPRYSIF KLFDSLTLLA SGRLMFHGPA QEALGYFESA
281 GYHCEAYNNP ADFFLDIING DSTAVALNRE EDFKATEIIE
321 PSKQDKPLIE KLAEIYVNSS FYKETKAELH QLSGGEKKKK
361 ITVFKEISYT TSFCHQLRWV SKRSFKNLLG NPQASIAQII
401 VTVVLGLVIG AIYFCLKNDS TGIQNRAGVL FFLTTNQCFS
441 SVSAVELFVV EKKLFIHEYI SGYYRVSSYF LGKLLSDLLP
481 MRMLPSIIFT CIVYFMLGLK AKADAFFVMM FTLMMVAYSA
521 SSMALAIAAG QSVVSVATLL MTICFVFMMI FSGLLVNLTT
561 IASWLSWLQY FSIPRYGFTA LQHNEFLGQN FCPGLNATGN
601 NPCNYATCTG EEYLVKQGID LSPWGLWKNH VALACMIVIF
641 LTIAYLKLLF LKKYS
```

A cDNA sequence that encodes the SEQ ID NO:11 human ABCG2 protein is shown below as SEQ ID NO:12 (NCBI accession number AY017168.1).

```
  1 ACCGTGCACA TGCTTGGTGG TCTTGTTAAG TGGAAACTGC
 41 TGCTTTAGAG TTTGTTTGGA AGGTCCGGGT GACTCATCCC
 81 AACATTTACA TCCTTAATTG TTAAAGCGCT GCCTCCGAGC
121 GCACGCATCC TGAGATCCTG AGCCTTTGGT TAAGACCGAG
161 CTCTATTAAG CTGAAAAGAT AAAAACTCTC AGATGTCTT
201 CCAGTAATGT CGAAGTTTTT ATCCCAGTGT CACAAGGAAA
241 CACCAATGGC TTCCCCGCGA CAGCTTCCAA TGACCTGAAG
281 GCATTTACTG AAGGAGCTGT GTTAAGTTTT CATAACATCT
321 GCTATCGAGT AAAACTGAAG AGTGGCTTTC TACCTTGTCG
361 AAAACCAGTT GAGAAAGAAA TATTATCGAA TATCAATGGG
401 ATCATGAAAC CTGGTCTCAA CGCCATCCTG GGACCCACAG
441 GTGGAGGCAA ATCTTCGTTA TTAGATGTCT TAGCTGCAAG
481 GAAAGATCCA AGTGGATTAT CTGGAGATGT TCTGATAAAT
521 GGAGCACCGC GACCTGCCAA TTTCAAATGT AATTCAGGTT
```

-continued

```
 561 ACGTGGTACA AGATGATGTT GTGATGGGCA CTCTGACGGT
 601 GAGAGAAAAC TTACAGTTCT CAGCAGCTCT TCGGCTTGCA
 641 ACAACTATGA CGAATCATGA AAAAAACGAA CGGATTAACA
 681 GGGTCATTCA AGAGTTAGGT CTGGATAAAG TGGCAGACTC
 721 CAAGGTTGGA ACTCAGTTTA TCCGTGGTGT GTCTGGAGGA
 761 GAAAGAAAAA GGACTAGTAT AGGAATGGAG CTTATCACTG
 801 ATCCTTCCAT CTTGTTCTTG GATGAGCCTA CAACTGGCTT
 841 AGACTCAAGC ACAGCAAATG CTGTCCTTTT GCTCCTGAAA
 881 AGGATGTCTA AGCAGGGACG AACAATCATC TTCTCCATTC
 921 ATCAGCCTCG ATATTCCATC TTCAAGTTGT TTGATAGCCT
 961 CACCTTATTG GCCTCAGGAA GACTTATGTT CCACGGGCCT
1001 GCTCAGGAGG CCTTGGGATA CTTTGAATCA GCTGGTTATC
1041 ACTGTGAGGC CTATAATAAC CCTGCAGACT TCTTCTTGGA
1081 CATCATTAAT GGAGATTCCA CTGCTGTGGC ATTAAACAGA
1121 GAAGAAGACT TTAAAGCCAC AGAGATCATA GAGCCTTCCA
1161 AGCAGGATAA GCCACTCATA GAAAAATTAG CGGAGATTTA
1201 TGTCAACTCC TCCTTCTACA AAGAGACAAA AGCTGAATTA
1241 CATCAACTTT CCGGGGGTGA GAAGAAGAAG AAGATCACAG
1281 TCTTCAAGGA GATCAGCTAC ACCACCTCCT TCTGTCATCA
1321 ACTCAGATGG GTTTCCAAGC GTTCATTCAA AAACTTGCTG
1361 GGTAATCCCC AGGCCTCTAT AGCTCAGATC ATTGTCACAG
1401 TCGTACTGGG ACTGGTTATA GGTGCCATTT ACTTTGGGCT
1441 AAAAAATGAT TCTACTGGAA TCCAGAACAG AGCTGGGGTT
1481 CTCTTCTTCC TGACGACCAA CCAGTGTTTC AGCAGTGTTT
1521 CAGCCGTGGA ACTCTTTGTG GTAGAGAAGA AGCTCTTCAT
1561 ACATGAATAC ATCAGCGGAT ACTACAGAGT GTCATCTTAT
1601 TTCCTTGGAA AACTGTTATC TGATTTATTA CCCATGAGGA
1641 TGTTACCAAG TATTATATTT ACCTGTATAG TGTACTTCAT
1681 GTTAGGATTG AAGGCAAAGG CAGATGCCTT CTTCGTTATG
1721 ATGTTTACCC TTATGATGGT GGCTTATTCA GCCAGTTCCA
1761 TGGCACTGGC CATAGCAGCA GGTCAGAGTG TGGTTTCTGT
1801 AGCAACACTT CTCATGACCA TCTGTTTTGT GTTTATGATG
1841 ATTTTTTCAG GTCTGTTGGT CAATCTCACA ACCATTGCAT
1881 CTTGGCTGTC ATGGCTTCAG TACTTCAGCA TTCCACGATA
1921 TGGATTTACG GCTTTGCAGC ATAATGAATT TTTGGGACAA
1961 AACTTCTGCC CAGGACTCAA TGCAACAGGA AACAATCCTT
2001 GTAACTATGC AACATGTACT GGCGAAGAAT ATTTGGTAAA
2041 GCAGGGCATC GATCTCTCAC CCTGGGGCTT GTGGAAGAAT
2081 CACGTGGCCT TGGCTTGTAT GATTGTTATT TTCCTCACAA
2121 TTGCCTACCT GAAATTGTTA TTTCTTAAAA AATATTCTTA
2161 AATTTCCCCT TAATTCAGTA TGATTTATCC TCACATAAAA
2201 AAGAAGCACT TTGATTGAAG TATTCAAAAA AAAAAAAAA
2241 AAAAAAA
```

Kinsin-13, MCAK, ABCC4, and/or ABCG2 proteins and nucleic acids can exhibit sequence variation. However, variants with less than 100% sequence identity to the amino acid and nucleic acid sequences shown herein can still have similar activities. For example, Kinsin-13, MCAK, ABCC4, and/or ABCG2 proteins and nucleic acid with at least 90%, at least 92%, at least 95%, at least 96%, at least 97%, at least 98%, at least 99%, or at least 99.5% sequence identity to any of SEQ ID NOs: 1-12 can still be used in the compositions and methods described herein.

The kinsin-13, MCAK, ABCC4, and/or ABCG2 proteins can be administered to subjects who may exhibit chromosomal instability, or who may be suffering from cancer or be suspected of developing cancer. Similarly, expression cassettes and/or expression vectors encoding kinsin-13, MCAK, ABCC4, and/or ABCG2 proteins can be administered to subjects who may exhibit chromosomal instability, or who may be suffering from cancer or be suspected of developing cancer.

In addition, kinsin-13, MCAK, ABCC4, and/or ABCG2 agonists can be administered to enhance kinesin-13 protein activities. For example, the Kinesin 13 agonist referred to as UMK57, which is specific for Kif2c/MCAK, can be administered to subjects who may exhibit chromosomal instability, or who may be suffering from cancer or be suspected of developing cancer. The structure of UMK57 is shown below, where X is a methyl ($CH_3$) group.

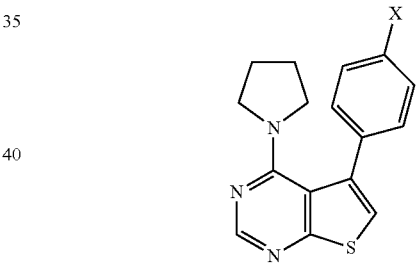

In some cases, the expression of various endogenous nucleic acids (mRNAs) and proteins can be inhibited. For example, the expression of the following can be inhibited STING, cGAS, NF-κB transcription factor p52, NF-κB transcription factor RelB, ENPP1, LTβR, BAFFR, CD40, RANK, FN14, NIK (MAP3K14), MST1, or any combination thereof.

One example of a human STING protein sequence (SEQ ID NO:13; NCBI accession number NP_938023 XP_291127) is shown below.

```
  1 MPHSSLHPSI PCPRGHGAQK AALVLLSACL VTLWGLGEPP
 41 EHTLRYLVLH LASLQLGLLL NGVCSLAEEL RHIHSRYRGS
 81 YWRTVRACLG CPLRRGALLL LSIYFYYSLP NAVGPPFTWM
121 LALLGLSQAL NILLGLKGLA PAEISAVCEK GNFNVAHGLA
161 WSYYIGYLRL ILPELQARIR TYNQHYNNLL RGAVSQRLYI
201 LLPLDCGVPD NLSMADPNIR FLDKLPQQTG DHAGIKDRVY
```

```
241  SNSIYELLEN GQRAGTCVLE YATPLQTLFA MSQYSQAGFS
281  REDRLEQAKL FCRTLEDILA DAPESQNNCR LIAYQEPADD
321  SSFSLSQEVL RHLRQEEKEE VTVGSLKTSA VPSTSTMSQE
361  PELLISGMEK PLPLRTDFS
```

A cDNA sequence that encodes the SEQ ID NO:13 human STING protein is shown below as SEQ ID NO:14 (NCBI accession number NM_198282 XM_291127).

```
   1 TATAAAAATA GCTCTTGTTA CCGGAAATAA CTGTTCATTT
  41 TTCACTCCTC CCTCCTAGGT CACACTTTTC AGAAAAAGAA
  81 TCTGCATCCT GGAAACCAGA AGAAAAATAT GAGACGGGCA
 121 ATCATCGTGT GATGTGTGTG CTGCCTTTGG CTGAGTGTGT
 161 GGAGTCCTGC TCAGGTGTTA GGTACAGTGT GTTTGATCGT
 201 GGTGGCTTGA GGGGAACCCG CTGTTCAGAG CTGTGACTGC
 241 GGCTGCACTC AGAGAAGCTG CCCTTGGCTG CTCGTAGCGC
 281 CGGGCCTTCT CTCCTCGTCA TCATCCAGAG CAGCCAGTGT
 321 CCGGGAGGCA GAAGATGCCC CACTCCAGCC TGCATCCATC
 361 CATCCCGTGT CCCAGGGGTC ACGGGCCCA GAAGGCAGCC
 401 TTGGTTCTGC TGAGTGCCTG CCTGGTGACC CTTTGGGGGC
 441 TAGGAGAGCC ACCAGAGCAC ACTCTCCGGT ACCTGGTGCT
 481 CCACCTAGCC TCCCTGCAGC TGGGACTGCT GTTAAACGGG
 521 GTCTGCAGCC TGGCTGAGGA GCTGCGCCAC ATCCACTCCA
 561 GGTACCGGGG CAGCTACTGG AGGACTGTGC GGGCCTGCCT
 601 GGGCTGCCCC CTCCGCCGTG GGGCCCTGTT GCTGCTGTCC
 641 ATCTATTTCT ACTACTCCCT CCCAAATGCG GTCGGCCCGC
 681 CCTTCACTTG GATGCTTGCC CTCCTGGGCC TCTCGCAGGC
 721 ACTGAACATC CTCCTGGGCC TCAAGGGCCT GGCCCCAGCT
 761 GAGATCTCTG CAGTGTGTGA AAAAGGGAAT TTCAACGTGG
 801 CCCATGGGCT GGCATGGTCA TATTACATCG GATATCTGCG
 841 GCTGATCCTG CCAGAGCTCC AGGCCCGGAT TCGAACTTAC
 881 AATCAGCATT ACAACAACCT GCTACGGGGT GCAGTGAGCC
 921 AGCGGCTGTA TATTCTCCTC CCATTGGACT GTGGGGTGCC
 961 TGATAACCTG AGTATGGCTG ACCCCAACAT TCGCTTCCTG
1001 GATAAACTGC CCCAGCAGAC CGGTGACCAT GCTGGCATCA
1041 AGGATCGGGT TTACAGCAAC AGCATCTATG AGCTTCTGGA
1081 GAACGGGCAG CGGGCGGGCA CCTGTGTCCT GGAGTACGCC
1121 ACCCCCTTGC AGACTTTGTT TGCCATGTCA CAATACAGTC
1161 AAGCTGGCTT TAGCCGGGAG GATAGGCTTG AGCAGGCCAA
1201 ACTCTTCTGC CGCACACTTG AGGACATCCT GGCAGATGCC
1241 CCTGAGTCTC AGAACAACTG CCGCCTCATT GCCTACCAGG
1281 AACCTGCAGA TGACAGCAGC TTCTCGCTGT CCCAGGAGGT
1321 TCTCCGGCAC CTGCGGCAGG AGGAAAAGGA AGAGGTTACT
1361 GTGGGCAGCT TGAAGACCTC AGCGGTGCCC AGTACCTCCA
1401 CGATGTCCCA AGAGCCTGAG CTCCTCATCA GTGGAATGGA
1441 AAAGCCCCTC CCTCTCCGCA CGGATTTCTC TTGAGACCCA
1481 GGGTCACCAG GCCAGAGCCT CCAGTGGTCT CCAAGCCTCT
1521 GGACTGGGGG CTCTCTTCAG TGGCTGAATG TCCAGCAGAG
1561 CTATTTCCTT CCACAGGGGG CCTTGCAGGG AAGGGTCCAG
1601 GACTTGACAT CTTAAGATGC GTCTTGTCCC CTTGGGCCAG
1641 TCATTTCCCC TCTCTGAGCC TCGGTGTCTT CAACCTGTGA
1681 AATGGGATCA TAATCACTGC CTTACCTCCC TCACGGTTGT
1721 TGTGAGGACT GAGTGTGTGG AAGTTTTTCA TAAACTTTGG
1761 ATGCTAGTGT ACTTAGGGGG TGTGCCAGGT GTCTTTCATG
1801 GCGCCTTCCA CACCCACTCC CCACCCTTCT CCCCTTCCTT
1841 TGCCCCGGGA CGCCGAACTC TCTCAATGGT ATCAACAGGC
1881 TCCTTCGCCC TCTGGCTCCT GGTCATGTTC CATTATTGGG
1921 GAGCCCCAGC AGAAGAATGG AGAGGAGGAG GAGGCTGAGT
1961 TTGGGGTATT GAATCCCCCG GCTCCCACCC TGCAGCATCA
2001 AGGTTGCTAT GGACTCTCCT GCCGGGCAAC TCTTGCGTAA
2041 TCATGACTAT CTCTAGGATT CTGGCACCAC TTCCTTCCCT
2081 GGCCCCTTAA GCCTAGCTGT GTATCGGCAC CCCCACCCCA
2121 CTAGAGTACT CCCTCTCACT TGCGGTTTCC TTATACTCCA
2161 CCCCTTTCTC AACGGTCCTT TTTTAAAGCA CATCTCAGAT
2201 TACCCAAAAA AAAAAAAAA AAA
```

A cGAS (cyclic GMP-AMP synthase) protein can include the following human sequence (SEQ ID NO:15; NCBI accession number NP_612450).

```
   1 MQPWHGKAMQ RASEAGATAP KASARNARGA PMDPTESPAA
  41 PEAALPKAGK FGPARKSGSR QKKSAPDTQE RPPVRATGAR
  81 AKKAPQRAQD TQPSDATSAP GAEGLEPPAA REPALSRAGS
 121 CRQRGARCST KPRPPPGPWD VPSPGLPVSA PILVRRDAAP
 161 GASKLRAVLE KLKLSRDDIS TAAGMVKGVV DHLLLRLKCD
 201 SAFRGVGLLN TGSYYEHVKI SAPNEFDVMF KLEVPRIQLE
 241 EYSNTRAYYF VKFKRNPKEN PLSQFLEGEI LSASKMLSKF
 281 RKIIKEEIND IKDTDVIMKR KRGGSPAVTL LISEKISVDI
 321 TLALESKSSW PASTQEGLRI QNWLSAKVRK QLRLKPFYLV
 361 PKHAKEGNGF QEETWRLSFS HIEKEILNNH GKSKTCCENK
 401 EEKCCRKDCL KLMKYLLEQL KERFKDKKHL DKFSSYHVKT
 441 AFFHVCTQNP QDSQWDRKDL GLCFDNCVTY FLQCLRTEKL
 481 ENYFIPEFNL FSSNLIDKRS KEFLTKQIEY ERNNEFPVFD
 521 EF
```

A cDNA sequence that encodes the SEQ ID NO:15 human cGAS protein is shown below as SEQ ID NO:16 (NCBI accession number NM_138441).

```
   1 AGCCTGGGGT TCCCCTTCGG GTCGCAGACT CTTGTGTGCC
  41 CGCCAGTAGT GCTTGGTTTC CAACAGCTGC TGCTGGCTCT
  81 TCCTCTTGCG GCCTTTTCCT GAAACGGATT CTTCTTTCGG
 121 GGAACAGAAA GCGCCAGCCA TGCAGCCTTG GCACGGAAAG
 161 GCCATGCAGA GAGCTTCCGA GGCCGGAGCC ACTGCCCCCA
 201 AGGCTTCCGC ACGGAATGCC AGGGGCGCCC CGATGGATCC
 241 CACCCAGTCT CCGGCTGCCC CCGAGGCCGC CCTGCCTAAG
 281 GCGGGAAAGT TCGGCCCCGC CAGGAAGTCG GGATCCCGGC
 321 AGAAAAAGAG CGCCCCGGAC ACCCAGGAGA GGCCGCCCGT
 361 CCGCGCAACT GGGGCCCGCG CCAAAAAGGC CCCTCAGCGC
 401 GCCCAGGACA CCCAGCCGTC TGACGCCACC AGCGCCCCTG
 441 GGGCAGAGGG GCTGGAGCCT CCTGCGGCTC GGGAGCCGGC
 481 TCTTTCCAGG GCTGGTTCTT GCCGCCAGAG GGGCGCGCGC
 521 TGCTCCACGA AGCCAAGACC TCCGCCCGGG CCCTGGGACG
 561 TGCCCAGCCC CGGCCTGCCG GTCTCGGCCC CCATTCTCGT
 601 ACGGAGGGAT GCGGCGCCTG GGGCCTCGAA GCTCCGGCG
 641 GTTTTGGAGA AGTTGAAGCT CAGCCGCGAT GATATCTCCA
 681 CGGCGGCGGG GATGGTGAAA GGGGTTGTGG ACCACCTGCT
 721 GCTCAGACTG AAGTGCGACT CCGCGTTCAG AGGCGTCGGG
 761 CTGCTGAACA CCGGGAGCTA CTATGAGCAC GTGAAGATTT
 801 CTGCACCTAA TGAATTTGAT GTCATGTTTA AACTGGAAGT
 841 CCCCAGAATT CAACTAGAGA AATATTCCAA CACTCGTGCA
 881 TATTACTTTG TGAAATTTAA AAGAAATCCG AAAGAAAATC
 921 CTCTGAGTCA GTTTTTAGAA GGTGAAATAT TATCAGCTTC
 961 TAAGATGCTG TCAAAGTTTA GGAAAATCAT TAAGGAAGAA
1001 ATTAACGACA TTAAAGATAC AGATGTCATC ATGAAGAGGA
1041 AAAGAGGAGG GAGCCCTGCT GTAACACTTC TTATTAGTGA
1081 AAAAATATCT GTGGATATAA CCCTGGCTTT GGAATCAAAA
1121 AGTAGCTGGC CTGCTAGCAC CCAAGAAGGC CTGCGCATTC
1161 AAAACTGGCT TTCAGCAAAA GTTAGGAAGC AACTACGACT
1201 AAAGCCATTT TACCTTGTAC CCAAGCATGC AAAGGAAGGA
1241 AATGGTTTCC AAGAAGAAAC ATGGCGGCTA TCCTTCTCTC
1281 ACATCGAAAA GGAAATTTTG AACAATCATG GAAAATCTAA
1321 AACGTGCTGT GAAAACAAAG AAGAGAAATG TTGCAGGAAA
1361 GATTGTTTAA AACTAATGAA ATACCTTTTA GAACAGCTGA
1401 AAGAAAGGTT TAAAGACAAA AAACATCTGG ATAAATTCTC
1441 TTCTTATCAT GTGAAAACTG CCTTCTTTCA CGTATGTACC
1481 CAGAACCCTC AAGACAGTCA GTGGGACCGC AAAGACCTGG
1521 GCCTCTGCTT TGATAACTGC GTGACATACT TTCTTCAGTG
1561 CCTCAGGACA GAAAAACTTG AGAATTATTT TATTCCTGAA
1601 TTCAATCTAT TCTCTAGCAA CTTAATTGAC AAAAGAAGTA
1641 AGGAATTTCT GACAAAGCAA ATTGAATATG AAAGAAACAA
1681 TGAGTTTCCA GTTTTTGATG AATTTTGAGA TTGTATTTTT
1721 AGAAAGATCT AAGAACTAGA GTCACCCTAA ATCCTGGAGA
1761 ATACAAGAAA AATTTGAAAA GGGGCCAGAC GCTGTGGCTC
1801 AC
```

An NF-κB transcription factor p52 protein can include the following human sequence (SEQ ID NO: 17; NCBI accession number NP_001309863 XP_005269917).

```
   1 MESCYNPGLD GIIEYDDFKL NSSIVEPKEP APETADGPYL
  41 VIVEQPKQRG FRFRYGCEGP SHGGLPGASS EKGRKTYPTV
  81 KICNYEGPAK IEVDLVTHSD PPRAHAHSLV GKQCSELGIC
 121 AVSVGPKDMT AQFNNLGVLH VTKKNMMGTM IQKLQRQRLR
 161 SRPQGLTEAE QRELEQEAKE LKKVMDLSIV RLRFSAFLRA
 201 SDGSFSLPLK PVISQPIHDS KSPGASNLKI SRMDKTAGSV
 241 RGGDEVYLLC DKVQKDDIEV RFYEDDENGW QAFGDFSPTD
 281 VHKQYAIVFR TPPYHKMKIE RPVTVFLQLK RKRGGDVSDS
 321 KQFTYYPLVE DKEEVQRKRR KALPTESQPF GGGSHMGGGS
 361 GGAAGGYGGA GGGGSLGFFP SSLAYSPYQS GAGPMGCYPG
 401 GGGGAQMAAT VPSRDSGEEA AEPSAPSRTP QCEPQAPEML
 441 QRAREYNARL FGLAQRSARA LLDYGVTADA RALLAGQRHL
 481 LTAQDENGDT PLHLAIIHGQ TSVIEQIVYV IHHAQDLGVV
 521 NLTNHLHQTP LHLAVITGQT SVVSFLLRVG ADPALLDRHG
 561 DSAMHLALRA GAGAPELLRA LLQSGAPAVP QLLHMPDFEG
 601 LYPVHLAVRA RSPECLDLLV DSGAEVEATE RQGGRTALHL
 641 ATEMEELGLV THLVTKLRAN VNARTFAGNT PLHLAAGLGY
 681 PTLTRLLLKA GADIHAENEE PLCPLPSPPT SDSDSDSEGP
 721 EKDTRSSFRG HTPLDLTCST KVKTLLLNAA QNTMEPPLTP
 761 PSPAGPGLSL GDTALQNLEQ LLDGPEAQGS WAELAERLGL
 801 RSLVDTYRQT TSPSGSLLRS YELAGGDLAG LLEALSDMGI
 841 EEGVRLLRGP ETRDKLPSTA EVKEDSAYGS QSVEQEAEKL
 881 GPPPEPPGGL CHGHPQPQVH
```

A cDNA sequence that encodes the SEQ ID NO:17 human NF-κB transcription factor p52 protein is shown below as SEQ ID NO: 18 (NCBI accession number NM_001322934 XM_005269860).

```
   1 GCCTCCCGCC CCTCCCGTCG CGAGGGCGGG GCCAGTGGCG
  41 TCATTTCCAG GCCCGCCCCC TCCGGCCCCG CCTCCCCTTG
  81 GTATTTTCGG GACTTTCCTA AGCTGCTCTA ACTTTCCTGC
```

```
121  CCCTTCCCCG GCCAAGCCCA ACTCCGGATC TCGCTCTCCA
161  CCGGATCTCA CCCGCCACAC CCGGACAGGC GGCTGGAGGA
201  GGCGGGCGTC TAAAATTCTG GGAAGCAGAA CCTGGCCGGA
241  GCCACTAGAC AGAGCCGGGC CTAGCCCAGA GACATGGAGA
281  GTTGCTACAA CCCAGGTCTG GATGGTATTA TTGAATATGA
321  TGATTTCAAA TTGAACTCCT CCATTGTGGA ACCCAAGGAG
361  CCAGCCCCAG AAACAGCTGA TGGCCCCTAC CTGGTGATCG
401  TGGAACAGCC TAAGCAGAGA GGCTTCCGAT TTCGATATGG
441  CTGTGAAGGC CCCTCCCATG GAGGACTGCC CGGTGCCTCC
481  AGTGAGAAGG GCCGAAAGAC CTATCCCACT GTCAAGATCT
521  GTAACTACGA GGGACCAGCC AAGATCGAGG TGGACCTGGT
561  AACACACAGT GACCCACCTC GTGCTCATGC CCACAGTCTG
601  GTGGGCAAGC AATGCTCGGA GCTGGGGATC TGCGCCGTTT
641  CTGTGGGGCC CAAGGACATG ACTGCCCAAT TTAACAACCT
681  GGGTGTCCTG CATGTGACTA AGAAGAACAT GATGGGGACT
721  ATGATACAAA AACTTCAGAG GCAGCGGCTC CGCTCTAGGC
761  CCCAGGGCCT TACGGAGGCC GAGCAGCGGG AGCTGGAGCA
801  AGAGGCCAAA GAACTGAAGA AGGTGATGGA TCTGAGTATA
841  GTGCGGCTGC GCTTCTCTGC CTTCCTTAGA GCCAGTGATG
881  GCTCCTTCTC CCTGCCCCTG AAGCCAGTCA TCTCCCAGCC
921  CATCCATGAC AGCAAATCTC CGGGGGCATC AAACCTGAAG
961  ATTTCTCGAA TGGACAAGAC AGCAGGCTCT GTGCGGGGTG
1001 GAGATGAAGT TTATCTGCTT TGTGACAAGG TGCAGAAAGA
1041 TGACATTGAG GTTCGGTTCT ATGAGGATGA TGAGAATGGA
1081 TGGCAGGCCT TTGGGGACTT CTCTCCCACA GATGTGCATA
1121 AACAGTATGC CATTGTGTTC CGGACACCCC CCTATCACAA
1161 GATGAAGATT GAGCGGCCTG TAACAGTGTT TCTGCAACTG
1201 AAACGCAAGC GAGGAGGGGA CGTGTCTGAT TCCAAACAGT
1241 TCACCTATTA CCCTCTGGTG GAAGACAAGG AAGAGGTGCA
1281 GCGGAAGCGG AGGAAGGCCT TGCCCACCTT CTCCCAGCCC
1321 TTCGGGGGTG GCTCCCACAT GGGTGGAGGC TCTGGGGGTG
1361 CAGCCGGGGG CTACGGAGGA GCTGGAGGAG GTGGCAGCCT
1401 CGGTTTCTTC CCCTCCTCCC TGGCCTACAG CCCCTACCAG
1441 TCCGGCGCGG GCCCCATGGG CTGCTACCCG GGAGGCGGGG
1481 GCGGGGCGCA GATGGCCGCC ACGGTGCCCA GCAGGGACTC
1521 CGGGGAGGAA GCCGCGGAGC CGAGCGCCCC CTCCAGGACC
1561 CCCCAGTGCG AGCCGCAGGC CCCGGAGATG CTGCAGCGAG
1601 CTCGAGAGTA CAACGCGCGC CTGTTCGGCC TGGCGCAGCG
1641 CAGCGCCCGA GCCCTACTCG ACTACGGCGT CACCGCGGAC
1681 GCGCGCGCGC TGCTGGCGGG ACAGCGCCAC CTGCTGACGG
1721 CGCAGGACGA GAACGGAGAC ACACCACTGC ACCTAGCCAT
```

```
1761 CATCCACGGG CAGACCAGTG TCATTGAGCA GATAGTCTAT
1801 GTCATCCACC ACGCCCAGGA CCTCGGCGTT GTCAACCTCA
1841 CCAACCACCT GCACCAGACG CCCCTGCACC TGGCGGTGAT
1881 CACGGGGCAG ACGAGTGTGG TGAGCTTTCT GCTGCGGGTA
1921 GGTGCAGACC CAGCTCTGCT GGATCGGCAT GGAGACTCAG
1961 CCATGCATCT GGCGCTGCGG GCAGGCGCTG GTGCTCCTGA
2001 GCTGCTGCGT GCACTGCTTC AGAGTGGAGC TCCTGCTGTG
2041 CCCCAGCTGT TGCATATGCC TGACTTTGAG GGACTGTATC
2081 CAGTACACCT GGCGGTCCGA GCCCGAAGCC CTGAGTGCCT
2121 GGATCTGCTG GTGGACACTG GGGCTGAAGT GGAGGCCACA
2161 GAGCGCCAGG GGGGACGAAC AGCCTTGCAT CTAGCCACAG
2201 AGATGGAGGA GCTGGGGTTG GTCACCCATC TGGTCACCAA
2241 GCTCCGGGCC AACGTGAACG CTCGCACCTT GCGGGAAAC
2281 ACACCCCTGC ACCTGGCAGC TGGACTGGGG TACCCGACCC
2321 TCACCCGCCT CCTTCTGAAG GCTGGTGCTG ACATCCATGC
2361 TGAAAACGAG GAGCCCCTGT GCCCACTGCC TTCACCCCCT
2401 ACCTCTGATA GCGACTCGGA CTCTGAAGGG CCTGAGAAGG
2441 ACACCCGAAG CAGCTTCCGG GGCCACACGC CTCTTGACCT
2481 CACTTGCAGC ACCAAGGTGA AGACCTTGCT GCTAAATGCT
2521 GCTCAGAACA CCATGGAGCC ACCCCTGACC CCGCCCAGCC
2561 CAGCAGGGCC GGGACTGTCA CTTGGTGATA CAGCTCTGCA
2601 GAACCTGGAG CAGCTGCTAG ACGGGCCAGA AGCCCAGGGC
2641 AGCTGGGCAG AGCTGGCAGA GCGTCTGGGG CTGCGCAGCC
2681 TGGTAGACAC GTACCGACAG ACAACCTCAC CCAGTGGCAG
2721 CCTCCTGCGC AGCTACGAGC TGGCTGGCGG GGACCTGGCA
2761 GGTCTACTGG AGGCCCTGTC TGACATGGGC CTAGAGGAGG
2801 GAGTGAGGCT CCTGAGGCCT CCAGAAACCC GAGACAAGCT
2841 GCCCAGCACA GCAGAGGTGA AGGAAGACAG TGCGTACGGG
2881 AGCCAGTCAG TGGAGCAGGA GGCAGAGAAG CTGGGCCCAC
2921 CCCCTGAGCC ACCAGGAGGG CTCTGCCACG GCACCCCCA
2961 GCCTCAGGTG CACTGACCTG CTGCCTGCCC CAGCCCCCT
3001 TCCCGGACCC CCTGTACAGC GTCCCCACCT ATTTCAAATC
3041 TTATTTAACA CCCCACACCC ACCCCTCAGT GGGACAAAT
3081 AAAGGATTCT CATGGGAAGG GGAGGACCCC TCCTTCCCAA
3121 CTTATGGCA
```

An NF-κB transcription factor RelB protein can include the following human sequence (SEQ ID NO:19; NCBI accession number NP 006500).

```
  1  MLRSGPASGP SVPTGRAMPS RRVARPPAAP ELGALGSPDL
 41  SSLSLAVSRS TDELEIIDEY IKENGFGLDG GQPGPGEGLP
```

```
 81  RLVSRGAASL STVTLGPVAP PATPPPWGCP LGRLVSPAPG
121  PGPQPHLVIT EQPKQRGMRF RYECEGRSAG SILGESSTEA
161  SKTLPAIELR DCGGLREVEV TACLVWKDWP HRVHPHSLVG
201  KDCTDGICRV RLRPHVSPRH SFNNLGIQCV RKKEIEAAIE
241  RKIQLGIDPY NAGSLKNHQE VDMNVVRICF QASYRDQQGQ
281  MRRMDPVLSE PVYDKKSTNT SELRICRINK ESGPCTGGEE
321  LYLLCDKVQK EDISVVFSRA SWEGRADFSQ ADVHRQIAIV
361  FKTPPYEDLE IVEPVTVNVF LQRLTDGVCS EPLPFTYLPR
401  DHDSYGVDKK RKRGMPDVLG ELNSSDPHGI ESKRRKKKPA
441  ILDHFLPNHG SGPFLPPSAL LPDPDFFSGT VSLPGLEPPG
481  GPDLLDDGFA YDPTAPTLFT MLDLLPPAPP HASAVVCSGG
521  AGAVVGETPG PEPLTTDSYQ APGPGDGGTA SLVGSNMFPN
541  HYREAAFGGG LLSPGPEAT
```

A cDNA sequence that encodes the SEQ ID NO:19 human NF-κB transcription factor RelB protein is shown below as SEQ ID NO:20 (NCBI accession number NM_006509).

```
   1  GGCCCCGCGC CCCGCGCAGC CCCGGGCGCC GCGCGTCCTG
  41  CCCGGCCTGC GGCCCCAGCC CTTGCGCCGC TCGTCCGACC
  81  CGCGATCGTC CACCAGACCG TGCCTCCCGG CCGCCCGGCC
 121  GGCCCGCGTG CATGCTTCGG TCTGGGCCAG CCTCTGGGCC
 161  GTCCGTCCCC ACTGGCCGGG CCATGCCGAG TCGCCGCGTC
 201  GCCAGACCGC CGGCTGCGCC GGAGCTGGGG GCCTTAGGGT
 241  CCCCCGACCT CTCCTCACTC TCGCTCGCCG TTTCCAGGAG
 281  CACAGATGAA TTGGAGATCA TCGACGAGTA CATCAAGGAG
 321  AACGGCTTCG GCCTGGACGG GGGACAGCCG GGCCCGGGCG
 361  AGGGCCTGCC ACGCCTGGTG TCTCGCCGGG CTCCGTCCCT
 401  GAGCACGGTC ACCCTGGGCC CTGTGGCGCC CCCAGCCACG
 441  CCGCCGCCTT GGGGCTGCCC CCTGGGCCGA CTAGTGTCCC
 481  CAGCGCCGGG CCCGGGCCCG CAGCCGCACC TGGTCATCAC
 521  GGAGCAGCCC AAGCAGCGCG GCATGCGCTT CCGCTACGAG
 561  TGCGAGGGCC GCTCGGCCGG CAGCATCCTT GGGGAGAGCA
 601  GCACCGAGGC CAGCAAGACG CTGCCCGCCA TCGAGCTCCG
 641  GGATTGTGGA GGGCTGCGGG AGGTGGAGGT GACTGCCTGC
 681  CTGGTGTGGA AGGACTGGCC TCACCGAGTC CACCCCCACA
 721  GCCTCGTGGG GAAAGACTGC ACCGACGGCA TCTGCAGGGT
 761  GCGGCTCCGG CCTCACGTCA GCCCCCGGCA CAGTTTTAAC
 801  AACCTGGGCA TCCAGTGTGT GAGGAAGAAG GAGATTGAGG
 841  CTGCCATTGA GCGGAAGATT CAACTGGGCA TTGACCCCTA
 881  CAACGCTGGG TCCCTGAAGA ACCATCAGGA AGTAGACATG
 921  AATGTGGTGA GGATCTGCTT CCAGGCCTCA TATCGGGACC
 961  AGCACCGACA GATGCGCCGG ATGGATCCTG TGCTTTCCGA
1001  GCCCGTCTAT GACAAGAAAT CCACAAACAC ATCAGAGCTG
1041  CGGATTTGCC AATTAACAA GGAAAGCGGG CCGTGCACCG
1081  GTGGCGAGGA GCTCTACTTG CTCTGCGACA AGGTGCAGAA
1121  AGAGGACATA TCAGTGGTGT TCAGCAGGGC CTCCTGGGAA
1161  GGTCGGGCTG ACTTCTCCCA GGCCGACGTG CACCGCCAGA
1201  TTGCCATTGT GTTCAAGACG CCGCCCTACG AGGAGCTGGA
1241  GATTGTCGAG CCCGTGACAG TCAACGTCTT CCTGCAGCGG
1281  CTCACCGATG GGGTCTGCAG CGAGCCATTG CCTTTCACGT
1321  ACCTGCCTCG CGACCATGAC AGCTACGGCG TGGACAAGAA
1361  GCGGAAACGG GGGATGCCCG ACGTCCTTGG GGAGCTGAAC
1401  AGCTCTGACC CCCATGGCAT CGAGAGCAAA CGGCGGAAGA
1441  AAAAGCCGGC CATCCTGGAC CACTTCCTGC CAACCACGG
1481  CTCAGGCCCG TTCCTCCCGC CGTCAGCCCT GCTGCCAGAC
1521  CCTGACTTCT TCTCTGGCAC CGTGTCCCTG CCCGGCCTGG
1561  AGGCCCCTGG CGGGCCTGAC CTCCTGGACG ATGGGTTTGC
1601  CTACGACCCT ACGGGCCCCA CACTCTTCAC CATGCTGGAC
1641  CTGCTGCCCC CGGCACCGCC ACACGCTAGC GCTGTTGTGT
1681  GCAGCGGAGG TGCCGGGGCC GTGGTTGGGG AGACCCCCGG
1721  CCCTCAACCA CTGACACTCG ACTCCTACCA GGCCCCGGGC
1761  CCCGGGGATG GAGGCACCGC CAGCCTTGTG GGCAGCAACA
1801  TGTTCCCCAA TCATTACCGC GAGGCGGCCT TTGGGGGCGG
1841  CCTCCTATCC CCGGGGCCTG AAGCCACGTA GCCCCGCGAT
1881  GCCAGAGGAG GGGCACTGGG TGGGGAGGGA GGTGGAGGAG
1921  CCGTGCAATC CCAACCACCA TGTCTAGCAC CCCCATCCCC
1961  TTGGCCCTTC CTCATGCTTC TGAAGTGGAC ATATTCAGCC
2001  TTGGCGAGAA GCTCCGTTGC ACGGGTTTCC CCTTGAGCCC
2041  ATTTTACAGA TGAGGAAACT GAGTCCGGAG AGGAAAAGGG
2081  AGATGGCTCC CGTGCAGTAG CTTGTTAGAG CTGCCTCTGT
2121  CCCCACATGT GGGGGCACCT TCTCCAGTAG GATTCGGAAA
2161  AGATTCTAGA TATGGGAGGA GGGGGCAGAT TCCTGGCCCT
2201  CCCTCCCCAG ACTTGAAGGT GGGGGGTAGG TTGGTTGTTC
2241  AGAGTCTTCC CAATAAAGAT GAGTTTTTGA GCCTCCGGGA
2281  AAAAAAAAAA AAAAAA
```

For example, a ENPP1 protein can include the following human sequence (SEQ ID NO:21; NCBI accession number NP 006199.2).

```
   1  MERDGCAGGG SRGGEGGRAP REGPAGNGRD RGRSHAAEAP
  41  GDPQAAASLL APMDVGEEPL EKAARARTAK DPNTYKVLSL
  81  VLSVCVLTTI LGCIFGLKPS CAKEVKSCKG RCFERTFGNC
 121  RCDAACVELG NCCLDYQETC IEPEHIWTCN KFRCGEKRLT
```

```
161  RSLCACSDDC KDKGDCCINY SSVCQGEKSW VEEPCESINE
201  PQCPAGFETP PTLLFSLDGF RAEYLHTWGG LLPVISKLKK
241  CGTYTKNMRP VYPTKTFPNH YSIVTGLYPE SHGIIDNKMY
281  DPKMNASFSL KSKEKFNPEW YKGEPIWVTA KYQGLKSGTF
321  FWPGSDVEIN GIFPDIYKMY NGSVPFEERI LAVLQWLQLP
361  KDERPHFYTL YLEEPDSSGH SYGPVSSEVI KALQRVDGMV
401  GMLMDGLKEL NLHRCLNLIL ISDHGMEQGS CKKYIYLNKY
441  LGDVKNIKVI YGPAARLRPS DVPDKYYSFN YEGIARNLSC
481  REPNQHFKPY LKHFLPKRLH FAKSDRIEPL TFYLDPQWQL
521  ALNPSERKYC GSGFHGSDNV FSNMQALFVG YGPGFKHGIE
561  ADTFENIEVY NLMCDLLNLT PAPNNGTHGS LNHLLKNPVY
601  TPKHPKEVHP LVQCPFTRNP RDNLGCSCNP SILPIEDFQT
641  QFNLTVAEEK IIKHETLPYG RPRVLQKENT ICLLSQHQFM
681  SGYSQDILMP LWTSYTVDRN DSFSTEDFSN CLYQDFRIPL
721  SPVHKCSFYK NNTKVSYGFL SPPQLNKNSS GIYSEALLTT
761  NIVPMYQSFQ VIWRYFHDTL LRKYAEERNG VNVVSGPVFD
801  FDYDGRCDSL ENLRQKRRVI RNQEILIPTH FFIVLTSCKD
841  TSQTPLHCEN LDTLAFILPH RTDNSESCVH GKHDSSWVEE
881  LLMLHRARIT DVEHITGLSF YQQRKEPVSD ILKLKTHLPT
921  FSQED
```

A cDNA sequence that encodes the SEQ ID NO:21 human ENPP1 protein is shown below as SEQ ID NO:22 (NCBI accession number NM_006208.2).

```
   1 CCGGAGCGGC CGGGGCCACG ATGGAGCGCG ACGGCTGCGC
  41 GGGGGGCGGG AGCCGCGGCG GCGAGGGCGG GCGCGCTCCC
  81 CGGGAGGGCC CGGCGGGGAA CGGCCGCGAT CGGGGCCGCA
 121 GCCACGCTGC CGAGGCGCCC GGGGACCCGC AGGCGGCCGC
 161 GTCCTTGCTG GCCCCTATGC ACGTGGGGGA GGAGCCGCTG
 201 GAGAAGGCGG CGCGCGCCCG CACTGCCAAG GACCCCAACA
 241 CCTATAAACT ACTCTCGCTG GTATTGTCAG TATGTGTCTT
 281 AACAACAATA CTTGGTTCTA TATTTGGGTT GAAACCAAGC
 321 TGTGCCAAAG AAGTTAAAAG TTGCAAAGGT CGCTGTTTCG
 361 AGAGAACATT TGGGAACTCT CGCTGTGATG CTGCCTGTGT
 401 TGAGCTTGGA AACTGCTCTT TAGATTACCA GGAGACGTGC
 441 ATAGAACCAG AACATATATG GACTTGCAAC AAATTCAGGT
 481 GTGGTGAGAA AAGGTTGACC AGAAGCCTCT GTGCCTGTTC
 521 AGATGACTGC AAGGACAAGG GCGACTGCTG CATCAACTAC
 561 AGTTCTGTGT GTCAAGGTGA GAAAAGTTGG GTAGAAGAAC
 601 CATGTGAGAG CATTAATGAG CCACAGTGCC AGCAGGGTT
 641 TGAAACGCCT CCTACCCTCT TATTTTCTTT GGATGGATTC
 681 AGGGCAGAAT ATTTACACAC TTGGGGTGGA CTTCTTCCTG
 721 TTATTAGCAA ACTAAAAAAA TGTGGAACAT ATACTAAAAA
 761 CATGAGACCG GTATATCCAA CAAAAACTTT CCCCAATCAC
 801 TACAGCATTG TCACCGGATT GTATCCAGAA TCTCATGGCA
 841 TAATCGACAA TAAAATGTAT GATCCCAAAA TGAATGCTTC
 881 CTTTTCACTT AAAAGTAAAG AGAAATTTAA TCCTGAGTGG
 921 TACAAAGGAG AACCAATTTC GGTCACAGCT AAGTATCAAG
 961 GCCTCAAGTC TGGCACATTT TTCTGGCCAG GATCAGATGT
1001 GGAAATTAAC GGAATTTTCC CAGACATCTA TAAAATGTAT
1041 AATGGTTCAG TACCATTTCA AGAAAGGATT TTAGCTGTTC
1081 TTCAGTGGCT ACAGCTTCCT AAAGATGAAA GACCACACTT
1121 TTACACTCTG TATTTAGAAG AACCAGATTC TTCAGGTCAT
1161 TCATATGGAC CAGTCAGCAG TGAAGTCATC AAAGCCTTGC
1201 ACACGGTTCA TGCTATGGTT GGTATGCTGA TGGATGGTCT
1241 GAAAGAGCTC AACTTGCACA GATGCCTGAA CCTCATCCTT
1281 ATTTCAGATC ATGGCATGGA ACAAGGCAGT TGTAAGAAAT
1321 ACATATATCT GAATAAATAT TTGGGGGATG TTAAAAATAT
1361 TAAAGTTATC TATGGACCTG CAGCTCGATT GAGACCCTCT
1401 GATGTCCCAG ATAAATACTA TTCATTTAAC TATGAAGGCA
1441 TTGCCCGAAA TCTTTCTTGC CGGGAACCAA ACCAGCACTT
1481 CAAACCTTAC CTGAAACATT TCTTACCTAA GCGTTTGCAC
1521 TTTGCTAAGA GTGATAGAAT TGAGCCCTTG ACATTCTATT
1561 TGGACCCTCA GTGGCAACTT GCATTGAATC CCTCAGAAAG
1601 GAAATATTGT GGAAGTGGAT TCATGGCTC TGACAATGTA
1641 TTTTCAAATA TGCAAGCCCT CTTTGTTGGC TATGGACCTG
1681 GATTCAAGCA TGGCATTGAG GCTGACACCT TTGAAAACAT
1721 TGAAGTCTAT AACTTAATGT GTGATTTACT GAATTTGACA
1761 CCGGCTCCTA ATAACGGAAC TCATGGAAGT CTTAACCACC
1801 TTCTAAAGAA TCCTGTTTAT ACGCCAAAGC ATCCCAAAGA
1841 AGTCCACCCC CTGGTACAGT GCCCCTTCAC AAGAAACCCC
1881 AGAGATAACC TTGGCTGCTC ATGTAACCCT TCGATTTTGC
1921 CGATTGAGGA TTTTCAAACA CAGTTCAATC TGACTGTGGC
1961 AGAAGAGAAG ATTATTAAGC ATGAAACTTT ACCCTATGGA
2001 AGACCTAGAG TTCTCCAGAA GGAAAACACC ATCTGTCTTC
2041 TTTCCCAGCA CCAGTTTATG AGTGGATACA GCCAAGACAT
2081 CTTAATGCCC CTTTGGACAT CCTATACCGT GGACAGAAAT
2121 GACAGTTTCT CTACGGAAGA CTTCTCCAAC TGTCTGTACC
2161 AGGACTTTAG AATTCCTCTT AGTCCTGTCC ATAAATGTTC
2201 ATTTTATAAA AATAACACCA AAGTGAGTTA CGGGTTCCTC
2241 TCCCCACCAC AACTAAATAA AAATTCAAGT GGAATATATT
2281 CTGAAGCTTT GCTTACTACA AATATAGTGC CAATGTACCA
```

-continued

```
2321 GAGTTTTCAA GTTATATGGC GCTACTTTCA TGACACCCTA
2361 CTGCGAAAGT ATGCTGAAGA AAGAAATGGT GTCAATGTCG
2401 TCAGTGGTCC TGTGTTTGAC TTTGATTATG ATGGACGTTG
2441 TGATTCCTTA GAGAATCTGA GGCAAAAAAG AAGAGTCATC
2481 CGTAACCAAG AAATTTTGAT TCCAACTCAC TTCTTTATTG
2521 TGCTAACAAG CTGTAAAGAT ACATCTCAGA CGCCTTTGCA
2561 CTGTGAAAAC CTAGACACCT TAGCTTTCAT TTTGCCTCAC
2601 AGGACTGATA ACAGCGAGAG CTGTGTGCAT GGGAAGCATG
2641 ACTCCTCATG GGTTGAAGAA TTGTTAATGT TACACAGAGC
2681 ACGGATCACA GATGTTGAGC ACATCACTGG ACTCAGCTTC
2721 TATCAACAAA GAAAGAGCC AGTTTCAGAC ATTTTAAAGT
2761 TGAAAACACA TTTGCCAACC TTTAGCCAAG AAGACTGATA
2801 TGTTTTTTAT CCCCAAACAC CATGAATCTT TTTGAGAGAA
2841 CCTTATATTT TATATAGTCC TCTAGCTACA CTATTGCATT
2881 GTTCAGAAAC TGTCGACCAG AGTTAGAACG GAGCCCTCGG
2921 TGATGCGGAC ATCTCAGGGA AACTTGCGTA CTCAGCACAG
2961 CAGTGGGAGA GTGTTCCTGTT GAATCTTGCA CATATTTGAA
3001 TGTGTAAGCA TTGTATACAT TGATCAAGTT CGGGGGAATA
3041 AAGACAGACC ACACCTAAAA CTGCCTTTCT GCTTCTCTTA
3081 AAGGAGAAGT AGCTGTGAAC ATTGTCTGGA TACCAGATAT
3121 TTGAATCTTT CTTACTATTG GTAATAAACC TTGATGGCAT
3161 TGGGCAAACA GTAGACTTAT AGTAGGGTTG GGGTAGCCCA
3201 TGTTATGTGA CTATCTTTAT GAGAATTTTA AAGTGGTTCT
3241 GGATATCTTT TAACTTGGAG TTTCATTTCT TTTCATTGTA
3281 ATCAAAAAAA AAATTAACAG AAGCCAAAAT ACTTCTGAGA
3321 CCTTGTTTCA ATCTTTGCTG TATATCCCCT CAAAATCCAA
3361 GTTATTAATC TTATGTGTTT TCTTTTTAAT TTTTTGATTG
3401 GATTTCTTTA GATTTAATGG TTCAAATGAG TTCAACTTTG
3441 AGGGACGATC TTTGAATATA CTTACCTATT ATAAAATCTT
3481 ACTTTGTATT TGTATTTAAA AAGAAAAAT ATTCCTATCC
3521 TGCTCACTGG TAATTAACAT AGGTTAAAA TGGCTTCAAA
3561 TGTGGCCCTA TAGACGGTTA AAATTGTACC TTATCTTGGC
3601 AAAACTTCAG AGCACCAGTC AGTGCATGCA AGGTGCCATT
3641 TTTTATTGAG ATGCTTAGAA TGTTTCTTTC TGTGCACAAG
3681 ACTTACCCTA CCAGCAGCAG AGCCATTCTC TGTTGAGTGG
3721 TTCATTTTGA AGTTCCACAG ATTGAAGAGA ACATGCCACC
3761 AATCACCTCA CATCTTCTTG GTGGACATGA TAAATGACAC
3801 AATGAACTTG ATTTCTTTAC TACCTTGACT GTACCTTTTT
3841 ATCCCTACCT GTGAACCTTC AAAGACTGCA TTAACTTTTA
3881 GGCTACATAG GTCCAATTGA GGTATAATAT CAGTACACCA
3921 AAGATTTTTA TATGTCCTTC GTGTGACCAT TCTTCAACGG
3961 CCTAAGGGCC AGCTGCAAAG ACTTTTGGAA AATACAATTT
4001 ACAACTCAAA ATTATTTAAT AATTTAGGAA GTTGCTTTTT
4041 TTTTTTTTTT TTTTCAGTCC TGCAGTTTCC TGAAGCTCTG
4081 TATATGATAT TTTTTTCAGC CTGCTTCTCT CTGTTGTTCA
4121 GATTAGGTAA TTTTATTCTT CTGTCTCGAA GCTCACTGAT
4161 TCTTTATTCT GTCTAATCTG TTCTGCTGTT GAGCCCATTT
4201 ATTCCTGATT TTTATATTTT AGTTATTGTA TGTTTTATTT
4241 CTAAAATTTC CATTCAGTTT TTCTTTATAT CTTCTATTTG
4281 CTGAGAATTT CTGTCTCTTT GCTGAGACTT TCTACGTTTT
4321 CATTTGTTTC AAGTGCATTT ATACTTGCTT GTTGAAGAAT
4361 TTTTATGATG GCTGCTGTAA ATCCTTATC AGATAATTCC
4441 AACATCTGTC ACCTCATTGT TTGCATCTAC TGATGGTCTT
4441 TTTTCCATTC GGAAACATTT TCCTGTTTCT TGGTGTGTGG
4481 AATGATTTTT TATTGAAACC TGGATATTTT TAGGTATTAT
4521 GTTATGAGAC TATGGGTCTT ATTTAAACCT TCTGCTTTAG
4561 CCAACTTTCT CAGATACCAC CACAGCAGGG GAATTGGGAG
4601 CACTGCTTCA TTATTACCAG GTGTCGCTAG GAGTCCAGGT
4641 TCCCAGTCA GCCTCCCTTT TACTGAGTA ACAGGGTCCC
4681 CTCATTACTA CTGGGCAAGG TGAGAATTCA GTTTCCCATT
4721 AGGTCTTTAT TGATTCTTCC CTGGCTGAA TGTGCAGCGG
4761 CACCTTTTGG TGCACCCTGG GAATCTCCAC TAATGCTATG
4801 GGACAGAGTG ACCAGGAAGA GCTTCATTAC ACCAGGTGGG
4841 AATGAAATTC CCAGTAGCCT ACACAGCCTT CTCCGACACC
4831 ACTCTGGAGT TGTATTCTTC CAGCACACA ACATACACAA
4921 TTTAACTCAA AGCATCTTAG CAGAGCTTAA TTAAATGGAT
4961 AGATGCCTGT TCCCTTTGCT GGATACCAAG AATACAAAAG
5001 TCAGGGAGTT GGGGCACCTC TTTACAGCTT GGTGAGAGTG
5041 TAAGTCTGGA CTCCCCACTC AGCATTTGCT GGTATGGGTC
5081 GGGCCATGGT GTTTTTCCAT GGTGTTTGGT TGGAGTACAG
5121 CCTTTTTTAC CCTTGCTTGG CTACCCTTTT CTGGTCCTTT
5161 GGCAGGAGAG AGCAGGACTC TCTTAGGGCT TTTTTTTCCC
5201 CTGCATTTAT TGACATTTCC AGGTTGCTGA CTTTTTCAGC
5241 TCCAAGTTGG AAATATATGA GCTGAAAGA AAATGTAGGG
5281 AACTCATCAC AGTGTTGTTA CTTGGGCCCC AATGTTCCTA
5321 GCCTATTTTC TGTCTACTAT TCAGAGTCTT GCTGTGTTTT
5361 AATATAATAT CCAGGATTTT TATATGCATT TAGCAGAAGG
5401 ATGTCTACTC TGCCTTTGTA GAAGTGTCTC ACTGATTTTT
5441 ACATATTTTT CCAGCACACA AACATACACA ATTTAACTCA
5481 AAGCATCTTA GCAGAGCTTA ATTAAATGGA TAGATGTCTG
5521 TTCCCTTTGC TGGACGCCAA GAATACAAAA AAGAACAAGT
```

```
5561 GACAATTTTC TCTGTCTTAG GGAGAAGAGA CAGCAGAAGT
5601 GTAAATGATC CCTAAAGAGT GATAGATGTT ATCATGAAGC
5641 CACAGGAGGG GTGCCAGGCT GCACAAAAGA GACACTGGAT
5681 GCTTCTTGGT AGTAGAGGCA GTGGCTTCCC AGCCTTGGGG
5721 CTAAGGCTTG TAGGGTGAAT TGGAACTTTT CAGATGAGCA
5761 AGGCAAAGAA GGGACCTTCT AACATTCCTT GGATGGAACA
5801 TTTTTGACAT TTTCCCATTT ACAGCTACTT ATATTTTCTA
5841 CAAGTGTCAC TGTGACCAAC TTATGTACAC ATACTTTTTC
5881 TTGCTTAGTT ATAATAATCT GTTCTTAAAG AAAATGTCAG
5921 TCTCTACATT CTATGCTGAC TGTTAAGGAA AGAGCACCCA
5961 CATCTGCTCC TACTTAGCTT TTTTTCTGTG GTTCTTACAC
6001 AGTATTCCTT TTTTTCTTTT CTTGAAAGAG ACTCCTCCTT
6041 TCTTTTCTTT TCTTGAAAGA GTTTTAAACA GATAAGATGG
6081 CAAAAGTGAC TGATCTCTAC TCCCCCAGTT TGAATGGTAA
6121 ATTTGAATGG TAAATTCCCA TGAACATATA TGGAAATGTC
6161 TTTATCCTAC TTTCTCCAAT AAAGGCTGTT CTTAGCTTTT
6201 CAAATGCAAA GTGAAACCTT TATTTATCTT GATTTCTTTT
6241 TTTTTTTTTT TTTTTTTTTT TTTTTGAGA TGCTCTGTCA
6281 CCCAGGCTGG AGTGCAGTGG CAAGATCTTG GCTCACTGCA
6321 AGCTCCGCCT CCCAGGTTCA CGCCATTCTC CTGGCTCAGC
6361 CTCCCGAGTA ACTGGGACTA CAGGCACCTG CCGTCACGCC
6401 TGGCTAATTT TTTGTATTTT TAGTAGAGAA TGGAGTTTCA
6441 CCGTGTTAGC CAGGATGGTC TCGATCTCCT GACCTTGTGA
6481 TCTGCCCGCC TCGGCCTCCC AAAGTGCTGG GATTACAGGC
6521 TCGAGCCACT GCCTCCAGCC TATCCTGATT TCTACTGTCA
6561 TGCCTCACAT CAGTCCTTTT TTTTTTTTTT GAGACAGAGT
6601 CTCGCTCTGT GGCCCAGGCT AGACTGCAGT GGCATGATCT
6641 CGGCTCACTG CAACCTCCAC CTCCGGGGTT CTAGCAATTC
6681 TCCTGCCTCA GCCTCCTGAG TAGCTGGGAT TATAGGCGCA
6721 TGCCACACCT GGCTTTTTGT ATTTTAGTGG AGATGGGGTT
6761 TCACTGTGTT GCTCAGGCTG GTCTTGATCT CCTGAGCTCA
6801 GACAATCCCC CCGCCTTGGC CTCCCAAAGT GCTAGGATTA
6841 TAGGCGAGAG CTGCTGTGTG CTTCTTAAGT GAGGTAAGTA
6881 AGTTCCATAG AAAATTTCCA TCAGTTCATT CATGAAAGAA
6921 CAAAGAACCT GGCAAAACTT AAAAAAACGT TTCCAAGAAT
6961 CAGATAAAAG AGGACAAACC TTAGGGAGAA GAAGGCAGCT
7001 GCTCATTTCC AGCAGGGGAA GTAGCTGCAT AGAGTACAAG
7041 GACTGGTAGG CCTGTTGGCT GTTCCTGTTT AAGGAGACAA
7081 GATGGGCATG AACAGGGAC CACCCCCTCC TCTGGGAGAA
7121 GCTGTTACCC CCTTCACTTT TCCTCCTCTG TCATTACCCA
7161 CAATCACTCT CCTTCTTTGC GCTATGGTAG GTGTTTACCC
7201 ATCATAGGAA TGGGCATTTG AACTTTGAAA CTGAATGTGG
7241 TGATTACACT TCATGCTGAA GCTTTTCACA TGAGTGCTTT
7281 CATAAGCATT AAGTAAAATT TTATAATGAC TGCAGTCCAA
7321 GGACATTTTC CCTGGTTTTT GGCCAGTCTA AATATTGTAA
7361 GAGAGAGAGA AGAAAAGTGT ACGGAATATA ATTGTCTCTA
7401 AGCTAAGAAA TGTGGATGTT CAAATAAAAC ATACGTACAG
7441 AA
```

For example, a LTβR protein can include the following human sequence (SEQ ID NO:23; NCBI accession number P36941.1).

```
  1 MLLPWATSAP GLAWGPLVLG LFGLLAASQP QAVPPYASEN
 41 QTCRDQEKEY YEPQHRICCS RCPPGTYVSA KCSRIRDTVC
 81 ATCAENSYNE HWNYLTICQL CRPCDPVMGL EEIAPCTSKR
121 KTQCRCQPGM FCAAWALECT HCELLSDCPP GTEAELKDEV
161 GKGNNHCVPC KAGHFQNTSS PSARCQPHTR CENQGLVEAA
201 PGTAQSDTTC KNPLEPLPPE MSGTMLMLAV LLPLAFFLLL
241 ATVFSCIWKS HPSLCRKLGS LLKRRPQGEG PNPVAGSWEP
281 PKAHPYFPDL VQPLLPISGD VSPVSIGLPA APVLEAGVPQ
321 QQSPLDLTRE PQLEPGEQSQ VAHGTNGIHV TGGSMTITGN
361 IYIYNGPVLG GPPGPGDLPA TPEPPYPIPE EGDPGPPGLS
401 TPHQEDGKAW HLAETEHCGA TPSNRGPRNQ FITHD
```

A cDNA sequence that encodes the SEQ ID NO:23 human LTβR protein is shown below as SEQ ID NO:24 (NCBI accession number NM 002342.2).

```
  1 GCTTTCCCGG CCGCCCCTCC CGCCCCGCAT CGAGGCAGAC
 41 AAGCCTGTTC CTCTTCCCTG GGCTGCGATT GCGACAGGCC
 81 GGCCTGGCTC CCAGCGCTCC CTGTCCCCGC CCCGCGGCCA
121 GCTCGCTCCA CTCCCACTTC CTGAGCTCCG CCATGGGAGC
161 CCTGGAGGCC CGGCCTGGCC GCTCCCGCC CTGGGGTGCA
201 CATCGGCCCT GAGTCCCGTC CCAGGCTCTG GGCTCGGGCA
241 GCCGCCGCCA CCGCTGCCCA GGACGTCGGG CCTCCTGCCT
281 TCCTCCCAGG CCCCCACGTT GCTGGCCGCC TGGCCGAGTG
321 GCCGCCATGC TCCTGCCTTG GCCACCTCT GCCCCCGGCC
361 TGGCCTGGGG GCCTCTGGTC CTGGGCCTCT TCGGGCTCCT
401 GGCAGCATCG CAGCCCCAGG CGGTGCCTCC ATATGCGTCG
441 GAGAACCAGA CCTGCAGGGA CCAGGAAAAG GAATACTATG
481 AGCCCCAGCA CCGCATCTGC TGCTCCCGCT GCCCGCCAGG
521 CACCTATGTC TCAGCTAAAT GTAGCCGCAT CCGGGACACA
561 GTTTGTGCCA CATGTGCCGA GAATTCCTAC AACGAGCACT
601 GGAACTACCT GACCATCTGC CAGCTGTGCC GCCCCTGTGA
```

```
641  CCCAGTGATG GGCCTCGAGG AGATTGCCCC CTGCACAAGC

681  AAACGGAAGA CCCAGTGCCG CTGCCAGCCG GGAATGTTCT

721  GTGCTGCCTG GGCCCTCGAG TGTACACACT GCGAGCTACT

761  TTCTGACTGC CCGCCTGGCA CTGAAGCCGA GCTCAAAGAT

801  GAAGTTGGGA AGGGTAACAA CCACTGCGTC CCCTGCAAGG

841  CCGGGCACTT CCAGAATACC TCCTCCCCCA GCGCCCGCTG

881  CCAGCCCCAC ACCAGGTGTG AGAACCAAGG TCTGGTGGAG

921  GCAGCTCCAG GCACTGCCCA GTCCGACACA ACCTGCAAAA

961  ATCCATTAGA GCCACTGCCC CCAGAGATGT CAGGAACCAT

1001 GCTGATGCTG GCCGTTCTGC TGCCACTGGC CTTCTTTCTG

1041 CTCCTTGCCA CCGTCTTCTC CTGCATCTGG AAGAGCCACC

1081 CTTCTCTCTG CAGGAAACTG GGATCGCTGC TCAAGAGGCG

1121 TCCGCAGGGA GAGGGACCCA ATCCTGTAGC TGGAAGCTGG

1161 GAGCCTCCGA AGGCCCATCC ATACTTCCCT GACTTGGTAC

1201 AGCCACTGCT ACCCATTTCT GGAGATGTTT CCCCAGTATC

1241 CACTGGGCTC CCCGCAGCCC CAGTTTTGGA GGCAGGGGTG

1281 CCGCAACAGC AGAGTCCTCT GGACCTGACC AGGGAGCCGC

1321 AGTTGGAACC CGGGGAGCAG AGCCAGGTGG CCCACGGTAC

1361 CAATGGCATT CATGTCACCG GCGGGTCTAT GACTATCACT

1401 GGCAACATCT ACATCTACAA TGGACCAGTA CTGGGGGGAC

1441 CACCGGGTCC TGGAGACCTC CCAGCTACCC CCGAACCTCC

1481 ATACCCCATT CCCGAAGAGG GGGACCCTGG CCCTCCCGGG

1521 CTCTCTACAC CCCACCAGGA AGATGGCAAG GCTTGGCACC

1561 TAGCGGAGAC AGAGCACTGT GGTGCCACAC CCTCTAACAG

1601 GGGCCCAAGG AACCAATTTA TCACCCATGA CTGACTGAGT

1641 CTGAGAAAAG GCAGAAGAAG GGGGCACAA GGGCACCTTC

1681 TCCCTTGAGG CTGCCCTGCC CACGTGGGAT TCACAGGGGC

1721 CTGAGTAGGG CCCGGGGAAG CAGAGCCCTA AGGGATTAAG

1761 GCTCAGACAC CTCTGAGAGC AGGTGGGCAC TGGCTGGGTA

1801 CGGTGCCCTC CACAGGACTC TCCCTACTGC CTGAGCAAAC

1841 CTGAGGCCTC CCGGCAGACC CACCCACCCC CTGGGCTGC

1881 TCAGCCTCAG GCACGGACAG GGCACATGAT ACCAACTGCT

1921 GCCCACTACG GCACGCCGCA CCGGAGCACG GCACCGAGGC

1961 AGCCGCCACA CGGTCACCTG CAAGGACGTC ACGGGCCCCT

2001 CTAAAGGATT CGTGGTGCTC ATCCCCAAGC TTCAGAGACC

2041 CTTTGGGGTT CCACACTTCA CGTGGACTGA GGTAGACCCT

2081 GCATGAAGAT GAAATTATAG GGAGGACGCT CCTTCCCTCC

2121 CCTCCTAGAG GAGAGGAAAG GGAGTGATTA ACAACTAGGG

2161 GGTTGGGTAG GATTCCTAGG TATGGGGAAG AGTTTTGGAA

2201 GGGGAGGAAA ATGGCAAGTG TATTTATATT GTAACCACAT

2241 CCAAATAAAA ACAATGGGAC CTAGATAAAA AAAAAAAAA

2281 AAA
```

STING, cGAS, NF-κB transcription factor p52, NF-κB transcription factor RelB, ENPP1, LTβR, BAFFR, CD40, RANK, FN14, NIK (MAP3K14), and MST1 proteins and nucleic acids can exhibit sequence variation. However, variants with less than 100% sequence identity to the amino acid and nucleic acid sequences shown herein can still have similar activities. For example, STING, cGAS, NF-κB transcription factor p52, NF-κB transcription factor RelB, ENPP1, LTβR, BAFFR, CD40, RANK, FN14, NIK (MAP3K14), and MST1 proteins and nucleic acid with at least 90%, at least 92%, at least 95%, at least 96%, at least 97%, at least 98%, at least 99%, or at least 99.5% sequence identity to any of SEQ ID NOs: 13-24 can still be used in the compositions and methods described herein.

Expression Systems

Nucleic acid segments encoding any kinsin-13, MCAK, ABCC4, and/or ABCG2 protein, as well as nucleic acids encoding STING, cGAS, NF-κB transcription factor p52, NF-κB transcription factor RelB proteins, ENPP1, LTβR, BAFFR, CD40, RANK, FN14, NIK (MAP3K14), MST1, or nucleic acid segments including any STING, cGAS, NF-κB transcription factor p52, NF-κB transcription factor RelB, ENPP1, LTβR, BAFFR, CD40, RANK, FN14, NIK (MAP3K14), MST1 inhibitory nucleic acid can be inserted into or employed with any suitable expression system. A therapeutically effective quantity of kinsin-13, MCAK, ABCC4, and/or ABCG2 protein can be generated from such expression systems. A therapeutically effective STING, cGAS, NF-κB transcription factor p52, NF-κB transcription factor RelB, ENPP1, LTβR, BAFFR, CD40, RANK, FN14, NIK (MAP3K14), and/or MST1 inhibitory nucleic acid can also be generated from such expression systems.

Recombinant expression of nucleic acids (or inhibitory nucleic acids) is usefully accomplished using a vector, such as a plasmid. The vector can include a promoter operably linked to nucleic acid segment encoding a kinsin-13, MCAK, ABCC4, and/or ABCG2 protein, or a protein such as a STING, cGAS, NF-κB transcription factor p52, and/or NF-κB transcription factor RelB, ENPP1, LTβR, BAFFR, CD40, RANK, FN14, NIK (MAP3K14), and/or MST1. In another example, a vector can include a promoter operably linked to nucleic acid segment that encodes a STING, cGAS, NF-κB transcription factor p52, and/or NF-κB transcription factor RelB, ENPP1, LTβR, BAFFR, CD40, RANK, FN14, NIK (MAP3K14), MST1 inhibitory nucleic acid.

The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing kinsin-13, KIF13A, MCAK, ABCC4, and/or ABCG2. A variety of prokaryotic and eukaryotic expression vectors suitable for carrying, encoding and/or expressing STING, cGAS, NF-κB transcription factor p52, and/or NF-κB transcription factor RelB, ENPP1, LTβR, BAFFR, CD40, RANK, FN14, NIK (MAP3K14), and/or MST1 inhibitory nucleic acids can be employed. Such expression vectors include, for example, pET, pET3d, pCR2.1, pBAD, pUC, and yeast vectors. The vectors can be used, for example, in a variety of in vivo and in vitro situations.

The expression cassette, expression vector, and sequences in the cassette or vector can be heterologous. As used herein, the term "heterologous" when used in reference to an expression cassette, expression vector, regulatory sequence, promoter, or nucleic acid refers to an expression cassette, expression vector, regulatory sequence, or nucleic acid that has been manipulated in some way. For example, a heterologous promoter can be a promoter that is not naturally linked to a nucleic acid of interest, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA forms; the cDNA sequences may be expressed in either a sense (to produce mRNA) or anti-sense orientation (to produce an anti-sense RNA transcript that is complementary to the mRNA transcript). Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase Il transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleic acid segment encoding a kinsin-13. MCAK, ABCC4, and/or ABCG2 protein. In another example, the promoter can be upstream of a STING, cGAS, NF-κB transcription factor p52, and/or NF-κB transcription factor RelB, ENPP1, LTβR, BAFFR, CD40, RANK, FN14, NIK (MAP3K14), and/or MST1 inhibitory nucleic acid segment.

A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences for the termination of transcription, which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The expression of a kinsin-13, KIF13A, MCAK, ABCC4, and/or ABCG2 protein, or of STING, cGAS, NF-κB transcription factor p52, and/or NF-κB transcription factor RelB, ENPP1, LTβR, BAFFR, CD40, RANK, FN14, NIK (MAP3K14), and/or MST1 inhibitory nucleic acids from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV.

The expression cassette or vector can include nucleic acid sequence encoding a marker product. This marker product is used to determine if the gene has been delivered to the cell and once delivered is being expressed. Marker genes can include the E. coli lacZ gene which encodes β-galactosidase, and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern P. and Berg, P., J. Molec. Appl. Genet. 1: 327 (1982)), mycophenolic acid, (Mulligan, R. C. and Berg, P. Science 209:1422 (1980)) or hygromycin, (Sugden, B. et al., Mol. Cell. Biol. 5: 410-413 (1985)).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991).

For example, the kinesin-13-related (e.g., kinsin-13, MCAK, ABCC4, ABCG2, or KIF13A), nucleic acid molecule, expression cassette and/or vector, and/or the STING, cGAS, NF-κB transcription factor p52, NF-κB transcription factor RelB, ENPP1, LTβR, BAFFR, CD40, RANK, FN14, NIK (MAP3K14), and/or MST1 inhibitory nucleic acid molecule, expression cassette and/or vector can be introduced to a cell by any method including, but not limited to, calcium-mediated transformation, electroporation, microinjection, lipofection, particle bombardment and the like. The cells can be expanded in culture and then administered to a subject, e.g. a mammal such as a human. The amount or number of cells administered can vary but amounts in the range of about $10^6$ to about $10^9$ cells can be used. The cells are generally delivered in a physiological solution such as saline or buffered saline. The cells can also be delivered in a vehicle such as a population of liposomes, exosomes or microvesicles.

In some cases, the transgenic cell can produce exosomes or microvesicles that contain kinesin-13-related (e.g., kinsin-13, MCAK, ABCC4, ABCG2, or KIF13A) nucleic acid molecules, expression cassettes and/or vectors, and/or that produce STING, cGAS, NF-κB transcription factor p52, NF-κB transcription factor RelB, ENPP1, LTβR, BAFFR, CD40, RANK, FN14, NIK (MAP3K14), and/or MST1 inhibitory nucleic acids. Microvesicles can mediate the secretion of a wide variety of proteins, lipids, mRNAs, and micro RNAs, interact with neighboring cells, and can thereby transmit signals, proteins, lipids, and nucleic acids from cell to cell (see, e.g., Shen et al., J Biol Chem. 286(16): 14383-14395 (2011); Hu et al., Frontiers in Genetics 3 (April 2012); Pegtel et al., Proc. Nat'l Acad Sci 107(14): 6328-6333 (2010); WO/2013/084000; each of which is incorporated herein by reference in its entirety. Cells producing such microvesicles can be used to express the STING, cGAS, NF-κB transcription factor p52, and/or NF-κB transcription factor kinesin-13-related (e.g., kinsin-13, MCAK, ABCC4, ABCG2, or KIF13A), RelB, ENPP1, LTβR, BAFFR, CD40, RANK, FN14, NIK (MAP3K14), and/or MST1 proteins and/or inhibitory nucleic acids.

Transgenic vectors or cells with a heterologous expression cassette or expression vector that expresses the kinesin-13 protein(s) (e.g., Kif2b, MCAK/Kif2c, kinsin-13, MCAK, ABCC4, ABCG2, or KIF13A) that can optionally also express STING, cGAS, NF-κB transcription factor p52, NF-κB transcription factor RelB, ENPP1, LTβR, BAFFR, CD40, RANK, FN14, and/or NIK (MAP3K14), and/or MST1 inhibitory nucleic acids can be administered to a subject. Transgenic vectors or cells with a heterologous expression cassette or expression vector can also optionally express ENPP1. Exosomes produced by transgenic cells can be used to deliver kinesin-13/MCAK nucleic acids or protein(s) (e.g., Kif2b, MCAK/Kif2c, ABCC4, ABCG2, and/or KIF13A nucleic acids or protein(s)) to tumor and cancer cells in the subject. Exosomes produced by transgenic cells can be used to deliver STING, cGAS, NF-κB transcription factor p52, NF-κB transcription factor RelB, ENPP1, LTβR, BAFFR, CD40, RANK, FN14, NIK (MAP3K14), and/or MST1 inhibitory nucleic acids to tumor and cancer cells in the subject.

Methods and compositions that include inhibitors of STING, cGAS, NF-κB transcription factor p52, NF-κB transcription factor RelB, ENPP1, LTβR, BAFFR, CD40, RANK, FN14, NIK (MAP3K14), MST1, or any combination thereof can involve use of antibodies or inhibitory nucleic acids directed against STING, cGAS, NF-κB transcription factor p52, NF-κB transcription factor RelB, ENPP1, LTβR, BAFFR, CD40, RANK, FN14, NIK (MAP3K14), MST1, or any combination thereof.

Inhibitory Nucleic Acids

The expression of the following can be inhibited STING, cGAS, NF-κB transcription factor p52, NF-κB transcription factor RelB, ENPP1, LTβR, BAFFR, CD40, RANK, FN14, NIK (MAP3K14), MST1, or any combination thereof, for example by use of an inhibitory nucleic acid that specifically recognizes a nucleic acid that encodes STING, cGAS, NF-κB transcription factor p52, NF-κB transcription factor RelB, ENPP1, LTβR, BAFFR, CD40, RANK, FN14, NIK (MAP3K14), or MST1.

An inhibitory nucleic acid can have at least one segment that will hybridize to a STING, cGAS, NF-κB transcription factor p52, NF-κB transcription factor RelB, ENPP1, LTβR, BAFFR, CD40, RANK, FN14, NIK (MAP3K14), or MST1 nucleic acid under intracellular or stringent conditions. The inhibitory nucleic acid can reduce expression of a nucleic acid encoding STING, cGAS, NF-κB transcription factor p52, NF-κB transcription factor RelB, ENPP1, LTβR, BAFFR, CD40, RANK, FN14, NIK (MAP3K14), or MST1. A nucleic acid may hybridize to a genomic DNA, a messenger RNA, or a combination thereof. An inhibitory nucleic acid may be incorporated into a plasmid vector or viral DNA. It may be single stranded or double stranded, circular or linear.

An inhibitory nucleic acid is a polymer of ribose nucleotides or deoxyribose nucleotides having more than 13 nucleotides in length. An inhibitory nucleic acid may include naturally-occurring nucleotides; synthetic, modified, or pseudo-nucleotides such as phosphorothiolates; as well as nucleotides having a detectable label such as $P^{32}$, biotin or digoxigenin. An inhibitory nucleic acid can reduce the expression and/or activity of a STING, cGAS, NF-κB transcription factor p52, NF-κB transcription factor RelB, ENPP1, LTβR, BAFFR, CD40, RANK, FN14, NIK (MAP3K14), or MST1 nucleic acid. Such an inhibitory nucleic acid may be completely complementary to a segment of the STING, cGAS, NF-κB transcription factor p52, NF-κB transcription factor RelB, ENPP1, LTβR, BAFFR, CD40, RANK, FN14, NIK (MAP3K14), or MST1 nucleic acid. Alternatively, some variability is permitted in the inhibitory nucleic acid sequences relative to STING, cGAS, NF-κB transcription factor p52, NF-κB transcription factor RelB, ENPP1, LTβR, BAFFR, CD40, RANK, FN14, NIK (MAP3K14), or MST1 sequences. An inhibitory nucleic acid can hybridize to a STING, cGAS, NF-κB transcription factor p52, NF-κB transcription factor RelB, ENPP1, LTβR, BAFFR, CD40, RANK, FN14, NIK (MAP3K14), or MST1 nucleic acid under intracellular conditions or under stringent hybridization conditions, and is sufficiently complementary to inhibit expression of a STING, cGAS, NF-κB transcription factor p52, NF-κB transcription factor RelB, ENPP1, LTβR, BAFFR, CD40, RANK, FN14, NIK (MAP3K14), or MST1 nucleic acid. Intracellular conditions refer to conditions such as temperature, pH and salt concentrations typically found inside a cell, e.g. an animal or mammalian cell. One example of such an animal or mammalian cell is a myeloid progenitor cell. Another example of such an animal or mammalian cell is a more differentiated cell derived from a myeloid progenitor cell. Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Inhibitory oligonucleotides that comprise, for example, 2, 3, 4, or 5 or more stretches of contiguous nucleotides that are precisely complementary to a STING, cGAS, NF-κB transcription factor p52, NF-κB transcription factor RelB, ENPP1, LTβR, BAFFR, CD40, RANK, FN14, NIK (MAP3K14), or MST1 coding sequence, each separated by a stretch of contiguous nucleotides that are not complementary to adjacent coding sequences, can inhibit the function of a STING, cGAS, NF-κB transcription factor p52, NF-κB transcription factor RelB, ENPP1, LTβR, BAFFR, CD40, RANK, FN14, NIK (MAP3K14), or MST1 nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an inhibitory nucleic acid hybridized to a sense nucleic acid to estimate the degree of mismatching that will be tolerated for inhibiting expression of a particular target nucleic acid. Inhibitory nucleic acids of the invention include, for example, a short hairpin RNA, a small interfering RNA, a ribozyme or an antisense nucleic acid molecule.

Examples of a nucleic acid encoding STING, cGAS, NF-κB transcription factor p52, NF-κB transcription factor RelB, ENPP1, LTβR, BAFFR, CD40, RANK, FN14, NIK (MAP3K14), or MST1 are shown herein. Example 1 provides examples of inhibitory nucleic acid sequences, including SEQ ID NOs:25-36. See also FIGS. 6 and 9.

The inhibitory nucleic acid molecule may be single or double stranded (e.g. a small interfering RNA (siRNA)), and may function in an enzyme-dependent manner or by steric blocking. Inhibitory nucleic acid molecules that function in an enzyme-dependent manner include forms dependent on RNase H activity to degrade target mRNA. These include single-stranded DNA, RNA, and phosphorothioate molecules, as well as the double-stranded RNAi/siRNA system that involves target mRNA recognition through sense-antisense strand pairing followed by degradation of the target mRNA by the RNA-induced silencing complex. Steric blocking inhibitory nucleic acids, which are RNase-H independent, interfere with gene expression or other mRNA-dependent cellular processes by binding to a target mRNA and getting in the way of other processes. Steric blocking inhibitory nucleic acids include 2'-0 alkyl (usually in chimeras with RNase-H dependent antisense), peptide nucleic acid (PNA), locked nucleic acid (LNA) and morpholino antisense.

Small interfering RNAs, for example, may be used to specifically reduce STING, cGAS, NF-κB transcription factor p52, NF-κB transcription factor RelB, ENPP1, LTβR, BAFFR, CD40, RANK, FN14, NIK (MAP3K14), or MST1 translation such that translation of the encoded polypeptide is reduced. SiRNAs mediate post-transcriptional gene silencing in a sequence-specific manner. See, for example, website at invitrogen.com/site/us/en/home/Products-and-Services/Applications/rnai.html. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the STING, cGAS, NF-κB transcription factor p52, NF-κB transcription factor RelB, ENPP1, LTβR, BAFFR, CD40, RANK, FN14, NIK (MAP3K14), or MST1 mRNA transcript. The region of homology may be 30 nucleotides or less in length, preferable less than 25 nucleotides, and more preferably about 21 to 23 nucleotides in length. SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411: 494-498 (2001); Harborth et al. *Antisense Nucleic Acid Drug Dev.* 13: 83-106 (2003).

The pSuppressorNeo vector for expressing hairpin siRNA, commercially available from IMGENEX (San Diego, Calif.), can be used to generate siRNA for inhibiting STING, cGAS, NF-κB transcription factor p52, NF-κB transcription factor RelB, ENPP1, LTβR, BAFFR, CD40, RANK, FN14, NIK (MAP3K14), or MST1 expression. The construction of the siRNA expression plasmid involves the selection of the target region of the mRNA, which can be a trial-and-error process. However, Elbashir et al. have provided guidelines that appear to work ~80% of the time. Elbashir, S. M., et al., *Analysis of gene function in somatic mammalian cells using small interfering RNAs*. Methods, 2002. 26(2): p. 199-213. Accordingly, for synthesis of synthetic siRNA, a target region may be selected preferably 50 to 100 nucleotides downstream of the start codon. The 5' and 3' untranslated regions and regions close to the start codon should be avoided as these may be richer in regulatory protein binding sites. As siRNA can begin with AA, have 3' UU overhangs for both the sense and antisense siRNA strands, and have an approximate 50% G/C content. An example of a sequence for a synthetic siRNA is 5'-AA(N19)UU, where N is any nucleotide in the mRNA sequence and should be approximately 50% G-C content. The selected sequence(s) can be compared to others in the human genome database to minimize homology to other known coding sequences (e.g., by Blast search, for example, through the NCBI website).

SiRNAs may be chemically synthesized, created by in vitro transcription, or expressed from an siRNA expression vector or a PCR expression cassette. See, e.g., website at invitrogen.com/site/us/en/home/Products-and-Services/Applications/mai.html. When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be of any appropriate lengths, for example, 3 to 30 nucleotides in length, preferably, 3 to 23 nucleotides in length, and may be of various nucleotide sequences including, AUG, CCC, UUCG, CCACC, CTCGAG, AAGCUU, CCACACC and UUCAAGAGA (SEQ ID NO:60). SiRNAs also may be produced in vivo by cleavage of double-stranded RNA introduced directly or via a transgene or virus. Amplification by an RNA-dependent RNA polymerase may occur in some organisms.

An inhibitory nucleic acid such as a short hairpin RNA siRNA or an antisense oligonucleotide may be prepared using methods such as by expression from an expression vector or expression cassette that includes the sequence of the inhibitory nucleic acid. Alternatively, it may be prepared by chemical synthesis using naturally-occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the inhibitory nucleic acid and the target STING, cGAS, NF-κB transcription factor p52, NF-κB transcription factor RelB, ENPP1, LTβR, BAFFR, CD40, RANK, FN14, NIK (MAP3K14), or MST1 nucleic acid.

An inhibitory nucleic acid may be prepared using available methods, for example, by expression from an expression vector encoding the sequence of the STING, cGAS, NF-κB transcription factor p52, NF-κB transcription factor RelB, ENPP1, LTβR, BAFFR, CD40, RANK, FN14, NIK (MAP3K14), and/or MST1 nucleic acid, or a complement thereof. Alternatively, it may be prepared by chemical synthesis using naturally-occurring nucleotides, modified nucleotides or any combinations thereof. In some embodiments, the STING, cGAS, NF-κB transcription factor p52, NF-κB transcription factor RelB, and ENPP1, LTβR, BAFFR, CD40, RANK, FN14, NIK (MAP3K14), and/or MST1 nucleic acids are made from modified nucleotides or non-phosphodiester bonds, for example, that are designed to increase biological stability of the STING, cGAS, NF-κB transcription factor p52, NF-κB transcription factor RelB, ENPP1, LTβR, BAFFR, CD40, RANK, FN14, NIK (MAP3K14), and/or MST1 nucleic acids or to increase intracellular stability of the duplex formed between the inhibitory nucleic acids and other (e.g., endogenous) nucleic acids.

For example, the STING, cGAS, NF-κB transcription factor p52, NF-κB transcription factor RelB, ENPP1, LTβR, BAFFR, CD40, RANK, FN14, NIK (MAP3K14), and/or MST1 nucleic acids can be peptide nucleic acids that have peptide bonds rather than phosphodiester bonds.

Naturally-occurring nucleotides that can be employed in STING, cGAS, NF-κB transcription factor p52, NF-κB transcription factor RelB, ENPP1, LTβR, BAFFR, CD40, RANK, FN14, NIK (MAP3K14), and/or MST1 nucleic acids include the ribose or deoxyribose nucleotides adenosine, guanine, cytosine, thymine and uracil. Examples of modified nucleotides that can be employed in STING, cGAS, NF-κB transcription factor p52, NF-κB transcription factor RelB, ENPP1, LTβR, BAFFR, CD40, RANK, FN14, NIK (MAP3K14), and/or MST1 nucleic acids include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3) w, and 2,6-diaminopurine.

Thus, STING, cGAS, NF-κB transcription factor p52, NF-κB transcription factor, RelB nucleic acids as well as the ENPP1, LTβR, BAFFR, CD40, RANK, FN14, NIK (MAP3K14), and/or MST1 inhibitory nucleic acids may include modified nucleotides, as well as natural nucleotides such as combinations of ribose and deoxyribose nucleotides. The inhibitory nucleic acids and may be of same length as wild type (e.g., SEQ ID NO:14, 16, 18, 20, 22 or 24) The STING, cGAS, NF-κB transcription factor p52, and NF-κB transcription factor RelB nucleic acids as well as the ENPP1, LTβR, BAFFR, CD40, RANK, FN14, NIK (MAP3K14), and/or MST1 inhibitory nucleic acids can also be longer and include other useful sequences. In some embodiments, the STING, cGAS, NF-κB transcription factor p52, NF-κB transcription factor RelB, ENPP1, LTβR, BAFFR, CD40, RANK, FN14, NIK (MAP3K14), and/or MST1 nucleic acids are somewhat shorter. For example, the STING, cGAS, NF-κB transcription factor p52, NF-κB transcription factor RelB, ENPP1, LTβR, BAFFR, CD40, RANK, FN14, NIK (MAP3K14), and/or MST1 inhibitory nucleic acids can include a segment that has nucleic acid sequence (e.g., SEQ ID NO:14, 16, 18, 20, 22, or 24) that can be missing up to 5 nucleotides, or missing up to 10 nucleotides, or missing up to 20 nucleotides, or missing up to 30 nucleotides, or missing up to 50 nucleotides, or missing up to 100 nucleotides from the 5' or 3' end.

Antibodies

Antibodies can be used as inhibitors of STING, cGAS, NF-κB transcription factor p52, NF-κB transcription factor RelB, ENPP1, LTβR, BAFFR, CD40, RANK, FN14, and NIK (MAP3K14), MST1. Antibodies can be raised against various epitopes of the STING, cGAS, NF-κB transcription factor p52, NF-κB transcription factor RelB, ENPP1, LTβR, BAFFR, CD40, RANK, FN14, and NIK (MAP3K14), MST1 proteins. Some antibodies for STING, cGAS, NF-κB transcription factor p52, NF-κB transcription factor RelB, ENPP1, LTβR, BAFFR, CD40, RANK, FN14, and NIK (MAP3K14), MST1 proteins may also be available commercially. However, the antibodies contemplated for treatment pursuant to the methods and compositions described herein are preferably human or humanized antibodies, and are highly specific for their targets.

In one aspect, the present disclosure relates to use of isolated antibodies that bind specifically to STING, cGAS, NF-κB transcription factor p52, NF-κB transcription factor RelB proteins, ENPP1, LTβR, BAFFR, CD40, RANK, FN14, NIK (MAP3K14), or MST1. Such antibodies may be monoclonal antibodies. Such antibodies may also be humanized or fully human monoclonal antibodies. The antibodies can exhibit one or more desirable functional properties, such as high affinity binding to STING, cGAS, NF-κB transcription factor p52, NF-κB transcription factor RelB proteins, ENPP1, LTβR, BAFFR, CD40, RANK, FN14, NIK (MAP3K14), or MST1, or the ability to inhibit binding of STING, cGAS, NF-κB transcription factor p52, NF-κB transcription factor RelB proteins, ENPP1, LTβR, BAFFR, CD40, RANK, FN14, NIK (MAP3K14), or MST1 receptor.

Methods and compositions described herein can include STING, cGAS, NF-κB transcription factor p52, NF-κB transcription factor RelB proteins, ENPP1, LTβR, BAFFR, CD40, RANK, FN14, NIK (MAP3K14), or MST1 antibodies, or a combination of STING, cGAS, NF-κB transcription factor p52, NF-κB transcription factor RelB proteins, ENPP1, LTβR, BAFFR, CD40, RANK, FN14, NIK (MAP3K14), MST1 antibodies.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g. a domain of STING, cGAS, NF-κB transcription factor p52, NF-κB transcription factor RelB proteins, ENPP1, LTβR, BAFFR, CD40, RANK, FN14, NIK (MAP3K14), or MST1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds STING, cGAS, NF-κB transcription factor p52, NF-κB transcription factor RelB proteins, ENPP1, LTβR, BAFFR, CD40, RANK, FN14, NIK (MAP3K14), or MST1 is substantially free of antibodies that specifically bind antigens other than STING, cGAS, NF-κB transcription factor p52, NF-κB transcription factor RelB proteins, ENPP1, LTβR, BAFFR, CD40, RANK, FN14, NIK (MAP3K14), or MST1). An isolated antibody that specifically binds STING, cGAS, NF-κB transcription factor p52, NF-κB transcription factor RelB proteins, ENPP1, LTβR, BAFFR, CD40, RANK, FN14, NIK (MAP3K14), or MST1 may, however, have cross-reactivity to other antigens, such as STING, cGAS, NF-κB transcription factor p52, NF-κB transcription factor RelB proteins, ENPP1, LTβR, BAFFR, CD40, RANK, FN14, NIK (MAP3K14), or MST1-family molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_L$ and $V_H$ regions of the recombinant antibodies are sequences that, while derived from and related to human germline $V_L$ and $V_H$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human STING, cGAS, NF-κB transcription factor p52, NF-κB transcription factor RelB proteins, ENPP1, LTβR, BAFFR, CD40, RANK, FN14, NIK (MAP3K14), or MST" is intended to refer to an antibody that binds to human STING, cGAS, NF-κB transcription factor p52, NF-κB transcription factor RelB proteins, ENPP1, LTβR, BAFFR, CD40, RANK, FN4, NIK (MAP3K14), or MST1 with a $K_D$ of $1 \times 10^{-7}$ M or less, more preferably $5 \times 10^{-8}$ M or less, more preferably $1 \times 10^{-8}$ M or less, more preferably $5 \times 10^{-9}$ M or less, even more preferably between $1 \times 10^{-8}$ M and $1 \times 10^{-10}$ M or less.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The antibodies of the invention are characterized by particular functional features or properties of the antibodies. For example, the antibodies bind specifically to human STING, cGAS, NF-κB transcription factor p52, NF-κB transcription factor RelB proteins, ENPP1, LTβR, BAFFR, CD40, RANK, FN14, NIK (MAP3K14), or MST1. Preferably, an antibody of the invention binds to STING, cGAS, NF-κB transcription factor p52, NF-κB transcription factor RelB proteins, ENPP1, LTβR, BAFFR, CD40, RANK, FN14, NIK (MAP3K14), or MST1 with high affinity, for example with a $K_D$ of $1 \times 10^{-7}$ M or less. The antibodies can exhibit one or more of the following characteristics:

(a) binds to human STING, cGAS, NF-κB transcription factor p52, NF-κB transcription factor RelB proteins, ENPP1, LTβR, BAFFR, CD40, RANK, FN14, NIK (MAP3K14), or MST1 with a $K_D$ of $1 \times 10^{-7}$ M or less;

(b) inhibits the function or activity of STING, cGAS, NF-κB transcription factor p52, NF-κB transcription factor RelB proteins, ENPP1, LTβR, BAFFR, CD40, RANK, FN14, NIK (MAP3K14), or MST1;

(c) inhibits cancer (e.g., metastatic cancer); or (d) a combination thereof.

Assays to evaluate the binding ability of the antibodies toward STING, cGAS, NF-κB transcription factor p52, NF-κB transcription factor RelB proteins, ENPP1, LTβR, BAFFR, CD40, RANK, FN14, NIK (MAP3K14), or MST1 can be used, including for example, ELISAs, Western blots and RIAs. The binding kinetics (e.g., binding affinity) of the antibodies also can be assessed by standard assays known in the art, such as by Biacore™. analysis.

Given that each of the subject antibodies can bind to STING, cGAS, NF-κB transcription factor p52, NF-κB transcription factor RelB proteins, ENPP1, LTβR, BAFFR, CD40, RANK, FN14, NIK (MAP3K14), or MST1, the $V_L$ and $V_H$ sequences can be "mixed and matched" to create other binding molecules that bind to STING, cGAS, NF-κB transcription factor p52, NF-κB transcription factor RelB proteins, ENPP1, LTβR, BAFFR, CD40, RANK, FN14, NIK (MAP3K14), or MST1. The binding properties of such "mixed and matched" antibodies can be tested using the binding assays described above and assessed in assays described in the examples. When $V_L$ and $V_H$ chains are mixed and matched, a $V_H$ sequence from a particular $V_H/V_L$ pairing can be replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence; and (b) alight chain variable region comprising an amino acid sequence;

wherein the antibody specifically binds STING, cGAS, NF-κB transcription factor p52, NF-κB transcription factor RelB proteins, ENPP1, LTβR, BAFFR, CD40, RANK, FN14, NIK (MAP3K14), or MST1.

In some cases, the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., British J. of Cancer 83(2):252-260 (2000) (describing the production of a humanized anti-CD30 antibody using only the heavy chain variable domain CDR3 of murine anti-CD30 antibody Ki-4); Beiboer et al., J. Mol. Biol. 296:833-849 (2000) (describing recombinant epithelial glycoprotein-2 (EGP-2) antibodies using only the heavy chain CDR3 sequence of the parental murine MOC-31 anti-EGP-2 antibody); Rader et al., Proc. Natl. Acad. Sci. U.S.A. 95:8910-8915 (1998) (describing a panel of humanized anti-integrin alpha$_v$beta$_3$ antibodies using a heavy and light chain variable CDR3 domain. Hence, in some cases a mixed and matched antibody or a humanized antibody contains a CDR3 antigen binding domain that is specific for STING, cGAS, NF-κB transcription factor p52, NF-κB transcription factor RelB proteins, ENPP1, LTβR, BAFFR, CD40, RANK, FN14, NIK (MAP3K14), or MST1.

Small Molecules

Small molecule modulators of STING, cGAS, NF-κB transcription factor p52, and NF-κB transcription factor RelB, ENPP1, LTβR, BAFFR, CD40, RANK, FN14, NIK (MAP3K14), and/or MST1 are also available. For example, the SK4A compound is a specific inhibitor of ENNP1 (Arad et al., *SAT0037An ENPP1-Specific Inhibitor Attenuates Extracellular Ecto-Pyrophosphatase Activity in Human Osteoarthritic Cartilage*, see website at ard.bmj.com/content/74/Suppl_2/662.1 (2015)).

In addition, the following compound (L524-0366) is an FN14 antagonist.

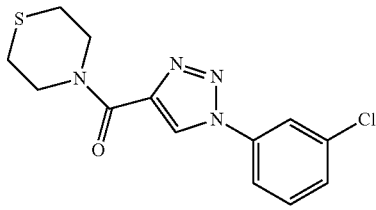 [SMILES: O=C(c1cn(-c2cccc(Cl)c2)nn1)N1CCSCC1]

Assays for Drug Development

Methods are also described herein for screening metastatic tumor samples for susceptibility to treatment with candidate compounds. Specifically, the methods can include assay steps for identifying a candidate compound that selectively interferes with proliferation or viability of cells exhibiting increased chromosomal instability (e.g., CIN-mutant cells) or metastatic cells that have elevated levels of cGAMP.

If proliferation or viability of cells exhibiting increased chromosomal instability (e.g., CIN-mutant cells) is decreased in the presence of a test compound as compared to a normal control cell then that test compound has utility for reducing the growth and/or metastasis of cells exhibiting such increased chromosomal instability.

Similarly, if a cell or population of cells has elevated levels cGAMP then that cell or cell population is cancerous or will develop cancer. When cGAMP levels of such a cell or population of cells exhibits decreased levels of cGAMP as compared to previous levels for the cGAMP secreting cells, then that test compound has utility for reducing the growth and/or metastasis of cells that have elevated levels of cGAMP.

An assay can include determining whether a compound can specifically cause decreased levels of cGAMP from metastatic or CIN cancer cells, or cell lines. If the compound does cause decreased levels, then the compound can be selected/identified for further study, such as for its suitability as a therapeutic agent to treat a cancer. For example, the candidate compounds identified by the selection methods featured in the invention can be further examined for their ability to target a tumor or to treat cancer by, for example, administering the compound to an animal model.

The cells that are evaluated can include cells from a patient with cancer (including a patient with metastatic cancer), or cells from a known cancer type or cancer cell line, or cells exhibiting an overproduction of cGAMP. A compound that can reduce the production of cGAMP from any of these cell types can be administered to a patient.

For example, one method can include (a) obtaining a cell or tissue sample from a patient; (b) measuring the amount or concentration of cGAMP produced from a known number or weight of cells or tissues from the sample to generate a reference cGAMP value; (c) mixing the same known number or weight of cells or tissues from the sample with a test compound to generate a test assay; (d) measuring the cGAMP amount or concentration in the test assay (either in the cell medium or in the cells or tissues) to generate a test assay cGAMP value; (e) optionally repeating steps (c) and (d); and selecting a test compound with a lower test assay cGAMP value than the reference cGAMP value. The method can further include administering a test compound to an animal model, for example, to further evaluate the toxicity and/or efficacy of the test compound. In some cases, the method can further include administering the test compound to the patent from whom the cell or tissue sample as obtained.

For example, another method can include assays useful for identifying KIF2B and KIF2C/MCAK agonists or activators. KIF2B and KIF2C/MCAK are related molecular kinesin motor proteins that utilize the energy of ATP hydrolysis to regulate microtubule dynamics and chromosome-kinetochore attachments. The central role of KIF2B and MCAK over expression or hyper activation is suppressing chromosomal instability (CIN) makes them attractive targets for cancer therapy. An in vitro assay and imaging method are described below that can be used to identify and assess potent activators of KIF2B and MCAK.

Measuring the kinetics of ATP hydrolysis can be used to screen for compounds that activate KIF2B and MCAK and that suppress CIN. This assay is based upon an absorbance shift (330 to 360 nm) that occurs when 2-amino-6-mercapto-7-methylpurine ribonucleoside (MESG) is converted to 2-amino-6-mercapto-7-methyl purine in the presence of inorganic phosphate. The reaction is catalyzed by purine nucleoside phosphorylase (PNP). One molecule of inorganic phosphate (Pi) will yield one molecule of 2-amino-6-mercapto-7-methyl purine in a irreversible reaction. Thus, the absorbance at 360 nm is directly proportional to the amount of Pi generated in the ATPase reaction, and can be used as a proxy for MCAK activity.

Alternatively, ADP production can also be monitored as a readout for MCAK activity using the Transcreener ADP assay from BellBrook Labs. This assay is based on the ability of ADP to displace a fluorescent tracer (633 nm) bound to an antibody the specifically recognizes ADP. Displacement of the tracer causes a decrease in fluorescence measured by laser excitation at 633 nm. Thus, activity of MCAK can be calculated by plotting the concentration of drug used and the amount of ADP produced/decrease in fluorescent intensity.

The following is another example of a method for identifying and assessing the potency of MCAK activators. MCAK negatively regulates microtubule length by binding microtubule tips and promoting microtubule depolymerization. Therefore, distance between γ-tubulin-labeled centrosomes can be measured as an indirect readout for MCAK activity in cells. Spindle length is inversely proportional to MCAK activity and can serve as proxy to evaluate potential compounds that promote MCAK activity. This method can be adapted for screening compounds by using a high-throughput imaging microscope.

Compounds (e.g., top hits identified by any method described herein) can be used in a cell-based assay using lagging chromosomes, micronuclei, or chromosome missegregation with Fluorescent in situ hybridization (FISH) as a readout of their efficacy. Cells having chromosomes with labeled γ-tubulin centromeres can be used. Alternatively, labeled antibodies that bind to γ-tubulin in centrosomes can be used in the assays.

Assay methods are also described herein for identifying and assessing the potency of inhibitors of NF-kB Inducing Kinase (NIK). NF-kB Inducing Kinase (NIK) mediates non-canonical NF-kB signaling and is associated with metastasis. Therefore, the inhibition of NIK may suppress CIN induced inflammatory responses and metastasis. Specific inhibition of the kinase function of NIK provides an approach to assess the potency of various compounds. Two methods are described below to identify and assess NIK inhibition.

ADP production can be monitored as a readout for MCAK activity using the Transcreener ADP assay from BellBrook Labs. This assay is based on the ability of ADP to displace a fluorescent tracer (633 nm) bound to an antibody the specifically recognizes ADP. Competitive displacement of the tracer causes a decrease in fluorescence, as measured by laser excitation at 633 nm. Thus, the activity of MCAK can be calculated by plotting the concentration of drug used and the amount of ADP produced/decrease in fluorescent intensity.

Inhibition of NIK provides an approach to directly inhibit the non-canonical NF-κB pathway. This assay relies on quantification of the nuclear translocation of p52 (RELB; non-canonical NF-kB signaling) using high content cellular imaging. For RELB nuclear translocation assay, cells are treated with different concentrations of compounds and stimulated with 100 ng/mL of an antagonistic antilymphotoxin beta receptor (LT-PR) antibody, a potent activator of non-canonical NF-kB signaling. The RELB translocation into the nucleus is quantified by the ratio of the nuclear over cytoplasmic signal intensity. Potent compounds are discovered that selectively inhibit the nuclear translocation of RELB.

The compounds so identified can be useful for selectively targeting tumors or treating cancers characterized by CIN. For example, the compounds are useful for treating tumors or cancer types that exhibit overproduction of cGAMP.

"Treatment" or "treating" refers to both therapeutic treatment, and prophylactic or preventative measures. Those in need of treatment include those already with the disorder as well as those prone to have the disorder, or those in whom the disorder is to be prevented.

"Subject" for purposes of treatment refers to any animal classified as a mammal or bird, including humans, domestic and farm animals, and zoo, sports, or pet animals, such as dogs, horses, cats, cows, etc. Preferably, the subject is human.

As used herein, the term "cancer" includes solid animal tumors as well as hematological malignancies. The terms "tumor cell(s)" and "cancer cell(s)" are used interchangeably herein.

"Solid animal tumors" include cancers of the head and neck, lung, mesothelioma, mediastinum, lung, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. In addition, a metastatic cancer at any stage of progression can be treated, such as micrometastatic tumors, megametastatic tumors, and recurrent cancers.

The term "hematological malignancies" includes adult or childhood leukemia and lymphomas, Hodgkin's disease, lymphomas of lymphocytic and cutaneous origin, acute and chronic leukemia, plasma cell neoplasm and cancers associated with AIDS.

The inventive methods and compositions can also be used to treat cancer of the breast, cancer of the lung, cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. A cancer at any stage of progression can be treated or detected, such as primary, metastatic, and recurrent cancers. In some cases, metastatic cancers are treated but primary cancers are not treated. Information regarding numerous types of cancer can be found, e.g., from the American Cancer Society (cancer.org), or from, e.g., Wilson et al. (1991) Harrison's Principles of Internal Medicine, 12th Edition, McGraw-Hill, Inc.

In some embodiments, the cancer and/or tumors to be treated are those that originate as breast or lung cancers.

Treatment of, or treating, metastatic cancer can include the reduction in cancer cell migration or the reduction in establishment of at least one metastatic tumor. The treatment also includes alleviation or diminishment of more than one symptom of metastatic cancer such as coughing, shortness of breath, hemoptysis, lymphadenopathy, enlarged liver, nausea, jaundice, bone pain, bone fractures, headaches, seizures, systemic pain and combinations thereof. The treatment may cure the cancer, e.g., it may prevent metastatic cancer, it may substantially eliminate metastatic tumor formation and growth, and/or it may arrest or inhibit the migration of metastatic cancer cells.

Anti-cancer activity can reduce the progression of a variety of cancers (e.g., breast, lung, or prostate cancer) using methods available to one of skill in the art. Anti-cancer activity, for example, can determined by identifying the lethal dose ($LD_{100}$) or the 50% effective dose (ED50) or the dose that inhibits growth at 50% ($GI_{50}$) of an agent of the present invention that prevents the migration of cancer cells. In one aspect, anti-cancer activity is the amount of the agent that reduces 50%, 60%, 70%, 80%, 90%, 95%, 97%, 98%, 99% or 100% of cancer cell migration, for example, when measured by detecting expression of a cancer cell marker at sites proximal or distal from a primary tumor site, or when assessed using available methods for detecting metastases.

In another example, agents that promote chromosomal instability can be administered to sensitize tumor cells to immune therapies. Chromosomal instability promotes a viral-like response that synergizes with immune checkpoint blockades. Hence, by administering an agent that promotes chromosomal instability, tumor cells can become more sensitive to the immune system and to various immune therapies.

Compositions

The invention also relates to compositions containing chemotherapeutic agents. Such an agent can be a polypeptide, a nucleic acid encoding a polypeptide (e.g., within an expression cassette or expression vector), a small molecule, a compound identified by a method described herein, or a combination thereof. The compositions can be pharmaceutical compositions. In some embodiments, the compositions can include a pharmaceutically acceptable carrier. By "pharmaceutically acceptable" it is meant that a carrier, diluent, excipient, and/or salt is compatible with the other ingredients of the formulation, and not deleterious to the recipient thereof.

The composition can be formulated in any convenient form. In some embodiments, the compositions can include a Kinsin-13, MCAK, ABCC4, and/or ABCG2 protein or polypeptide having at least 90% amino acid sequence identity to SEQ ID NO:1, 3, 5, 7, 9, 11, or a combination of such Kinsin-13, MCAK, ABCC4, and/or ABCG2 proteins or polypeptides. In other embodiments, the compositions can include a Kinsin-13, MCAK, ABCC4, and/or ABCG2 nucleic acid or expression cassette that includes a nucleic acid segment encoding a Kinsin-13, MCAK, ABCC4, and/or ABCG2 protein. For example, the nucleic acid or expression cassette can have a nucleic acid sequence with at least 90% sequence identity to any of SEQ ID NO: 2, 4, 6, 8, 10, 12.

In some embodiments, the chemotherapeutic agents of the invention (e.g., polypeptide, a nucleic acid encoding a polypeptide (e.g., within an expression cassette or expression vector), a small molecule, a compound identified by a method described herein, or a combination thereof), are administered in a "therapeutically effective amount." Such a therapeutically effective amount is an amount sufficient to obtain the desired physiological effect, such a reduction of at least one symptom of cancer. For example, chemotherapeutic agents can reduce cell metastasis by 5%, or 10%, or 15%, or 20%, or 25%, or 30%, or 35%, or 40%, or 45%, or 50%, or 55%, or 60%, or 65%, or %70, or 80%, or 90%, 095%, or 97%, or 99%, or any numerical percentage between 5% and 100%. Symptoms of cancer can also include tumor cachexia, tumor-induced pain conditions, tumor-induced fatigue, tumor growth, and metastatic spread. Hence, the chemotherapeutic agents may also reduce tumor cachexia, tumor-induced pain conditions, tumor-induced fatigue, tumor growth, or a combination thereof by 5%, or 10%, or 15%, or 20%, or 25%, or 30%, or 35%, or 40%, or 45%, or 50%, or 55%, or 60%, or 65%, or %70, or 80%, or 90%, 095%, or 97%, or 99%, or any numerical percentage between 5% and 100%.

To achieve the desired effect(s), the chemotherapeutic agents may be administered as single or divided dosages. For example, chemotherapeutic agents can be administered in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the type of small molecules, compounds, peptides, or nucleic acid chosen for administration, the disease, the weight, the physical condition, the health, and the age of the mammal. Such factors can be readily determined by the clinician employing animal models or other test systems that are available in the art.

Administration of the chemotherapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the chemotherapeutic agents and compositions of the invention may be essentially continuous over a preselected period of time or may be in a series of spaced doses. Both local and systemic administration is contemplated.

To prepare the composition, small molecules, compounds, polypeptides, nucleic acids, expression cassettes, and other agents are synthesized or otherwise obtained, purified as necessary or desired. These small molecules, compounds, polypeptides, nucleic acids, expression cassettes, and other agents can be suspended in a pharmaceutically acceptable carrier and/or lyophilized or otherwise stabilized. The small molecules, compounds, polypeptides, nucleic acids, expression cassettes, other agents, and combinations thereof can be adjusted to an appropriate concentration, and optionally combined with other agents. The absolute weight of a given small molecule, compound, polypeptide, nucleic acid, and/or other agents included in a unit dose can vary widely. For example, about 0.01 to about 2 g, or about 0.1 to about 500 mg, of at least one molecule, compound, polypeptide, nucleic acid, and/or other agent, or a plurality of molecules, compounds, polypeptides, nucleic acids, and/or other agents can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the chemotherapeutic agents of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of chemotherapeutic agent for use in treatment will vary not only with the particular carrier selected but also with the route of administration, the nature of the cancer condition being treated and the age and condition of the patient. Ultimately the attendant health care provider can determine proper dosage. In addition, a pharmaceutical composition can be formulated as a single unit dosage form.

Thus, one or more suitable unit dosage forms comprising the chemotherapeutic agent(s) can be administered by a variety of routes including parenteral (including subcutaneous, intravenous, intramuscular and intraperitoneal), oral, rectal, dermal, transdermal, intrathoracic, intrapulmonary and intranasal (respiratory) routes. The chemotherapeutic agent(s) may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the chemotherapeutic agent with liquid carriers, solid matrices, semi-solid carriers, finely divided solid carriers or combinations thereof, and then, if necessary, introducing or shaping the product into the desired delivery system. For example, the chemotherapeutic agent(s) can be linked to a convenient carrier such as a nanoparticle, albumin, polyalkylene glycol, or be supplied in prodrug form. The chemotherapeutic agent(s), and combinations thereof can be combined with a carrier and/or encapsulated in a vesicle such as a liposome.

The compositions of the invention may be prepared in many forms that include aqueous solutions, suspensions, tablets, hard or soft gelatin capsules, and liposomes and other slow-release formulations, such as shaped polymeric gels. Administration of inhibitors can also involve parenteral or local administration of the in an aqueous solution or sustained release vehicle.

Thus, while the chemotherapeutic agent(s) and/or other agents can sometimes be administered in an oral dosage form, that oral dosage form can be formulated so as to protect the small molecules, compounds, polypeptides, nucleic acids, expression cassettes, and combinations thereof from degradation or breakdown before the small molecules, compounds, polypeptides, nucleic acids encoding such polypeptides, and combinations thereof provide therapeutic utility. For example, in some cases the small molecules, compounds, polypeptides, nucleic acids encoding such polypeptide, and/or other agents can be formulated for release into the intestine after passing through the stomach. Such formulations are described, for example, in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives. The pharmaceutical compositions may take such forms as suspensions, solutions, or emulsions in oily or aqueous vehicles, and may contain formulatory agents such as suspending, stabilizing and/or dispersing agents. Suitable carriers include saline solution, encapsulating agents (e.g., liposomes), and other materials. The chemotherapeutic agent(s) and/or other agents can be formulated in dry form (e.g., in freeze-dried form), in the presence or absence of a carrier. If a carrier is desired, the carrier can be included in the pharmaceutical formulation, or can be separately packaged in a separate container, for addition to the inhibitor that is packaged in dry form, in suspension or in soluble concentrated form in a convenient liquid.

A chemotherapeutic agent(s) and/or other agents can be formulated for parenteral administration (e.g., by injection, for example, bolus injection or continuous infusion) and may be presented in unit dosage form in ampoules, prefilled syringes, small volume infusion containers or multi-dose containers with an added preservative.

The compositions can also contain other ingredients such as chemotherapeutic agents, anti-viral agents, antibacterial agents, antimicrobial agents and/or preservatives. Examples of additional therapeutic agents that may be used include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compositions can also be used in conjunction with radiation therapy.

The present description is further illustrated by the following examples, which should not be construed as limiting in any way. The contents of all cited references (including literature references, issued patents, published patent applications as cited throughout this application) are hereby expressly incorporated by reference.

Example 1: Materials and Methods

This Examples describes some of the materials and methods employed in the development of the invention.

Genomic Analysis of Primary-Metastasis Matched Pairs.

Whole exome DNA sequence data from 61 brain metastases with matched primary tumor and normal (Brastianos et al. *Cancer Discovery* 5, 1164-1177 (2015)) was downloaded from the database of Genotypes and Phenotypes (dbGAP) and processed as described (McGranahan et al. *Science* 351, 1463-1469 (2016)) to derive allele specific segmented DNA copy number data for each sample. The weighted Genome Instability Index (wGII), describing the proportion of the genome that was classified as aberrant relative to tumor ploidy, was determined as described (Burrell et al., *Nature* 494, 492-496 (2013)).

Mitelman Database analysis.

All available breast adenocarcinoma cases in the Mitelman database (Mitelman et al. Database of Chromosome Aberrations and Gene Fusions in Cancer. cgap.nci.nih.gov Available at: cgap.nci.nih.gov/Chromosomes/Mitelman) were analyzed. Primary literature was reviewed to determine the source of the sample (primary tumor or metastasis). When clonal karyotype was reported as a range, the average value was used for this clone. Karyotype aberrations included structural aberrations as well as numerical deviations from the overall karyotype of the clone.

Analysis of Chromosome Segregation in HNSCC.

Primary tumor specimens were analyzed from 60 patients with head and neck squamous cell carcinoma (HNSCC) (Chung et al. *Cancer Cell* 5, 489-500 (2004)). Forty patients had Hematoxylin and Eosin-stained (H&E) primary tumor samples of sufficient quality for high-resolution microscopy analysis. Analysis was restricted to cells fixed while undergoing anaphase as previously described (Bakhoun et al. *Clin. Cancer Res.* 17, 7704-7711 (2011); Zaki et al. *Cancer* 120, 1733-1742 (2014)). Chromosome missegregation was defined by hematoxylin staining presence in between the remaining segregating chromosomes during anaphase and it was reported as the percentage of cells undergoing anaphase with evidence of chromosome missegregation. Clinical lymph node status was defined by clinical examination or radiographic evidence of lymph node tumor involvement (Chung et al. *Cancer Cell* 5, 489-500 (2004)).

Single-Cell Karyotyping.

Cultures were treated with colcemid at a final concentration of 0.1 µg ml$^{-1}$. Following 45 min incubation at 37° C., the cultures were trypsinized, resuspended in pre-warmed 0.075M KCl, incubated for an additional 10 minutes at 37° C. and fixed in methanol-acetic acid (3:1). The fixed cell suspension was then dropped onto slides, stained in 0.08 µg/ml DAPI in 2×SSC for 5 minutes and mounted in antifade solution (Vectashield, Vector Labs). Metaphase spreads were captured using the Nikon Eclipse E800 epifluorescence microscope equipped with GenASI Cytogenetic suite (Applied Spectral Imaging, Carlsbad). For each sample a minimum of 20 inverted DAPI-stained metaphases were fully karyotyped and analyzed according to the International System of Human Cytogenetic Nomenclature (ISCN) 2013.

Cell culture.

Cell lines were purchased from the American Type Culture Collection (ATCC). Tumor (MDA-MB-231 and H2030) and 293T cells were cultured in DMEM supplemented with 10% FBS and 2 mM of L-Glutamine in the presence of penicillin (50 Uml$^{-1}$) and streptavidin (50 µgml$^{-1}$). All cells tested negative for mycoplasma. Cell confluence was measured using IncuCyte live-cell analysis system (Essen Bioscience).

Immunofluorescence Microscopy.

Cell fixation and antibody staining were performed as described (Bakhoun et al. *Nat Commun* 6, 5990 (2015)). Briefly, cells were fixed with ice-cold (−30 C) methanol for 15 minutes—when staining for centromeres, centrosomes, cGAS, Vimentin, β-actin, or α-tubulin—or 4% paraformaldehyde—when staining for RelB, p65, IRF3, ssDNA, dsDNA, CoxIV, or β-catenin. Subsequently, cells were permeabilized using 1% triton for 4 minutes. See Table 1 for antibody information.

TABLE 1

Antibodies used for immunofluorescence

| Antibody Target | Source | Catalog No. |
|---|---|---|
| α-tubulin | Sigma Aldrich | T9026 |
| β-actin | Abcam | ab8227 |
| β-catenin | Abcam | ab16051 |
| cGAS | Sigma Aldrich | HPA031700 |
| Cox IV | Abcam | ab16056 |
| dsDNA | Abcam | AB27156 |
| dsDNA (FIG. 5f) | Thermo Fisher Scientific | MAB1293MI |
| Human centromere proteins | Antibodies Incorporated | 15-234-0001 |
| IRF3 | Abcam | ab68481 |
| p65 | Abcam | ab16502 |
| Pericentrin | Abcam | ab4448 |
| RelB | Cell Signaling Technology | 4922 |
| ssDNA | Thermo Fisher Scientific | MAB3299MI |
| Vimentin | Abcam | ab201637 |

For selective plasma membrane permeabilization used for cytosolic dsDNA and ssDNA staining, cells were treated with 0.02% saponin for 5 minutes after fixation. For single-stranded (Thermo Fisher FEREN0321) and double stranded (Life Technologies—EN0771)-specific nuclease treatment, cells were also permeabilized with 0.02% saponin for 2 minutes and treated with either nucleases for 10 minutes before fixation using 4% paraformaldehyde. TBS-BSA was used as a blocking agent during antibody staining. DAPI was added together with secondary antibodies. Cells were mounted with Prolong Diamond Antifade Mountant (Life Technologies—P36961).

Immunoblotting.

Cells were pelleted and lysed using RIPA buffer. Protein concentration was determined using BCA protein assay and 20-30 mg of total protein were loaded in each lane. Proteins were separated by gradient SDS-PAGE and transferred to PVDF membranes. See Table 2 for antibody information.

TABLE 2

Antibodies used for immunoblots

| Antibody Target | Company | Catalog No. |
|---|---|---|
| β-actin | Abcam | ab8227 |
| cGAS | Sigma Aldrich | HPA031700 |
| GFP | Life Technologies | A11122 |
| IRF3 | Abcam | ab68481 |
| p100/p52 | Cell Signaling | 4882 |
| p65 | Abcam | ab16502 |
| phospho-IRF3 | Cell Signaling | 4947 |
| phospho-p100 | Abcam | 194919 |
| phospho-p65 | Cell Signaling | 3033 |
| phospho-TBK1 | Cell Signaling | 5483 |
| RelB | Cell Signaling | 4922 |
| STING | Cell Signaling | 13647 |
| TBK1 | Cell Signaling | 3013 |
| TRAF2 | Cell Signaling | 4712 |
| TRAF3 | Cell Signaling | 4729 |

Figure 6A:
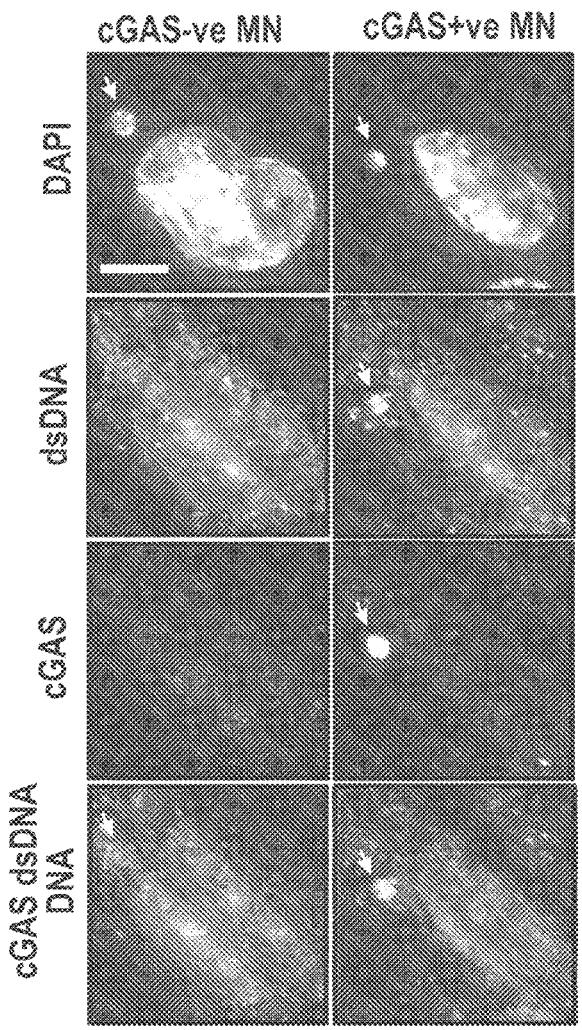
Figure 6B:
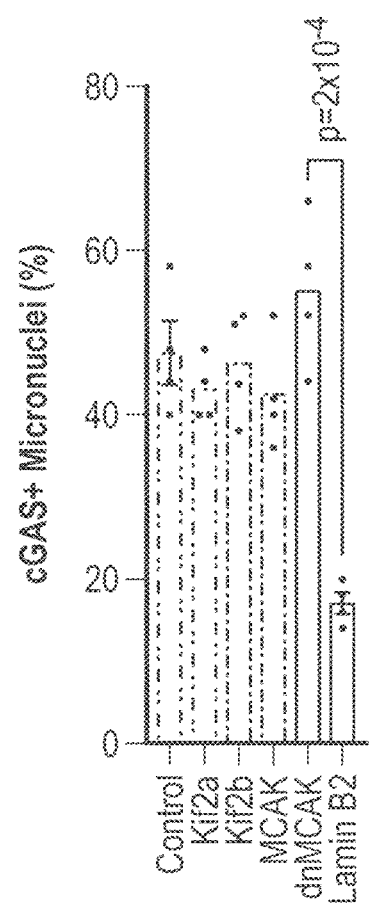
Figure 6C:
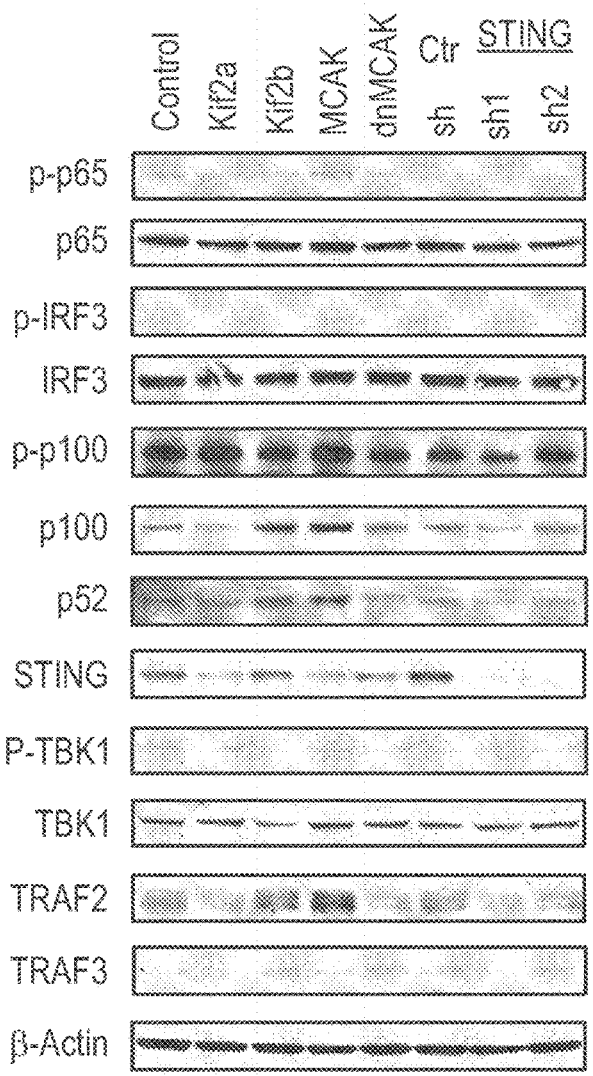
Figure 6D:
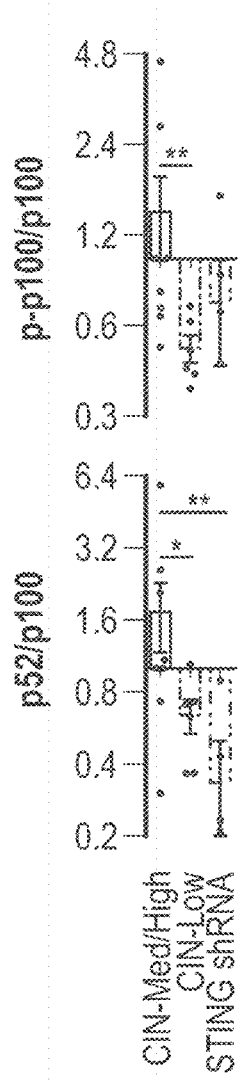

For quantitative comparisons shown in FIG. 6D, immunoblots from three biological replicates were used. Band intensities were obtained using ImageJ (see website at imagej.nih.gov/ij), normalized to β-actin (loading control) and background was subtracted. Ratios were normalized to control cells.

Knockdown and Overexpression Constructs.

Luciferase expression was achieved using pLVX plasmid (expressing tdTomato) and cells stably expressing luciferase were sorted for tdTomato expression. Kinesin-13 expression was achieved using plasmid (pEGFP) transfection or lentiviral (pLenti-GIII-CMV-GFP-2A-Puro) expression where cells were selected using G418 (0.5mgml$^{-1}$) or puromycin (5 µgml$^{-1}$), respectively. Dnase2 overexpression was achieved using a pLenti-GIII-CMV-RFP-2A-Puro plasmid with puromycin used for selection. Plasmids containing kinesin-13 or Lamin B2 (pQCXIB-mCherry-lmnb2) constructs were kindly offered by the Compton and Hetzer Laboratories, respectively. Blasticidin was used to select for lmnb2 expressing cells at 10 µgml$^{-1}$. All other plasmids were purchased from Applied Biological Materials Inc. (www.abmgood.com). Stable knockdown of STING, NFKB2, RelB, and cGAS were achieved using shRNAs in pRRL (SGEP or SGEN) plasmids and were obtained from the MSKCC RNA Interference Core. Two to four distinct shRNA hairpins were screened per target. Targeted shRNA sequences are listed in Table 3.

TABLE 3

Anti-sense shRNA sequences

| Gene Name | Entrez ID | shRNA ID | shRNA anti-sense sequence |
|---|---|---|---|
| cGAS | 115004 | 2 | TTCATATTCAATTTGCTTTGTC (SEQ ID NO: 25) |
| | | 1 | TTAGTTTTAAACAATCTTTCCT (SEQ ID NO: 26) |
| | | 3 | TTCTAAAAACTGACTCAGAGGA (SEQ ID NO: 27) |
| NFKB2 | 4791 | 1 | TTCAGTTGCAGAAACACTGTTA (SEQ ID NO:28) |
| | | 3 | TCATCATATTCAATAATACCAT (SEQ ID NO: 29) |
| | | 2 | TGAAGTTTTTGTATCATAGTCC (SEQ ID NO: 30) |

TABLE 3-continued

Anti-sense shRNA sequences

| Gene Name | Entrez ID | shRNA ID | shRNA anti-sense sequence |
|---|---|---|---|
| RelB | 5971 | 3 | TTCCTCATCTGTAAAATGGGCT (SEQ ID NO: 31) |
| | | 1 | TAATGATTGGGGAACATGTTGC (SEQ ID NO: 32) |
| | | 4 | TTTCTTGTCATAGACGGGCTCG (SEQ ID NO: 33) |
| | | 2 | TCAAAAACTCATCTTTATTGGG (SEQ ID NO: 34) |
| STING | 340061 | 2 | TTATGATCCCATTTCACAGGTT (SEQ ID NO: 35) |
| | | 1 | TCTCAAGAGAAATCCGTGCGGA (SEQ ID NO: 36) |

Animal Studies.

Animal experiments were performed in accordance with protocols approved by the Weill Cornell Medicine Institutional Animal Care and Use Committee. For disease-specific survival, power analysis indicated that 10 mice per group will be sufficient to detect a difference at relative hazard ratios of <0.2 or >5 with 80% power and 95% confidence, given a median disease-specific survival of 3 months in the control group and a total follow up period of 250 days. There was no need to randomize animals. Investigators were not blinded to group allocation. Intracardiac injection was performed as previously described (Chen et al. Nature 533, 493-498 (2016)). Briefly, cells were trypsinized and washed with PBS and a $1\times10^5$ cells (in 100 µl of PBS) were injected into the left cardiac ventricle of female athymic 6-7-week-old athymic nude (nu/nu) mice (Jackson Laboratory strain 002019). Mice were then immediately injected with D-luciferin (150 mgkg$^{-1}$) and subjected to bioluminescence imaging (BLI) using tan IVIS Spectrum Xenogen instrument (Caliper Life Sciences) to ensure systemic dissemination of tumor cells. Metastatic burden was measured at week 5 after injection using BLI and in the case of MDA-MB-231 mice BLI images were taken every 1-2 weeks for up to 17 weeks. BLI images were analyzed using Living Image Software v.2.50. Disease-specific survival endpoint was met when the mice died or met the criteria for euthanasia under the IACUC protocol and had radiographic evidence of metastatic disease. For Orthotopic tumor implantation, $2.5\times10^5$ cells in 50p of PBS were mixed 1:1 with Matrigel (BD Biosciences) and injected into the fourth mammary fat pad. Only one tumor was implanted per animal. Primary tumors were surgically excited when they reached ~1.5 cm in the largest dimension and metastatic dissemination was assessed using BLI imaging at 1-week to 3-week intervals for up to 30 weeks. Distant metastasis-free survival endpoint was met when BLI signal was seen outside of site of primary tumor transplantation. To derive short-term culture from primary tumors and metastases, anesthetized animals (isofluorane) were imaged then sacrificed. Ex-vivo BLI was subsequently performed on harvested organs to define the precise location of the metastatic lesion. Primary tumors and metastases were subsequently mechanically dissociated and cultured in DMEM with selection media to select for tumor cells. All subsequent assays were performed after one passage.

Patient-Derived Xenografts (PDX) Assays.

PDX models of human metastatic breast cancers were successfully generated by transplanting the freshly obtained surgically excised tumor specimens from patients consented under the IRB approved protocol (MSKCC IRB #97-094) in female NOD-scid IL2Rgamma$^{null}$ (NSG) (Jackson Laboratories strain 005557). The estrogen receptor-positive PDX was derived from breast cancer metastatic to the bone. The triple-negative PDX was established out of an axillary lymph node metastasis from a patient with inflammatory breast cancer. PDXs were maintained for a maximum of three serial passages. Briefly, freshly obtained tumor tissue specimens were either directly transplanted in the mammary fat-pad of the mice or minced into 1-2 mm pieces in serum free MEM medium with nonessential amino acids (Cat #41500018, Thermofisher) transduced with lentiviral vectors expressing either GFP-luciferase or pUltra-Chili-Luc plasmid (Addgene plasmid: 48688) followed by transplantation into mice. Typically, PDX tumor growth became evident during the first 1-3 weeks post engrafting and tumor continued to grow for additional 4-8 weeks. Primary tumor growth and metastases were followed using BLI or spectrum CT imaging. At the time of harvesting of primary tumors and metastases, we derived primary cell cultures directly from primary tumors as well as lung and liver metastases. Briefly, 500 mg of fresh bulk tumor tissues were chopped into 1-2 mm$^3$ sized pieces and incubated in Accutase (AT104; Innovative Cell Technologies) for cell detachment and separation over 1-2 hours. The dissociated tissues were sieved through 100-µm cell strainers and pelleted the cells by centrifugation at 1200 RPM. The pellets are washed and resuspended in the above MEM buffer with 3% FBS. Cells were analyzed for chromosome missegregation after one passage.

RNA sequencing and analysis. Bulk RNA was extracted from cells using the QIAShredder (Qiagen—79654) and the RNA extraction kit (Qiagen—74106) and sequenced using HiSeq2500 or HiSeq4000 (Illumina Inc.). The quality of the raw FASTQ files were checked with FastQC (see website at bioinformatics.babraham.ac.uk/projects/fastqc/), then mapped to human reference GRCh38 using STAR (v2.4.1d, 2-pass mode) (Dobin et al. Bioinformatics 29, 15-21 (2013)). Gene expression was estimated using cufflinks (v2.2.1, default parameters) and HTSeq (v0.6.1) (Trapnell et al. Nat Biotechnol 28, 511-515 (2010); Anders et al. Bioinformatics 31, 166-169 (2015)). Differential expression analyses were performed using DESeq2 (v.14.1) (Love et al. Genome Biol. 15, 550 (2014)). Prior to any unsupervised analyses, expression counts were transformed using variance-stabilizing transformation using the DESeq2 R package. All custom code, statistical analysis, and visualizations were performed in Python or R. We used Nextflow to manage some of the computational pipelines (see website at nextflow.io).

Single-Cell RNA Sequencing.

Cells were trypsinized and resuspended in PBS. 21 ul of a cellular suspension at 400 cells/ul, >95% viability, were loaded onto to the 10× Genomics Chromium platform to generate barcoded single-cell GEMs. Single-cell RNA sequencing (scRNA-seq) libraries were prepared according to 10× Genomics specifications (Single Cell 3' Reagent Kits User Guide PN-120233, 10× Genomics, Pleasanton, Calif., USA). GEM-Reverse Transcription (RT) (55° C. for 2 h, 85° C. for 5 min; held at 4° C.) was performed in a C1000 Touch Thermal cycler with 96-Deep Well Reaction Module (Bio-Rad, Hercules). After RT, GEMs were broken and the single-strand cDNA was cleaned up with DynaBeads MyOne Silane Beads (Thermo Fisher Scientific, Waltham, Mass.) and SPRIselect Reagent Kit (0.6×SPRI; Beckman Coulter). cDNA was amplified for 14 cycles using the C1000 Touch Thermal cycler with 96-Deep Well Reaction Module (98° C. for 3 min; 98° C. for 15 s, 67° C. for 20 s, and 72° C. for 1 min×14 cycles; 72° C. for 1 min; held at 4° C.). Quality of the cDNA was analyzed using an Agilent Bioanalyzer 2100 (Santa Clara, Calif.). The resulting cDNA was sheared to ~200 bp using a Covaris S220 instrument (Covaris, Woburn, Mass.) and cleaned using 0.6× SPRI beads. The products were end-repaired, 'A'-tailed and ligated to adaptors provided in the kit. A unique sample index for each library was introduced through 10 cycles of PCR amplification using the indexes provided by in the kit (98° C. for 45 s; 98° C. for 20 s, 60° C. for 30 s, and 72° C. for 20 s×14 cycles; 72° C. for 1 min; held at 4° C.). After two SPRI cleanups, libraries were quantified using Qubit fluorometric quantification (Thermo Fisher Scientific, Waltham, Mass.) and the quality assessed on an Agilent Bioanalyzer 2100. Four libraries were pooled and clustered on a HiSeq2500 rapid mode at 10 pM on a pair end read flow cell and sequenced for 98 cycles R1, followed by 14 bp I7 Index (10× Barcode), 8 bp I5 Index (sample Index) and 10 bp on R2 (UMI). Primary processing of sequencing images was done using Illumina's Real Time Analysis software (RTA). Demultiplexing and post processing was done using the 10× Genomics Cell Ranger pipeline as per the manufacturer recommendations. Single cell RNA sequencing data (scRNA-seq) was processed from raw reads to a molecule count array using the Cell Ranger pipeline (Zheng et al. *Nat Commun* 8, 14049 (2017)). Additionally, to minimize the effects of experimental artifacts on the analysis, data was pre-processed to filter out cells with low total molecule counts (library size), low complexity and high mitochondrial content, identified by a bimodal fit. Remaining cells were normalized by dividing the expression level of each gene in a cell by its total library size and then scaling by the median library size of all cells). After normalizing by library size; principal component analysis (PCA) was performed to improve robustness of the constructed Markov Matrix generated when computing diffusion eigenvalues for imputation of dropout noise (van Dijk et al. *bioRxiv* (2017)). The number of principle components was chosen to retain approximately 80% of variance in the data and excluded the first principal component, which was highly correlated with library size. Imputation of both he normalized and unnormalized count matrix was performed using a Markov matrix raised to the power of 3 (power corresponds the approximate number of weighted nearest neighbors) and with a gene expression distribution computed according to 21 nearest neighboring cells as described (van Dijk et al. *bioRxiv* (2017)). Subpopulations were identified using Phenograph (Levine et al. *Cell* 162, 184-197 (2015)) and genes differentially expressed in at least one subpopulation were identified by the Kruskal-Wallis rank statistic using a bootstrapping method for random down-sampling of matched molecule and cell counts from each subpopulation. t-Distributed Stochastic Neighbor Embedding (t-SNE) was used to visualize subpopulation structure based on the first 20 principle components of the imputed count matrix, subsetted by the top 5,150 differentially expressed genes (False Discovery Rate (FDR) q of Kruskal Wallis rank statistic <0.05). Mean expression of key gene signatures in population M versus other subpopulations were z-normalized and visualized by violin plots. All gene signatures are annotated near the end of Example 1. The correlation between gene signatures was computed using the Spearman Rank Correlation Coefficient according to mean expression of all genes per signature per cell. Ward's minimum variance method was applied to hierarchically cluster cells by their normalized expression of differentially expressed epithelial-to-mesenchymal transition (EMT) genes.

Patient Survival Analysis.

Genes used for survival analysis include PELI2, BMP2, SHH, TNS4, RAB3B, ROBO1, ARHGAP28, CHN2, CST1, F13A1, CPVL, SEMA6D, NHSL2, GTF2IP7, DPYSL3, PCDH7, KHDRBS3, TRAC, TMEM156, CST4, CD24, FGF5, (optionally NTN4) (see Table 5).

Two independent datasets were used to evaluate survival markers. The first was a meta-analysis (Györffy et al., Breast Cancer Res. Treat. 123, 725-731 (2010)) and a validation cohort (Hatzis et al. J. Am. Med. Assoc. 305, 1873-1881 (2011)). For the meta analysis, publicly available microarray gene expression datasets deposited in the KM-Plotter database (www.kmplot.com) were used, with the following microarray probes for each gene (note that some genes have multiple names and alternate names could be listed below): 219132_at (PELI2), 205289_at (BMP2), 207586_at (SHH), 230398_at (TNS4), 227123_at (RAB3B), 213194_at (ROBO1), 227911_at (ARHGAP28), 213385_at (CHN2), 206224_at (CST1), 203305_at (F3A1), 208146_s_at (CPVL), 226492_at, (SEMA6D), 201431_s_at (DPYSL3), 228640_at (PCDH7), 209781_s_at (etoile), 210972_x_at (TRA@), 220169_at (TMEM156), 206994_at (CST4), 266_s_at (CD24), 210311_at (FGF5), 200948_at (MLF2). For the meta-analysis cohort, the JetSet best probe set was used and auto-selection was used for best cutoff between the 25$^{th}$ and 75th percentile. For the validation cohort in which DMFS data was available (Hatzis et al. *JAMA* 305, 1873-1881 (2011)), the z-normalized expression data for a dataset and the median value was used as a cutoff. DMFS curves were compared using the log-rank test. For the first dataset, the best cutoff value was determined to be the 36-percentile was then used such that the patients with cumulative expression of the genes above that were in the bottom 36-percentile had higher metastasis-free survival. In the second data set, publicly deposited gene expression data was used that was derived from next-gen sequencing and the median expression values were used as a cutoff and obtained similar results. In this type of analysis, it is typical to use cutoff values ranging from the 25-percentile to the 75-percentile depending on the patient population and assay used thus we should include that.

In Vitro Invasion and Migration Assays.

For the invasion and migration/chemotaxis assays the CytoSelect cell invasion (CBA-110) and cell migration (CBA-100) kits, respectively, were used. Briefly, 3×10$^5$ cells were suspended in serum-free media and placed on top of the membrane. Media containing serum was placed at the bottom and cells, which have invaded to the inferior surface of the collagen membrane, were stained and counted 18-24 hours later. For the chemotaxis assay, we used a colorimetric approach (OD 560 nm) for quantification. For the scratch assay, cells were treated with mitomycin C (10 µgml$^{-1}$) for 1 hour when they reached >90% confluence and then placed in DMEM containing 1% FBS. Wounds were applied using p200 pipette tip and images of the wound were taken immediately and at subsequent regular intervals. ImageJ was used for quantification of wound surface area.

Quantification of Cytosolic DNA.

Approximately 1×10$^7$ cells were lysed and the nuclear, cytosolic, and mitochondrial fractions were obtained using the mitochondrial isolation kit (Thermo Fisher—89874). Protease inhibitors were not used to enable subsequent DNA purification. Mitochondria were purified at 12,000×g to minimize their contamination in the cytosolic fraction. DNA was subsequently isolated from the nuclear, cytosolic, mitochondrial fractions using the Qiagen DNeasy blood and tissue kit (Qiagen—69506) and dsDNA was quantified using Qubit 2.0 (Invitrogen) using Qubit dsDNA HS Reagent.

Data Availability.

All RNA sequencing data was deposited in the Sequence Read Archive (SRA, www.ncbi.nlm.nih.gov/sra). Single-cell RNAseq data was deposited under the following accession number: SRP104750. Bulk RNAseq data was deposited under the following accession number: SRP104476. Access link at website ftp://ftp-trace.ncbi.nlm.nih.gov/sra/review/SRP104476_20170424_100917_3d522deaf85 577451c01974654b36ad3

CIN Gene Expression Signature for Assessing Survival: PELI2, BMP2, SHH, TNS4, RAB3B, ROBO1, ARHGAP28, CHN2, CST1, F13A1, CPVL, SEMA6D, NHSL2, GTF2IP7, DPYSL3, PCDH7, KHDRBS3, TRAC, TMEM156, CST4, CD24, FGF5, (optionally NTN4). Examples of sequences for the proteins and nucleic acids encoding these proteins, are illustrated in Table 5.

TABLE 5

CIN Gene Expression Signature Genes

| Gene Name | Example CIN Gene Expression Signature Human Sequence |
|---|---|
| PELI2 | mfspgqeehc apnkepvkyg elvvlgynga lpngdrqrrk srfalykrpk angvkpstvh vistpqaska isckgqhsis ytlsrnqtvv veythdkdtd mfqvgrstes pidfvvtdti sgsqntdeaq itqstisrfa crivcdrnep ytarifaagf dsskniflge kaakwknpdg hmdglttngv lvmhprggft eesqpgvwre isvcgdvytl retrsaqqrg klvesetnvl qdgslidlcg atllwrtadg lfhtptqkhi ealrqeinaa rpgcpvglnt lafpsinrke vveekqpway lscghvhgyh nwghrsdtea nerecpmcrt vgpyvplwlg ceagfyvdag ppthaftpcg hvcseksaky wsqiplphgt hafhaacpfc atqlvgeqnc iklifqgpid (SEQ ID NO: 37; cDNA sequence NCBI accession no. NM_021255.2) |
| BMP2 | mvagtrclla lllpqvllgg aaglvpelgr rkfaaassgr pssqpsdevl sefelrllsm fglkqrptps rdavvppyml dlyrrhsgqp gspapdhrle raasrantvr sfhheeslee lpetsgkttr rfffnlssip teefitsael qvfreqmqda lqnnssfhhr iniyeiikpa tanskfpvtr lldtrivnqn asrwesfdvt pavmrwtaqg hanhgfvvev ahleekqgvs krhvrisrsl hqdehswsqi rpllvtfghd gkghplhkre krqakhkqrk rlkssckrhp lyvdfsdvgw ndwivappgy hafychgecp fpladhlnst nhaivqtlvn svnskipkac cvptelsais mlyldenekv vlknyqdmvv egcgcr (SEQ ID NO: 38; cDNA sequence NCBI accession no. NM_001200.3) |
| SHH | mlllarclll vlvssllvcs glacgpgrgf gkrrhpkklt playkqfipn vaektlgasg ryegkisrns erfkeltpny npdiifkdee ntgadrlmtq rckdklnala isvmnqwpgv klrvtegwde dghhseeslh yegravditt sdrdrskygm larlaveagf dwvyyeskah ihcsvkaens vaaksggcfp gsatvhleqg gtklvkdlsp gdrvlaaddq grllvsdflt fldrddgakk vfyvietrep rerllltaah llfvaphnds atgepeassg sgppsggalg pralfasrvr pgqrvyvvae rdgdrrllpa avhsvtlsee aagayaplta qgtilinrvl ascyavieeh swahrafapf rlahallaal apartdrggd sqggdrgggg grvaltapga adapgagata gihwysqlly qigtwlldse alhplgmavk ss (SEQ ID NO: 39; cDNA sequence NCBI accession no. NM_000193.3) |
| TNS4 | mgskassphg lgsplvaspr lekrlgglap qrgsrisvls aspvsdvsym fgssgsllhs snsshqsssr slespansss slhslgsysl ctrpsdfqap rnptltmgqp rtphspplak ehasscppsi tnsmvdipiv lingcpepgs sppqrtpghq nsvqpgaasp snpcpatrsn sqtlsdapft tcpegpardm qptmkfvmdt skywfkpnit reqaiellrk eepgafvird sssyrgsfgl alkvqevpas aqsrpqedsn dlirhflies sakgvhlkga deepyfgsls afvcqhsima lalpckitip grelggadga sdstdspasc qkksagchtl ylssysvetl |
| | tgalavqkai sttferdilp tptvvhfkvt eqgitltdvq rkvffrrhyp ltttlrfcgmd peqrkwqkvc kpswifgfva ksqtepqenv chlfaevdmv qpasqviglv tallqdaerm (SEQ ID NO: 40; cDNA sequence NCBI accession no. BC013706.1) |
| RAB3B | masvtdgktg vkdasdqnfd ymfklliign ssvgktsflf ryaddtftpa fvstvgidfk vktvyrhekr vklqiwdtag qervrtitta yyrgamgfil myditneesf navqdwatqi ktyswdnaqv ilvgnkcdme eervvptekg qllaeqlgfd ffeasakeni svrqaferlv daicdkmsds ldtdpsmigs skntrlsdtp pllqqncsc (SEQ ID NO: 41; cDNA sequence NCBI accession no. NM_002867.3) |
| ROBO1 | miaepahfyl fgliclcsgs rlrqedfppr ivehpsdliv skgepatlnc kaegrptpti ewykggerve tdkddprshr mllpsgslff lrivhgrksr pdegvyvcva rnylgeavsh naslevailr ddfrqnpsdv mvavgepavm ecqpprghpe ptiswkkdgs plddkderit irggkimity trksdagkyv cvgtnmvger esevaeltvl erpsfvkrps nlavtvddsa efkceargdp vptvrwrkdd gelpksryei rddhtlkirk vtagdmgsyt cvaenmvgka easatltvqv gsepphfvvk prdqvvalgr tvtfqceatq npqpaifwrr egsqnllfsy qppqsssrfs vsqtgdltit nvqrsdvgyy icqtinvags iitkaylevt dviadrpppv irqgpvnqtv avdgtfvlsc vatgspvpti lwrkdgvlvs tqdsrikqle ngvlqiryak lgdtgrytci astpsgeatw sayievqefg vpvqpprptd pnlipsapsk pevtdvsrnt vtlswqpnln sgatptsyii eafshasgss wqtvaenvkt etsaikglkp naiylflvra anavgisdps qisdpvktqd vlptsqgvdh kqvqrelgna vlhlhnptvl ssssievhwt vdqqsqyiqg ykilvrpsga nhgesdwlvf evrtpaknsv vipdlrkgvn yeikarpffn efgqgadseik faktleeaps appqqvlvsk ndgngtailv swqpppedtq ngmvqevkvw clgnetryhi nktvdgstfs vvipflvpgi rysvevaast gagsgyksep gfigldahgn pvspedqvsl aqqisdvvkq pafiagigaa cwiilmvfsi wlyrhrkkrn gltstyagir kvtyqrggea vssggrpgll nisepaaqpw ladtwpntgn nhndcsiscc tagngnsdsn lttysrpadc ianynnqldn kqtnlmlpes tvygdvdlsn kinemktfns pnlkdgrfvn psgqptpyat tqliqsnlsn nmnngsgdsg ekhwkplgqq kqevapvqyn iveqnklnkd yrandtvppt ipyngsydqn tggsynssdr gsstsgsqqh kkggartpkv pkqggmawad llppppahpp phsnseeyni svdesydqem pcpvpparmy lqqdeleeee dergptppvr gaasspaays yshqstatlt pspqeelqpm lqdcpeetgh mqhqpdrrrq pvspppppp ispphtygyi sqplvsdmdt dapeeeedea dmevakmqtr rllrglegt passvgdles svtgesmingw qsaseednis sgrssyssssd gsfftdadfa qavaaaaeya glkvarrqmq daagrrhfha sqcprptspv stdsnmsaav mqktrpakkl khqpghlrre tytddlpppp vpppaikspt aqsktglevr pvvvpklpsm dartdrssdr kgssvkgrev ldgrqvvdmr tnpgdpreaq eqqndgkgrg nkaakrdlpp akthliqedi lpvcrptfpt snnprdpsss ssmssrgsgs rqreqanvgr rniaemqvlg gyergednne eleetes (SEQ ID NO: 42; cDNA sequence NCBI accession no. BC112336.1) |
| ARHGAP28 | mnelprdtcg nhtnqldgtk eerelprvik tsgsmpddas lnsttlsdas qdkegsfavp rsdsvailet ipvlpvhsng spepgqpvqn aisdddflek nippeaeels fevsysemvt ealkrnklkk seikkedyvl tkfnvqktrf glteagdlsa edmkkirhls lieltaffda fgiqlkrnkt ekvkgrdngi fgvpltvlld gdrkkdpgvk vplvlqkffe kveesglese gifrlsgcta kvkqyreeld akfnadkfkw dkmchreaav mlkaffrelp tslfpveyip afislmergp hvkvqfqalh lmvmalpdan rdaaqalmtf fnkvianesk nrmslwnist vmapnlffsr skhsdyeell lantaahiir lmlkyqkilw kvpsflitqv rrmneatmll kkqlpsvrkl lrrktleret aspktskvlq ksspsarrmsd vpegvirvha pllskvsmai qlnnqtkakd ilakfqyenr ilhwqraals flngkwvkke reestetnrs pkhvflftig ldist (SEQ ID NO: 43; cDNA sequence NCBI accession no. BC065274.1) |

TABLE 5-continued

CIN Gene Expression Signature Genes

| Gene Name | Example CIN Gene Expression Signature Human Sequence |
|---|---|
| CHN2 | maassnssls gssyssdaee yqppiwksyl yqlqqeaprp kriicpreve nrpkyvgref hgiisreqad ellggvegay ilresqrqpg cytlalrfgn qtlnyrlfhd gkhfvgekrf esihdlvtdg litiyietka aeyiskmttn piyehiqyat llrekvsrri srskneprkt nvtheehtav ekisslvrra althndnhfn yekthnfkvh tfrgphwcey canfmwglia ggvrcsdcgl nvhkqcskhv pndcqpdlkr ikkvyccdlt tlvkahntgr pmvvdicire iearglkseg lyrvsgfteh iedvkmafdr dgekadisan vypdiniitg alklyfrdlp ipvitydtys kfidaakisn aderleavhe vlmllppahy etlrylmihl kkvtmnekdn fmnaenlgiv fgptimrrpe dstittlhdm ryqklivqil ienedvif SEQ ID NO: 44; nucleotide sequence NCBI accession no. LS482359.1) |
| CST1 | maqylstlll llatlavala wspkeedrii pggiynadln dewvqralhf aiseynkatk ddyyrrplrv lrarqqttvgg vnyffdvevg rticktksqpn idtcafheqp elqkkqlcsf eiyevpwenr rslvksrcqe s (SEQ ID NO: 45; nucleotide sequence NCBI accession no. NM_001898.2) |
| F13A1 | msetsrtafg grravppnns naaeddlptv elqgvvprgv nlqeflnvts vhlfkerwdt nkvdhhtdky ennkIivrrg gsfyvqidfs rpydprrdlf rveyvigryp genkgtyipv pivselqsgk wgakivmred rsvrlsiqss pkcivgkfrm yvavwtpygv lrtsrnpetd tyilfnpwce ddavyldnek ereeyvlndi gvifygevnd iktrswsygq fedgiidtcl yvmdraqmdl sgrgnpikvs rvgsamvnak ddegvlvgsw dniyaygvpp sawtgsvdil levrssenpv rygqcwvfag vfntflrclg iparivtnyf sahdndanlq mdifleedgn vnskltkdsv wnyhcwneaw mtrpdlpvgf qwqavdstp qensdgmyrc gpasvgaikh ghvcfqfdap fvfaevnsdl iyitakkdgt hvvenvdath igklivtkqi gqdgmmditd tykfqegqee erlaletalm ygakkplnte gvmksrsnvd mdfevenavl gkdfklsitf rnnshnvyri taylsanitf ytgvpkaefk ketfdvtlep lsfkkeavli qageymgqll eqaslhffvt arinetrdvl akqkstvlti peiiikvrgt qvvgsdmtvt veftnplket lrnvwvhldg pgvtrpmkkm freirpnstv qweevcrpwv sghrkliasm ssdslrhvyg elavqiqrrp sm (SEQ ID NO: 46; nucleotide sequence NCBI accession no. NM_000129.3) |
| CPVL | mvgamwkviv slvllmpgpc dglfrslyrs vsmppkgdsg qplfltpyie agkiqkgrel slvgpfpgln mksyagfltv nktynsnlff wffpaqiqpe dapvvlwlqg gpggssmfql fvehgpyvvt snmtlrdrdf pwtttlsmly idnpvgtqfs ftddthgyav neddvardly saliqffqif peyknndfyv tgesyagkyv paiahlihsl npvrevkinl ngiaigdgys dpesiiggya eflyqiglld ekqkkyfqkq checiehirk qnwfeafeil dkllddgdlts dpsyfqnvtg csnyynflrc tepedqlyyv kflslpevrq aihvgnqtfn dgtivekylr edtvqsvkpw lteimnnykv liyngqldii vaaaltersl mgmdwkgsqe ykkaekkvwk ifksdsevag yirqagdfhq viirggghil pydqplrafd minrfiygkg wdpyvg (SEQ ID NO: 47; nucleotide sequence NCBI accession no. AY358549.2) |
| SEMA6D | mrvfllcayi lllmvsqlra vsfpeddepl ntvdyhysrq ypvfrgrpsg nesqhrldfq lmlkirdtly iagrdqvytv nlnempktev ipnkkltwrs rqqdrencam kgkhkdechn fikvfvprnd emvfvcgtna fnpmcryyrl stleydgeei sglarcpfda rqtnvalfad gklysatvad flasdaviyr smgdgsalrt ikydskwike phflhaieyg nyvyfffrei avehnnlgka vysrvarick ndmggsqrvl ekhwtsflka rlncsvpgds ffyfdvlqsi tdiiqingip tvvgvfttql nsipqsavca fsmddiekvf kgrfkeqktp dsvwtavped kvpkprpgcc akhglaeayk tsidfpdetl sfikshplmd savpiadep wftktrvryr ltaisvdhsa gpyqnytvif vgseagmvik vlaktgpfsl ndsvlleeie aynhakcsae needkkvisl qldkdhhaly vafssciiri plsrcerygs ckksciasrd pycgwlsqgs cgrvtpgmll ltedffafhn hsaegyeqdt efgntahlgd chgvrwevqs qesnqmvhmn vlitcvfaaf vlgafiagva vycyrdmfvr knrrkihkdae |
| | saqsctdssg sfaklnglfd spvkeyqqni dspklysnll tsrkelppng dtksmvmdhr gqppelaalp tpestpvlhq ktlqamkshs ekahghgasr ketpqffpss ppphspllshg hipsaivlpn athdyntsfs nsnahkaekk lqnidhpltk ssskrdhrrs vdsrntlndl lkhlndpnsn pkaimgdiqm ahqnlmldpm gsmsevppkv pnreaslysp pstlprnspt krvdvpttpg vpmtslerqr gyhknssqrh sisampknln spngvllsrq psmnrggymp tptgakvdyi qgtpvsvhlq pslsrqssyt sngtlprtql krtpslkpdv ppkpsfvpqt psvrplnkyt v (SEQ ID NO: 48; nucleotide sequence NCBI accession no. BC150253.1) |
| C9orf152 | maegsrtqap gkgpplsiqf lraqyeglkr qqrtqahllv lpkgqntpap aesmvnavwi nkerrsslsl eeadsevegr leeaaqgclq apkspwhthl emhclvqtsp qdtshqvhhr gklvgsdqrl ppegdthlfe tnqmtqqgtg ipeaaqlpcq vgntqtkave sglkfstqcp lsiknphrsg kpayypfpqr ktprisqaar nlglygsa (SEQ ID NO: 49; nucleotide sequence NCBI accession no. NM_001012993.2) |
| NHSL2 | mesmgmvysv psscngptes tfstswkgda ftymtpsats qsnqvnengk npscgnswvs lnkvpplvpk eaatllvard npagcsgsag yperliqqrh mperpskigl ltsgtsrlet gppgasrfre rslsvqqrdsg ttdvdydeeq kaneacalpf astsegsns adniasisaq qeaqhrrqrs ksislrkakk kpspptrsvs lvkdepgllp eggsalpkdq rpkslclsle hqghhsshpd aqghpaipnh kdpestqfsh hwyltdwksg dtyqslssss tatgttviec tqvqgssesl aspstsratt psqlsievea reissspgrpp glmspssgvs sqsetptptv smsltlghlp ppsssvrvrp vvperksslp ptspmekfpk srlsfdlplt sspnldlsgm sisirsktkv srhhsetnfg vklaqktnpn qpimpmvtqs dlrsvrlrsv sksepeddie speyaeepra eevftlperk tkppvaekpp varrppslvh kppsvpeeya ltsptlampp rssigharpl pqdsytvvrk pkpssfpdgr spgestapss lvftpfassss daffsgtqqp pqgsvedegp kvrvlperis lqsqeeaekk kgkipppvpk kpsvlylplt sptaqmeayv aeprlplspi itleedtkcp atgddlqsig qrvtstpqad sereasplg (SEQ ID NO: 50; nucleotide sequence NCBI accession no. BC136756.1) |
| GTF21P7 | TGCCTCCAGA AAGGGTTGAG AAGATAATGG ATCAGATTGA AAAGTACATC ATGACTCATC TCTGTAAATA TGCGTTCTGT CCAGAACCCC AGTGAGCCTG GAAGACTGGG TGCTATGGGA AATGTCATCA ATCCAATGCT AGTGAAAGAT GTGACTGGGG AATGCTGAAA ATGCGCACCC CTGGGAGGA ATGAGGAAAG ATGACATCCA CTGACTGTT ATTTTTTTGA GAAGGAGTCT TGCTCTGTTG CCCAGGCTAG AGTGTGGTGG CACGATCTCG GCTCACTGAT GATGAGAAGA AAGTGCTTGC CATTCAAAAG AGGATCACAG IGCAACCTTC TCTCCTCT CACAAACACC ACGAATGTCG TCACCTCACC TATCCATCTC CCTCAAGCCA GCTTTTGACC TGAACTGGTT ATTTCCTACT TGCCTCCTGG ACTTGCTAAT AAAATAAACA CTAAAGCTTC CCACTTTCTA AAAACACCAT CAACCCCTGA GAGTAATCAA AACCITCCTC AAATTGAGGT CACTGTGGAA GGAGAATCTA ATGCCTGATG ATCTGTCACT ATCTCCCATC ACCCCCAGAT GGGACCATCT AGTTGCAGGA AAAGAAGGTC AAGACTCCCA GTCATTCTAC ATTATGCCTC AGCCAAGATG TCTCACCCCA CTCTCTCTGA TGCAACAAGA AGCCCCTGGA GAACGTTTCA GTCCCATTTT GTACTTCTGT CATGTGCTCA TCACAGTCTG |
| DPYSL3 | masgrrgwds sheddlpvyl arpgttdqvp rqkyggmfcn vegafesktl dfdalsvgqr gaktprsgqg sdrgsgsrpg iegdtprrgq greesrepap aspapagvei rsatgkevlq nlgpkdksdr llikggrivn ddqsfyadiy medglikqig dnlivpggvk tieangkmvi pggidvhthf qmpyvkgmttv ddffqgtkaa laggttmiid hvypepessl teayekwrew adgksccdya lhvdithwnd svkqevqnli kdkgvnsfmv ymaykdlyqv snteiyeift clgelgaiaq vhaengdiia qeqtrmlkmg itgpeghvls rpeeleaeav fraitiasqt naplyvtkvm sksaadlisq arkkgnvvfg epitaslgid gthvwsknwa kaafvtspp lspdpttpdy insllasgdl qlsgsahctf staqkaigkd nftaipegtn gveermsviw dkavatgkmd enqfvavtst naakifnlyp rkgrisvgsd |

TABLE 5-continued

CIN Gene Expression Signature Genes

| Gene Name | Example CIN Gene Expression Signature Human Sequence |
|---|---|
| | sdlviwdpda vkivsaknhq saaeynifeg melrgaplvv icqgkimled gnlhvtqgag rfipcspfsd yvykrikarr kmadlhavpr gmydgpvfdl tttpkggtpa gsargsptrp nppyrnlhqs gfslsgtqvd egvrsaskri vappggrsni tsls (SEQ ID NO: 51; nucleotide sequence NCBI accession no. BC077077.1) |
| PCDH7 | mlrmrtagwa rgwclgccll lplslslaaa kqllryrlae egpadvrign vasdlgivtg sgevtfsles gseylkidnl tgelstserr idreklpqcq mifdenecfl dfevsvigps qswvdlfegq vivldindnt ptfpspvltl tveenrpvgt lyllptatdr dfgrngiery ellqepgggg sggesrraga adsapypggg gngasgggsg gskrrldase ggggtnpggr ssvfelqvad tpdgekqpql ivkqaldreq rdsyeltlrv rdggdpprss qailrvlitd vndnsprfek svyeadlaen sapgtpilql raadldvgvn gqieyvfgaa tesvrrllrl detsgwlsvl hridreevnq lrftvmardr qqppktdkat vvlnikdend nvpsieirki griplkdgva nvaedvlvdt pialvqvsdr dqgengvvtc tvvgdvpfql kpasdteqdq nkkkvflhts tpldyeatre fnvvivavds gspslssnns livkvgdtnd nppmfgqsvv evvfpennip gervatvlat dadsgknaei aysldssvmg ifaidpdsgd ilvntvldre gtdryefkvn akdkgipvlq gsttvivqva dkndndpkfm qdvftfyvke nlqpnspvgm vtvmdadkgr naemslyiee nnnifsiend tgtiystmsf drehqttytf rvkavdggdp prsatatvsl fvmdendnap tvtlpknisy tllppssnvr tvvatvlatd sddginadln ysivggnpfk lfeidptsqv vslvgkltqk hyglhrlvvq vndsgqpsqs tttlvhvfvn esvsnataid sqiarslhip ltqdiagdps yeiskqrlsi vigvvagimt viliilivvm arycrsknkn gyeagkkdhe dfftpqqhdk skkpkkdkkn kkskqplyss ivtveaskpn gqrydsvnek lsdspsmgry rsvnggpgsp dlarhyksss plptvqlhpq sptagkkhqa vqdlppantf vgagdnisig sdhcseyscq tnnkyskqmr lhpyitvfg (SEQ ID NO: 52; nucleotide sequence NCBI accession no. NM_002589.2) |
| KHDRBS3 | meekylpelm aekdsidpsf thalrlvnQe iekfqkgegk eekyidvvin khmklgqkvl ipvkqfpkfn fvgkllgprg nslkrlgeet ltkmsilgkg smrdkakeee lrksgeakyf hlnddlhvli evfappaeay armghaleei kkflipdynd eirqaqlqel tylnggsena dvpvvrgkpt lrtrgvpapa itrgrgqvta rpvgvvvprq tptprqvlst rqpvsrgrql itprargvpp tqyrpppppp tqetygeydy ddgygtayde qsydsydnsy stpaqsgady ydyghqlsee tydsygqeew tnsrhkapsa rtakgvyrdq pygry (SEQ ID NO: 53; nucleotide sequence NCBI accession no. BC063536.1) |
| TRAC | pniqnpdpav yqlrdskssd ksvclftdfd sqtnvsgskd sdvyitdktv ldmrsmdfks nsavawsnks dfacanafnn siipedtffp spesscdvkl veksfetdtn lnfgnlsvig frilllkvag fnllmtlrlw ss (SEQ ID NO: 54; nucleotide sequence NCBI accession no. X02592.1) |
| TMEM156 | mtktallklf vaivitfili lpeyfktpke rtlelsclev clgsnftysl sslnfsfvtf lqpvretqii mriflnpsnf rnftrtcqdi tgefkmcssc lvcepkgnmd fisqeqtskv lirrgsmevk andfhspcqh fnfsvaplvd hleeyntchh lknhtgrsti medepskeks inytcrimey pndcihislh lemdiknitc smkitwyilv llvfifliil tirkilegqr rvqkwqshrd kptsvllrgs dseklralnv qvlsaettqr lpldqvqevl ppipel (SEQ ID NO: 55; nucleotide sequence NCBI accession no. BC030803.1) |
| CST4 | marplctlll lmatlagala ssskeenrii pggiydadln dewygralhf aiseynkate deyyrrplqv lrareqtfgg vnyffdvevg rtictksqpn ldtcafheqp elqkkqlcsf eiyevpwedr mslvnsrcqe a (SEQ ID NO: 56; nucleotide sequence NCBI accession no. NM001899.2) |
| CD24 | mgramvarlg lgllllalll ptqiyssett tqtssnssqs tsnsglapnp tnattkaaqg algstaslfv vslsllhlys (SEQ ID NO: 57; nucleotide sequence NCBI accession no. FJ226006.1) |
| FGF5 | mslsfllllf fshlilsawa hgekrlapkg qpgpaatdrn prgsssrqss ssamssssas sspaaslgsq gsgleqssfq wspsgrrtgs lycrvgigfh lqiypdgkvn gsheanmlsv leifaysqgi vgirgvfsnk flamskkgkl hasakftddc kfrerfqens yntyasaihr tektgrewyv alnkrgkakr gcsprvkpqh isthflprfk gseqpelsft vtvpekkkpp spikpkipls aprkntnsvk yrlkfrfg (SEQ ID NO: 58; nucleotide sequence NCBI accession no. NM_004464.3) |

CIN-Responsive Noncanonical NF-kB Signature:
PPARG, DDIT3, NUPR1, RAB3B, IGFBP4, LRRC8C, TCP11L2, MAFK, NRG1, F2R, KRT19, CTGF, ZFC3H1, MACROD1, GSTA4, SCN9A, BDNF, LACTB Genes in bold were suppressed (negative values were used in survival and TCGA analyses)

Noncanonical NF-kB Regulatory Genes:
NFKB2, RelB, MAP3K14, TRAF2, TRAF3, BIRC2, BIRC3

Genes in bold were suppressed (negative values were used in survival analysis)

Canonical NF-kB Regulatory Genes:
NFKB1, RelA, TRAF1, TRAF4, TRAF5, TRAF6

Interferon Regulatory Genes
IRF1, IRF3, IRF7, TBK1

Regulators of Epithelial-to-Mesenchymal Transition (EMT): VIM, ZEB2, SNAI2, ZEB1

Inflammation Genes:
RGS16, DENND5A, BTG2, STAT3, IFITM3, CD47, SLAMF7, REL, BCL6, IL18BP, NAMPT, PDE4B, I18, PSME2, P2RX4, IFI44, CCR7, KLF10, ADRM1, KLF9, NFIL3, CNP, LDLR, HES1, HLA-A, PARP9, NUB1, STAT2, VIP, TGIF1, PVR, MOV10, PSMA2, EIF4E3, IER3, PLA2G4A, TRAFD1, MYD88, VAMP5, TRIM14, TUBB2A, BPGM, B2M, HRH1, PSMB9, LATS2, PTPN6, DCBLD2, PSMB8, IL1R1, PSMB2, SQSTM1, PTX3, ITGA5, EDN1, SLC31A1, SAMHD1, PNPT1, CSF1, TNFRSF9, SOCS1, RELB, VEGFA, ARL4A, DUSP5, CMKLR1, CD38, SLC4A4, SP110, PLAU, DDX58, PSME1, TRAF1, SPSB1, TDRD7, F2RL1, EPSTI1, SAMD9L, NINJ1, RNF19B, LIF, RIPK1, SLC2A6, IRF7, PTAFR, IRAK2, CD14, ITGB8, SCARF, KIF1B, FOSL2, SOCS3, DUSP1, IRF1, SLC2A3, HBEGF, CXCL3, TNIP1, AHR, SGMS2, FZD5, GCH1, SLC25A28, OSMR, RSAD2, APOL6, ICOSLG, JAG1, GOS2, GEM, KLF4, NFKB1, STAT1, HLA-C, IFIH1, LY6E, EFNA1, SLC16A6, BHLHE40, TRIM26, CD82, CYBB, IL15RA, GABBR1, RELA, PHLDA2, MAP3K8, NUP93, IL7R, PTPRE, IF127, SNN, NR4A2, SPPL2A, RHOG, SAT1, SLC7A1, IL6, IL15, RAF1, CCL20, ACVR1B, BIRC2, RBCK1, LAP3, ID2, TNFSF10, SIK1, BST2, PANX1, GADD45A, PML, CD40, TRIM21, SECTM1, SSPN, TXNIP, BTG1, AREG, KYNU, PTGS2, IRS2, C3AR1, STAT4, ATP2A2, BIRC3, MAP2K3, CXCL1, NFKBIA, IFNAR1, MET, NR4A1, CXCL2, EB13, CD83, DNAJB4, CASP7, PHLDA1, NLRC5, IL1B, TRIM25, IERS, RNF213, IL10, NFAT5, ADAR, PNP, MMP14, ICAM4, PPAP2B, SDC4, ABCA1, DUSP2, EIF2AK2, IER2, HERC6, BMP2, IL7, ISG20, GMPR, PSEN1, XAF1, SERPINB8, MTHFD2, EREG, TNFAIP3, TMEM140, KDM6B, CXCL11, CASP1, CYR61, IRF9, GBP2, ADM, TRIP10, PTGER2, METTL7B, SOD2, OAS2, CSF3, SERPINE1, MXD1, ICAM1, ZC3H12A, BCL3, PFKFB3, OGFR, SRI, IFNAR2, FUT4, IL6ST, TNIP2, DUSP4, PROCR, TLR2, OASL, JAK2, C1S, NMI, UBE2L6, LAMP3, TRIB1, TIPARP, IFIT3, GFPT2, IFI30, PPP1R15A, FAM46A, ELF1, UPP1, NOD1, CCL5, FOS, VAMP8, RTP4, TPBG, IL23A, BEST1, CEBPB, TNFSF1S, SCN1B, P2RY2, STAT5A, CHST2, HIF1A, ZFP36, KLF2, LPAR1, EHD1, PLSCR1, PDLIMS, OAS1, CXCL10, JUNB, PFKP, CD274, CD55, TNFSF9, ADORA2B, ETS2, OAS3, CASP8, ISG15, WARS, SLC7A2, TNFRSF1B, PARP14, FAS, SAMD9, EIF1, CD74, TORiB, PTPN2, MARCKS, ST8SIA4, SEMA4D, LYSMD2, ATF3, FOSB, PSMB10, ISOC1, PSMA3, IFNGR2, SMAD3, RIPK2, MARCHI, DHX58, IL4R, TRIM5, LITAF, B4GALT5, NLRP3, ITGB3, CIITA, IFIM1, PIM1, BTG3, CD44, PLK2, DRAM1, FPR1, RHOB, EGR1, GNAl3, C1R, NCOA3, PARP12, ABI1, RCAN1, EMP3, IRF2, HLA-DMA, LAMB3, MYC, ATP2B1, YRDC, HLA-DRB1, NDP, MCL1, F3, MT2A, IF144L, SERPINB2, MAFF, FJX1, LGALS3BP, I118, GADD45B, TLR1, CEBPD, GNA15, CSF2, SPHK1, IF135, LYN, PNRC1, IRF5, IFITM2, BANK1, AXL, KLF6, PTGER4, CASP3, PMEPA1, TNC, ZBTB10, PCDH7, CCRL2, CDKN1A, CCNL, PER1, TLR3, B4GALT1, CLCF1, MVP, CFB, NFKBIE, PTPN1, USP18, NFKB2, CASP4, TNFAIP2, ACVR2A, $CX3C_L1$, IFIT1, EMR1, CFLAR, DDX60, IDO1, CFH, IFIT2, NCOA7, INHBA, TIMP1, RNF144B, MX1, ATP2C1, TSC22D1, PELI1, TAPBP, GBP4, CCND1, SLC31A2, SGK1, ZNFX1, RAPGEF6, CCL2, HLA-B, NFE2L2, UBA7, HAS2, JUN, SLC11A2, FOSL1, SELL, PLAUR, BATF2, TNFAIP8, ST3GAL5, TANK, ARID5B, MX2, TAP1.

Migration and Motility Genes:
CALD1, CAV2, EGFR, FN1, ITGB1, JAG1, MSN, MST1R, NODAL, PDGFRB, RAC1, STAT3, TGFB1, VIM.

Example 2: Increased Chromosomal Instability in Human Metastases

This Example describes experiments illustrating that chromosomal instability is associated with human metastases.

To investigate whether chromosomal instability is associated with human metastases, whole-exome sequence data was compared from 61 primary tumors, comprising 13 tumor types, and matched with brain metastases using data from a recently published cohort (Brastianos et al. Cancer Discovery 5, 1164-1177 (2015)). These data were reanalyzed using the weighted-genomic integrity index (wGII) as a genomic proxy for chromosomal instability. wGII assesses copy number heterogeneity by measuring the percentage of the genome that deviates from the average tumor ploidy (Burrell et al. Nature 494, 492-496 (2013)). There was a significant bias whereby metastases were more likely to have higher wGII scores compared to their matched primary tumors (FIGS. 1A-1B-1 to 1B-4, 1H).

Figure 1C:
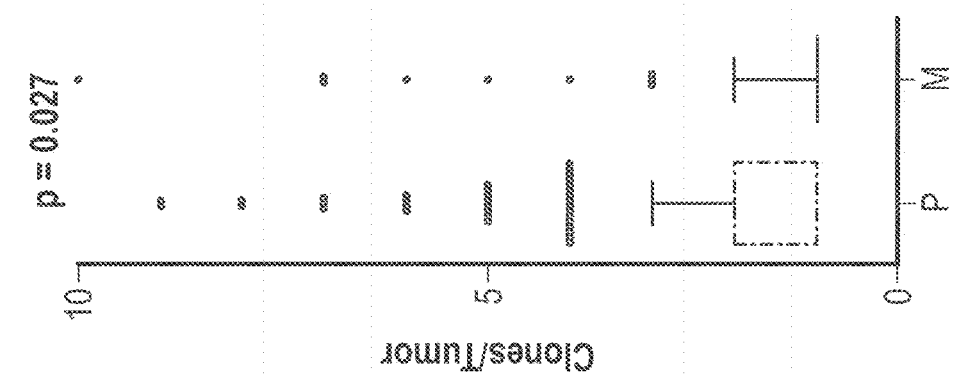
Figures 1, 1B, 2, 3, 4:
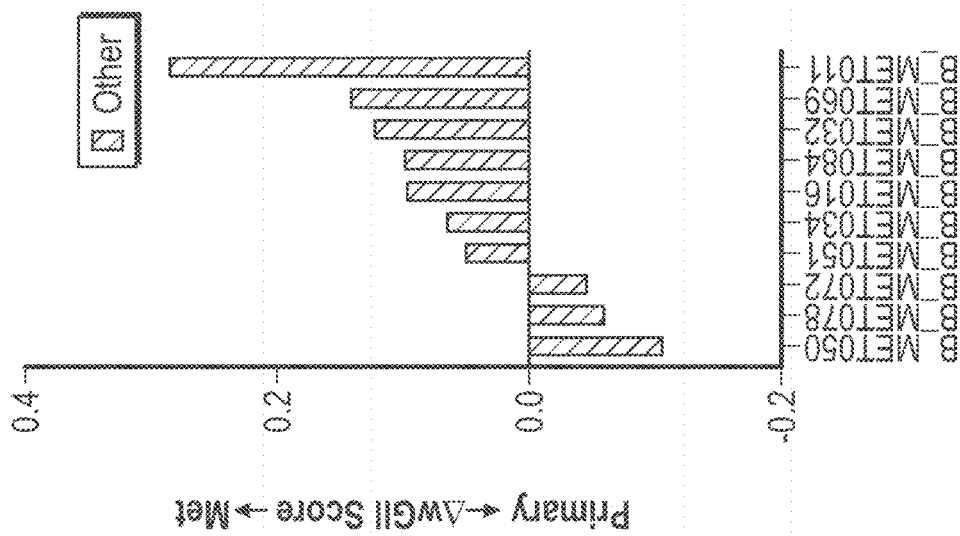
Figure 1G:
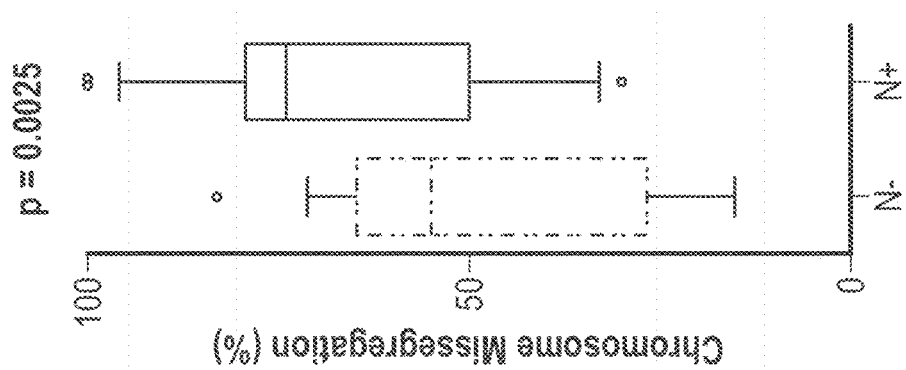
Figure 1F:
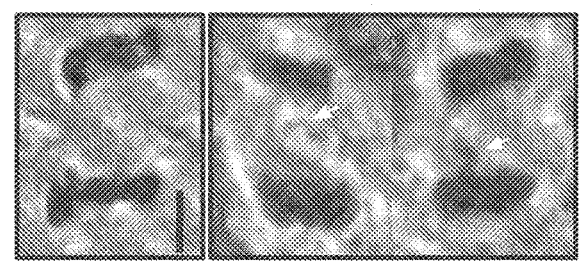
Figure 1E:
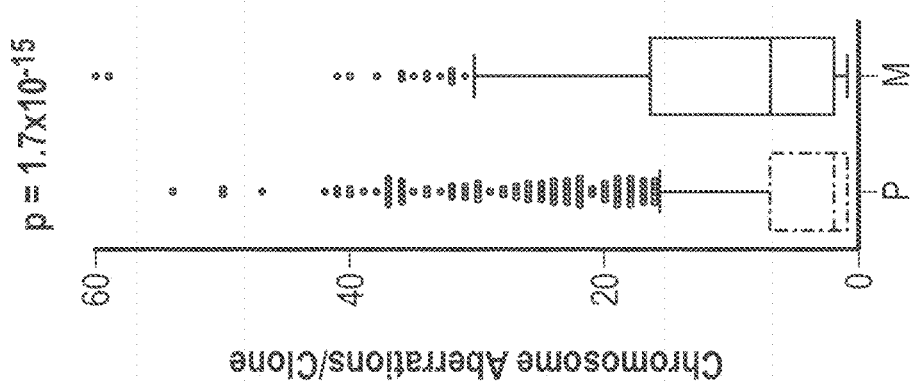
Figures 1H, 1I, 1J:
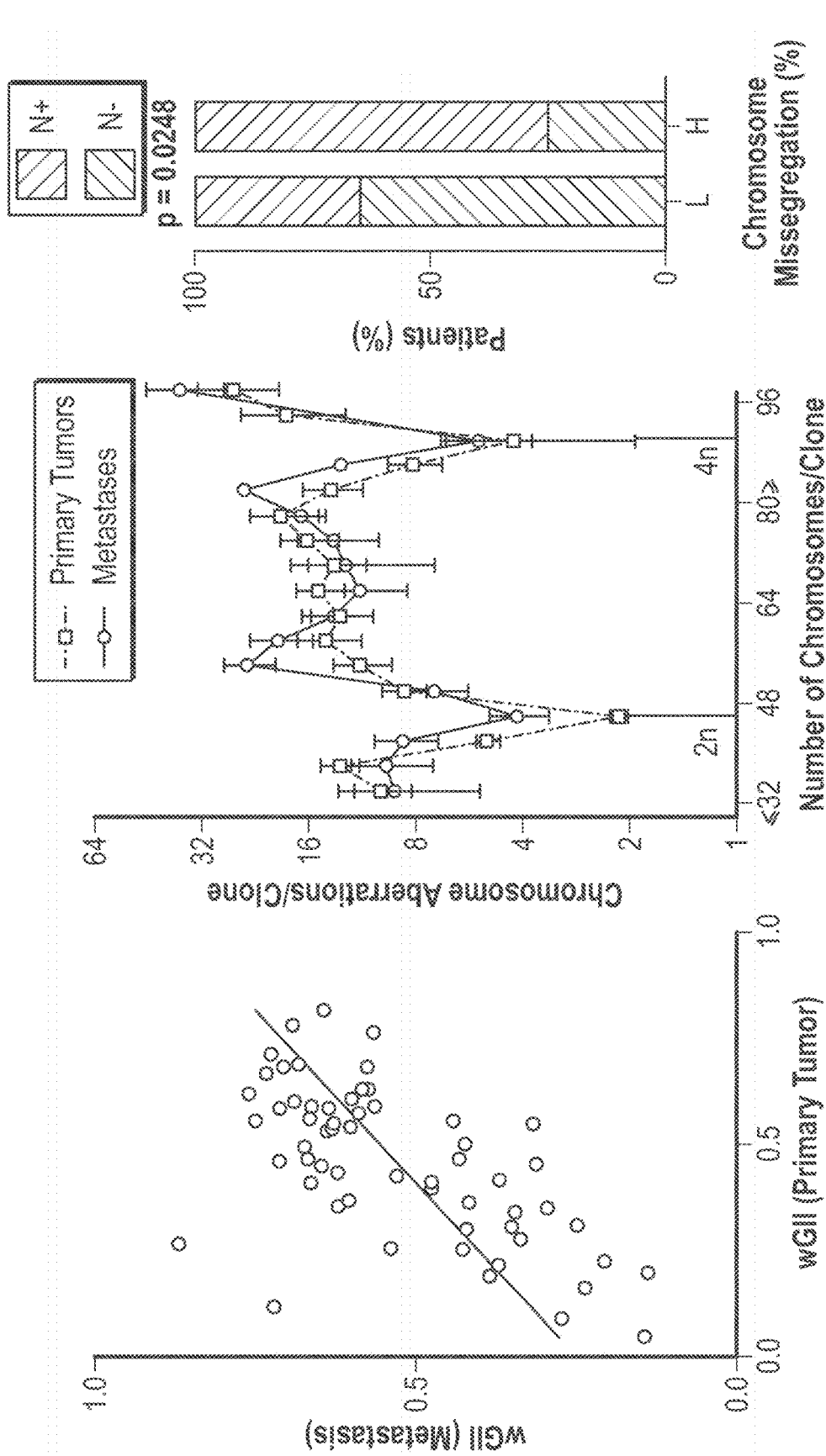

Using a second approach, karyotype information was analyzed from 637 primary breast tumors and 131 breast cancer metastases archived in the Mitelman Database of chromosomal translocations (Mitelman et al. website at cgap.nci.nih.gov/Chromosomes/Mitelman). Primary breast tumors contained more clones, as defined by single-cell karyotype analysis, yet they exhibited a strong predilection for normal, near-diploid (2n), karyotypes. On the other hand, samples derived from breast cancer metastases showed significant enrichment for near-triploid (3n) karyotypes and had, on average, twice as many chromosomal aberrations per clone as compared to primary tumors (FIGS. 1C-1E). It has been postulated that near-triploid karyotypes represent a convergent optimized evolutionary state where chromosomal instability is maximized (Carter et al. Nat Biotechnol 30, 413-421 (2012); Laughney et al. Cell Rep 12, 809-820 (2015); Storchova et al. J Cell Sci 121, 3859-3866 (2008)). Accordingly, the number of chromosomal aberrations was highest in tumor samples with karyotypes ranging between the diploid and tetraploid (4n) range (FIG. 1I).

Using a third approach, we analyzed data from primary tumor samples taken from patients with locally advanced head and neck squamous cell carcinoma (SCC) for which clinical data on lymph node metastasis at the time of diagnosis was available (Chung et al. Cancer Cell 5, 489-500 (2004)). As a measure of the dynamic nature of chromosomal instability, we directly assessed chromosome segregation integrity in cells fixed while undergoing anaphase (Bakhoun et al. Clin. Cancer Res. 17, 7704-7711 (2011)). The presence of chromatin between normally segregating chromosomes was taken as evidence for chromosome missegregation (FIG. 1F). Primary tumors with associated lymph node metastases had higher rates of chromosome missegregation compared with tumors without lymph node spread. Similarly, patients, whose tumors demonstrated high chromosome missegregation rates, were more likely to present with clinically involved lymph node metastases (FIGS. 1F, 1J). Using these three orthogonal approaches, we conclude that chromosomal instability is enriched in human metastases and when present in primary tumors, it is associated with a higher predilection for spread.

Example 3: Chromosomal Instability Drives Metastasis

Figure 2A:
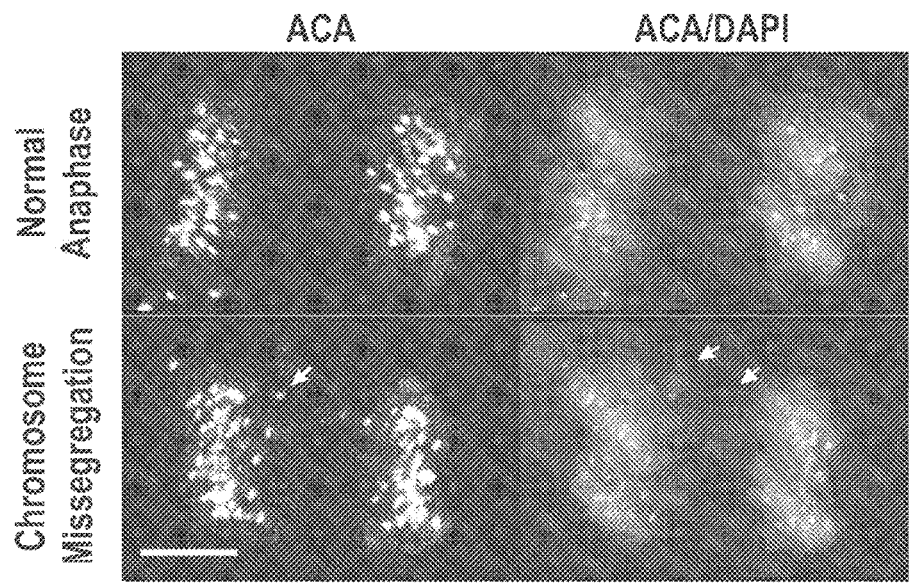
Figures 1, 2B:
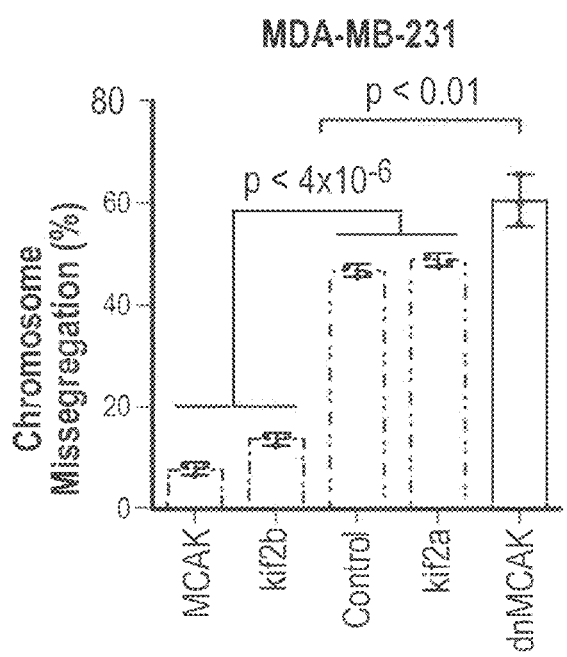
Figures 2, 2B:
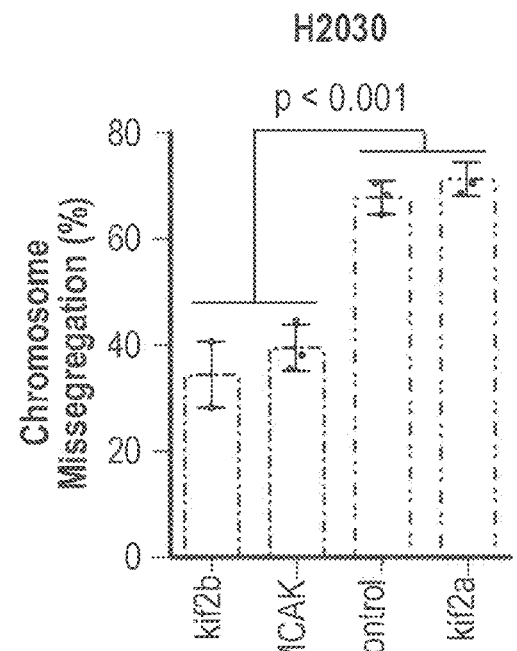
Figure 2D:
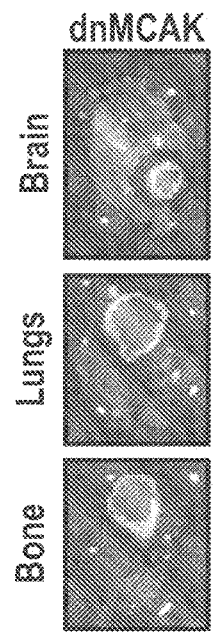
Figure 2E:
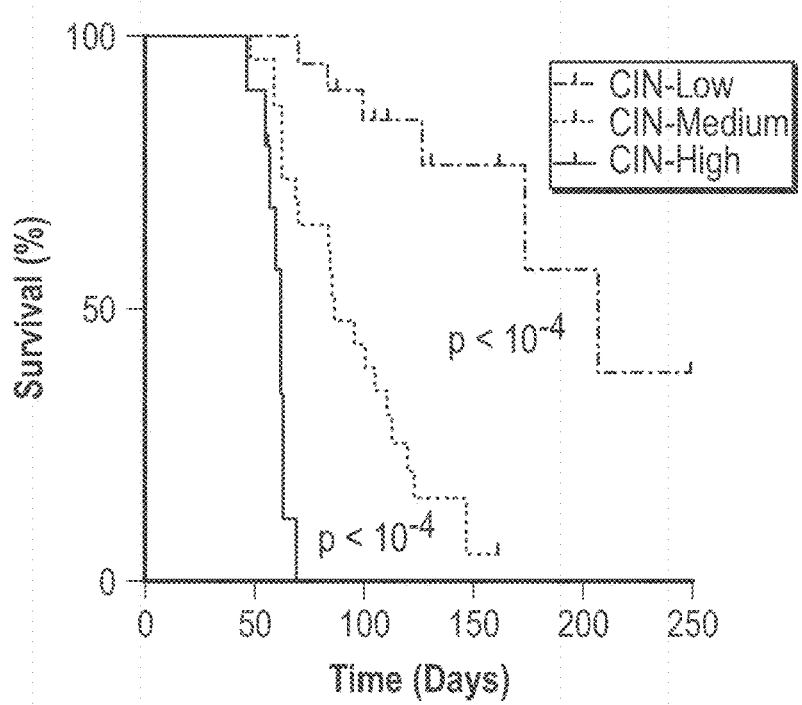

To determine whether chromosomal instability is causally involved in metastasis, we devised a genetic approach (Bakhoun et al., Nat. Cell Biol. 11, 27-35 (2009); Bakhoun et al., Nat Commun 6, 5990 (2015)) to alter the rate of chromosome missegregation in transplantable tumor models of human TNBC (MDA-MB-231) and lung adenocarcinoma (H2030). Cells from these highly metastatic tumor models exhibit elevated basal rates of chromosomal instability with 47% and 67% of anaphase cells, respectively, showing evidence of chromosome segregation errors during anaphase (FIGS. 2A, 2B-1 to 2B-2). These cells, with unperturbed chromosome segregation rates, are referred to a as CIN-medium cells. Overexpression of either Kif2b or MCAK/Kif2c in these cells led to significant suppression of chromosome segregation errors (referred to as CIN-low cells). Conversely, overexpression of a dominant negative form of MCAK[24] (dnMCAK) led to a further increase in chromosome segregation errors in MDA-MB-231 cells—referred to as CIN-high (FIGS. 2B-1 to 2B-2, FIG. 1L). Overexpression of Kinesin-13 proteins did not alter cellular proliferation rates in culture or the number of centrosomes per cell (FIGS. 1K, 1M). As an important control, Kif2a was overexpressed, Kif2a is a third member of the microtubule-depolymerizing kinesin-13 proteins that lacks any kinetochore or centromere localization domains (Ems-McClung et al. Semin. Cell Dev. Biol. 21, 276-282 (2010)). Kif2a overexpression had no effect on chromosomal instability despite exhibiting microtubule-depolymerizing activity on interphase microtubules similar to that of Kif2b and MCAK (FIGS. 2B-1 and 2B-2).

Figures 1, 2F:
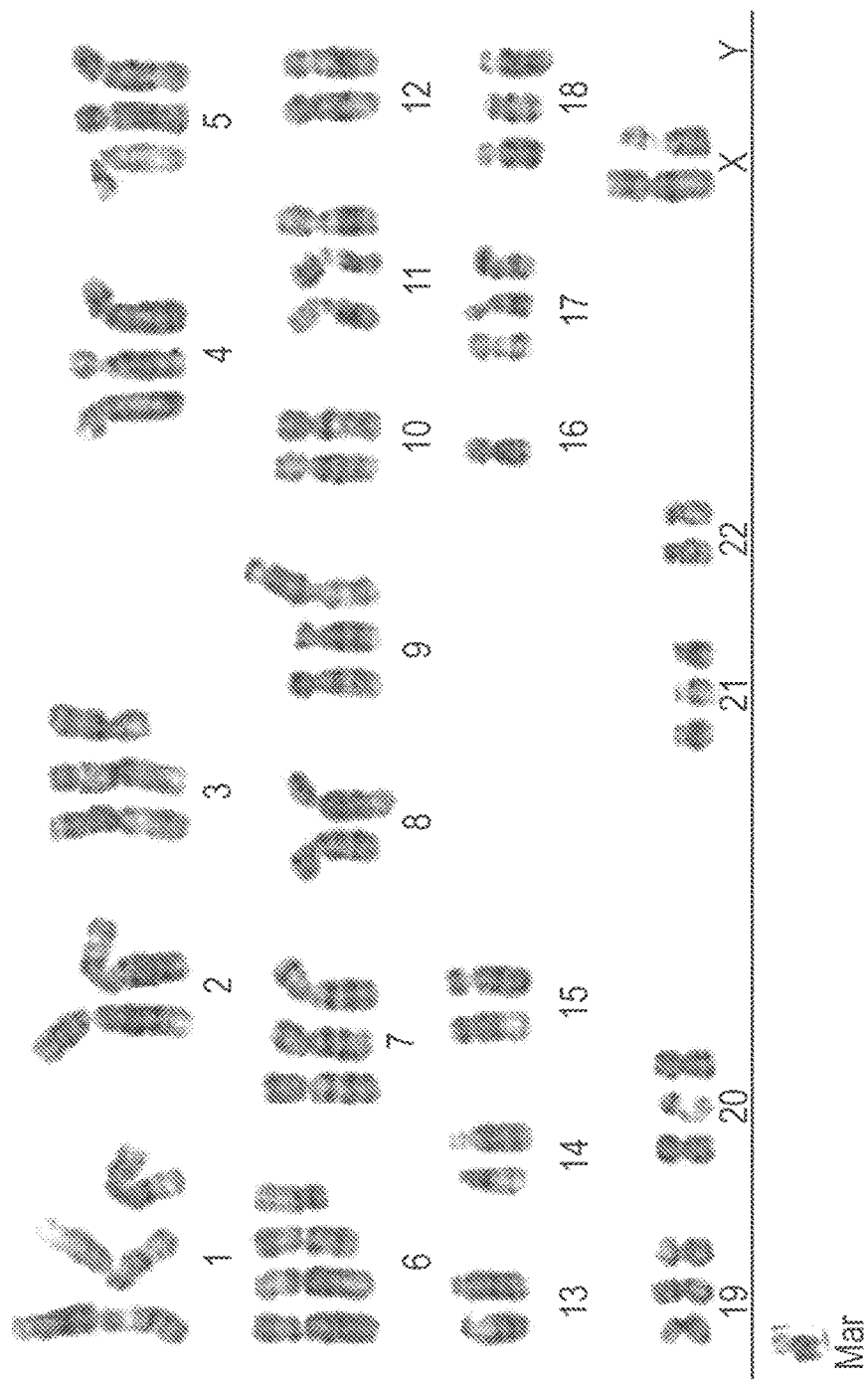
Figures 2, 2F:
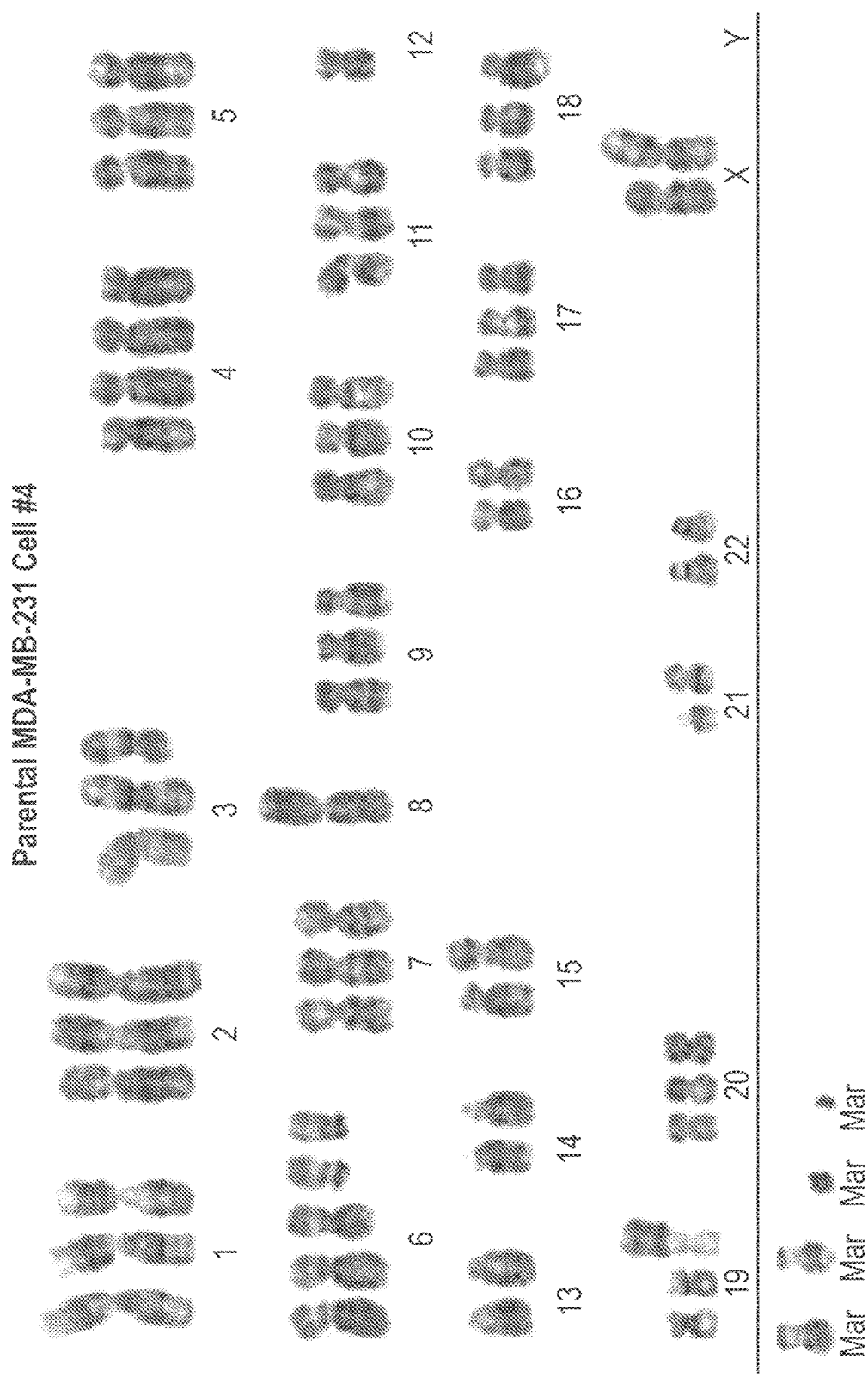
Figure 2G:
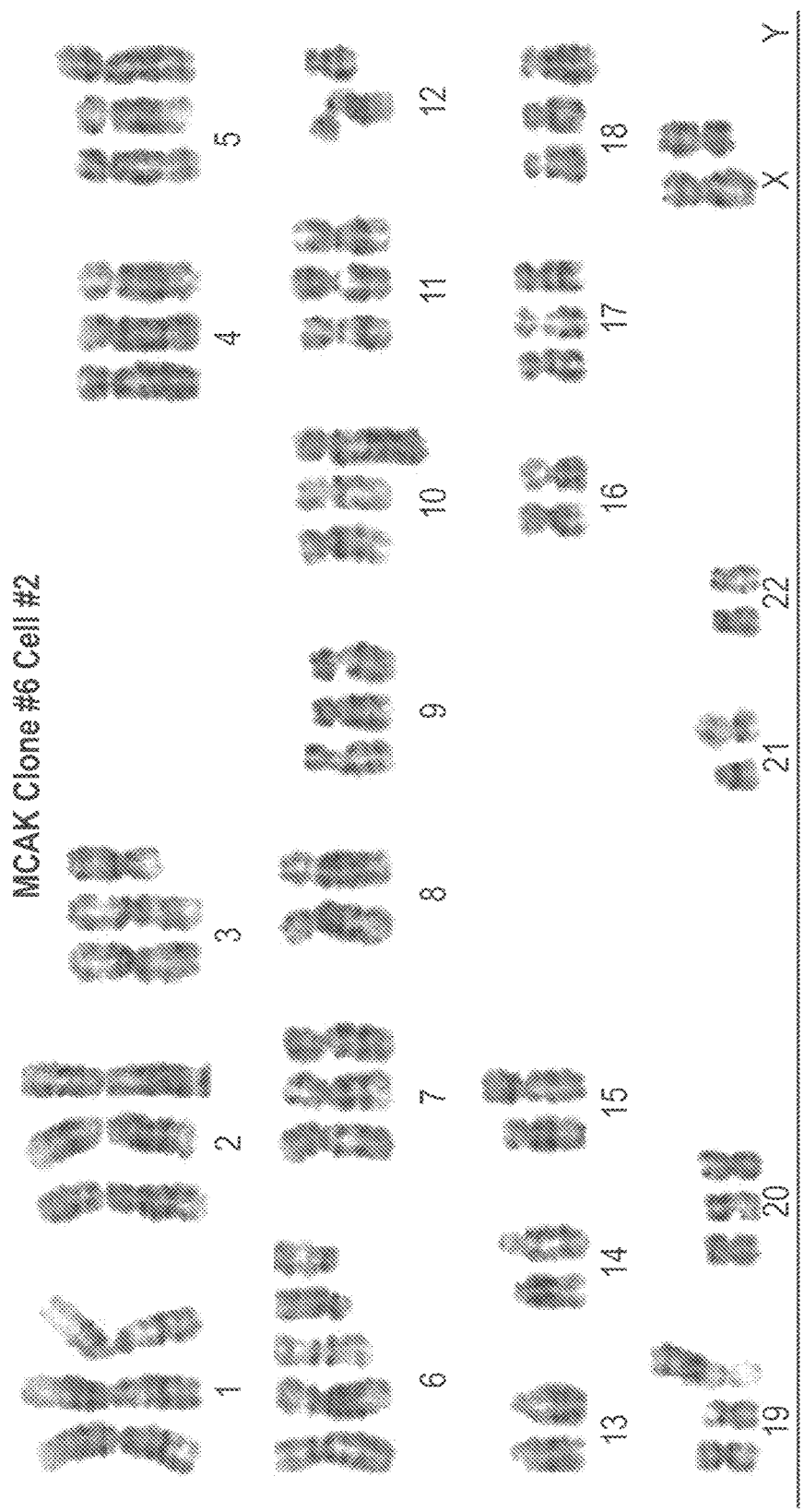
Figure 2H:
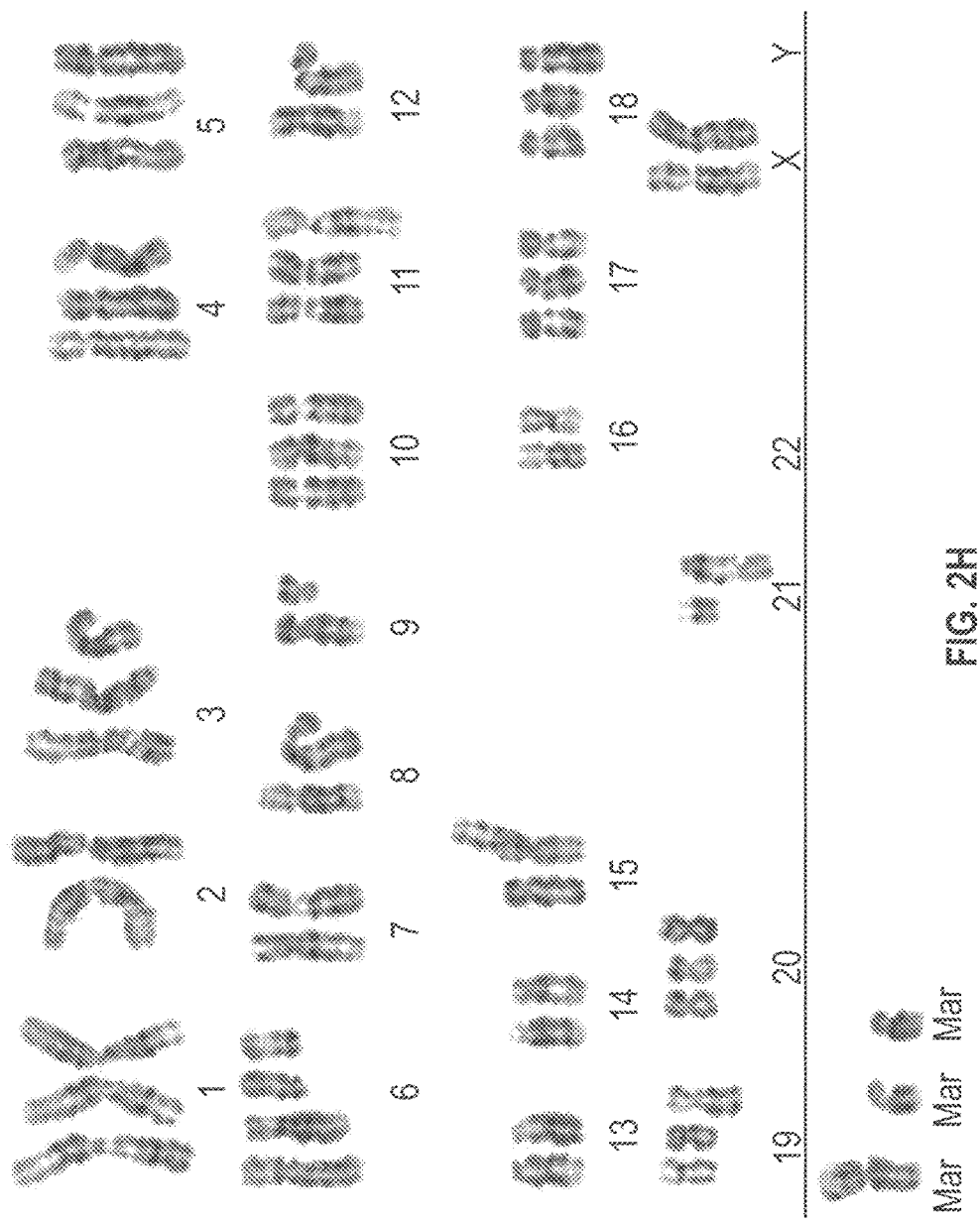
Figure 2I:
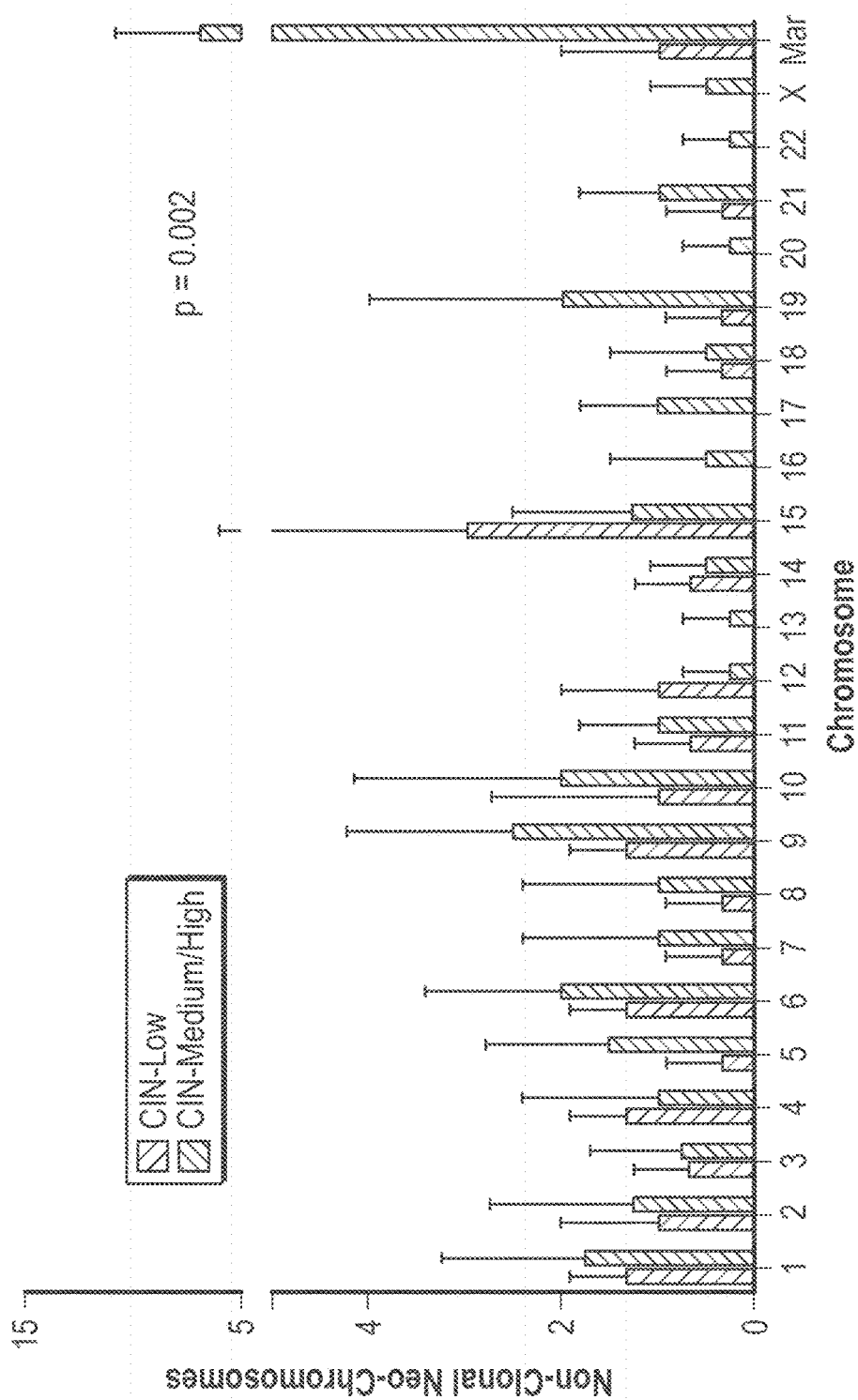
Figure 2J:
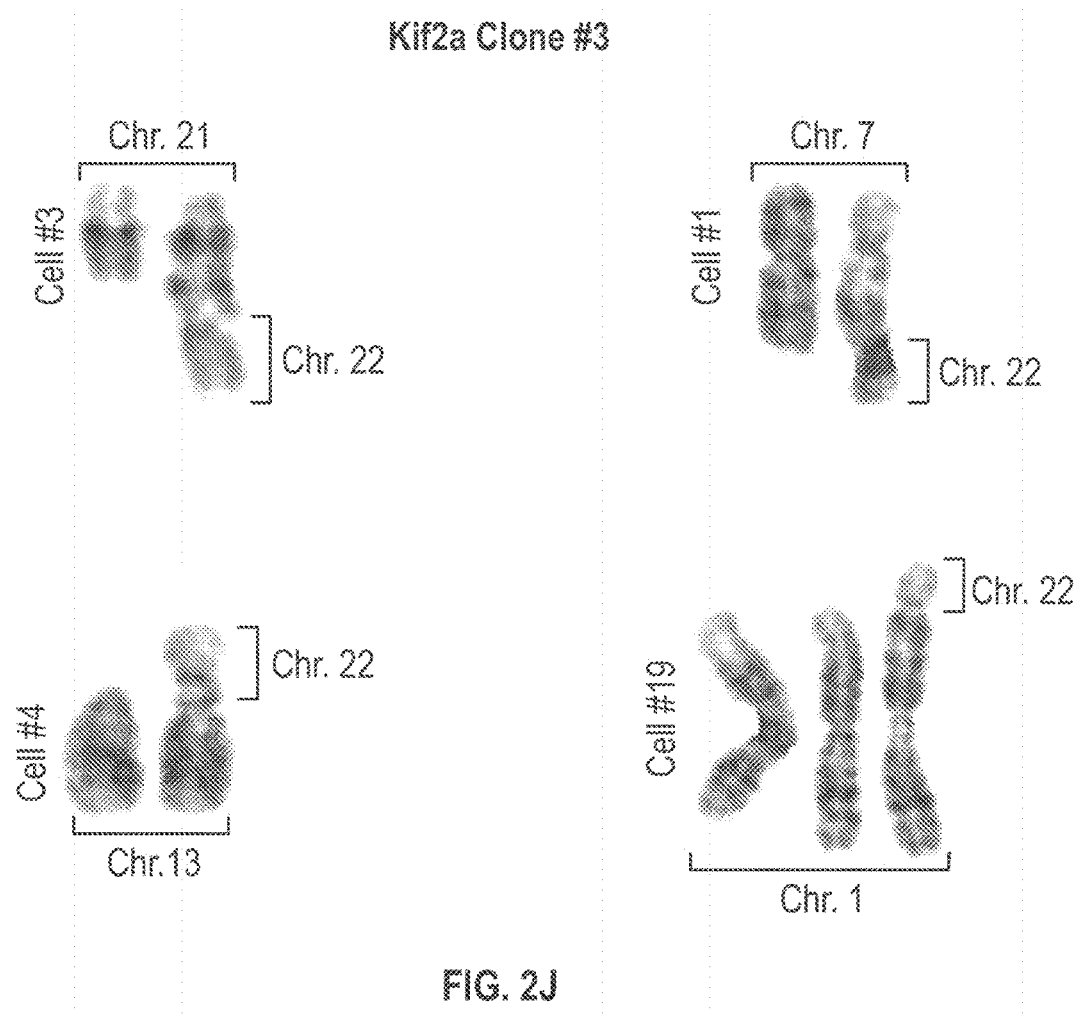

Karyotyping of the parental MDA-MB-231 cell line revealed widely aneuploid (near-triploid) chromosome content and demonstrated significant karyotypic heterogeneity as well as chromosomal abnormalities, as expected from a chromosomally unstable cell line (FIGS. 2F-1 to 2F-2). Suppression of chromosomal instability in these cells led to a reduction in karyotypic heterogeneity in single-cell derived clones, as evidenced by the presence of fewer neo-chromosomes (chromosomes exhibiting non-clonal structural abnormalities) in CIN-low cells as compared to CIN-medium or CIN-high (FIGS. 2G-2I). For instance, chromosome 22 was fused with other chromosomes leading to unique chromosomal combinations in different cells within the same Kif2a-expressing clonal population (FIG. 2J), indicating convergent karyotypic evolution conferred by chromosomal instability. Conversely, such events were uncommon in CIN-low clones. Nonetheless, CIN-low cells maintained highly aneuploid karyotypes, yet they faithfully propagated these abnormal karyotypes in a stable manner (FIGS. 2G, 2I). By comparing chromosomally stable aneuploid cells to their chromosomally unstable aneuploid counterparts, we can experimentally examine the role of chromosomal instability, independently of aneuploidy, in metastasis.

Figure 3D:
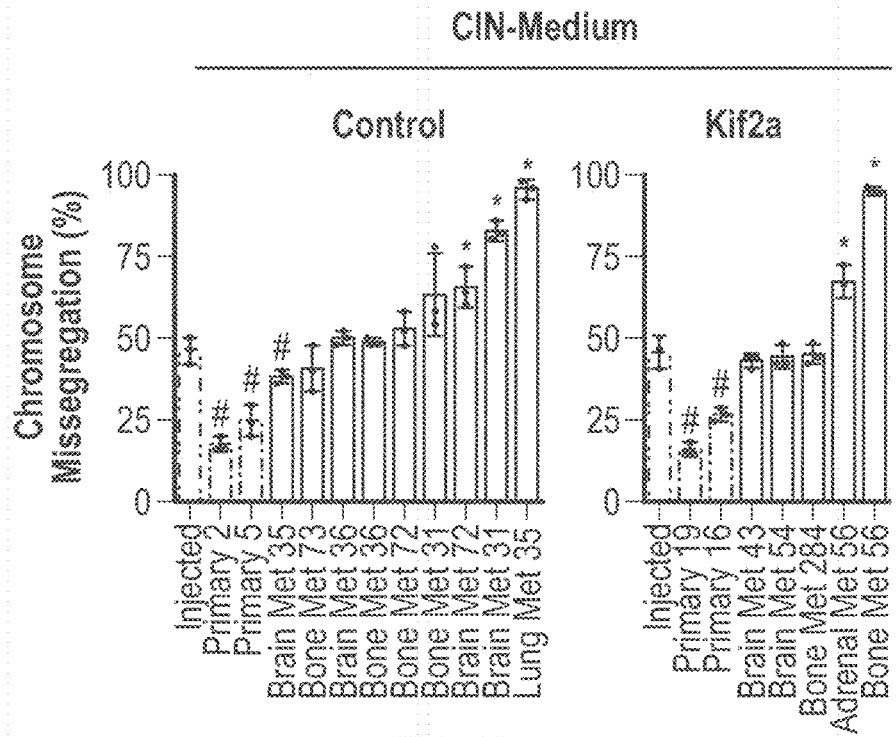
Figure 3E:
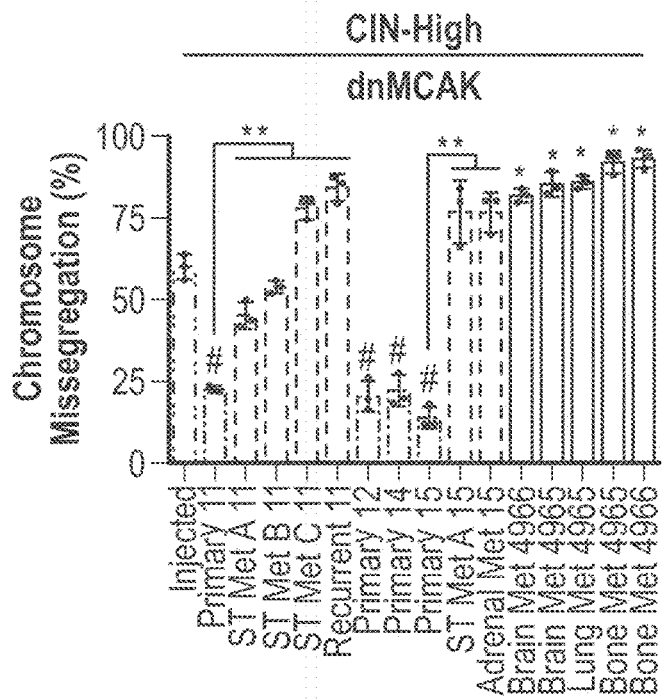
Figure 3F:
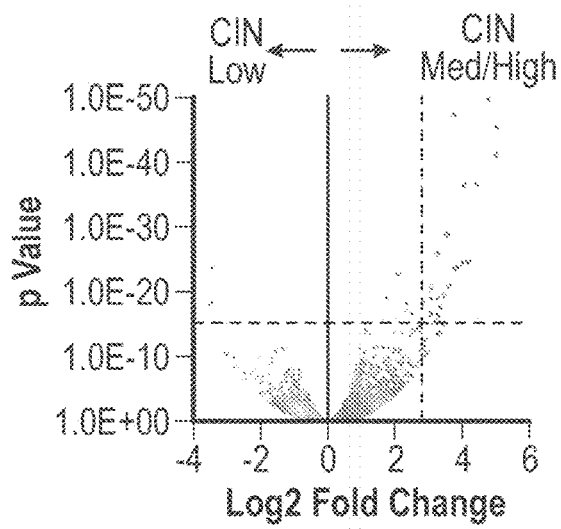
Figure 3G:
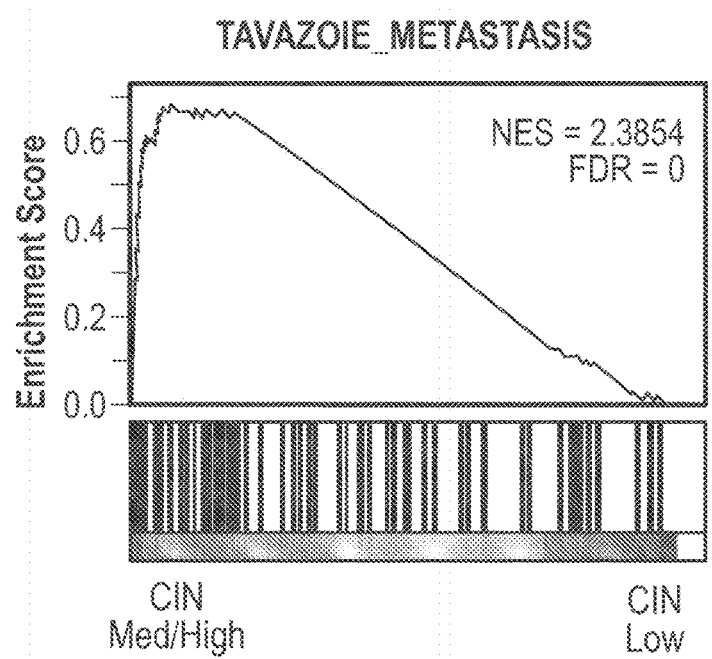
Figures 3H, 3I:
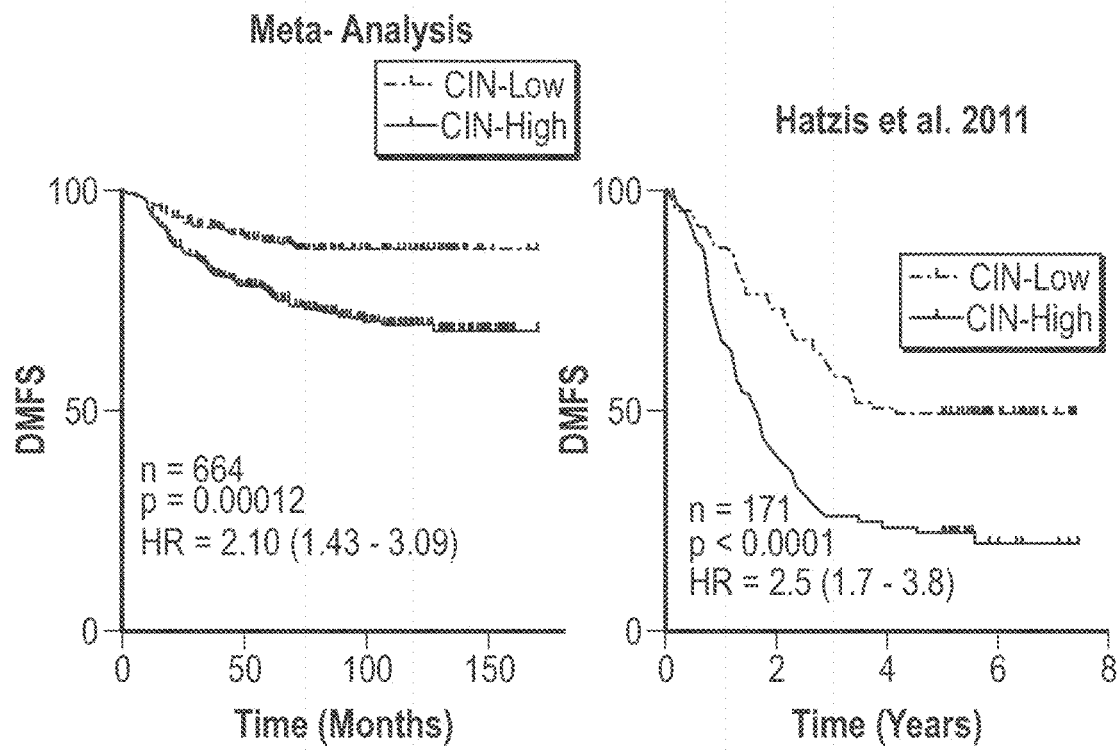
Figures 1, 3J:
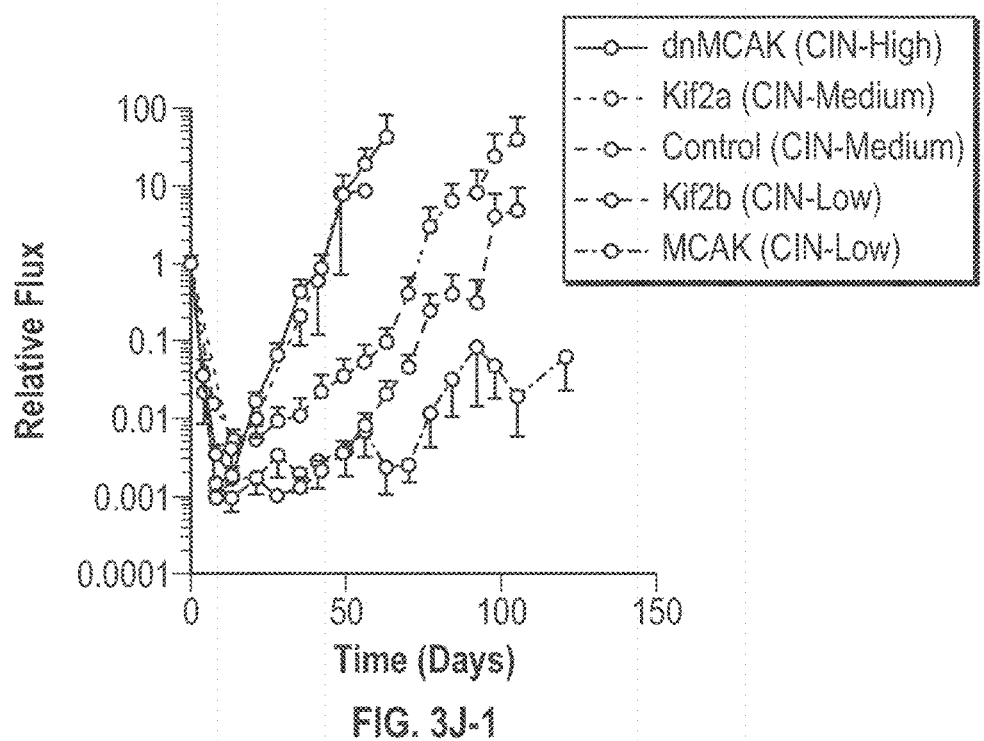
Figures 2, 3J:
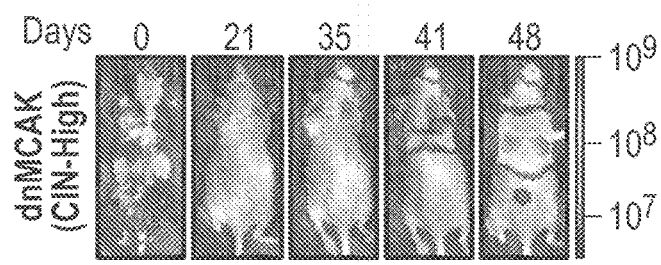
Figures 3, 3J:
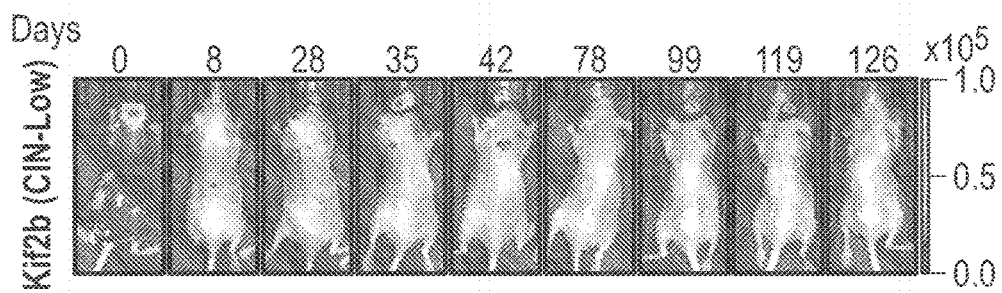
Figure 3K:
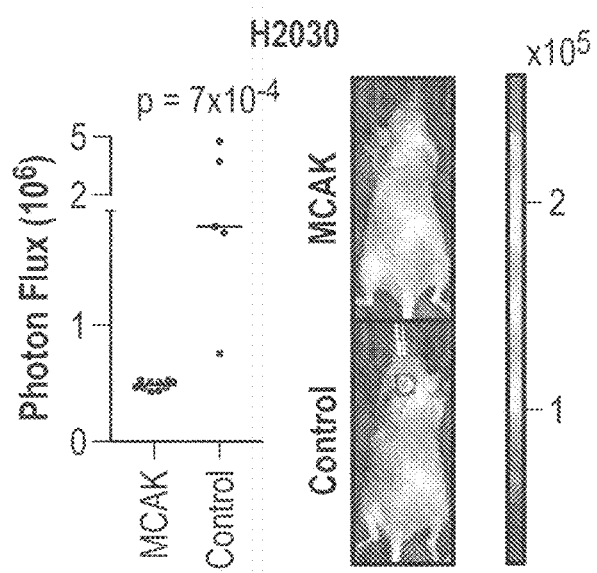

MDA-MB-231 cells were directly injected in the left cardiac ventricles of athymic mice to enable systemic dissemination (FIGS. 3J-1 and 3J-2, Day 0). Metastatic colonization was then tracked using a bioluminescence reporter assay. Experimentally altering chromosome missegregation rates had a dramatic effect on metastatic colonization, whereby mice harboring CIN-high cells rapidly succumbed to widespread disease within 60 days of injection with metastases present in the brain, bone, lungs, adrenal glands, and soft tissues. Conversely, mice injected with CIN-low cells exhibited a strikingly lower metastatic tumor burden and had a median survival of 207 days with some living over 290 days (FIGS. 2C-2E, 3J). In some animals, CIN-low metastases waxed-and-waned and, at times, spontaneously resolved, whereas CIN-high metastases involved multiple organs and rapidly progressed leading to death (FIGS. 3J-1 and 3J-2), indicating a potential role for chromosomal instability in the initiation as well as maintenance of metastases. Similar results were obtained after intraventricular injection of lung adenocarcinoma H2030 cells (FIG. 3K).

Figure 3L:
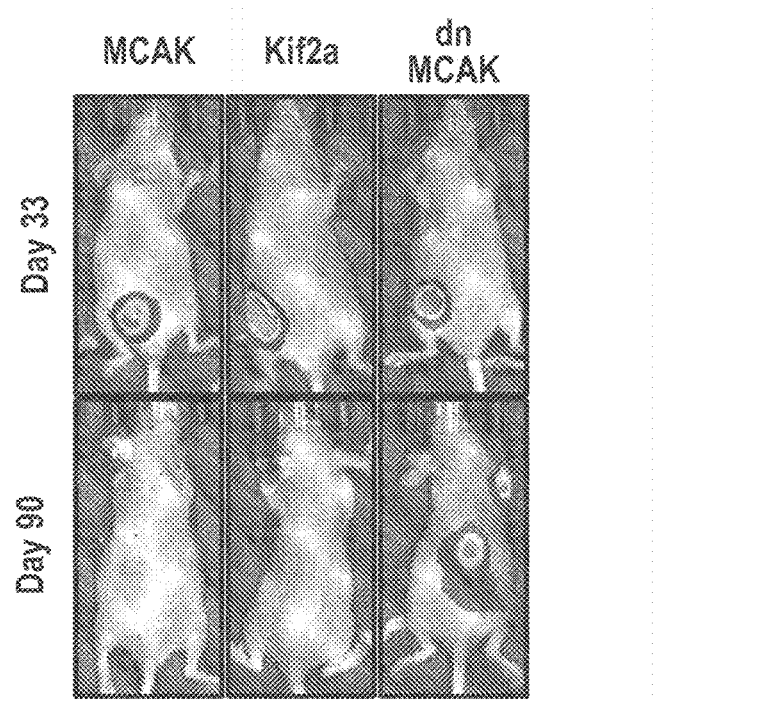
Figure 3M:
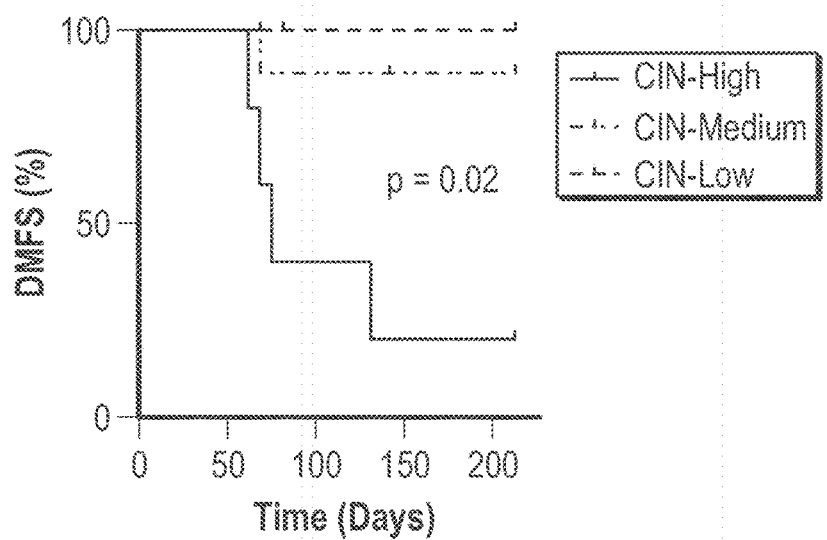

To assess the role of chromosomal instability in metastasis starting from the primary tumor setting, we performed orthotopic injections of MDA-MB-231 in the mammary fat pad followed by surgical excision of the primary tumor to enable time for metastatic dissemination (FIG. 3L, see methods described in Example 1). Chromosomal instability status did not noticeably alter primary tumor implantation efficiency as both CIN-low, CIN-medium, and CIN-high tumors were capable of forming palpable tumors at similar rates (not shown), however mice orthotopically injected with CIN-high cells exhibited a significantly shorter distant metastasis-free survival (DMFS) compared to animals injected with CIN-low tumor cells, which had no metastatic events (FIG. 3M). Collectively, these results show that chromosomal instability is a critical factor in tumor metastasis and that suppressing chromosomal instability reduces metastatic potential even in highly abnormal and aneuploid cells.

To evaluate the selection dynamics with respect to chromosomal instability during tumor dissemination, we assessed chromosome missegregation in the injected cells as well as cells (passage 1) derived from primary tumors or metastatic colonies (FIGS. 3J-1 and 3J-2). This analysis was first performed in two metastasis-competent patient-derived xenografts (PDX) belonging to two breast cancer subtypes: ER+ and TNBC (see Example 1). In both PDX tumor models, cells derived from orthotopically transplanted primary tumors had lower chromosome missegregation rates compared to matched metastases derived from the same animal (FIG. 3B). This analysis was then repeated using MDA-MB-231 cells and found that regardless of the chromosomal instability status of the injected cells, the majority of metastases enriched for cells that had significantly higher rates of chromosome missegregation compared to the injected cells (FIGS. 3C-3E). Conversely, cells derived from most primary tumors had significantly lower rates of chromosome missegregation compared to the injected cells (FIGS. 3D-3E). When CIN-high cells were injected (FIG. 3e, left-most bar) in the mammary fat pad, chromosome missegregation rates significantly decreased in the primary tumors (FIG. 3E, bars labeled 'primary') before increasing once more in the metastases spontaneously arising in the same animal (FIG. 3E, corresponding bars labeled 'met'). These results reveal the potential for rapid genomic plasticity arising from chromosomal instability and demonstrate a strong selective pressure for high rates of chromosome missegregation during the evolution of metastasis.

Example 4: Chromosomal Instability Enriches Mesenchymal Traits

Figure 4A:
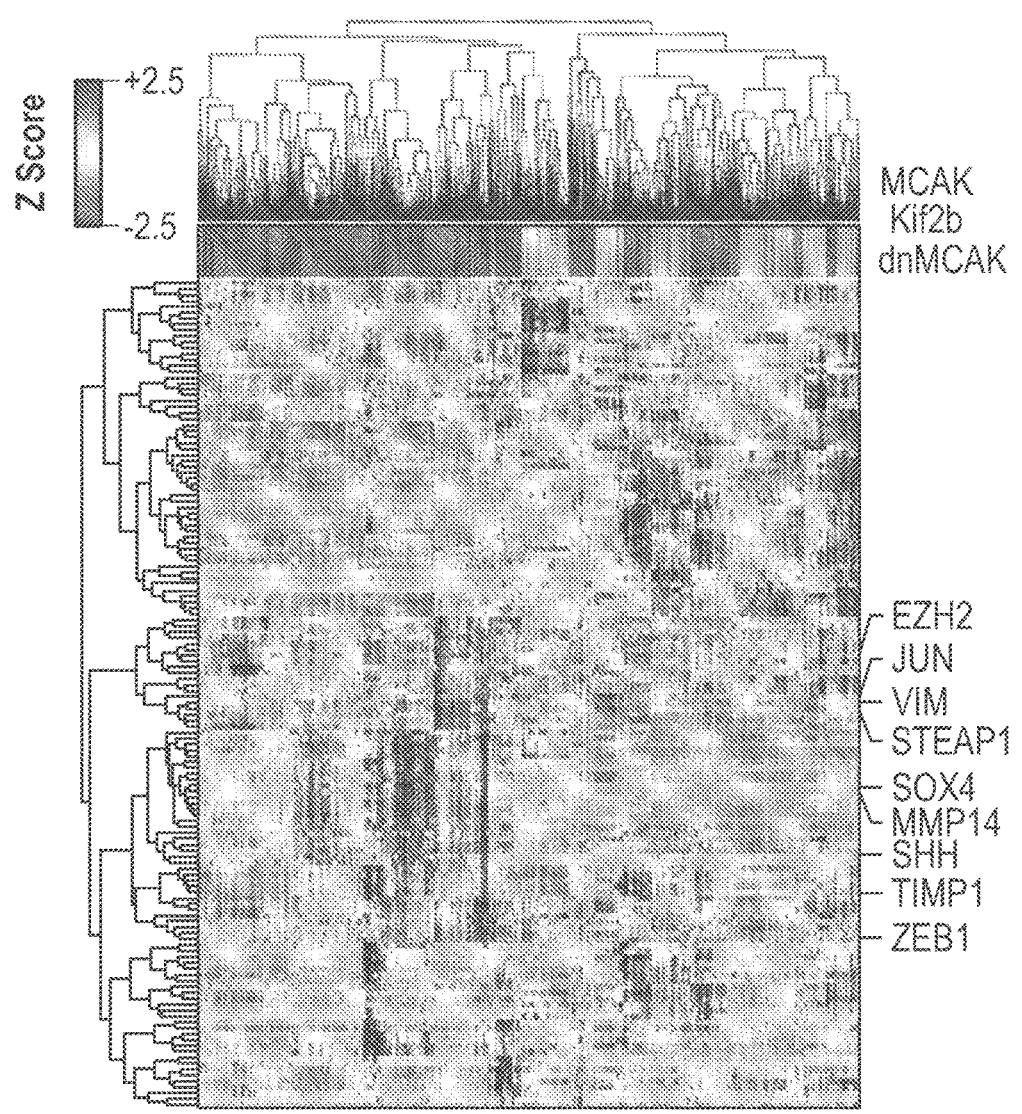
FIGS. 4A-4H illustrate that chromosomal instability enriches for mesenchymal cell traits.
Figure 4B:
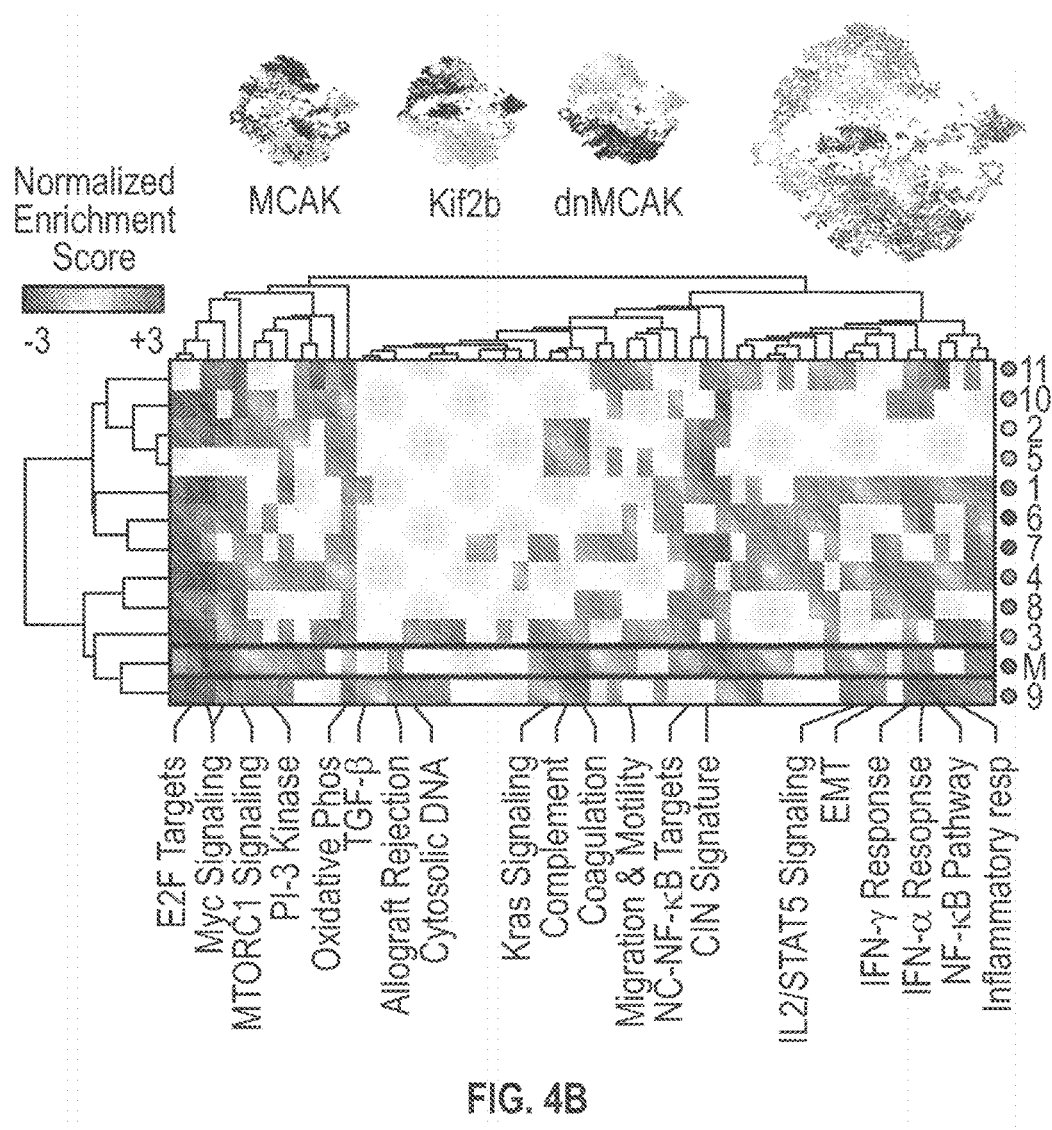
Figure 4C:
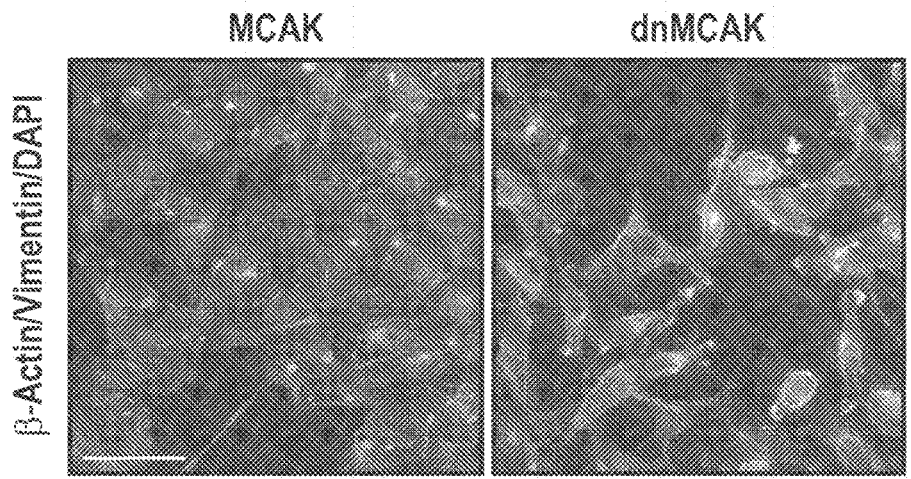
Figure 4D:
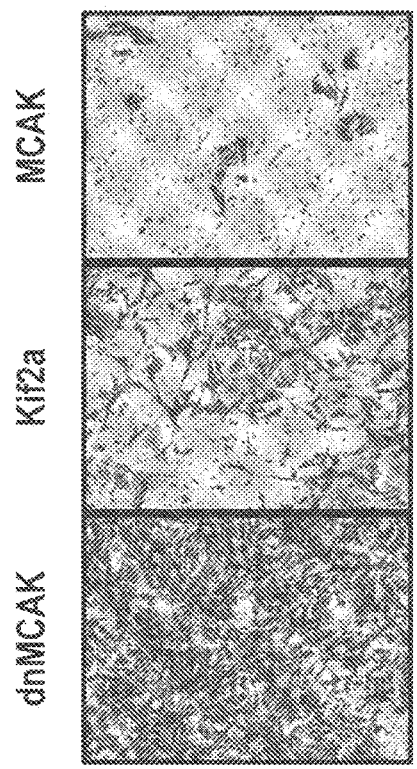
Figure 4E:
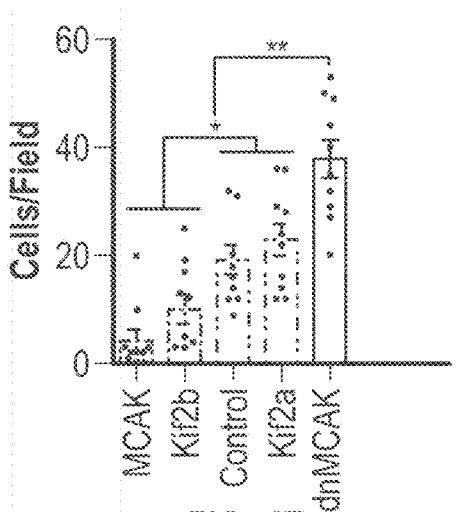
Figure 4F:
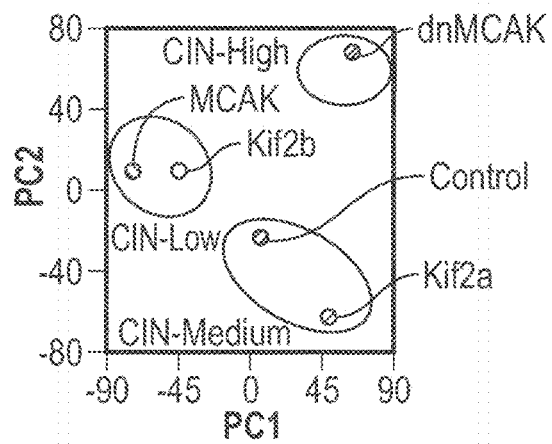

To examine the cellular changes in response to chromosomal instability, we performed bulk RNA sequencing (RNA-seq) of CIN-low, CIN-medium, and CIN-high MDA-MB-231 cells and found 1,584 differentially expressed genes when comparing CIN-low to CIN-medium/high (FIG. 3F). Principle component analysis (PCA) on gene-expression accurately separated samples according to their chromosomal instability status (FIG. 4F). Gene set enrichment analysis (GSEA) revealed that metastasis-related gene sets were amongst the most highly enriched in CIN-medium/high cells compared with CIN-low (FIG. 3G), indicating that chromosome missegregation induces a transcriptional change similar to that observed in metastasis. Indeed, the top 23 differentially expressed genes in CIN-medium/high compared with CIN-low were highly prognostic in human breast cancer patients as they predicted distant-metastasis-free survival (DMFS) in a meta-analysis (Györffy et al. Breast Cancer Res. Treat. 123, 725-731 (2010)) as well as a validation cohort (Hatzis et al., JAMA 305, 1873-1881 (2011)) (FIGS. 3H-3I).

This list of 23 genes whose elevated expression PREDICTS increased distant-metastasis free survival in breast cancer is referred to as the chromosomal instability (CIN) signature and includes elevated expression of: PELI2, BMP2, SHH, TNS4, RAB3B, ROBO1, ARHGAP28, CHN2, CST1, F3A1, CPVL, SEMA6D, C9orf152, NHSL2, GTF2IP7, DPYSL3, PCDH7, KHDRBS3, TRAC, TMEM156, CST4, CD24, FGF5, and NTN4. Such predictive power was largely preserved across tumor subtypes, grades, and lymph node status. For example, the 23-gene chromosomal instability (CIN) signature accurately identified that CIN-low patients had increased distant-metastasis free survival compared to CIN-high patients with a variety of breast cancers including node-negative, node-positive, grade 2, grade 3, grade 1/2, grade 3, ER+, ER−, and Her2+ breast cancers.

Figure 4G:
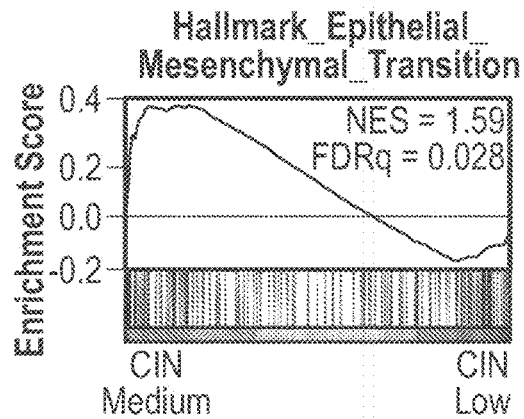

Epithelial-to-mesenchymal (EMT) transcriptional programs were also highly enriched in CIN-medium/high cells (FIG. 4G). To further understand how chromosomal instability influences cellular heterogeneity, single-cell RNA sequencing (scRNA-seq) was performed using a bead-based molecular barcoding technology (Klein et al. *Cell* 161, 1187-1201 (2015)) on two CIN-low MDA-MB-231 cell lines (Kif2b and MCAK) and one CIN-high cell line (dnMCAK) comprising a total of 6,821 cells. Single-cell library size was consistent across samples. Clustering of single cells using key EMT genes successfully classified most cells based on their CIN-status and it revealed a fraction of cells that was highly enriched in mesenchymal markers including key EMT regulators such as vimentin and ZEB1. This fraction was primarily comprised of dnMCAK expressing CIN-high cells (FIG. 4A). Conversely, CIN-low cells were highly enriched in epithelial markers.

Unsupervised graph-based clustering (Levine et al. *Cell* 162, 184-197 (2015)) based on all genes was then employed to identify intrinsic subpopulations in an unbiased manner. A subpopulation (referred to as subpopulation 'M') was identified that exhibited increased expression of genes involved in epithelial-to-mesenchymal transition (EMT) and metastasis and it was concomitantly enriched for the chromosomal instability (CIN) gene signature. Subpopulation M included 45% of the total dnMCAK expressing cells compared to only 6% of the CIN-low cells, respectively (FIG. 4B, FIGS. 6I-6J).

Figure 7A:
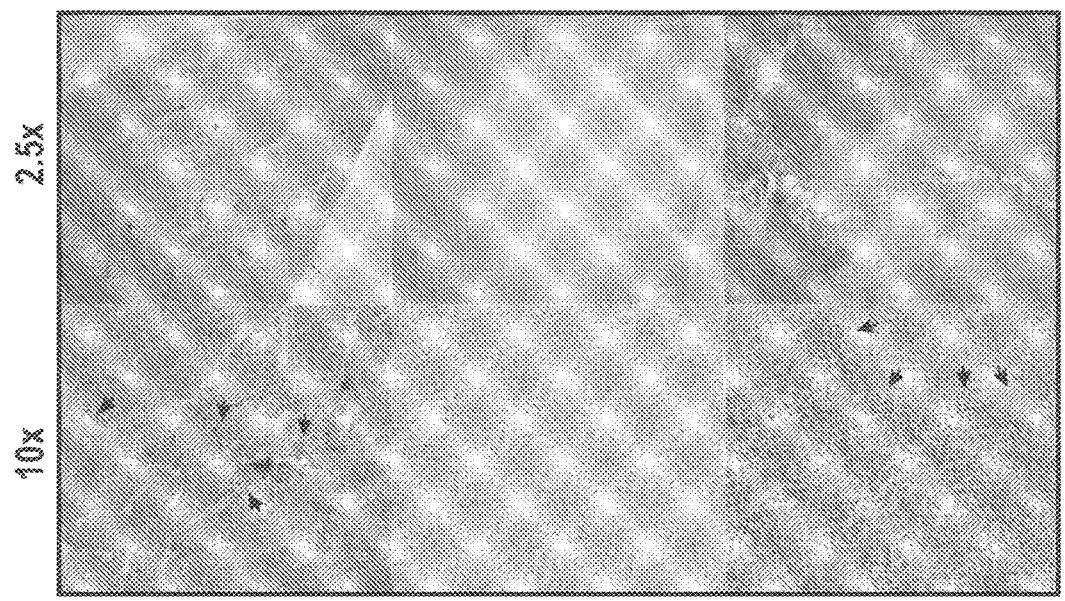
Figure 7B:
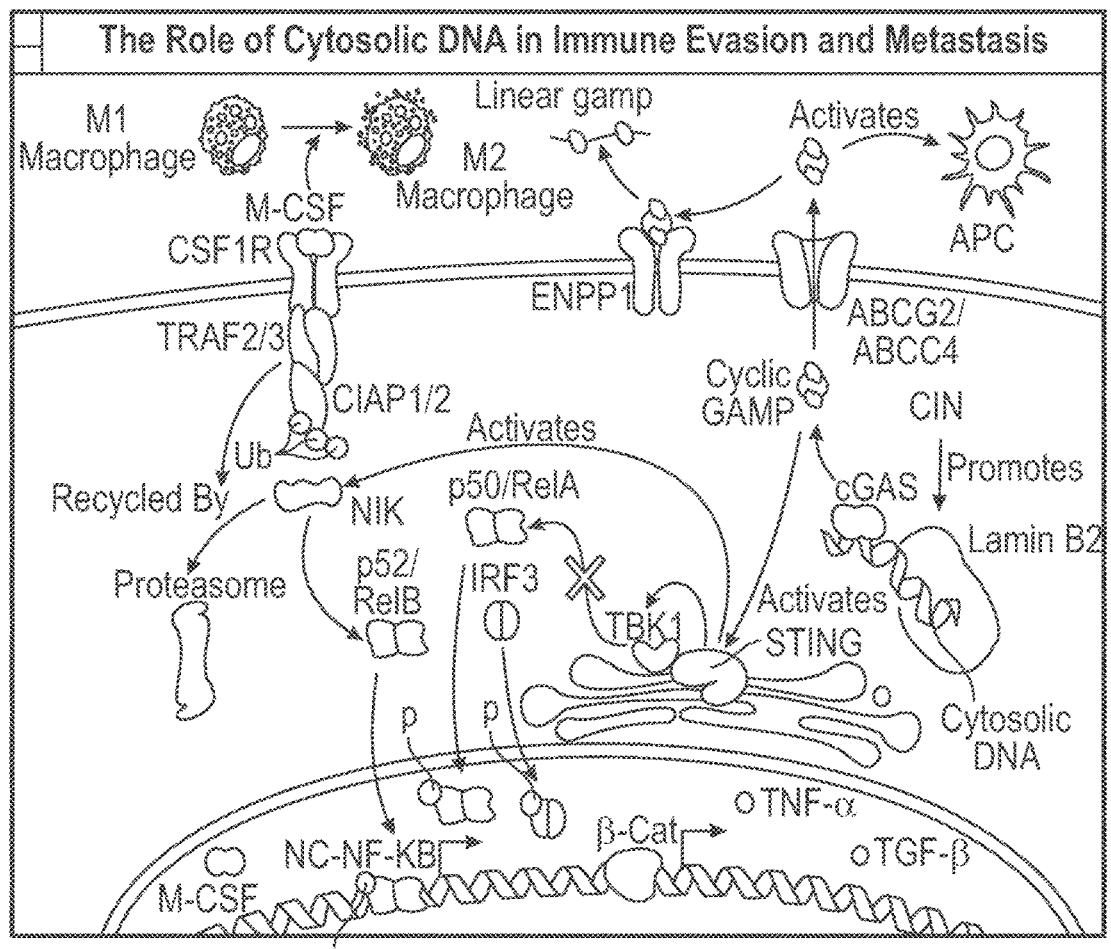
Figures 1, 7C:
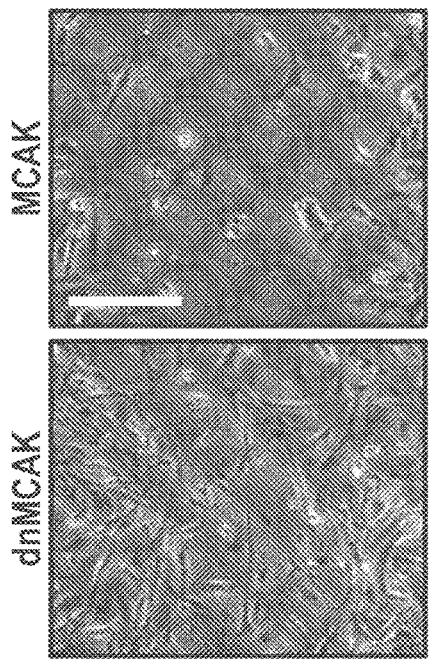
Figures 2, 7C:
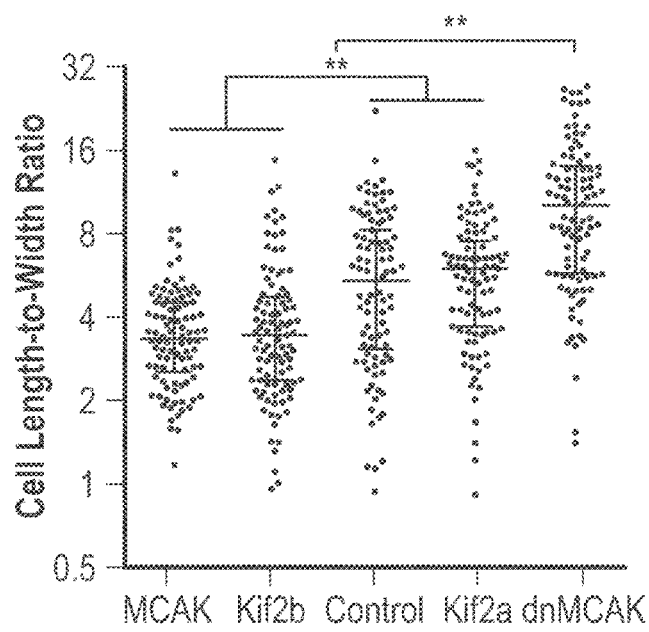
Figures 1, 2, 7D:
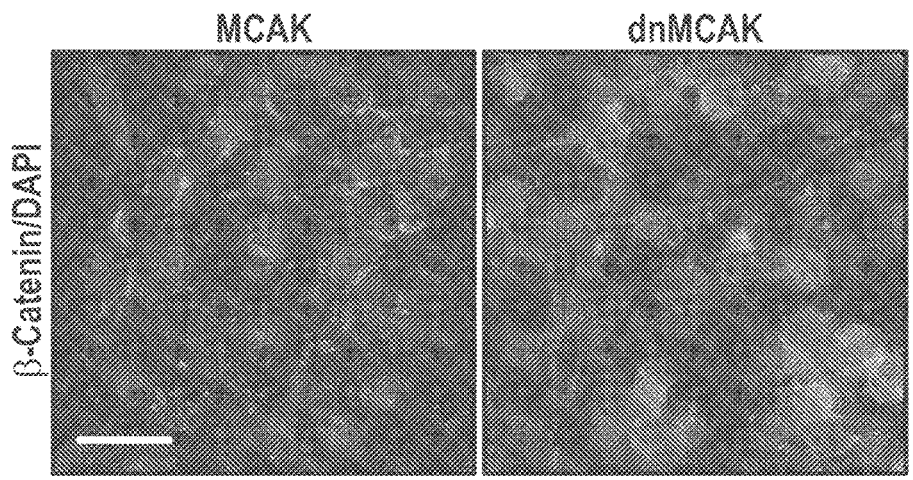
Figures 1, 7E:
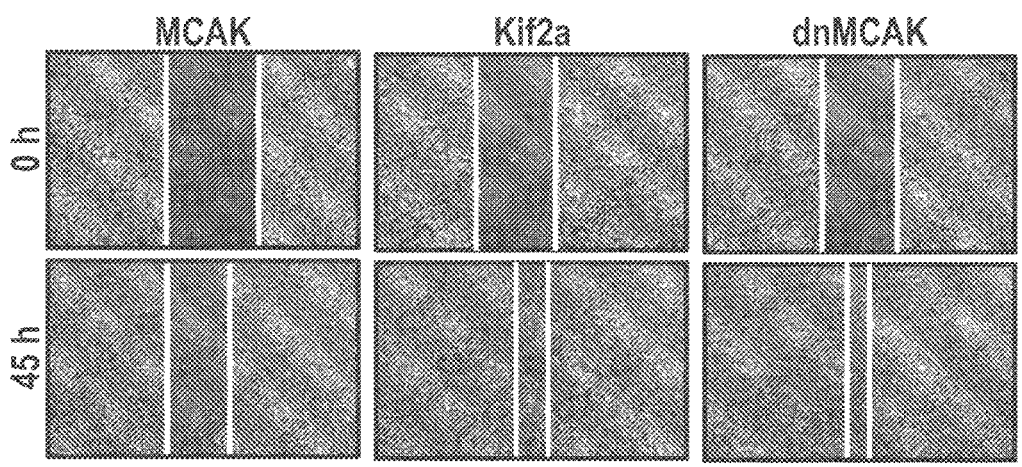
Figures 2, 7E:
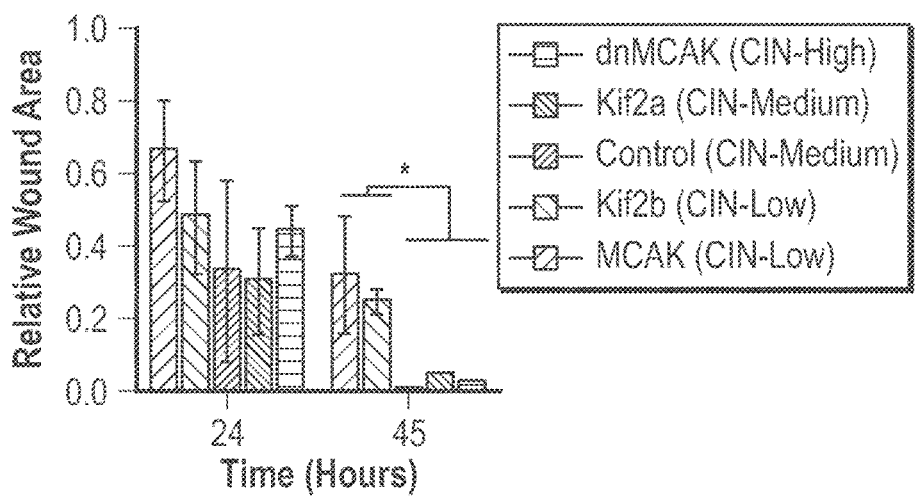
Figures 1, 7F:
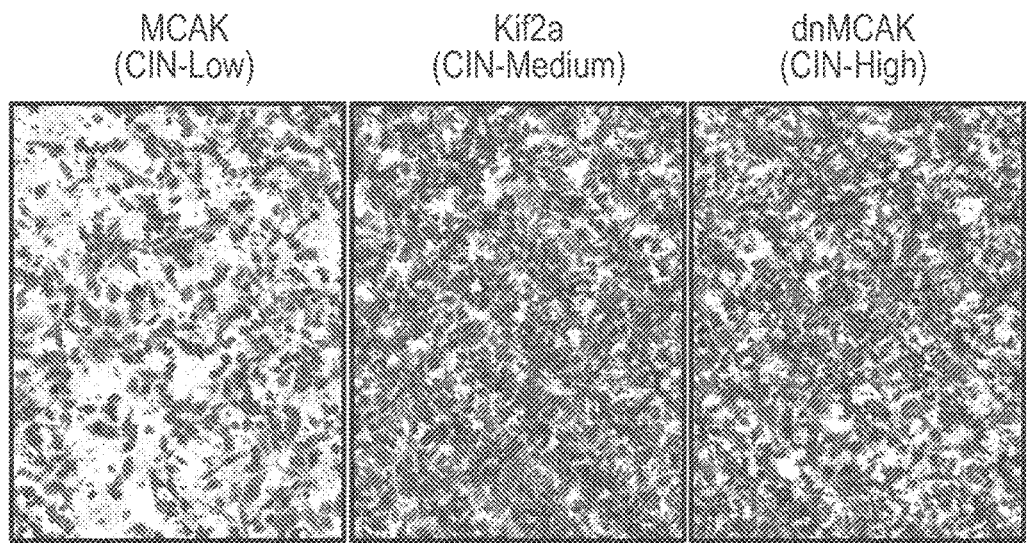
Figures 2, 7F:
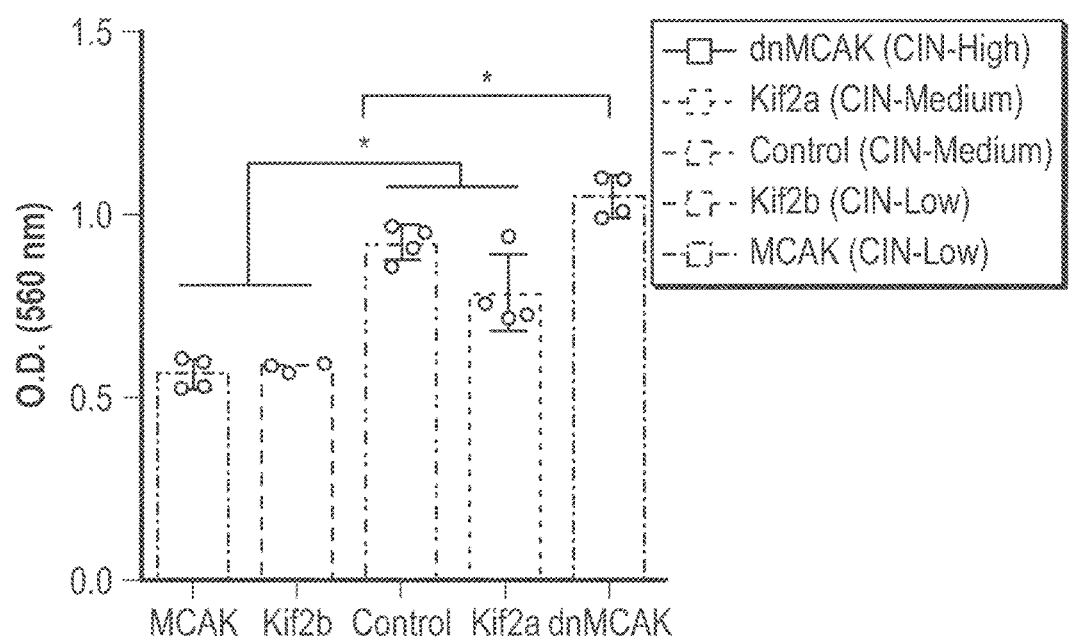
Figure 8A:
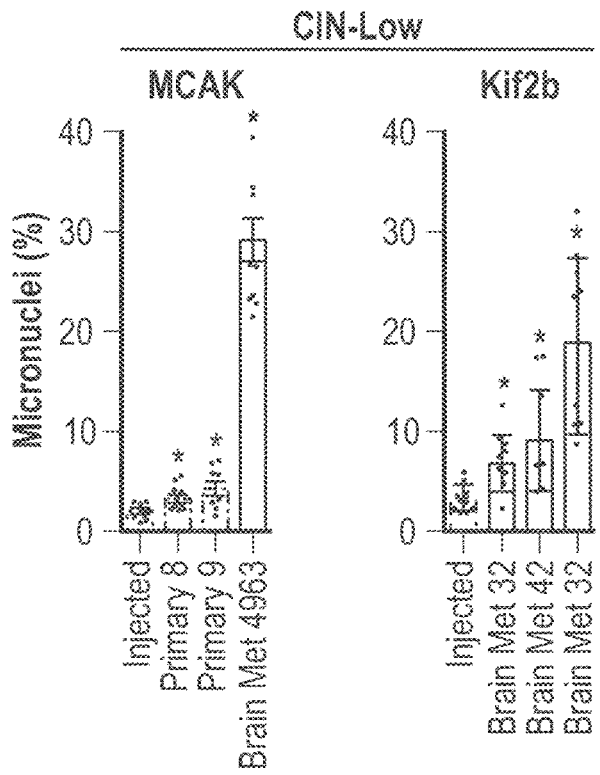
FIGS. 8A-8C illustrate that chromosomal instability generates micronuclei and cytosolic dsDNA.
Figure 8B:
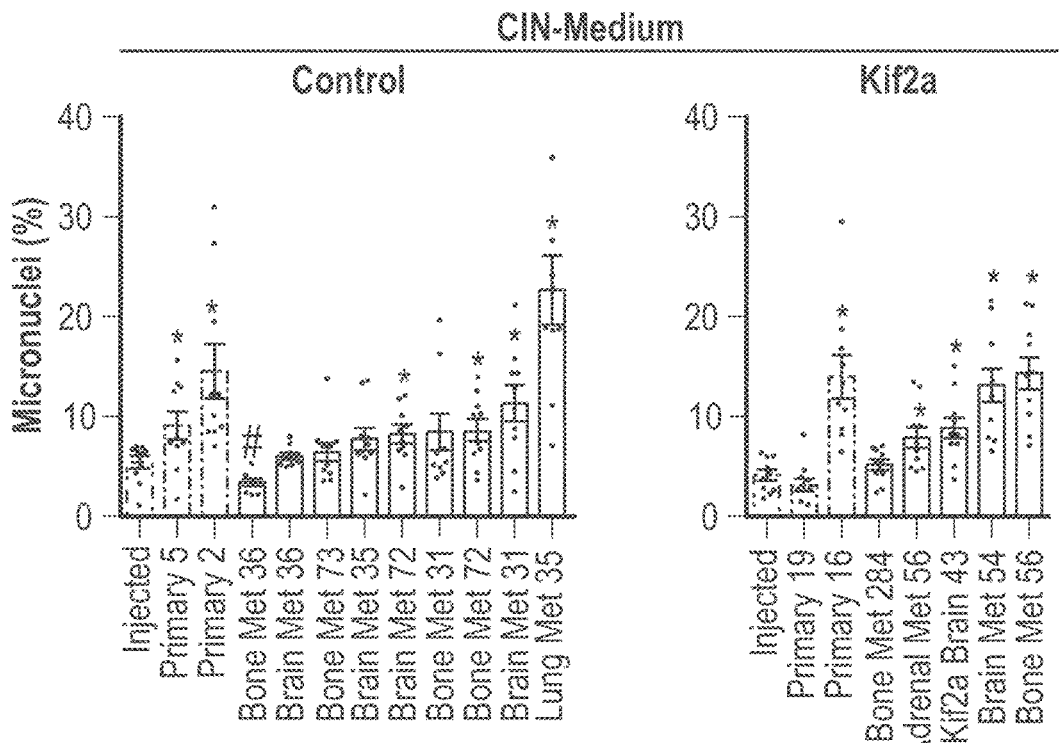
Figure 8C:
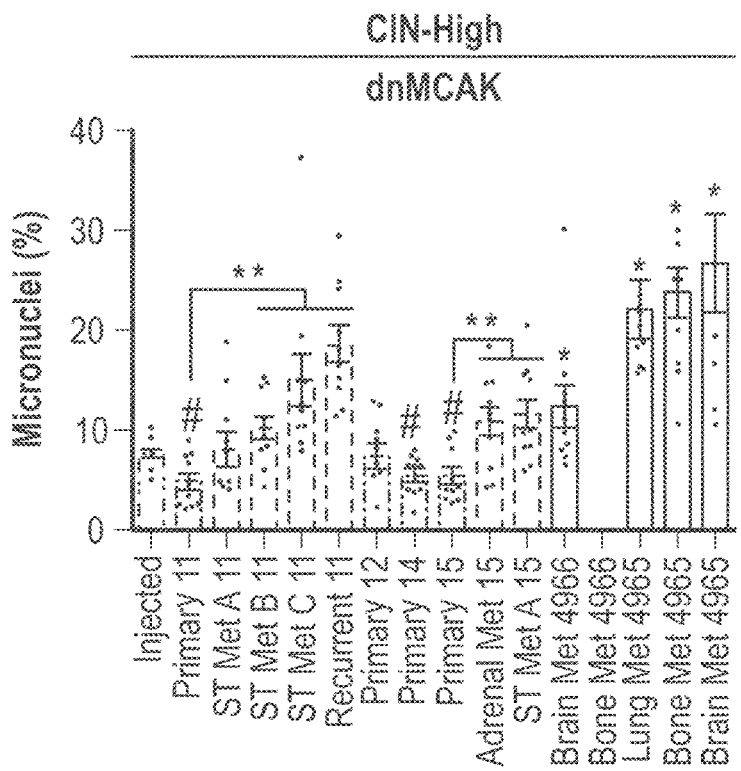
Figure 9A:
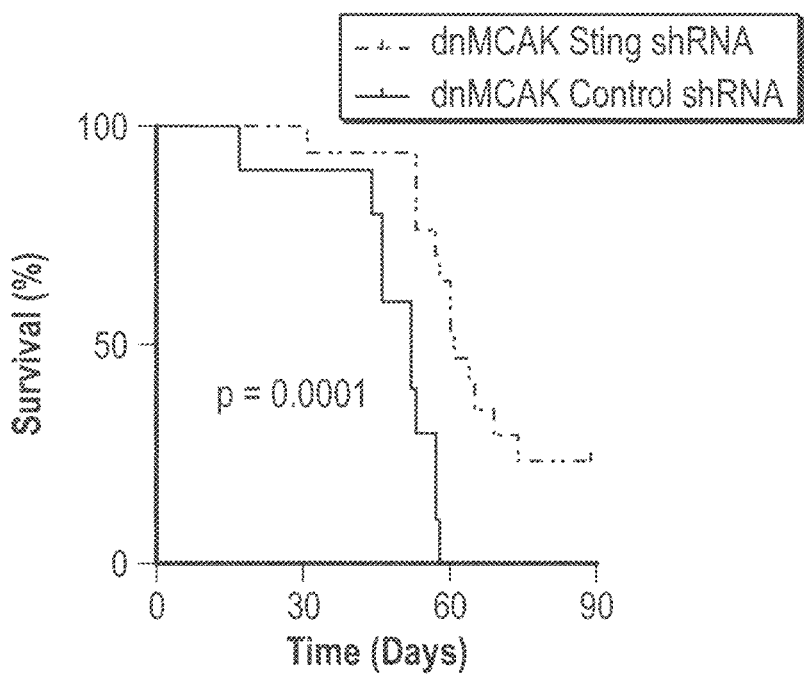
FIGS. 9A-9M illustrate the effects of cytosolic DNA sensing pathways on prognosis.
Figure 9B:
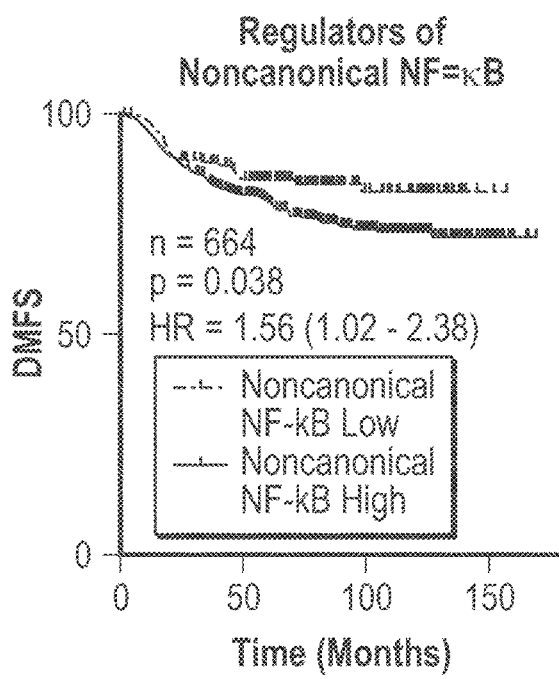
Figure 9C:
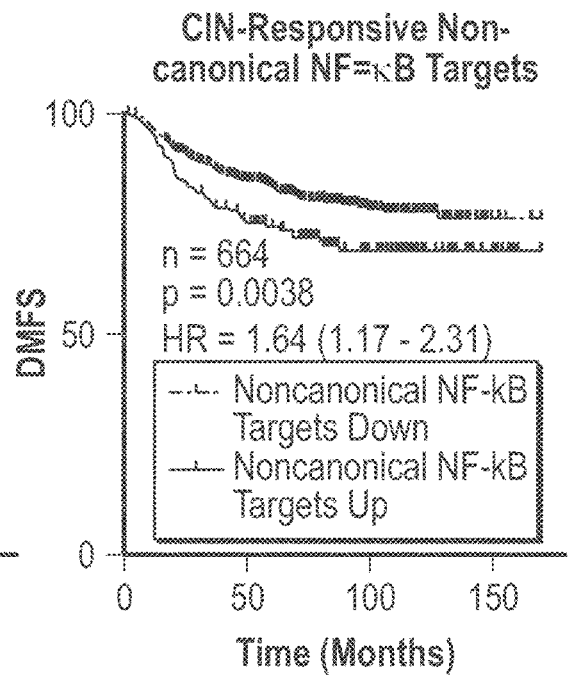
Figure 9D:
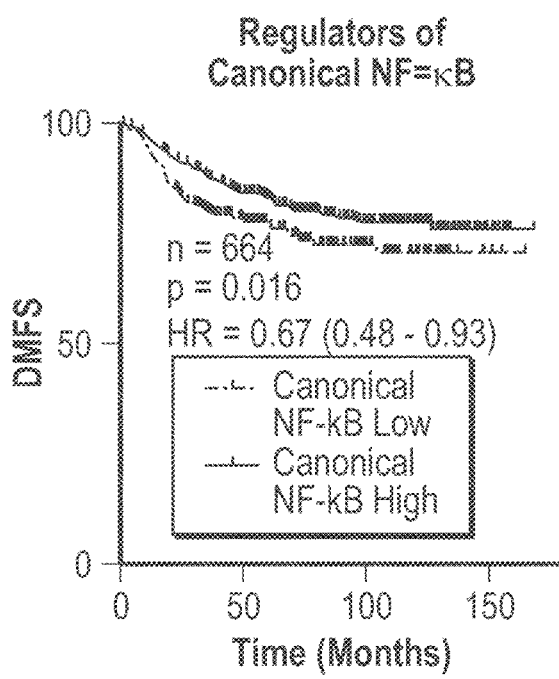
Figure 9E:
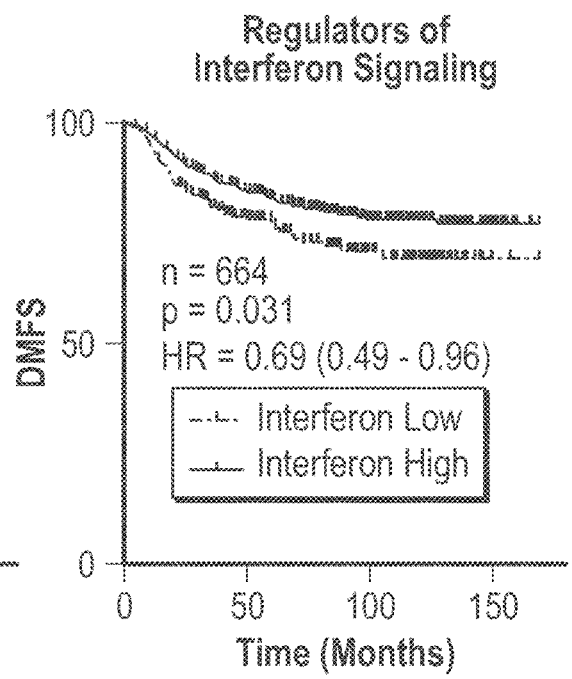
Figure 9F:
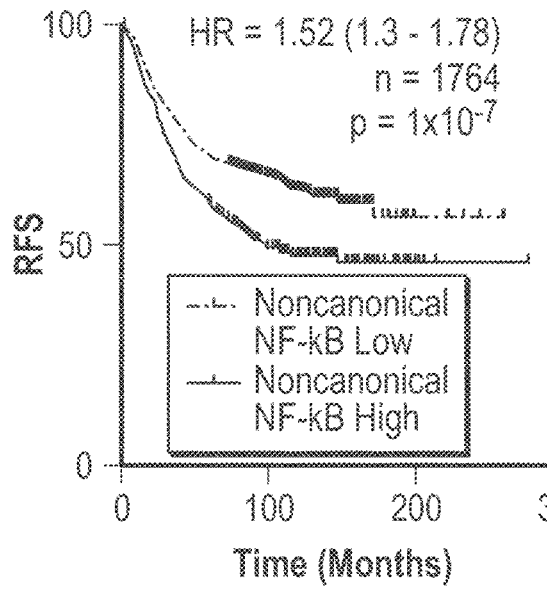
Figure 9G:
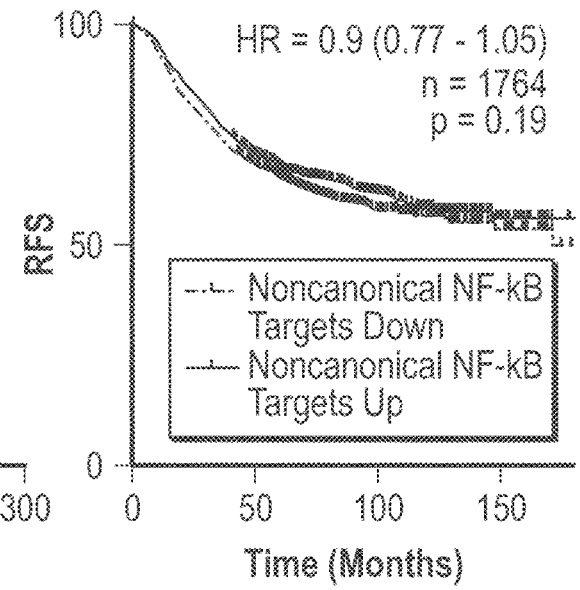
Figure 9H:
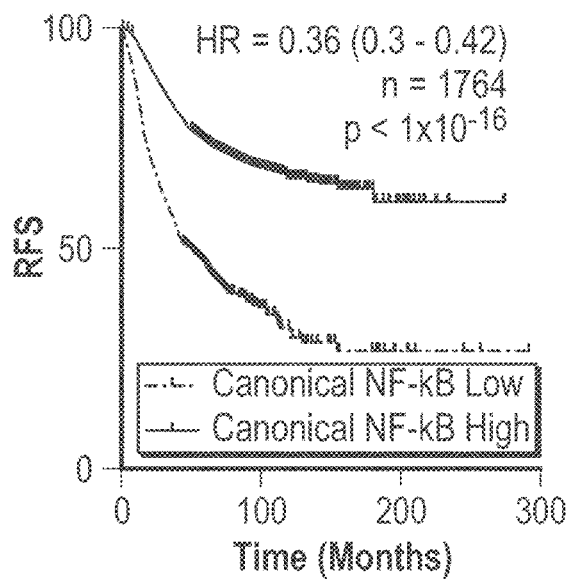
Figure 9I:
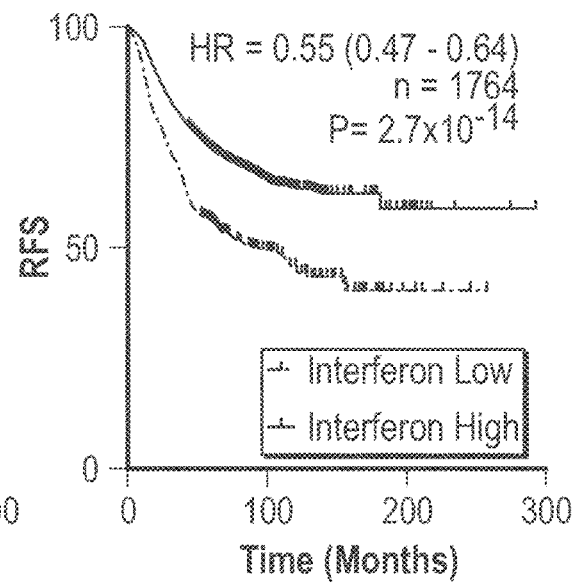
Figures 9J, 9K:
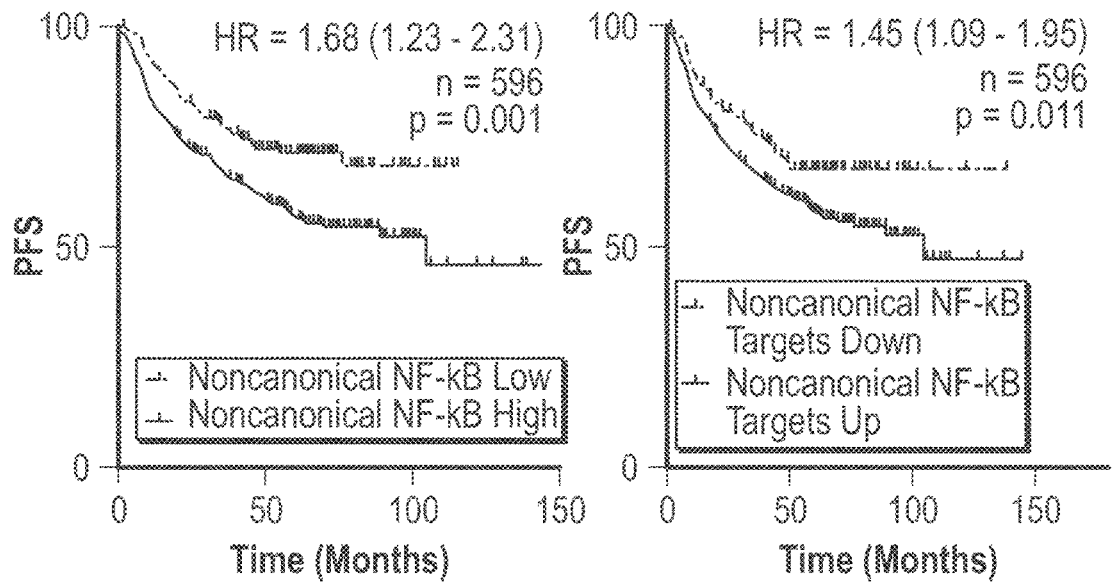
Figures 9L, 9M:
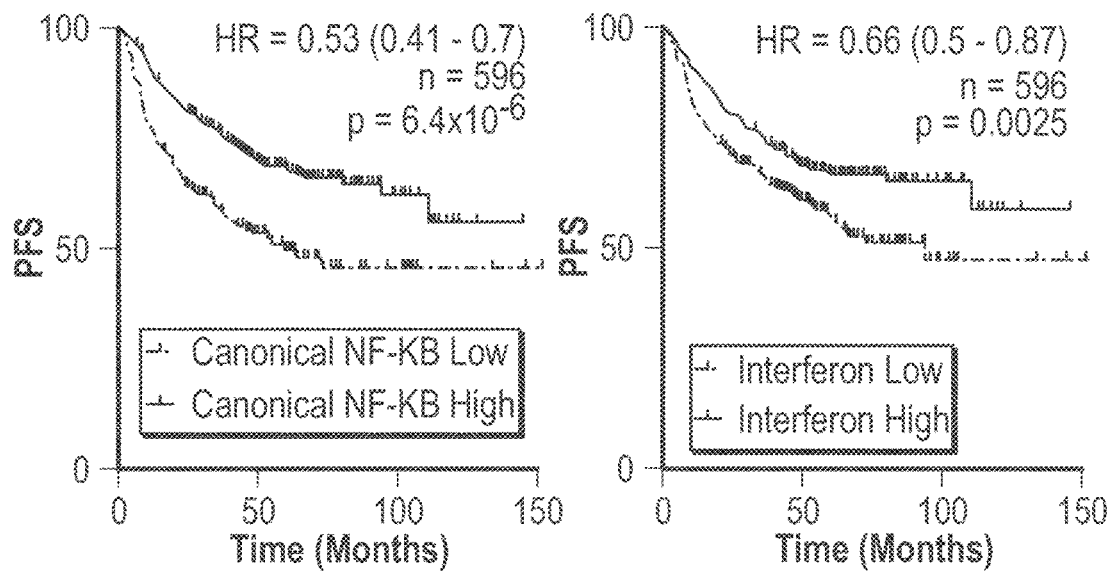

These results were validated experimentally using high-resolution fluorescence microscopy whereby we found cells expressing dnMCAK to have more elongated features (defined by length-to-width ratio) exhibiting actin cytoskeletal reorganization. They also exhibited mesenchymal characteristics such as diffuse vimentin staining and changes in localization of β-catenin: from cell-to-cell junctions in MCAK expressing cells to the cytoplasm and nucleus of dnMCAK expressing cells (FIG. 4C, FIGS. 7C-7D). Accordingly, cells with high levels of chromosomal instability exhibited increased migratory capacity and were significantly more invasive through collagen basement membranes in vitro (FIG. 4D, FIGS. 7E-7F). Collectively, these results demonstrate that chromosomal instability promotes a cell-autonomous invasive program that facilitates the metastatic process.

Example 5: Chromosomal Instability-Induced Cell-Intrinsic Inflammation

This Example illustrates that chromosomal instability induces intrinsic inflammation.

Figure 5A:
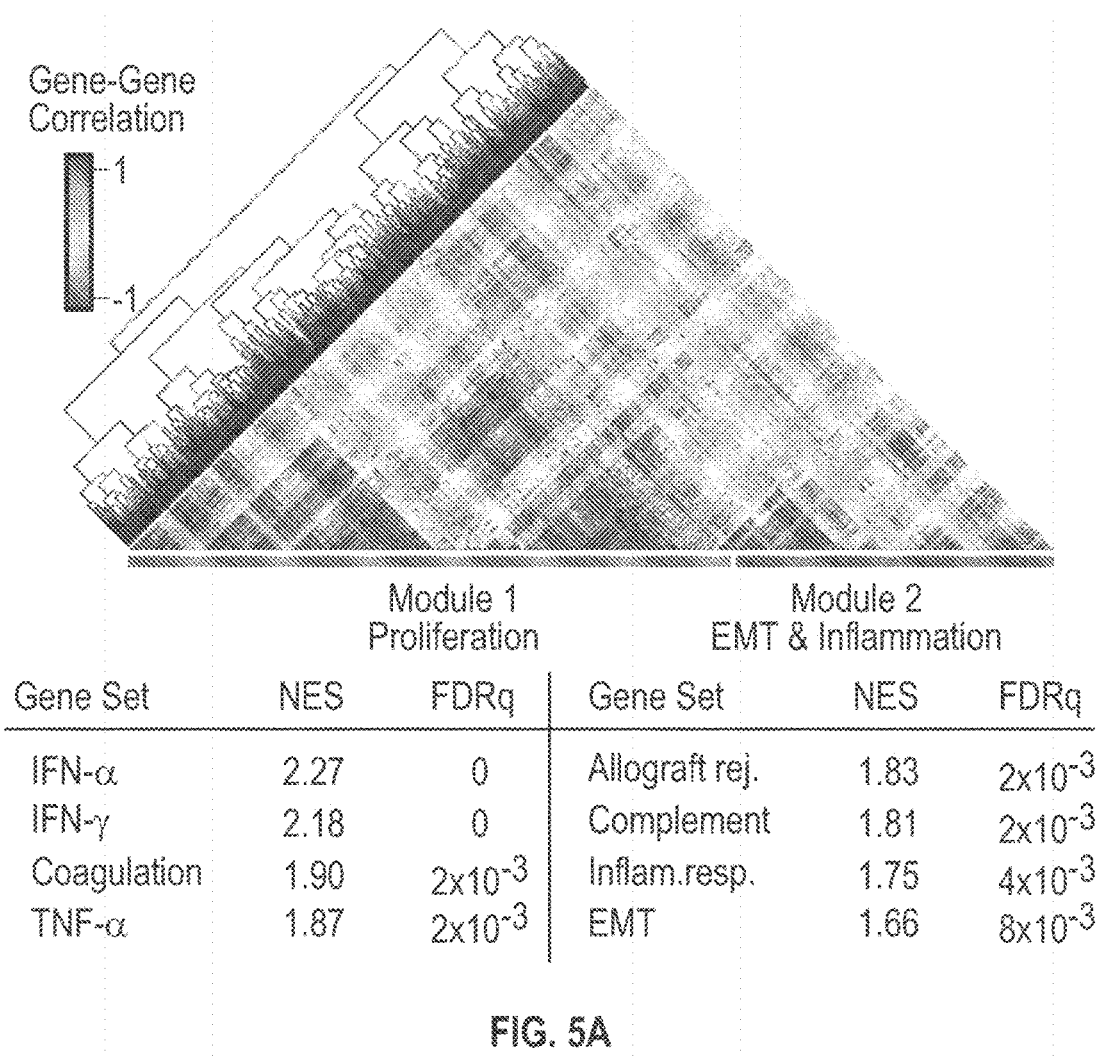

To further define chromosomal instability-responsive pathways, a gene-gene Pearson correlation analysis was performed using scRNA-seq data and identified two large gene modules. Module 2 contained genes involved in epithelial-to-mesenchymal transition (EMT) as well as a large number of inflammatory pathways (FIG. 5A).

As described in Example 1, the EMT genes include VIM, ZEB2, SNA12, and ZEB1. The inflammatory pathway genes include RGS16, DENND5A, BTG2, STAT3, IFITM3, CD47, SLAMF7, REL, BCL6, IL18BP, NAMPT, PDE4B, IL8, PSME2, P2RX4, IF144, CCR7, KLF10, ADRM1, KLF9, NFIL3, CNP, LDLR, HES1, HLA-A, PARP9, NUB1, STAT2, VIP, TGIF1, PVR, MOV10, PSMA2, EIF4E3, IER3, PLA2G4A, TRAFD1, MYD88, VAMP5, TRIM14, TUBB2A, BPGM, B2M, HRH1, PSMB9, LATS2, PTPN6, DCBLD2, PSMB8, IL1R1, PSMB2, SQSTM1, PTX3, ITGA5, EDN1, SLC31A1, SAMHD1, PNPT1, CSF1, TNFRSF9, SOCS1, RELB, VEGFA, ARL4A, DUSP5, CMKLR1, CD38, SLC4A4, SP110. PLAU, DDX58, PSME1, TRAF1, SPSB1, TDRD7, F2RL1, EPSTI1, SAMD9L, NINJ1, RNF19B, LIF, RIPK1, SLC2A6, IRF7, PTAFR, IRAK2, CD14, ITGB8, SCARF1, KIF1B, FOSL2, SOCS3, DUSP1, IRF1, SLC2A3, HBEGF, CXCL3, TNIP1, AHR, SGMS2, FZD5, GCH1, SLC25A28, OSMR, RSAD2, APOL6, ICOSLG, JAG1, GOS2, GEM, KLF4, NFKB1, STAT1, HLA-C, IFIH1, LY6E, EFNA1, SLC16A6, BHLHE40, TRIM26, CD82, CYBB, IL15RA, GABBR1, RELA, PHLDA2, MAP3K8, NUP93, IL7R, PTPRE, IF127, SNN, NR4A2, SPPL2A, RHOG, SAT1, SLC7A1, 1L6, IL15, RAF1, CCL20, ACVR1B, BIRC2, RBCK1, LAP3, ID2, TNFSF10, SIK1, BST2, PANX1, GADD45A, PML, CD40, TRIM21, SECTM1, SSPN, TXNIP, BTG1, AREG, KYNU, PTGS2, IRS2, C3AR1, STAT4, ATP2A2, BIRC3, MAP2K3, CXCL1, NFKBIA, IFNAR1, MET, NR4A1, CXCL2, EB1I3, CD83, DNAJB4, CASP7, PHLDA1, NLRC5, IL1B, TRIM25, IERS, RNF213, IL10, NFAT5, ADAR, PNP, MMP14, ICAM4, PPAP2B, SDC4, ABCA1, DUSP2, EIF2AK2, IER2, HERC6, BMP2, 1L7, ISG20, GMPR, PSEN1, XAF1, SERPINB8, MTHFD2, EREG, TNFAIP3, TMEM140, KDM6B, CXCL11, CASP1, CYR61, IRF9, GBP2, ADM, TRIP10, PTGER2, METTL7B, SOD2, OAS2, CSF3, SERPINE1, MXD1, ICAM1, ZC3H12A, BCL3, PFKFB3, OGFR, SRI, IFNAR2, FUT4, IL6ST, TNIP2, DUSP4, PROCR, TLR2, OASL, JAK2, C1S, NMI, UBE2L6, LAMP3, TRIB1, TIPARP, IFIT3, GFPT2, IF130, PPP1R15A, FAM46A, ELF1, UPP1, NOD1, CCL5, FOS, VAMP8, RTP4, TPBG, IL23A, BEST1, CEBPB, TNFSF15, SCN1B, P2RY2, STAT5A, CHST2, HIF1A, ZFP36, KLF2, LPAR1, EHD1, PLSCR1, PDLIMS, OAS1, CXCL10, JUNB, PFKP, CD274, CD55, TNFSF9, ADORA2B, ETS2, OAS3, CASP8, ISG15, WARS, SLC7A2, TNFRSF1B, PARP14, FAS, SAMD9, EIF1, CD74, TOR1B, PTPN2, MARCKS, ST8SIA4, SEMA4D, LYSMD2, ATF3, FOSB, PSMB10, ISOC1, PSMA3, IFNGR2, SMAD3, RIPK2, MARCHI, DHX58, IL4R, TRIM5, LITAF, B4GALT5, NLRP3, ITGB3, CIITA, IFITM1, PIM1, BTG3, CD44, PLK2, DRAM1, FPR1, RHOB, EGR1, GNAI3, C1R, NCOA3, PARP12, ABI1, RCAN1, EMP3, IRF2, HLA-DMA, LAMB3, MYC, ATP2B1, YRDC, HLA-DRB1, NDP, MCL1, F3, MT2A, IFI44L, SERPINB2, MAFF, FJX1, LGALS3BP, 1L18, GADD45B, TLR1, CEBPD, GNA15, CSF2, SPHK1, IFI35, LYN, PNRC1, IRF5, IFITM2, BANK1, AXL, KLF6, PTGER4, CASP3, PMEPA1, TNC, ZBTB10, PCDH7, CCRL2, CDKN1A, CCNL1, PER1, TLR3, B4GALT1, CLCF1, MVP, CFB, NFKBIE, PTPN1, USP18, NFKB2, CASP4, TNFAIP2, ACVR2A, CX3CL1, IFIT1, EMR1, CFLAR, DDX60, IDO1, CFH, IFIT2, NCOA7, INHBA, TIMP1, RNF144B, MX1, ATP2C1, TSC22D1, PELI1, TAPBP, GBP4, CCND1, SLC31A2, SGK1, ZNFX1, RAPGEF6, CCL2, HLA-B, NFE2L2, UBA7, HAS2, JUN, SLC11A2, FOSL1, SELL, PLAUR, BATF2, TNFAIP8, ST3GAL5, TANK, ARID5B, MX2, and TAP1.

The chromosomal instability signature genes include PELI2, BMP2, SHH, TNS4, RAB3B, ROBO1, ARHGAP28, CHN2, CST1, F13A1, CPVL, SEMA6D, NHSL2, GTF2IP7, DPYSL3, PCDH7, KHDRBS3, TRAC, TMEM156, CST4, CD24, FGF5, and NTN4. This list of 23 genes whose elevated expression predicts increased distant-metastasis free survival in breast cancer is referred to as the chromosomal instability (CIN) signature when elevated expression of these genes is detected.

Figure 4H:
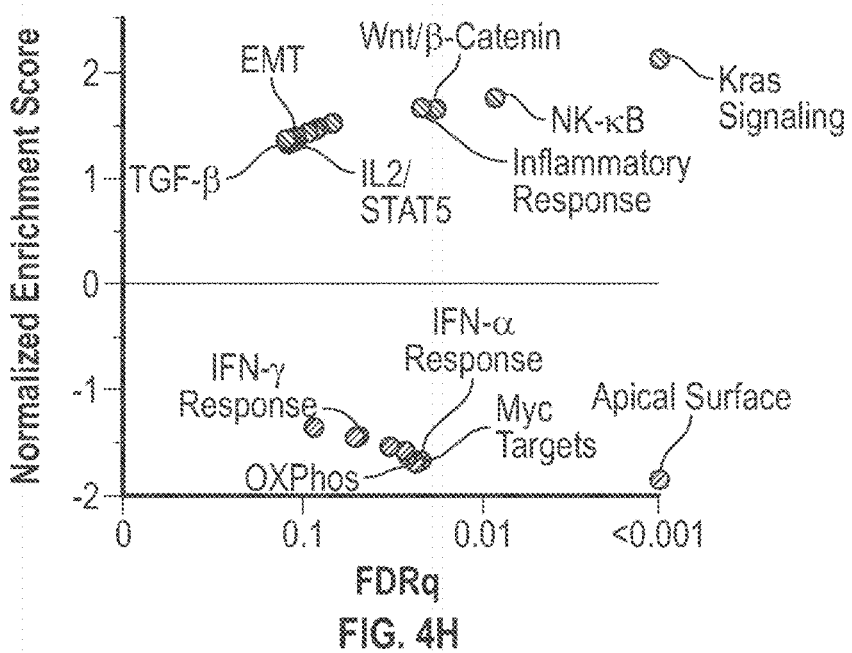
Figure 5B:
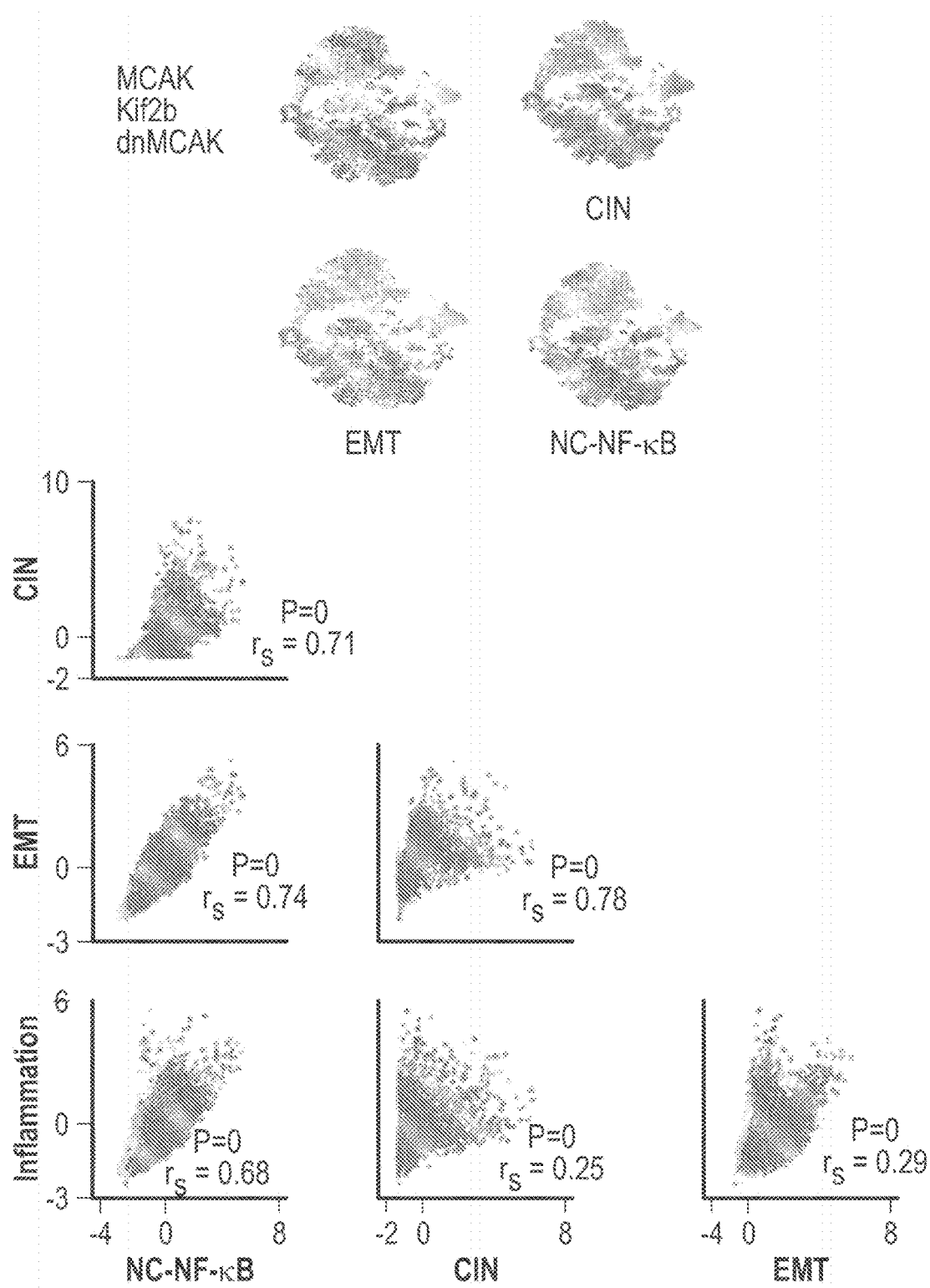
Figures 1, 5C:
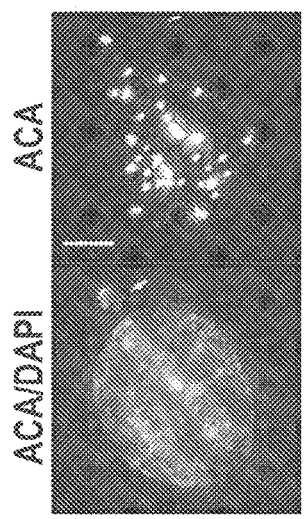
Figures 2, 5C:
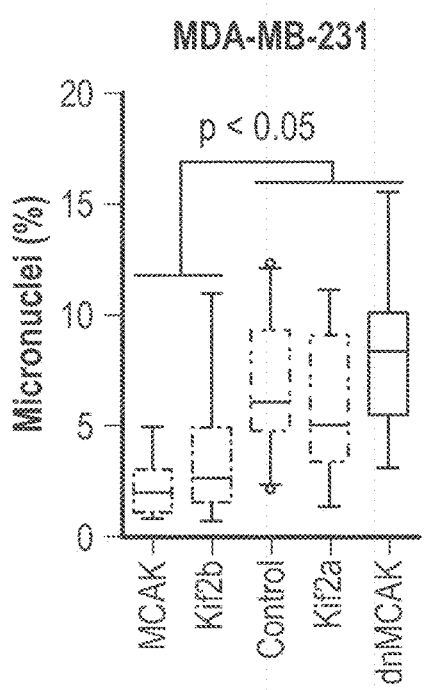
Figures 3, 5C:
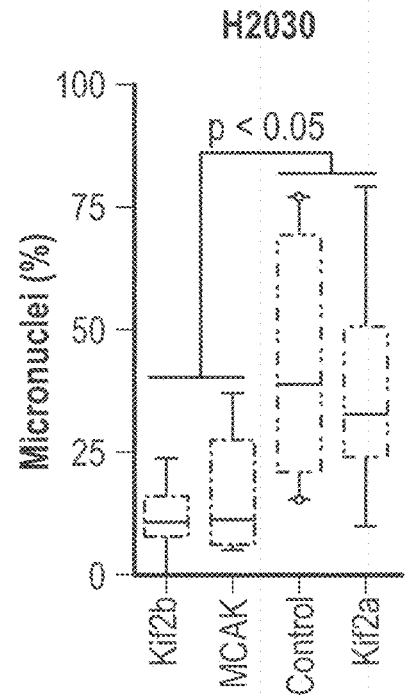
Figure 5D:
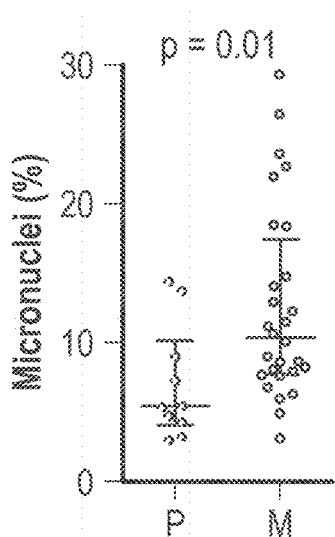
Figure 5E:
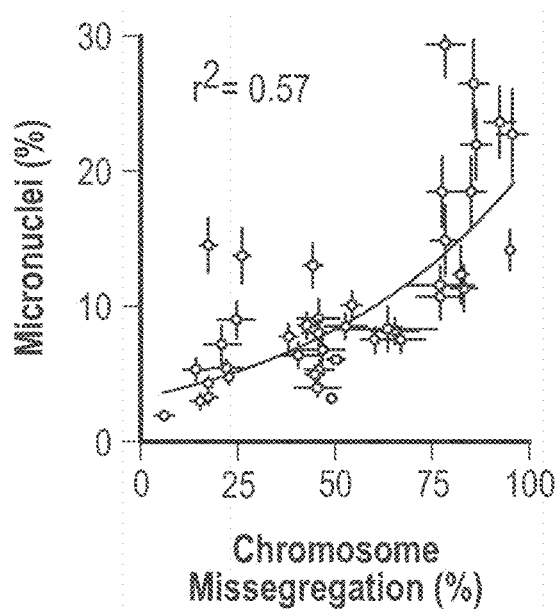
Figure 5F:
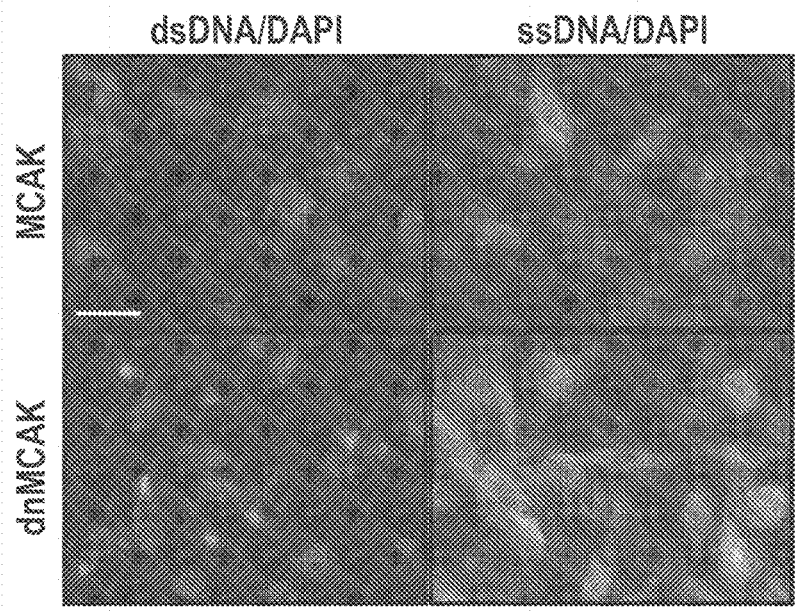

There was a significant correlation between inflammation-related genes, the chromosomal instability signature genes, and EMT genes, all of which were highly enriched in subpopulation M (FIG. 4B, black box; FIG. 5B). Bulk RNA-seq data also revealed significant enrichment for genes involved in the inflammatory response and TNF-α/NF-κB pathways in chromosomal instability-medium/high cells (FIG. 4H). These data indicate that a relationship may exist between chromosomal instability and tumor cell-intrinsic inflammation.

Induction of cell-intrinsic inflammation in response to chromosomal instability, even prior to in vivo transplantation, is unexpected and is reminiscent of a viral infection. We then asked whether chromosomal instability might induce cellular inflammation by introducing genomic DNA into the cytosol, thus eliciting intrinsic cellular inflammation normally reserved for anti-viral immunity.

Chromosomal instability-medium/high exhibited a higher preponderance for micronuclei, as seen when comparing cells derived from metastatic lesions as compared to primary tumors. There was an overall significant correlation between chromosome missegregation rates and the frequency of micronuclei (FIGS. 5C-5E, FIGS. 8A-8C).

Figure 5G:
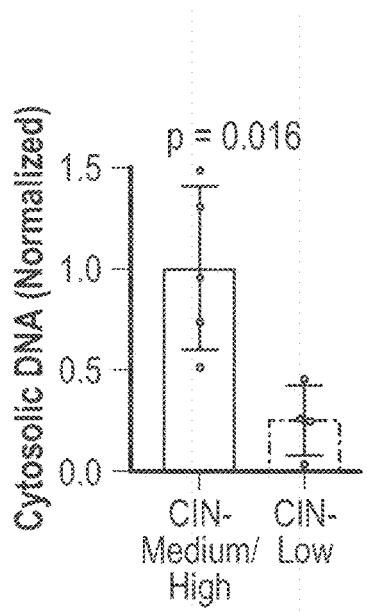
Figure 5H:

To determine if the presence of rupture-prone micronuclei contributed to the generation of cytosolic DNA, cells were stained using two different anti-dsDNA antibodies after selective plasma membrane permeabilization. In each case, cells expressing dnMCAK exhibited significantly increased levels of cytosolic dsDNA and single-stranded DNA (ssDNA) compared to cells exhibiting low levels of chromosomal instability (FIG. 5G). The dsDNA signal, which was distinct from mitochondrial staining, disappeared after treatment with double-strand-specific—but not single-strand-specific—nuclease and after overexpression of Dnase2, confirming the specificity of these antibodies (FIG. 5H).

Figure 5I:
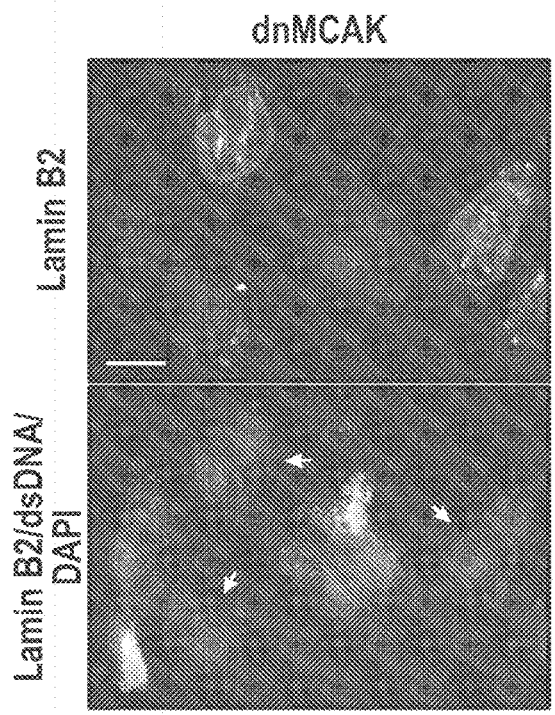

Direct quantification of dsDNA levels after subcellular fractionation revealed a four-fold reduction in cytosolic DNA in cells exhibiting low levels of chromosomal instability compared to cells exhibiting medium to high levels of chromosomal instability (CIN-medium/high cells; FIG. 5G). Finally, whole-genome sequencing at 30× coverage of subcellular fractions confirmed the genomic origin of cytosolic DNA (not shown). To further ascertain that cytosolic dsDNA arises from micronuclear rupture, mCherry-Lamin B2 was overexpressed as a means to stabilize micronuclear envelopes (Hatch et al. Cell 154, 47-60 (2013)) and cells were observed to ascertain whether there was selective reduction in cytosolic dsDNA staining in Lamin B2 overexpressing cells (FIG. 5I). Collectively, these results demonstrate that chromosomal instability induces cytosolic DNA of genomic origin through micronuclear rupture.

Example 6: Metastasis from Cytosolic DNA Response

This Example illustrates that exposure of DNA to cytosol can lead to cancer cell metastasis.

Cytosolic dsDNA elicits a distinct signaling pathway leading to the induction of type I interferon signaling used to combat viral infection. To explore the downstream consequences of cytosolic dsDNA in chromosomally unstable cells, cells were stained for cyclic GMP-AMP synthase (cGAS), a key sensor of cytosolic DNA (Sun et al. Science 339, 786-791 (2013)). cGAS exhibited a striking localization to approximately half of all micronuclei that were present regardless of the level of chromosomal instability (FIGS. 6A-6B).

cGAS-plus micronuclei were positively stained using anti-dsDNA antibody after selective plasma membrane permeabilization whereas cGAS-minus micronuclei did not (FIG. 6A). Furthermore, stabilizing micronuclear envelopes through Lamin B2 overexpression (Hatch et al., Cell 154, 47-60 (2013)), significantly diminished the relative fraction of micronuclei with cGAS staining (FIG. 6B). Collectively, these results demonstrate that micronuclear rupture is required for cytosolic DNA sensing by cGAS. And, although chromosomal instability does not influence micronuclear integrity per se, it increases the overall number of micronuclei per cell and consequently the probability of cGAS activation (FIGS. 5C-5E, FIGS. 6A-6B). cGAS catalyzes the formation of 2'3'-cyclic GMP-AMP (cGAMP), which in turn activates stimulator of interferon genes (STING, also known as TMEM173) to induce Type I interferon production. Increased STING protein levels were observed in CIN-high cells (FIG. 6C). However, there was no evidence for activation of downstream interferon-regulatory factors or the canonical NF-κB pathway as evidenced by the lack of significant changes in p65 or IRF phosphorylation as well as absence of their nuclear translocation (FIG. 6C). This is consistent with observations that cancer cells suppress interferon production downstream of cytosolic DNA sensing (Stetson et al., Cell 134, 587-598 (2008); Lau et al. Science 350, 568-571 (2015)). Cytosolic DNA, however, can activate the noncanonical NF-κB pathway in a STING-dependent and a TBK1-independent manner (Abe et al. J. Virol. 88, 5328-5341 (2014)).

Evidence was observed for noncanonical NF-κB pathway activation in cells exhibiting medium to high levels of chromosomal instability (CIN-medium/high cells). These cells had lower levels of the noncanonical NF-κB precursor protein, p100, as well as increased quantities of phosphorylated p100 and its cleaved product, p52, relative to the total p100 pool, in line with activation of the noncanonical pathway (FIGS. 6C-6D). There was also significant reduction in the levels of the noncanonical NF-κB pathway inhibitor, TRAF2 (FIG. 6C). Nuclear translocation was observed of RelB, the binding partner of p52, in CIN-medium/high cells cells exhibiting medium to high levels of chromosomal instability (FIG. 6E).

Figure 6E:
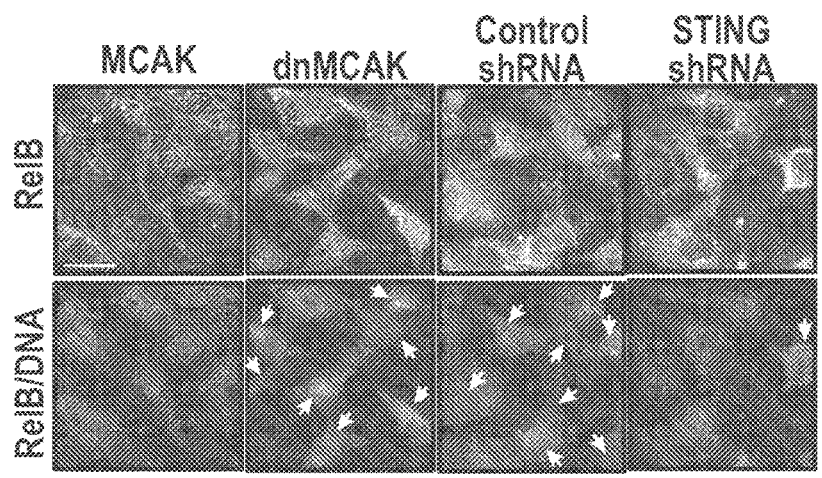

Interestingly, STING depletion abolished noncanonical NF-κB activation and RelB nuclear translocation and it was associated with negative enrichment in the TNF-α/NF-κB as well as other inflammatory and EMT pathways (FIGS. 6D-6E).

Bulk RNA-seq data revealed a number of noncanonical NF-κB target genes, which were upregulated in response to chromosomal instability (hence referred to as CIN-responsive NC-NF-κB genes, which include PPARG, DDIT3, NUPR1, RAB3B, IGFBP4, LRRC8C, TCP11L2, MAFK, NRG1, F2R, KRT19, CTGF, ZFC3H1, MACROD1, GSTA4, SCN9A, BDNF, LACTB). Similarly, the single-cell analysis showed that there was a significant correlation between the chromosomal instability-signature genes and the CIN-responsive NC-NF-κB genes (FIG. 4B and FIG. 5B).

Figure 6F:
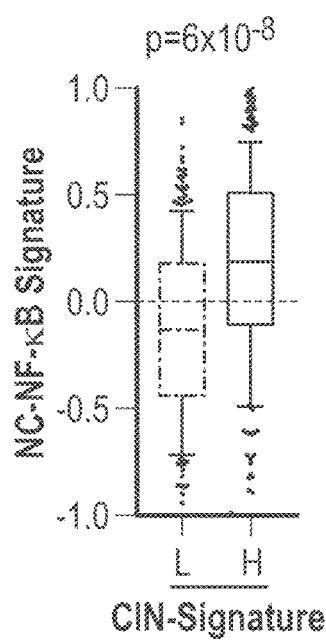
Figures 1, 6G:
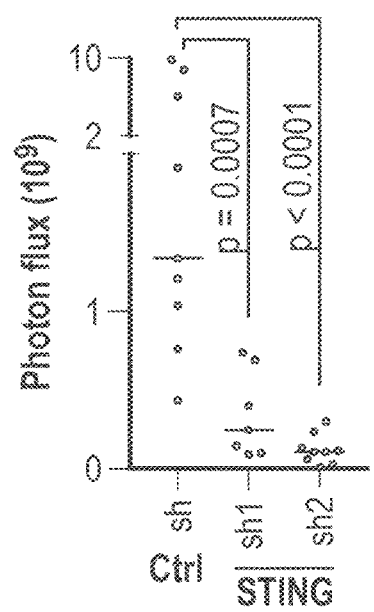
Figures 2, 6G:
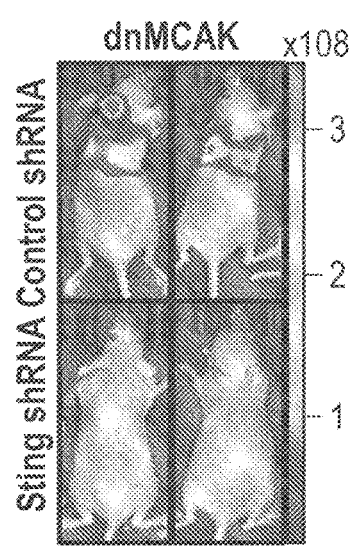

To validate the relationship between chromosomal instability-signature genes and the CIN-responsive NC-NF-κB genes in an independent dataset, RNA-seq data were analyzed from the TCGA breast cancer database. Significant upregulation of CIN-responsive NC-NF-κB genes was observed in tumors with higher levels of the CIN-signature genes (FIG. 6F). Furthermore, higher expression of key regulators of the noncanonical NF-κB pathway or its CIN-responsive target genes was associated with shorter DMFS and disease-free survival in breast and lung cancers. Conversely, upregulation of canonical NF-κB pathway (NFKB1, RelA, TRAF1, TRAF4, TRAF5, TRAF6) or interferon-regulatory factors (IRF1, IRF3, IRF7, TBK1) were associated with improved prognosis (FIG. 9).

Collectively, these data show that chromosomal instability induces a cytosolic dsDNA response manifested in the selective activation of the noncanonical NF-κB pathway and these features are associated with poor prognosis.

To test whether STING activity is important for metastasis in a tumor cell-autonomous manner, intracardiac injection of STING-depleted cells that exhibit high levels of chromosomal instability was performed. There was significant reduction in metastatic dissemination and lifespan extension in mice injected with STING-depleted cells compared to mice injected with their STING-replete counterparts (FIGS. 6G-1 and 6G-2, FIG. 9A).

Similarly, depletion of STING, cGAS, or the noncanonical NF-κB transcription factors p52 and RelB led to a significant decrease in the invasive potential of cells exhibiting high levels of chromosomal instability (CIN-high cells; FIG. 6H).

On the other hand, addition of cGAMP increased the ability of MCAK (CIN-low) cells to migrate and invade through a collagen membrane (FIG. 6H).

Therefore, tumor-cell autonomous STING activation in response to cytosolic DNA promotes invasion and metastasis, in part, through the noncanonical NF-κB pathway.

Example 7: Chromosomal Instability is Also Correlated with Immune Infiltrate

The data provided herein shown that a novel pathway exists that links chromosomal instability (CIN) to metastasis and formation of tumor immune infiltrate through tumor-cell intrinsic inflammatory response to cytosolic DNA. The pathway identified by the inventors is summarized in FIG. 7B. Briefly, the inventors found that CIN promotes the formation of chromosome-containing micronuclei, which often rupture exposing their DNA content to the cellular cytoplasm (or cytosol). This unusual situation—which does not occur in normal cells—is reminiscent of a viral infection. After sensing cytosolic DNA through cGAS, cancer cells promote the formation of cGAMP (a small molecule) that in turn activates STING. Instead of upregulating the canonical pathways cancer cells activate the noncanonical NF-kB pathway (NIK and RelB/p52) which leads to upregulation of pro-metastasis programs. In the meantime, cGAMP can exit tumor cells and activate neighboring stroma, in particular antigen presenting cells by directly engaging with their STING protein.

There are currently pre-clinical efforts underway exploring the use of intratumoral cGAMP injection in activating the immune system to attack tumor cells. The inventors think this effort might not be without its own risk as they have found that cGAMP in tumor cells themselves promotes metastasis—as opposed to its anti-tumor role in activating the immune cells.

The finding that chromosomal instability promotes a viral-like immune response that promotes metastasis yet at the same time recruits a large amount of an immune infiltrate (FIG. 7A) is significant, showing that chromosomally unstable cells are able to survive, thrive and metastasize in the presence of this immune activation.

Cells exhibiting chromosomal instability appear to be proficient at preserving the cytosolic DNA signal (and its byproducts) as much as possible within their own cytoplasm. In other words, they down regulate putative cGAMP transporters ABCG2 and ABCC4. Furthermore, these cells produce significantly higher amounts of ENPP1, a hydrolase that efficiently breaks down cGAMP and is only present on the extracellular leaflet of the plasma membrane. Therefore, these chromosomally unstable tumor cells preserve cGAMP in the intracellular milieu, reduce its export and, if necessary, degrade it when it leaks out. Furthermore, these tumor cells also produce large amounts of M-CSF, which is a cytokine that promotes the generation of pro-tumor M2 macrophages.

Such immune activation can be mobilized to facilitate treatment of cancers associated with chromosomal infiltration.

For example, instead of injecting tumors with cGAMP directly (and risking activating metastasis in tumor cells), the cGAMP produced by chromosomally unstable tumor cells can be against them: by inhibiting ENPP1, which underlies their ability to destroy it once it exists the cells. Another approach would be to use agonists to the ABC transporters to increase cGAMP export to the extracellular space and to activate neighboring immune cells.

Example 8: cGAMP Detection and Quantification Using Liquid Chromatography-Mass Spectrometry (LC-MS)

This Example illustrates that liquid chromatography-tandem mass spectrometry (LC-MS/MS) is a viable technology for the determination of cGAMP due to its specificity, reproducibility and sensitivity. LC-MS/MS is highly specific, thus minimizing interferences from other nucleotides. The greater specificity of LC-MS/MS is derived from analyte specific precursor to product ion mass-to-charge (m/z) values and/or analyte specific retention time.

Materials & Methods:

A cGAMP solution was used as a standard. The cGAMP standard solution was prepared in 70% acetonitrile in ddH$_2$O for LC-MS/MS analysis.

For cell culture, cells were grown in 10 cm plates.

Collection and Sample Preparation:

Cells were washed twice with PBS and once with LC/MS grade water (to remove salts). Plates were then flash frozen on liquid nitrogen to preserve metabolic state of the cells. Cells were then collected/scraped into 2 ml of cold 80% LC-MS grade methanol (−80C). Methanolic metabolite extracts were then purified by Solid Phase Extraction (SPE) using HyperSep aminopropyl solid phase columns as previously described by Collins, A. C. et al. 2015. Effluents were dried to completeness in a vacuum centrifuge and reconstituted in 70% acetonitrile in ddH$_2$O at a concentration of 100 µg protein/µL. 15 µL were subjected to LC-MS/MS analysis.

Serum/Media Sample Preparation:

To detect secreted cGAMP in culture media, 500 µl aliquots of conditioned media can be collected, mixed 80:20 with methanol, and centrifuged at 3,000 rpm for 20 minutes at 4 degrees Celsius. The resulting supernatant can be collected and stored at −80 degrees Celsius prior to LC-MS/MS to assess cGAMP levels. To measure whole-cell associated metabolites, media can be aspirated and cells can be harvested, e.g., at a non-confluent density. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions.

Analysis of cGAMP.

After Solid Phase Extraction (SPE), the samples were dried using a vacuum centrifuge (Eppendorf Vacufuge, Eppendorf, Germany) and reconstituted in 70% acetonitrile in ddH$_2$O. To remove unsolubilized particles, samples were centrifuged at 21,130 g for 10 min at 4° C. The supernatant was injected into an LC/MS-system comprised of an Agilent 1260 HPLC and an Agilent 6460 triple quadrupole mass spectrometer (Agilent Technologies, Santa Clara, Calif.) equipped with a JetStream electrospray ionization source, using positive ion-monitoring in dynamic multiple reaction monitoring (dMRM). The analyte cGAMP was resolved from interfering signals on an aqueous neutral phase column (Cogent™ Diamond Hydride, 4 µm particle size, 150 mm×2.1 mm; Microsolv Technology Corporation, NJ), at a column compartment temperature of 40° C. The samples were maintained at 4° C. and the injection volume was 15 µL. The gradient-chromatography previously described by Chen et al. (PLoS One 7(6): p. e37149 (2012)) was optimized to achieve chromatographic separation from interfering peaks. The aqueous mobile phase (A) was 50% isopropanol with 0.025% acetic acid, the organic mobile phase (B) was 90% acetonitrile containing 5 mM ammonium acetate. To eliminate the interference of metal ions on the chromatographic peak integrity and ESI ionization, EDTA was added to the mobile phase in a final concentration of 6 uM. The final gradient applied was: 0-1.0 min 99% B, 1.0-10.0 min to 60% B, 10.1-20 min 0% B and 20.1 min 99% B for 10 min to regenerate the column. The flow rate was 0.4 mL/min. Data was saved in centroid mode using Agilent Masshunter workstation acquisition software (B.06.00 Build 6.0.6025.4 SP4). Acquired raw data files were processed with Agilent MassHunter Qualitative Analysis Software (B.07.00 Build 7.0.7024.0, Agilent Technologies) and Quantitative Analysis Software (B.07.01 Build 7.1.524.0). The operating source parameters for MS-analysis were: gas temperature 280° C.; gas flow 11 L/min; nebulizer pressure 35 psi; sheath gas temperature 350° C.; sheath gas flow 11 L/min; capillary voltage 4000 V; nozzle voltage 300 V; fragmentor voltage 145V; cell accelerator voltage 2 V. dMRM data was acquired starting at a run time of 4 min in when the LC-flow was directed to the MS.

Compound specific parameters were optimized using Agilent Optimizer Software (for 6400 Series Triple Quadupole Version B.06.00 Build 6.0.6025.4 SP4).

Figure 10A:
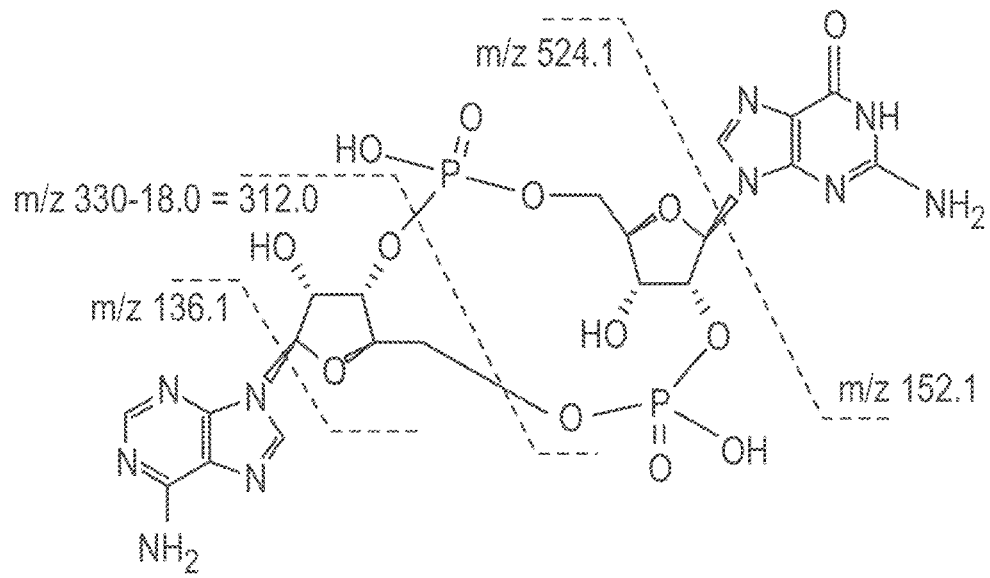
FIGS. 10A-10B illustrate quantification of cGAMP

Optimized dMRM transitions resulted in the deglycosylated base ions: for cGAMP the transition 675.1→136.1* (CE 65 eV) represented the formation of adenine and 675.1→152.1** (CE 65 eV) the formation of guanine. Additionally, the dMRM transitions of 675.1→312.0 (CE 61 eV) and 675.1→524.1 (CE 35 eV) were recorded. * indicate quantifier transitions, * indicate the qualifier transitions (see FIG. 10A). Because all the cGAMP transitions were derived from the same parent ion, all four transitions were summed into a final TIC (total ion current) to increase signal abundances and signal-to-noise ratios.

Results

Figure 10B:
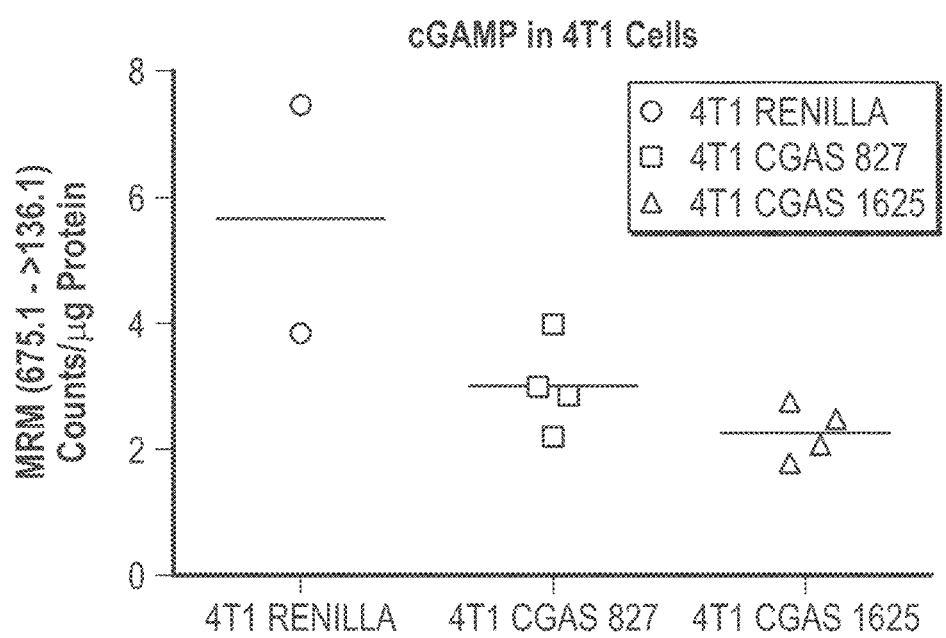

FIG. 10B graphically illustrates quantification of cGAMP in chromosomally unstable urine triple-negative breast cancer cells (4T1) using targeted LC-MS metabolomics. As shown, knockdown of cGAS in 4T1 cells reduced the abundance of cGAMP. These results show that cGAMP can be quantified in a variety of samples, and that cGAMP can be a marker for detecting and monitoring metastatic disease in patients.

Example 9: ATPase Assays for Identifying/Assessing KIF2B and MCAK Agonists

KIF2B and KIF2C/MCAK are related molecular kinesin motor proteins that utilize the energy of ATP hydrolysis to regulate microtubule dynamics and chromosome-kinetochore attachments. The central role of KIF2B and MCAK over expression or hyper activation is to suppress chromosomal instability (CIN), which makes them attractive targets for cancer therapy. Here, two methods (an in vitro assay and an imaging method) are outlined in this Example to identify and assess potent activators of KIF2B and MCAK.

Method 1 In Vitro Assay for KIF2B or MCAK Activity:

Measuring the kinetics of ATP hydrolysis is a strategy to screen for compounds that activate KIF2B and MCAK and suppress CIN. This assay is based upon an absorbance shift (330 to 360 nm) that occurs when 2-amino-6-mercapto-7-methylpurine ribonucleoside (MESG) is converted to 2-amino-6-mercapto-7-methyl purine in the presence of inorganic phosphate (Pi) (see, e.g., Webb, M. R. 1992. A continuous spectrophotometric assay for inorganic phosphate and for measuring phosphate release kinetics in biological systems. Proc. Natl. Acad. Sci. USA 89: 4884-4887). The reaction is catalyzed by purine nucleoside phosphorylase (PNP). One molecule of inorganic phosphate will yield one molecule of 2-amino-6-mercapto-7-methyl purine in an irreversible reaction. Thus, the absorbance at 360 nm is directly proportional to the amount of Pi generated in the ATPase reaction, and can be used as a proxy for MCAK activity.

Alternatively, ADP production can also be monitored as a readout for MCAK activity using the Transcreener ADP assay from BellBrook Labs. This assay is based on the ability of ADP to displace a fluorescent tracer (633 nm) bound to an antibody the specifically recognizes ADP. Displacement of the tracer causes a decrease in fluorescence measured by laser excitation at 633 nm. Thus, activity of MCAK can be calculated by plotting the concentration of drug used and the amount of ADP produced/decrease in fluorescent intensity.

Method 2 Cell-Based Assay for KIF2B or MCAK Activity:

MCAK negatively regulates microtubule length by binding microtubule tips and promoting microtubule depolymerization. Therefore, distance between γ-tubulin-labeled centrosomes can be measured as an indirect readout for MCAK activity in cells. Spindle length would be inversely proportional to MCAK activity and can serve as proxy to evaluate potential compounds that promote MCAK activity (see, e.g., Lockhart, A & Cross, R. A. 1996. Kinetics and Motility of the Eg5 Microtubule Motor. Biochemistry 35: 2365-2373). This method can be adapted for screening compounds by using a high-throughput imaging microscope.

Compounds (e.g., top hits identified via any of the methods described herein) can subsequently be used in a cell-based assay using lagging chromosomes, micronuclei, or chromosome missegregation using FISH as a readout of their efficacy. Fluorescent in situ hybridization (FISH) is a molecular cytogenetic technique that uses fluorescent probes that bind to only those parts of the chromosome with a high degree of sequence complementarity. Probes can include a portion of sequence of any of the chromosomes or genes described herein.

Example 10: ATPase Assays for Identifying/Assessing NF-kB Inducing Kinase (NIK) Inhibitors NF-kB Inducing Kinase (NIK) mediates non-canonical NF-kB signaling and is associated with metastasis. Therefore, the inhibition of NIK may suppress CIN-induced inflammatory responses and metastasis. This Example outlines two methods that can be used to identify and assess NIK inhibition.

Method 1:

Specific inhibition of the kinase function of NIK provides an approach to assess the potency of various compounds. Therefore, ADP production can be monitored as a readout for NIK activity using the Transcreener ADP assay from BellBrook Labs. This assay is based on the ability of ADP to displace a fluorescent tracer (633 nm) bound to an antibody the specifically recognizes ADP. Competitive displacement of the tracer causes a decrease in fluorescence, as measured by laser excitation at 633 nm. Thus, the activity of NIK can be calculated by plotting the concentration of drug used and the amount of ADP produced/decrease in fluorescent intensity.

Method 2:

Inhibition of NIK provides an approach to directly inhibit the non-canonical NF-κB pathway. This assay relies on quantification of the nuclear translocation of p52 (RELB; non-canonical NF-kB signaling) using high content cellular imaging. An example of a sequence for human RELB is shown below as SEQ ID NO:59.

```
  1  MLRSGPASGP SVPTGRAMPS RRVARPPAAP ELGALGSPDL
 41  SSLSLAVSRS TDELEIIDEY IKENGFGLDG GQPGPGEGLP
 81  RLVSRGAASL STVTLGPVAP PATPPPWGCP LGRLVSPAPG
121  PGPQPHLVIT EQPKQRGMRF RYECEGRSAG SILGESSTEA
161  SKTLPAIELR DCGGLREVEV TACLVWKDWP HRVHPHSLVG
201  KDCTDGICRV RLRPHVSPRH SFNNLGIQCV RKKEIEAAIE
241  RKIQLGIDPY NAGSLKNHQE VDMNVVRICF QASYRDQQGQ
281  MRRMDPVLSE PVYDKKSTNT SELRICRINK ESGPCTGGEE
321  LYLLCDKVQK EDISVVFSRA SWEGRADFSQ ADVHRQIAIV
361  FKTPPYEDLE IVEPVTVNVF LQRLTDGVCS EPLPFTYLPR
401  DHDSYGVDKK RKRGMPDVLG ELNSSDPHGI ESKRRKKKPA
441  ILDHFLPNHG SGPFLPPSAL LPDPDFFSGT VSLPGLFPPG
481  GPDLLDDGFA YDPTAPTLFT MLDLLPPAPP HASAVVCSGG
521  AGAVVGETPG PEPLITDSYQ APGPGDGGTA SLVGSNMFPN
561  HYREAAFGGG LLSPGPEAT
```

For RELB nuclear translocation assay, cells are treated with different concentrations of compounds and stimulated with 100 ng/mL of an antagonistic anti-lymphotoxin beta receptor (LT-PR) antibody (e.g., from Sigma Aldrich), a potent activator of non-canonical NF-kB signaling. RELB translocation into the nucleus is quantified by the ratio of the nuclear over cytoplasmic signal intensity. Potent compounds are discovered that selectively inhibit the nuclear translocation of RELB.

REFERENCES

1. Nowell, P. C. The clonal evolution of tumor cell populations. *Science* 194, 23-28 (1976).
2. Turajlic, S., Turajlic, S., Swanton, C. & Swanton, C. Metastasis as an evolutionary process. *Science* 352, 169-175 (2016).
3. Burrell, R. A., McGranahan, N., Bartek, J. & Swanton, C. The causes and consequences of genetic heterogeneity in cancer evolution. *Nature* 501, 338-345 (2013).
4. Makohon-Moore, A. P. et al. Limited heterogeneity of known driver gene mutations among the metastases of individual patients with pancreatic cancer. *Nat. Genet.* (2017). doi:10.1038/ng.3764
5. Campbell, P. J. et al. The patterns and dynamics of genomic instability in metastatic pancreatic cancer. *Nature* 467, 1109-1113 (2010).
6. Notta, F. et al. A renewed model of pancreatic cancer evolution based on genomic rearrangement patterns. *Nature* 538, 378-382 (2016).
7. Crasta, K. K. et al. DNA breaks and chromosome pulverization from errors in mitosis. *Nature* 482, 53-58 (2012).
8. Burrell, R. A. et al. Replication stress links structural and numerical cancer chromosomal instability. *Nature* 494, 492-496 (2013).
9. Bakhoum, S. F., Kabeche, L., Murnane, J. P., Zaki, B. I. & Compton, D. A.
DNA-Damage Response during Mitosis Induces Whole-Chromosome Missegregation. *Cancer Discovery* 4, 1281-1289 (2014).
10. Maciejowski, J., Li, Y., Bosco, N., Campbell, P. J. & de Lange, T. Chromothripsis and Kataegis Induced by Telomere Crisis. *Cell* 163, 1641-1654 (2015).
11. Thompson, S. L., Thompson, S. L., Compton, D. A. & Compton, D. A.
Examining the link between chromosomal instability and aneuploidy in human cells. *J Cell Biol* 180, 665-672 (2008).
12. Cimni, D. et al. Merotelic kinetochore orientation is a major mechanism of aneuploidy in mitotic mammalian tissue cells. *J Cell Biol* 153, 517-527 (2001).
13. Bakhoum, S. F., Thompson, S. L., Manning, A. L. & Compton, D. A. Genome stability is ensured by temporal control of kinetochore-microtubule dynamics. *Nat. Cell Biol.* 11, 27-35 (2009).
14. Bakhoum, S. F. et al. Numerical chromosomal instability mediates susceptibility to radiation treatment. *Nat Commun* 6, 5990 (2015).
15. Bakhoum, S. F. et al. The mitotic origin of chromosomal instability. *Curr. Biol.* 24, R148-9 (2014).
16. Lengauer, C., Kinzler, K. W. & Vogelstein, B. Genetic instabilities in human cancers. *Nature* 396, 643-649 (1998).
17. Brastianos, P. K. et al. Genomic Characterization of Brain Metastases Reveals Branched Evolution and Potential Therapeutic Targets. *Cancer Discovery* 5, 1164-1177 (2015).
18. Mitelman, F., Johansson, B. & Mertens, F. Mitelman Database of Chromosome Aberrations and Gene Fusions in Cancer. cgap.nci.nih.gov Available at: http-/cgap.nci.nih.gov/Chromosomes/Mitelman. (Accessed: 24 Oct. 2014)
19. Carter, S. L. S. et al. Absolute quantification of somatic DNA alterations in human cancer. *Nat Biotechnol* 30, 413-421 (2012).

20. Laughney, A. M., Elizalde, S., Genovese, G. & Bakhoum, S. F. Dynamics of Tumor Heterogeneity Derived from Clonal Karyotypic Evolution. *Cell Rep* 12, 809-820 (2015).
21. Storchova, Z., Storchova, Z., Kuffer, C. & Kuffer, C. The consequences of tetraploidy and aneuploidy. *J Cell Sci* 121, 3859-3866 (2008).
22. Chung, C. H. et al. Molecular classification of head and neck squamous cell carcinomas using patterns of gene expression. *Cancer Cell* 5, 489-500 (2004).
23. Bakhoum, S. F., Danilova, O. V., Kaur, P., Levy, N. B. & Compton, D. A. Chromosomal instability substantiates poor prognosis in patients with diffuse large B-cell lymphoma. *Clin. Cancer Res.* 17, 7704-7711 (2011).
24. Moore, A. T. et al. MCAK associates with the tips of polymerizing microtubules. *J Cell Biol* 169, 391-397 (2005).
25. Ems-McClung, S. C. & Walczak, C. E. Kinesin-13s in mitosis: Key players in the spatial and temporal organization of spindle microtubules. Semin. *Cell Dev. Biol.* 21, 276-282 (2010).
26. Györffy, B. et al. An online survival analysis tool to rapidly assess the effect of 22,277 genes on breast cancer prognosis using microarray data of 1,809 patients. *Breast Cancer Res. Treat.* 123, 725-731 (2010).
27. Hatzis, C. et al. A genomic predictor of response and survival following taxane-anthracycline chemotherapy for invasive breast cancer. *JAMA* 305, 1873-1881 (2011).
28. Klein, A. M. et al. Droplet barcoding for single-cell transcriptomics applied to embryonic stem cells. *Cell* 161, 1187-1201 (2015).
29. Levine, J. H. et al. Data-Driven Phenotypic Dissection of AML Reveals Progenitor-like Cells that Correlate with Prognosis. *Cell* 162, 184-197 (2015).
30. Abe, T., Abe, T., Barber, G. N. & Barber, G. N. Cytosolic-DNA-mediated, STING-dependent proinflammatory gene induction necessitates canonical NF-κB activation through TBK1. *J. Virol.* 88, 5328-5341 (2014).
31. Hatch, E. M., Fischer, A. H., Deerinck, T. J. & Hetzer, M. W. Catastrophic nuclear envelope collapse in cancer cell micronuclei. *Cell* 154, 47-60 (2013).
32. Cai, X., Chiu, Y.-H. & Chen, Z. J. The cGAS-cGAMP-STING pathway of cytosolic DNA sensing and signaling. *Mol. Cell* 54, 289-296 (2014).
33. Sun, L. et al. Cyclic GMP-AMP synthase is a cytosolic DNA sensor that activates the type I interferon pathway. *Science* 339, 786-791 (2013).
34. Stetson, D. B., Ko, J. S., Heidmann, T. & Medzhitov, R. Trex1 Prevents Cell-Intrinsic Initiation of Autoimmunity. *Cell* 134, 587-598 (2008).
35. Lau, L., Gray, E. E., Brunette, R. L. & Stetson, D. B. DNA tumor virus oncogenes antagonize the cGAS-STING DNA-sensing pathway. *Science* 350, 568-571 (2015).
36. Sun, S.-C. Controlling the fate of NIK: a central stage in noncanonical NF-kappaB signaling. *Sci Signal* 3, pe18 (2010).
37. Chen, Q. et al. Carcinoma-astrocyte gap junctionspromote brain metastasis by cGAMPtransfer. *Nature* 533, 493-498 (2016).
38. Fernandes-Alnemri, T., Yu, J.-W., Datta, P., Wu, J. & Alnemri, E. S. AIM2 activates the inflammasome and cell death in response to cytoplasmic DNA. *Nature* 458, 509-513 (2009).
39. Vitak, N., Hume, D. A., Chappell, K. J., Sester, D. P. & Stacey, K. J. Induction of interferon and cell death in response to cytosolic DNA in chicken macrophages. *Dev. Comp. Immunol.* 59, 145-152 (2016).
40. Wang, J., Yi, S., Zhou, J., Zhang, Y. & Guo, F. The NF-κB subunit RelB regulates the migration and invasion abilities and the radio-sensitivity of prostate cancer cells. *Int. J. Oncol.* 49, 381-392 (2016).
41. Demirci, H., Reed, D. & Elner, V. M. Tissue-based microarray expression of genes predictive of metastasis in uveal melanoma and differentially expressed in metastatic uveal melanoma. *J Ophthalmic Vis Res* 8, 303-307 (2013).
42. Fritz, R. D. & Radziwill, G. CNK1 promotes invasion of cancer cells through NF-kappaB-dependent signaling. *Mol. Cancer Res.* 8, 395-406 (2010).
43. Qin, H. et al. Prognostic significance of RelB overexpression in non-small cell lung cancer patients. *Thorac Cancer* 7, 415-421 (2016).
44. Yakubov, B. et al. Extracellular tissue transglutaminase activates noncanonical NF-κB signaling and promotes metastasis in ovarian cancer. *Neoplasia* 15, 609-619 (2013).
45. Rangaswami, H. & Kundu, G. C. Osteopontin stimulates melanoma growth and lung metastasis through NIK/MEKK1-dependent MMP-9 activation pathways. *Oncol. Rep.* 18, 909-915 (2007).
46. Qu, L. L., He, L., Zhao, X. & Xu, W. Downregulation of miR-518a-3p activates the NIK-dependent NF-κB pathway in colorectal cancer. *Int. J. Mol. Med.* 35, 1266-1272 (2015).
47. Thu, Y. M. et al. NF-κB inducing kinase (NIK) modulates melanoma tumorigenesis by regulating expression of pro-survival factors through the β-catenin pathway. *Oncogene* 31, 2580-2592 (2012).
48. Zhang, X. et al. Expression of NF-κB-inducing kinase in breast carcinoma tissue and its clinical significance. *Int J Clin Exp Pathol* 8, 14824-14829 (2015).
49. Tchoghandjian, A., Jennewein, C., Eckhardt, I., Rajalingam, K. & Fulda, S. Identification of non-canonical NF-κB signaling as a critical mediator of Smac mimetic-stimulated migration and invasion of glioblastoma cells. *Cell Death Dis* 4, e564 (2013).
50. Yu, J. et al. Noncanonical NF-κB activation mediates STAT3-stimulated IDO upregulation in myeloid-derived suppressor cells in breast cancer. *J. Immunol.* 193, 2574-2586 (2014).
51. Yang, C. et al. Antagonism of inhibitor of apoptosis proteins increases bone metastasis via unexpected osteoclast activation. *Cancer Discovery* 3, 212-223 (2013).
52. McGranahan, N. et al. Clonal neoantigens elicit T cell immunoreactivity and sensitivity to immune checkpoint blockade. *Science* 351, 1463-1469 (2016).
53. Zaki, B. I. et al. Chromosomal instability portends superior response of rectal adenocarcinoma to chemoradiation therapy. *Cancer* 120, 1733-1742 (2014).
54. Dobin, A. et al. STAR: ultrafast universal RNA-seq aligner. *Bioinformatics* 29, 15-21 (2013).
55. Trapnell, C. et al. Transcript assembly and quantification by RNA-Seq reveals unannotated transcripts and isoform switching during cell differentiation. *Nat Biotechnol* 28, 511-515 (2010).
56. Anders, S., Pyl, P. T. & Huber, W. HTSeq-a Python framework to work with high-throughput sequencing data. *Bioinformatics* 31, 166-169 (2015).
57. Love, M. I., Huber, W. & Anders, S. Moderated estimation of fold change and dispersion for RNA-seq data with DESeq2. *Genome Biol.* 15, 550 (2014).

58. Zheng, G. X. Y. et al. Massively parallel digital transcriptional profiling of single cells. *Nat Commun* 8, 14049 (2017).
59. van Dijk, D., Nainys, J., Sharma, R., Kathail, P. & Carr, A. J. MAGIC: A diffusion-based imputation method reveals gene-gene interactions in single-cell RNA-sequencing data. *bioRxiv* (2017).
60. Gyorffy, B., Surowiak, P., Budczies, J. & Lanczky, A. Online survival analysis software to assess the prognostic value of biomarkers using transcriptomic data in non-small-cell lung cancer. *PLoS ONE* 8, e82241 (2013).
61. Chen, Q., et al., Untargeted plasma metabolite profiling reveals the broad systemic consequences of xanthine oxidoreductase inactivation in mice. PLoS One, 2012.7 (6): p. e37149.
62. Collis, A. C., et al., Cyclic GMP-AMP Synthase Is an Innate Immune DNA Sensor for *Mycobacterium tuberculosis*. Cell Host & Microbe, 2015. 17(6): p. 820-828.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

Statements:

2) A method comprising administering a metastatic chemotherapeutic agent to a patient with a cell sample or bodily fluid sample:
   a. having at least 10%, or at least 11%, or at least 12%, or at least 13%, or at least 14%, or at least 15% detectable chromosomal missegregations within one or cells of the cell sample;
   b. having at least 3%, at least 4% or at least 5% of cells detectable micronuclei within one or cells of the cell sample;
   c. having detectable cytosolic double-stranded DNA within one or cells of the cell sample; or
   d. having at least 10%, or 20%, or 30%, or 50%, or 70%, or 80%, or 90% greater concentration or amount of cGAMP in the cell sample or bodily fluid sample;
   to thereby treat metastatic cancer in the patient.
3) The method of statement 1, comprising administering a metastatic chemotherapeutic agent to a patient with 15-20% of chromosomes in anaphase cells of the cell sample exhibiting missegregations.
4) The method of statement 1 or 2, comprising administering a metastatic chemotherapeutic agent to a patient with 5-8% of cells in the cell sample exhibiting micronuclei.
5) The method of statement 1, 2, or 3, comprising administering a metastatic chemotherapeutic agent to a patient with 1-fold to 2-fold increase in staining intensity within the cytosol compared to a normal non-cancer tissue.
6) The method of statement 1, 2, 3, or 4, comprising administering a metastatic chemotherapeutic agent to a patient with 1-fold to 2-fold greater concentration or amount of cGAMP in the bodily fluid sample than a non-cancerous bodily fluid sample.
7) The method of statement 1-4 or 5, further comprising monitoring samples from the patient over time to quantify chromosomal missegregations, micronuclei, cytosolic double-stranded DNA, or cGAMP within cells or bodily fluids of the patient.
8) The method of statement 1-5 or 6, wherein the metastatic chemotherapeutic agent is a composition comprising kinesin-13 protein(s) with at least 90%, at least 91%, at least 92%, at least 93%, at least 94%, at least 95%, at least 96%, at least 97%, at least 98%, at least 99% sequence identity to any of SEQ ID NO:1, 3, or 5.
9) The method of statement 1-6 or 7, wherein the metastatic chemotherapeutic agent is a composition comprising a kinesin-13 nucleic acid comprising a sequence with at least 90%, at least 91%, at least 92%, at least 93%, at least 94%, at least 95%, at least 96%, at least 97%, at least 98%, at least 99% sequence identity to any of SEQ ID NO:2, 4, or 6.
10) The method of statement 1-7 or 8, wherein the metastatic chemotherapeutic agent is a composition comprising a MCAK protein with at least 90%, at least 91%, at least 92%, at least 93%, at least 94%, at least 95%, at least 96%, at least 97%, at least 98%, at least 99% sequence identity to any of SEQ ID NO: 7, or a MCAK nucleic acid with at least 90%, at least 91%, at least 92%, at least 93%, at least 94%, at least 95%, at least 96%, at least 97%, at least 98%, at least 99% sequence identity to SEQ ID NO:8.
11) The method of statement 1-8 or 9, wherein the metastatic chemotherapeutic agent is a composition comprising at least one STING, cGAS, NF-κB transcription factor p52, NF-κB transcription factor RelB, ENPP1, LTβR, BAFFR, CD40, RANK, FN14, NIK (MAP3K14), or MST1 inhibitory nucleic acid.
12) The method of statement 1-9 or 10, wherein the metastatic chemotherapeutic agent is a composition comprising at least one inhibitory nucleic acid having at least 90%, at least 91%, at least 92%, at least 93%, at least 94%, at least 95%, at least 96%, at least 97%, at least 98%, at least 99% sequence identity to any of SEQ ID NO: 10, 12, 14, 16, 18, 20, 22, 24, 25, 26, 27, 28, 29, 30, 31, 32, 33, 34, 35, or 36.
13) The method of statement 1-10 or 11, wherein the metastatic chemotherapeutic agent is a composition comprising at least one antibody that binds with affinity to a STING, cGAS, NF-κB transcription factor p52, NF-κB transcription factor RelB, ENPP1, LTβR, BAFFR, CD40, RANK, FN14, NIK (MAP3K14), or MST1 protein.
14) The method of statement 1-11 or 12, wherein the metastatic chemotherapeutic agent is a composition comprising an expression vector having a promoter operably linked to a nucleic acid segment encoding a kinesin-13 or MCAK protein with at least 90%, at least 91%, at least 92%, at least 93%, at least 94%, at least 95%, at least 96%, at least 97%, at least 98%, at least 99% sequence identity to any of SEQ ID NO:1, 3, 5, or 7.
15) The method of statement 1-12 or 13, wherein the metastatic chemotherapeutic agent is a composition comprising an agonist of kinesin-13 with the following structure, wherein X is a methyl group:

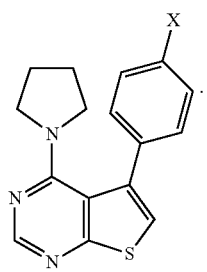

16) The method of statement 1-13 or 14, wherein the concentration or amount of cGAMP in the bodily fluid sample or the cell sample is quantified in a method comprising liquid chromatography (LC) with mass spectrometry (MS).

17) The method of statement 1-14 or 15, wherein the cGAMP in the bodily fluid sample or the cell sample is extracted and/or dissolved in an alcohol to produce an alcohol extract, the alcohol extract can be subjected to chromatography, and the effluent from the chromatography can be suspended in acetonitrile, water or a combination thereof before measuring the concentration or amount of the cGAMP.

18) A method comprising administering to a subject at least one kinesin-13 protein, at least one MACK protein, at least one agonist of kinesin-13, at least one agonist of MACK, or a combination thereof.

19) The method of statement 17, wherein the at least one kinesin-13 protein or MCAK has at least 90%, at least 91%, at least 92%, at least 93%, at least 94%, at least 95%, at least 96%, at least 97%, at least 98%, at least 99% sequence identity to any of SEQ ID NO:1, 3, 5, or 7.

20) The method of statement 17 or 18, wherein at least one agonist of kinesin-13 is the following, wherein X is a methyl group:

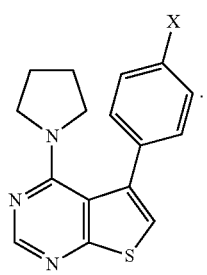

21) The method of statement 17, 18, or 19, further comprising administering an inhibitor of STING, cGAS, NF-κB transcription factor p52, NF-κB transcription factor RelB, ENPP1, LTβR, BAFFR, CD40, RANK, FN14, NIK (MAP3K14), MST1, or any combination thereof to the subject.

22) A method comprising inhibiting STING, cGAS, NF-κB transcription factor p52, NF-κB transcription factor RelB, ENPP1, LTβR, BAFFR, CD40, RANK, FN14, NIK (MAP3K14), MST1, or any combination thereof in a mammalian cell.

23) A method comprising administering to a subject an expression vector comprising a promoter operably linked to a nucleic acid segment encoding a kinesin-13 or MACK protein.

24) The method of statement 22, wherein the at least one kinesin-13 protein or MACK protein has at least 90%, at least 91%, at least 92%, at least 93%, at least 94%, at least 95%, at least 96%, at least 97%, at least 98%, at least 99% sequence identity to any of SEQ ID NO:1, 3, 5, or 7.

25) The method of statement 17-23 or 23, comprising administering an expression vector comprising a promoter operably linked to an inhibitory nucleic acid segment with at least 90%, at least 91%, at least 92%, at least 93%, at least 94%, at least 95%, at least 96%, at least 97%, at least 98%, at least 99% sequence identity or complementarity to any of SEQ ID NO: 9, 11, 13, or 15.

26) The method of statement 1-23, or 24, further comprising administering an inhibitor of STING, cGAS, NF-κB transcription factor p52, NF-κB transcription factor RelB, ENPP1, LTβR, BAFFR, CD40, RANK, FN14, NIK (MAP3K14), MST1, or any combination thereof to the subject.

27) The method of statement 1-24 or 25, further comprising administering an agonist of ABCC4, ABCG2, or a combination thereof; administering an expression cassette or vector comprising a promoter operably linked to a nucleic acid segment that encodes ABCC4 or ABCG2; or a combination thereof.

28) The method of statement 1-25, or 26, wherein cells in the patient exhibits chromosomal instability prior to administration.

29) The method of statement 1-26 or 27, wherein the patient is suspected of having cancer.

30) The method of statement 1-27 or 28, wherein the patient is suspected of developing cancer.

31) The method of statement 1-28 or 29, wherein the patient has cancer.

32) The method of statement 1-29 or 30, wherein the patient has metastatic cancer.

33) The method of statement 1-30 or 31, wherein the method inhibits metastasis of cancer in the subject.

34) The method of statement 1-31 or 32, wherein the method inhibits metastasis of cancer in the subject compared to a control subject that did not receive the protein or the expression vector.

35) The method of statement 1-32 or 33, wherein the method inhibits chromosomal instability.

36) A method comprising quantifying expression levels of at least one of the following genes in a test sample from a patient: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5, to generate at least one quantified expression level of at least one following genes in the test sample: PELI2, BMP2, SHH, TNS4, RAB3B, ROBO1, ARHGAP28, CHN2, CST1, F3A1, CPVL, SEMA6D, C9orf152, NHSL2, GTF2IP7, DPYSL3, PCDH7, KHDRBS3, TRAC, TMEM156, CST4, CD24, or FGF5.

37) The method of statement 35, further comprising determining at least one difference in at least one quantified expression level of at least one following genes in the test sample: PELI2, BMP2, SHH, TNS4, RAB3B, ROBO1, ARHGAP28, CHN2, CST1, F3A1, CPVL, SEMA6D, C9orf152, NHSL2, GTF2IP7, DPYSL3, PCDH7, KHDRBS3, TRAC, TMEM156, CST4, CD24, or FGF5 compared to a control expression level of at least one corresponding gene in a healthy or non-cancerous sample.

38) The method of statement 35 or 36, wherein the healthy or non-cancerous sample does not exhibit chromosomal instability.

39) The method of statement 35, 36, or 37, further comprising determining at least one difference in at least one quantified expression level of at least one following genes in the test sample: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5 compared to a control expression level of at least one corresponding gene in a sample (or set of samples) from a patient with metastatic cancer.

40) The method of statement 35-37, or 38, comprising quantifying expression levels of two or more, or three or more, or four or more, or five or more, or six or more, or seven or more, or eight or more, or nine or more, ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more of the following genes in the test sample: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5.

41) The method of statement 35-38, or 39, wherein the difference in at least one quantified expression level of at least one following genes in the test sample: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5 compared to a control expression level of at least one corresponding gene in a healthy or non-cancerous sample is at least a 10%, or 20% or 30%, or 40%, or 50%, or 60%, or 75%, or 100% increase in expression.

42) The method of statement 35-39, or 40, wherein the difference in at least one quantified expression level of at least one following genes in the test sample: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5 compared to a mean control expression level of at least one corresponding gene in a sample (or set of samples from one or more patients with metastatic cancer) is at least a 10%, or 20% or 30%, or 40%, or 50%, or 60%, or 75%, or 100% increase in expression.

43) The method of statement 35-40, or 41, wherein the difference in at least one quantified expression level of at least one following genes in the test sample: PELI2, BMP2, SHH, TNS4, RAB3B, ROBO1, ARHGAP28, CHN2, CST1, F13A1, CPVL, SEMA6D, C9orf152, NHSL2, GTF2IP7, DPYSL3, PCDH7, KHDRBS3, TRAC, TMEM156, CST4, CD24, or FGF5 compared to a control expression level is at least an increase of expression of these corresponding genes of at least a 1.2-fold, or 1.5-fold, or 2-fold, or 3-fold, or 5-fold, or 7-fold, or 10-fold increase in expression.

44) A method comprising administering STING proteins to a subject or expressing STING proteins from an expression cassette or expression vector in a subject to restore and/or activate canonical pathways downstream of cytosolic DNA sensing as a therapeutic tool against chromosomally unstable tumor cells and induce cell-intrinsic cytotoxic pathways.

45) A method comprising administering on or more STING agonists to a subject to restore and/or activate canonical pathways downstream of cytosolic DNA sensing as a therapeutic tool against chromosomally unstable tumor cells and induce cell-intrinsic cytotoxic pathways.

46) The method of statement 43 or 44, which sensitizes tumor cells to immune therapies.

47) A composition comprising a carrier and a kinesin-13 protein with at least 90%, at least 91%, at least 92%, at least 93%, at least 94%, at least 95%, at least 96%, at least 97%, at least 98%, at least 99% sequence identity to any of SEQ ID NO:1, 3, or 5.

48) A composition comprising a carrier and a kinesin-13 nucleic acid comprising a sequence with at least 90%, at least 91%, at least 92%, at least 93%, at least 94%, at least 95%, at least 96%, at least 97%, at least 98%, at least 99% sequence identity to any of SEQ ID NO:2, 4, or 6.

49) The composition of statement 46 or 47, further comprising a MCAK protein with at least 90%, at least 91%, at least 92%, at least 93%, at least 94%, at least 95%, at least 96%, at least 97%, at least 98%, at least 99% sequence identity to SEQ ID NO: 7, or a MCAK nucleic acid with at least 90%, at least 91%, at least 92%, at least 93%, at least 94%, at least 95%, at least 96%, at least 97%, at least 98%, at least 99% sequence identity to SEQ ID NO:8.

50) The composition of statement 46, 47, or 48, comprising at least one STING, cGAS, NF-κB transcription factor p52, NF-κB transcription factor RelB, ENPP1, LTβR, BAFFR, CD40, RANK, FN14, NIK (MAP3K14), or MST1 inhibitory nucleic acid.

51) The composition of statement 46-48 or 49, comprising at least one inhibitory nucleic acid having at least 90%, at least 91%, at least 92%, at least 93%, at least 94%, at least 95%, at least 96%, at least 97%, at least 98%, at least 99% sequence identity to any of SEQ ID NO: 10, 12, 14, 16, 18, 20, 22, 24, 25, 26, 27, 28, 29, 30, 31, 32, 33, 34, 35, or 36.

52) The composition of statement 46-49, or 50, comprising at least one antibody that binds with affinity to a STING, cGAS, NF-κB transcription factor p52, NF-κB transcription factor RelB, ENPP1, LTβR, BAFFR, CD40, RANK, FN14, NIK (MAP3K14), or MST1 protein.

53) The composition of statement 46-50, or 51, comprising at least one antibody that binds with affinity to a protein with at least 90%, at least 91%, at least 92%, at least 93%, at least 94%, at least 95%, at least 96%, at least 97%, at least 98%, at least 99% sequence identity to any of SEQ ID NO: 9, 11, 13, 15, 17, 19, 21, or 23.

54) An expression vector comprising a promoter operably linked to a nucleic acid segment encoding a kinesin-13 or MCAK protein with at least 90%, at least 91%, at least 92%, at least 93%, at least 94%, at least 95%, at least 96%, at least 97%, at least 98%, at least 99% sequence identity to any of SEQ ID NO:1, 3, 5, or 7.

55) An expression vector comprising a promoter operably linked to an inhibitory nucleic acid segment with at least 90%, at least 91%, at least 92%, at least 93%, at least 94%, at least 95%, at least 96%, at least 97%, at least 98%, at least 99% sequence identity or complementarity to any of SEQ ID NO:10, 12, 14, 16, 18, 20, 22, 24, 25, 26, 27, 28, 29, 30, 31, 32, 33, 34, 35, or 36.

56) A method comprising: (a) mixing a test compound with cancer (or metastatic cancer) cells in a culture medium to produce a test assay; (b) incubating the test assay for a time and under conditions sufficient for the test compound to associate with or penetrate the cells; (c) measuring cGAMP amounts or concentrations in the culture medium, in the cells, or in a combination thereof to produce a test assay cGAMP value; and (d) selecting a test compound with a lower test assay cGAMP value than a reference cGAMP value to thereby produce an effective test compound.

57) The method of statement 55, wherein the reference cGAMP value is the amount or concentration of cGAMP in the culture medium, in the cells, or in a combination thereof of an assay mixture that does not contain a test compound.

58) A method comprising: (a) obtaining a cell or tissue sample from a patient; (b) measuring the amount or concentration of cGAMP produced from a known number or weight of cells or tissues from the sample to generate a reference cGAMP value; (c) mixing the same known number or weight of cells or tissues from the sample with a test compound to generate a test assay; (d) measuring the cGAMP amount or concentration in the test assay (either in the cell medium or in the cells or tissues) to generate a test assay cGAMP value; (e) optionally repeating steps (c) and (d); and selecting a test compound with a lower test assay cGAMP value than the reference cGAMP value to thereby identify an effective test compound.

59) The method of statement 55, 56 or 57, wherein the metastatic cancer cells or metastatic tissues are mixed in the culture medium to produce the test assay.

60) The method of statement 55-57 or 58, further comprising extracting the cell or tissue sample with an alcohol (e.g., methanol, ethanol, or isopropanol) to produce an alcohol extract before measuring the cGAMP.

61) The method of statement 59, further comprising purifying the alcohol extract by Solid Phase Extraction (SPE) using one or more HyperSep aminopropyl solid phase columns to produce a semi-pure test sample before measuring the cGAMP of the semi-pure test sample 62) The method of statement 59 or 60, further comprising suspending the cGAMp in acetonitrile, water or a combination thereof before measuring the cGAMP.

63) The method of statement 55-60 or 61, wherein measuring cGAMP amounts or concentrations comprises liquid chromatography and/or mass spectroscopy to measure the level of cGAMP.

64) The method of statement 55-61 or 62, further comprising administering the effective test compound to an animal model, for example, to further evaluate the toxicity and/or efficacy of the effective test compound.

65) The method of statement 55-62 or 63, further comprising administering the effective test compound to a patient or to the patent from whom the cell or tissue sample as obtained.

66) An effective test compound produced by a method comprising: (a) mixing a test compound with cancer (or metastatic cancer) cells in a culture medium to produce a test assay; (b) incubating the test assay for a time and under conditions sufficient for the test compound to affect cGAMP production in the cells; (c) measuring cGAMP amounts or concentrations in the culture medium, in the cells, or in a combination thereof to produce a test assay cGAMP value; and (d) selecting a test compound with a lower test assay cGAMP value than a reference cGAMP value to thereby produce an effective test compound.

67) The effective test compound produced of statement 65, wherein the metastatic cancer cells or metastatic tissues are mixed in the culture medium to produce the test assay.

68) The effective test compound produced of statement 65 or 66, wherein the method further comprises extracting the cells with an alcohol (e.g., methanol, ethanol, or isopropanol) to produce an alcohol extract before measuring the cGAMP.

69) The effective test compound produced of statement 65, 66 or 67, wherein the method further comprises extracting the cell or tissue sample with methanol to produce a methanol extract and measuring the cGAMP in the methanol extract.

70) The effective test compound produced of statement 67 or 68, wherein the method further comprises purifying the alcohol extract or the methanol extract by Solid Phase Extraction (SPE) using one or more HyperSep aminopropyl solid phase columns to produce a semi-pure test sample before measuring the cGAMP of the semi-pure test sample.

71) The effective test compound produced of statement 65-68 or 69, wherein measuring cGAMP amounts or concentrations comprises liquid chromatography and/or mass spectroscopy to measure the level of cGAMP.

72) The effective test compound produced of statement 65-69 or 70. wherein the method further comprises administering the effective test compound to an animal model, for example, to further evaluate the toxicity and/or efficacy of the effective test compound.

73) The effective test compound produced of statement 65-70 or 71, wherein the method further comprises administering the effective test compound to a patient or to the patent from whom the cell or tissue sample as obtained.

74) A method comprising: (a) mixing a test compound with KIF2B or MCAK in a test assay mixture that contains 2-amino-6-mercapto-7-methylpurine ribonucleoside (MESG); (b) incubating the test assay mixture to produce an incubated test assay; (c) measuring an amount of inorganic phosphate to provide an inorganic phosphate test result; and (d) comparing the inorganic phosphate test result to a control or reference.

75) The method of statement 74, wherein the control is the amount of inorganic phosphate (Pi) present in a control assay that contains the KIF2B or MCAK and the 2-amino-6-mercapto-7-methylpurine ribonucleoside (MESG), but that does not contain the test compound.

76) The method of statement 74, wherein the reference is a mean amount of inorganic phosphate (Pi) present in two or more control assays that contain the KIF2B or MCAK and the 2-amino-6-mercapto-7-methylpurine ribonucleoside (MESG), but that does not contain the test compound.

77) The method of statement 74, 75 or 76, further comprising selecting a test compound that has an inorganic phosphate test result higher than the control or reference.

78) The method of statement 74-76 or 77, further comprising selecting a test compound that has an inorganic phosphate test result higher than the control or reference, and evaluating the test compound in a second assay to assess test compound as an activator of KIF2B or MCAK.

79) A method comprising: (a) mixing a test compound with cancer cells having γ-tubulin-labeled centrosomes to produce a test assay; (b) incubating the test assay for a time and under conditions sufficient for the test compound to penetrate the cancer cells to produce incubated test cancer cells; (c) measuring the distance between γ-tubulin-labeled centrosomes within a series of incubated test cancer cells to produce a mean distance result; and (d) comparing the mean distance result to a control or reference.

80) The method of statement 79, wherein the distance is measured by fluorescent in situ hybridization (FISH).

81) The method of statement 79 or 80, wherein the control is the distance between γ-tubulin-labeled centrosomes in cancer cells of a control assay that does not contain the test compound.

82) The method of statement 79 or 80, wherein the reference is a mean distance between γ-tubulin-labeled centrosomes within a series of γ-tubulin-labeled cancer cells in a control assay that does not contain the test compound.

83) The method of statement 79, 80 or 81, further comprising selecting a test compound that has a lower mean distance result than the control or reference.

84) The method of statement 74-76 or 77, further comprising selecting a test compound that has a lower mean distance result than the control or reference, and evaluating the test compound in a second assay to assess test compound as an activator of MCAK.

85) A method comprising (a) mixing NF-kB Inducing Kinase with a test compound, ATP, and an antibody with a fluorescent tracer (633 nm) bound to the antibody, where the antibody specifically recognizes ADP; (b) incubating the test assay mixture to produce an incubated test assay; (c) measuring an amount of fluorescence in the incubated test assay; and (d) comparing the amount of fluorescence in the incubated test assay to a control or reference.

86) The method of statement 85, wherein the control is the amount of fluorescence in a control assay that does not contain the test compound.

87) The method of statement 85, wherein the reference is a mean amount of fluorescence in a series of control assays that do not contain the test compound.

88) The method of statement 85, 86 or 87, further comprising selecting a test compound that has a higher amount of fluorescence in one or more incubated test assays than the control or reference.

89) The method of statement 85-87 or 88, further comprising selecting a test compound that has a higher amount of fluorescence in one or more incubated test assays than the control or reference, and evaluating the test compound in a second assay to assess the test compound as an inhibitor of NF-kB Inducing Kinase.

90) A method comprising: (a) mixing cancer cells with a test compound and an anti-lymphotoxin beta receptor (LT-PR) antibody; (b) incubating the test assay for a time and under conditions sufficient for the test compound to penetrate the cancer cells to produce incubated test cancer cells; (c) measuring the quantity of RELB translocation into nuclei of the incubated test cancer cells; and (d) comparing the amount quantity of RELB translocation into nuclei of the incubated test cancer cells to a control or reference.

91) The method of statement 90, wherein measuring the quantity of RELB translocation into nuclei of the incubated test cancer cells further comprises obtaining a ratio of the nuclear over cytoplasmic signal intensity.

92) The method of statement 90 or 91, wherein the control is the amount of RELB translocation into nuclei in a control assay that does not contain the test compound.

93) The method of statement 90 or 91, wherein the reference is a mean amount of RELB translocation into nuclei in a series of control assays that do not contain the test compound.

94) The method of statement 90-92 or 93, further comprising selecting a test compound that has a lower quantity of RELB translocation into nuclei of the incubated test cancer cells than the control or reference.

95) The method of statement 85-87 or 88, further comprising selecting a test compound that has a lower quantity of RELB translocation into nuclei of the incubated test cancer cells than the control or reference, and evaluating the test compound in a second assay to assess the test compound as an inhibitor of NF-kB Inducing Kinase.

96) An effective test compound produced by the method of statement 74-94 or 95.

97) The effective test compound of statement 96 wherein the method further comprises administering the effective test compound to an animal model, for example, to further evaluate the toxicity and/or efficacy of the effective test compound.

98) The effective test compound of statement 96 or 97, wherein the method further comprises administering the effective test compound to a patient or to the patent from whom the cancer cells were obtained.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "an expression cassette" or "a cell" includes a plurality of such nucleic acids, expression vectors or cells (for example, a solution or dried preparation of nucleic acids or expression cassettes, or a population of cells), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method for determining whether a test compound is effective for treatment of chromosomal instability, the method comprising:
 (a) mixing a test compound with a metastatic cancer cell sample in a culture medium to produce a test assay;
 (b) incubating the test assay for a time and under conditions sufficient for the test compound to associate with or penetrate the cells;
 (c) measuring:
 cGAMP amounts or concentrations in the culture medium, in the cells, or in a combination thereof to produce a test assay value;
 distances between centrosomes within a series of he cells to produce a mean distance result;
 a quantity of RELB translocation into nuclei of the cells; and
 (d) determining the test compound is effective for treatment of chromosomal instability when presence of the test compound results in:
 a lower test assay cGAMP value than a reference cGAMP value;
 a lower mean distance result than a reference distance;
 lower quantity of RELB translocation into nuclei of the cells than a reference quantity.

2. The method of claim 1, wherein the reference is
 a. the amount or concentration of cGAMP in an assay mixture that does not contain a test compound;
 b. the distance between centromeres in metastatic cancer cells within an assay mixture that does not contain a test compound; or
 c. the quantity of RELB translocation into nuclei of metastatic cancer cells within an assay mixture that does not contain a test compound.

3. The method of claim 1, comprising:
 (c) measuring cGAMP amounts or concentrations in the culture medium, in the cells, or in a combination thereof to produce a test assay value; and
 (d) selecting a test compound with a lower test assay cGAMP value than a reference cGAMP value, wherein the reference cGAMP value is the amount or concentration of cGAMP in an assay mixture that does not contain a test compound, and further comprising extracting the sample or culture medium with an alcohol to produce an alcohol extract before measuring the cGAMP.

4. The method of claim 3, further comprising purifying the alcohol extract by Solid Phase Extraction (SPE) using one or more aminopropyl solid phase columns to produce a semi-pure test sample before measuring the cGAMP of the semi-pure test sample.

5. The method of claim 4, wherein measuring cGAMP amounts or concentrations comprises liquid chromatography and/or mass spectroscopy to measure the level of cGAMP.

6. The method of claim 5, wherein the liquid chromatography comprises an aqueous mobile phase comprising isopropanol and acetic acid and an organic mobile phase comprising acetonitrile and ammonium acetate.

7. The method of claim 6, further comprising adding EDTA to the mobile phase before measuring the cGAMP.

8. The method of claim 4, wherein the alcohol is methanol.

9. The method of claim 4, wherein cells of the sample are frozen in liquid nitrogen before production of the alcohol extract.

10. The method of claim 1, further comprising administering the test compound to an animal model to further identify the in vivo activity of the test compound.

11. The method of claim 1, wherein the metastatic cancer cell originated from breast cancer or lung cancer.

12. The method of claim 1, wherein metastatic cancer cells of the sample comprise at least 10% chromosomal finis-segregations.

13. The method of claim 1, wherein step (b) comprises incubating die test assay for a time and under conditions sufficient for the test compound penetrate the cells.

14. The method of claim 1; wherein step (b) comprises incubating the test assay for a time and under conditions sufficient for the test compound to associate with the cells.

15. A method for determining whether a test compound is effective for treatment of chromosomal instability, the method comprising:
 (a) measuring in a test assay comprising a test compound that associates with or penetrates cells and a sample comprising metastatic cancer cells,
 cGAMP amounts or concentrations in the culture medium, in the cells, or in a combination thereof to produce a test assay value;
 distances between centrosomes within a series of the cells to produce a mean distance result;
 a quantity of RELB translocation into nuclei of the cells; and
 (b) determining the test compound is effective for treatment of chromosomal instability when presence of the test compound results in:
 a lower test assay cGAMP value than a reference cGAMP value;
 a lower mean distance result than a reference distance;
 lower quantity of RELB translocation into nuclei of the cells than a reference quantity.

* * * * *